(12) United States Patent
Zhang et al.

(10) Patent No.: US 8,575,363 B2
(45) Date of Patent: Nov. 5, 2013

(54) AMINO-PYRROLIDINE-AZETIDINE DIAMIDES AS MONOACYLGLYCEROL LIPASE INHIBITORS

(75) Inventors: Yue-Mei Zhang, Belle Mead, NJ (US); Peter J. Connolly, New Providence, NJ (US); Shu-Chen Lin, Doylestown, PA (US); Mark J. MacIelag, Gwynedd Valley, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 13/277,734

(22) Filed: Oct. 20, 2011

(65) Prior Publication Data

US 2012/0101081 A1 Apr. 26, 2012

(51) Int. Cl.
*C07D 207/10* (2006.01)
*A61K 31/397* (2006.01)

(52) U.S. Cl.
USPC ..................................... 548/518; 514/210.18

(58) Field of Classification Search
USPC ..................................... 548/518; 514/210.18
See application file for complete search history.

(56) References Cited

U.S. PATENT DOCUMENTS

| 7,217,705 B2 | 5/2007 | Benavides et al. |
| 2033/0119810 | 6/2003 | Achard et al. |
| 2004/0167224 A1 | 8/2004 | Ozaki et al. |
| 2006/0148844 A1 | 7/2006 | Nakade et al. |
| 2007/0142394 A1 | 6/2007 | Solomon et al. |
| 2007/0197654 A1 | 8/2007 | Benavides et al. |
| 2007/0293496 A1 | 12/2007 | Ozaki et al. |
| 2009/0269785 A1 | 10/2009 | Schubert et al. |
| 2010/0041651 A1 | 2/2010 | Even et al. |

FOREIGN PATENT DOCUMENTS

| EP | 2180048 | 4/2010 |
| FR | 2915199 A1 | 10/2008 |
| WO | WO 98/37077 | 8/1998 |
| WO | WO 99/19297 | 4/1999 |
| WO | WO 00/63168 | 10/2000 |
| WO | WO 01/77101 | 10/2001 |
| WO | WO 03/020314 | 3/2003 |
| WO | WO 2004/056800 A1 | 7/2004 |
| WO | WO 2006/097175 A1 | 9/2006 |
| WO | WO 2008/025736 | 3/2008 |
| WO | WO 2008/145842 A2 | 12/2008 |
| WO | WO 2008/145843 A1 | 12/2008 |
| WO | WO 2009/117444 A1 | 9/2009 |
| WO | WO 2009/132267 A1 | 10/2009 |
| WO | WO 2010/124082 A1 | 10/2010 |
| WO | WO 2010/124108 A1 | 10/2010 |
| WO | WO 2010/124121 A1 | 10/2010 |

OTHER PUBLICATIONS

International Search Report relating to International application No. PCT/US2011/057090, which corresponds to U.S. Appl. No. 13/277,734. Date of Mailing of International Search Report: Jan. 27, 2012.
Written Opinion of the International Searching Authority relating to International application No. PCT/US2011/057090, which corresponds to U.S. Appl. No. 13/277,734. Date of Mailing of Written Opinion: Jan. 27, 2012.
Benito et al., "Cannabinoid CB2 receptors in human braininflammation.", Brit. J. Pharmacol., 2008, pp. 277-285, vol. 153.
Ben-Shabat et al., "An entourage effect: inactive endogenous fatty acid glycerol esters enhance 2-arachidonoyl-glycerol cannabinoid activity.", Eur. J. Pharmacol., 1998, pp. 23-31, vol. 353.
Cavuoto et al.,"The expression of receptors for endocannabinoids in human and rodent skeletal muscle.", Biochem. Biophys. Res. Commun., 2007, pp. 105-110, vol. 364.
Comelli et al., "The inhibition of monoacylglycerol lipase by URB602 showed an anti-inflammatory and anti-nociceptive effect in a murine model of acute inflammation.", Brit. J. Pharmacol., 2007, pp. 787-794, vol. 152.
Cravatt et al.,"The Endogenous Cannabinoid System and Its Role in Nociceptive Behavior.", J. Neurobiol., 2004, pp. 149-160, vol. 61.
Devane et al., "Isolation and Structure of a Brain Constituent That Binds to the Cannabinoid Receptor.", Science, 1992, pp. 1946-1969, vol. 258.
Di Marzo et al., "Endocannabinoids and the Regulation of their levels in Health and Disease.", Curr. Opin. Lipidol., 2007, pp. 129-140, vol. 18.
Di Marzo et al., "Endocannabinoids: New Targets for Drug Development.", Curr. Pharm. Des., 2000, pp. 1361-1380, vol. 6.
Dogrul et al., "'Knock-down' of spinal CB1 receptors produces abnormal pain and elevates spinal dynorphin content in mice.", Pain, 2002, pp. 203-209, vol. 100.
Guindon et al.,"Cannabinoid CB2 receptors: a therapeutic target for the treatment of inflammatory and neuropathic pain.", Brit. J. Pharmacol., 2008, pp. 319-334, vol. 153.
Hajrasouliha et al., "Endogenous cannabinoids contribute to remote ischemic preconditioning via cannabinoid CB2 receptors in the rat heart.", Eur. J. Pharmacol., 2008, pp. 246-252, vol. 579.
Jhaveri et al., "Endocannabinoid metabolism and uptake: novel targets for neuropathic and inflammatory pain.", Brit. J. Pharmacol., 2007, pp. 624-632, vol. 152.

(Continued)

*Primary Examiner* — Robert Havlin
(74) *Attorney, Agent, or Firm* — Thomas J. Dodd

(57) ABSTRACT

Disclosed are compounds, compositions and methods for treating various diseases, syndromes, conditions and disorders, including pain. Such compounds, and enantiomers, diastereomers, and pharmaceutically acceptable salts thereof, are represented by Formula (I) as follows:

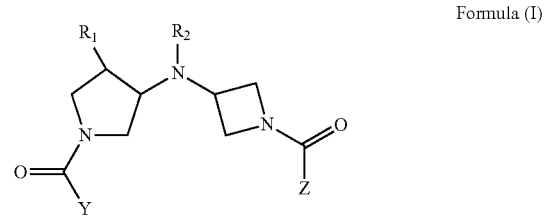

Formula (I)

wherein Y, Z, and $R_1$, and $R_2$ are defined herein.

10 Claims, No Drawings

(56) References Cited

OTHER PUBLICATIONS

Kathuria et al., "Modulation of anxiety through blockade of anandamide hydrolysis.", *Nat. Med.*, 2003, pp. 76-81, vol. 9.
Lichtman et al., "Pharmacological Activity of Fatty Acid Amides is Regulated, but Not Mediated, by Fatty Acid Amide Hydrolase in Vivo.", *J. Pharmacol. Exp. Ther.*, 2002, pp. 73-79, vol. 302(1).
Matsuda et al., "Structure of a Cannabinoid Receptor and Functional Expression of the cloned cDNA.", *Nature*, 1990, pp. 561-564, vol. 346.
Matulis et al., "Thermodynamic Stability of Carbonic Anhydrase: Measurements of Binding Affinity and Stoichiometry Using ThermoFluor.", *Biochemistry*, 2005, pp. 5258-5266, vol. 44.
McCarberg et al., "The Future of Cannabinoids as Analgesic Agents: A Pharmacologic, Pharmacokinetic, and Pharmacodynamic Overview.", *Amer. J. Ther.*, 2007, pp. 475-483, vol. 14.
Mechoulam et al., "Identification of an Endogenous 2-Monoglyceride, Present in Canine Gut, that Binds to Cannabinoid Receptors.", *Biochem. Pharmacol.*, 1995, pp. 83-90, vol. 50.
Munro et al., "Molecular Characterization of a Peripheral Receptor for Cannabinoids.", *Nature*, 1993, pp. 61-665, vol. 365.
Njie et al., "Aqueous humor outflow effects of 2-arachidonylglycerol.", *Exp. Eye Res.*, 2008, pp. 106-114, vol. 87(2).
Pacher et al., "Pleiotropic effects of the $CB_2$ cannabinoid receptor activation on human monocyte migration: implications for atherosclerosis and inflammatory diseases." *Amer. J. Physiol.*, 2008, pp. H1133-H1134, vol. 294.
Pantoliano et al., "High Density Miniaturized Thermal Shift Assays as a General Strategy for Drug Discovery*.", *Journal of Biomolecular Screening*, 2001, pp. 429-440, vol. 6(6).
Pertwee, R.G.,"The diverse CB1 and CB2 receptor pharmacology of three plant cannabinoids: $D^9$-tetrahydrocannabinol, cannabidiol and $D^9$-tetrahydrocannabivarin." *Brit. J. Pharmacol.*, 2008, pp. 199-215, vol. 153.
Piomelli D., "The Molecular Logic of Endocannabinold Signalling.", *Nat. Rev. Neurosci.*, 2003, pp. 873-884, vol. 4.
Schlosser et al., "In Search of Simplicity and flexibility: A Rational Access to Twelve Fluoroindolecarboxylic Acids.", *Eur. J. Org. Chem.*, 2006, pp. 2956-2969, Issue 13.
Sugiura et al., "2-Arachidonoylglycerol: A Possible Endogenous Cannabinoid Receptor Ligand in Brain.", *Biochem. Biophys. Res. Commun.*, 1995, pp. 89-97, vol. 215.
Walker et al., "Pain modulation by release of the endogenous cannabinoid anandamide.", *Proc. Natl. Acad. Sci.*, USA, 1999, pp. 12198-121203, vol. 96.
Bennett et al., "A peripheral mononeutopathy in rat that produces disorders of pain sensation like those seen in man.", Pain, 1988, vol. 33(1), pp. 87-107.
Chaplan et al., "Quantitative assessment of tactile allodynia in the rat paw", J. Neurosci Methods, 1994, vol. 53(1), pp. 55-63.
Dixon, W. J., "Efficient analysis of experimental observations", Annu. Rev. Pharmacol. Toxicol., 1980, vol. 20, pp. 441-462.
Lichtman et al., "Mice lacking fatty acid amide hydrolase exhibit a cannabinoid receptor-mediated phenotypic hypoalgesia", Pain, 2004, vol. 109, pp. 319-327.
PCT counterpart to U.S. Appl. No. 12/765,617, International Search Report and Written Opinion, PCT/US2010/032098, dated Jun. 18, 2010.
International Preliminary Report, PCT/US2010/032098, dated Oct. 25, 2011.
PCT counterpart to U.S. Appl. No. 12/765,675, International Search Report and Written Opinion, PCT/US2010/032100, dated Jun. 15, 2010.
International Preliminary Report, PCT/US2010/032100, dated Oct. 25, 2011.
PCT counterpart to U.S. Appl. No. 13/224,654, International Search Report and Written Opinion, PCT/US2011/049885, dated Oct. 11, 2011.
International Preliminary Report, PCT/US2011/049885, dated Mar. 5, 2013.
PCT counterpart to U.S. Appl. No. 13/246,232, International Search Report and Written Opinion, PCT/US2011/053442, dated Jan. 10, 2012.
International Preliminary Report, PCT/US2011/053442, dated Apr. 2, 2013.
PCT counterpart to U.S. Appl. No. 13/277,734, International Search Report and Written Opiniln, PCT/US2011/057090, dated Jan. 27, 2012.
International Preliminary Report, PCT/US2011/057090, dated Apr. 23, 2013.
PCT counterpart to U.S. Appl. No. 13/277,702, International Search Report and Written Opinion, PCT/US2011/057085, dated Jan. 27, 2012.
International Preliminary Report, PCT/US2011/057085, dated Apr. 23, 2013.
PCT counterpart to U.S. Appl. No. 13/628,331, International Search Report and Written Opinion, PCT/US2012/057461, dated Dec. 4, 2012.
PCT counterpart to U.S. Appl. No. 13/628,428, International Search Report and Written Opinion, PCT/US2012/057465, dated Dec. 12, 2012.
PCT counterpart to U.S. Appl. No. 13/628,452, International Search Report and Written Opinion, PCT/US2012/057470, dated Dec. 3, 2012.

AMINO-PYRROLIDINE-AZETIDINE DIAMIDES AS MONOACYLGLYCEROL LIPASE INHIBITORS

CROSS-REFERENCE TO RELATED APPLICATIONS

Not applicable.

STATEMENT REGARDING FEDERALLY SPONSORED RESEARCH OR DEVELOPMENT

The research and development of the invention described below was not federally sponsored.

BACKGROUND OF THE INVENTION

*Cannabis sativa* has been used for the treatment of pain for many years. $\Delta^9$-tetrahydrocannabinol is a major active ingredient from *Cannabis sativa* and an agonist of cannabinoid receptors (Pertwee, *Brit J Pharmacol,* 2008, 153, 199-215). Two cannabinoid G protein-coupled receptors have been cloned, cannabinoid receptor type 1 ($CB_1$ Matsuda et al., *Nature,* 1990, 346, 561-4) and cannabinoid receptor type 2 ($CB_2$ Munro et al., *Nature,* 1993, 365, 61-5). $CB_1$ is expressed centrally in brain areas, such as the hypothalamus and nucleus accumbens as well as peripherally in the liver, gastrointestinal tract, pancreas, adipose tissue, and skeletal muscle (Di Marzo et al., *Curr Opin Lipidol,* 2007, 18, 129-140). $CB_2$ is predominantly expressed in immune cells, such as monocytes (Pacher et al., *Amer J Physiol,* 2008, 294, H1133-H1134), and under certain conditions, also in the brain (Benito et al., *Brit J Pharmacol,* 2008, 153, 277-285) and in skeletal (Cavuoto et al., *Biochem Biophys Res Commun,* 2007, 364, 105-110) and cardiac (Hajrasouliha et al., *Eur J Pharmacol,* 2008, 579, 246-252) muscle. An abundance of pharmacological, anatomical and electrophysiological data, using synthetic agonists, indicate that increased cannabinoid signaling through $CB_1/CB_2$ promotes analgesia in tests of acute nociception and suppresses hyperalgesia in models of chronic neuropathic and inflammatory pain (Cravatt et al., *J Neurobiol,* 2004, 61, 149-60; Guindon et al., *Brit J Pharmacol,* 2008, 153, 319-334).

Efficacy of synthetic cannabinoid receptor agonists is well documented. Moreover, studies using cannabinoid receptor antagonists and knockout mice have also implicated the endocannabinoid system as an important modulator of nociception. Anandamide (AEA) (Devane et al., *Science,* 1992, 258, 1946-9) and 2-arachidinoylglycerol (2-AG) (Mechoulam et al., *Biochem Pharmacol,* 1995, 50, 83-90; Sugiura et al., *Biochem Biophys Res Commun,* 1995, 215, 89-97) are two major endocannabinoids. AEA is hydrolyzed by fatty acid amide hydrolase (FAAH) and 2-AG is hydrolyzed by monoacylglycerol lipase (MGL) (Piomelli, *Nat Rev Neurosci,* 2003, 4, 873-884). Genetic ablation of FAAH elevates endogenous AEA and results in a $CB_1$-dependent analgesia in models of acute and inflammatory pain (Lichtman et al., *Pain,* 2004, 109, 319-27), suggesting that the endocannabinoid system functions naturally to inhibit pain (Cravatt et al., *J Neurobiol,* 2004, 61, 149-60). Unlike the constitutive increase in endocannabinoid levels using FAAH knockout mice, use of specific FAAH inhibitors transiently elevates AEA levels and results in antinociception in vivo (Kathuria et al., *Nat Med,* 2003, 9, 76-81). Further evidence for an endocannabinoid-mediated antinociceptive tone is demonstrated by the formation of AEA in the periaqueductal grey following noxious stimulation in the periphery (Walker et al., *Proc Natl Acad Sci USA,* 1999, 96, 12198-203) and, conversely, by the induction of hyperalgesia following antisense RNA-mediated inhibition of $CB_1$ in the spinal cord (Dogrul et al., *Pain,* 2002, 100, 203-9).

With respect to 2-AG, intravenous delivery of 2-AG produces analgesia in the tail flick (Mechoulam et al., *Biochem Pharmacol,* 1995, 50, 83-90) and hot plate (Lichtman et al., *J Pharmacol Exp Ther,* 2002, 302, 73-9) assays. In contrast, it was demonstrated that 2-AG given alone is not analgesic in the hot plate assay, but when combined with other 2-monoacylglycerols (i.e., 2-linoleoyl glycerol and 2-palmitoyl glycerol), significant analgesia is attained, a phenomenon termed the "entourage effect" (Ben-Shabat et al., *Eur J Pharmacol,* 1998, 353, 23-31). These "entourage" 2-monoacylglycerols are endogenous lipids that are co-released with 2-AG and potentiate endocannabinoid signaling, in part, by inhibiting 2-AG breakdown, most likely by competition for the active site on MGL. This suggests that synthetic MGL inhibitors will have a similar effect. Indeed, URB602, a relatively weak synthetic MGL inhibitor, showed an antinociceptive effect in a murine model of acute inflammation (Comelli et al., *Brit J Pharmacol,* 2007, 152, 787-794).

Although the use of synthetic cannabinoid agonists has conclusively demonstrated that increased cannabinoid signaling produces analgesic and anti-inflammatory effects, it has been difficult to separate these beneficial effects from the unwanted side effects of these compounds. An alternative approach is to enhance the signaling of the endocannabinoid system by elevating the level of 2-AG, the endocannabinoid of highest abundance in the central nervous system (CNS) and gastrointestinal tract, which may be achieved by inhibition of MGL. Therefore, MGL inhibitors are potentially useful for the treatment of pain, inflammation, and CNS disorders (Di Marzo et al., *Curr Pharm Des,* 2000, 6, 1361-80; Jhaveri et al., *Brit J Pharmacol,* 2007, 152, 624-632; McCarberg Bill et al., *Amer J Ther,* 2007, 14, 475-83), as well as glaucoma and disease states arising from elevated intraocular pressure (Njie, Ya Fatou; He, Fang; Qiao, Zhuanhong; Song, Zhao-Hui, *Exp. Eye Res.,* 2008, 87(2):106-14).

SUMMARY OF THE INVENTION

The present invention is directed to a compound of Formula (I)

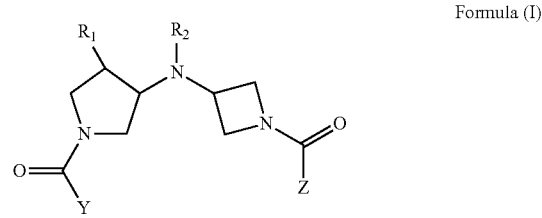

Formula (I)

wherein

Y is a $C_{6-10}$aryl or a heteroaryl selected from the group consisting of thiazolyl, thienyl, isothiazolyl, pyrrolyl, benzofuranyl, and benzothienyl; wherein Y is unsubstituted or substituted with one or two substituents independently selected from the group consisting of fluoro, chloro, $C_{1-4}$alkyl, $C_{1-4}$alkoxy, cyano, and trifluoromethyl;

Z is i) a $C_{6-10}$aryl;

ii) 9H-fluorenyl;

iii) phenyl-($R_a$)-phenyl wherein the phenyl ring on phenyl-($R_a$)— is unsubstituted or substituted with one substituent selected from the group consisting of trifluoromethyl, chloro, $C_{1-4}$alkyl, and fluoro;

$R_a$ is CH(F), $CF_2$, or CH(OH);

iv) a benzo-fused heterocyclyl selected from the group consisting of 1,2,3,4-tetrahydroisoquinolinyl, isoindolinyl, indolinyl, and indazolinyl;

wherein the benzo-fused heterocyclyl is unsubstituted or substituted with one substituent that is phenyl or bromo, wherein said phenyl is unsubstituted or substituted with one substituent selected from the group consisting of bromo, chloro, fluoro, iodo, $C_{1-4}$alkyl, $C_{2-4}$alkenyl, $C_{1-4}$alkoxy, trifluoromethyl, and trifluoromethoxy; or v) a heteroaryl selected from the group consisting thiazolyl, benzothienyl, benzofuranyl, benzothiazolyl, quinazolinyl, indolyl, and indazolyl;

wherein the $C_{6-10}$aryl and the heteroaryl of Z are unsubstituted or substituted with one or two substitutents each of which is independently selected from the group consisting of bromo, chloro, fluoro, iodo, $C_{1-4}$alkyl, $C_{2-4}$alkenyl, $C_{1-4}$alkoxy, trifluoromethyl, trifluoromethoxy, and $R_b$; provided that no more than one substituent is $R_b$; and $R_b$ is selected from the group consisting of 2,2-difluoroethyl; phenylmethyl; $C_{3-6}$cycloalkyl; N-methyl-N-phenylaminocarbonyl-methyl; thienyl; pyridinyl; pyrimidinyl; and phenyl; wherein the phenyl portion of phenylmethyl, and said thienyl, pyridinyl, pyrimidinyl, and phenyl of $R_b$ are unsubstituted or substituted with one or two substitutents each of which is independently selected from the group consisting of trifluoromethyl, trifluoromethoxy, $C_{1-4}$alkyl, chloro, and fluoro;

$R_1$ is hydrogen, fluoro, hydroxy, or methoxy;

$R_2$ is hydrogen, $C_{1-6}$ alkyl, hydroxy, or formyl;

and enantiomers, diastereomers, solvates and pharmaceutically acceptable salts thereof.

The present invention also provides, inter alia, a pharmaceutical composition comprising, consisting of and/or consisting essentially of a pharmaceutically acceptable carrier, a pharmaceutically acceptable excipient, and/or a pharmaceutically acceptable diluent, and a compound of Formula (I), or a pharmaceutically acceptable salt form thereof.

Also provided are processes for making a pharmaceutical composition comprising, consisting of, and/or consisting essentially of admixing a compound of Formula (I) or a pharmaceutically acceptable salt form thereof, and a pharmaceutically acceptable carrier, a pharmaceutically acceptable excipient, and/or a pharmaceutically acceptable diluent.

The present invention further provides, inter alia, methods for treating or ameliorating a MGL-modulated disorder in a subject, including a human or other mammal in which the disease, syndrome, or condition is affected by the modulation of the MGL enzyme, such as pain and the diseases that lead to such pain, inflammation and CNS disorders, using a compound of Formula (I) or a pharmaceutically acceptable salt form thereof.

The present invention also provides, inter alia, methods for producing the instant compounds and pharmaceutical compositions and medicaments thereof.

DETAILED DESCRIPTION OF THE INVENTION

With reference to substituents, the term "independently" refers to the situation where when more than one substituent is possible, the substituents may be the same or different from each other.

The term "alkyl" whether used alone or as part of a substituent group, refers to straight and branched carbon chains having 1 to 8 carbon atoms. Therefore, designated numbers of carbon atoms (e.g., $C_{1-8}$) refer independently to the number of carbon atoms in an alkyl moiety or to the alkyl portion of a larger alkyl-containing substituent. In substituent groups with multiple alkyl groups such as, ($C_{1-6}$alkyl)$_2$-amino-, the $C_{1-6}$alkyl groups of the dialkylamino may be the same or different.

The term "alkoxy" refers to an —O-alkyl group, wherein the term "alkyl" is as defined above.

The terms "alkenyl" and "alkynyl" refer to straight and branched carbon chains having 2 to 8 carbon atoms, wherein an alkenyl chain contains at least one double bond and an alkynyl chain contains at least one triple bond.

The term "cycloalkyl" refers to saturated or partially saturated, monocyclic or polycyclic hydrocarbon rings of 3 to 14 carbon atoms. Examples of such rings include cyclopropyl, cyclobutyl, cyclopentyl, cyclohexyl, cycloheptyl, and adamantyl.

The term "benzo-fused cycloalkyl" refers to a 5- to 8-membered monocyclic cycloalkyl ring fused to a benzene ring. The carbon atom ring members that form the cycloalkyl ring may be fully saturated or partially saturated.

The term "heterocyclyl" refers to a nonaromatic monocyclic or bicyclic ring system having 3 to 10 ring members that include at least 1 carbon atom and from 1 to 4 heteroatoms independently selected from N, O, and S. Included within the term heterocyclyl is a nonaromatic cyclic ring of 5 to 7 members in which 1 to 2 members are N, or a nonaromatic cyclic ring of 5 to 7 members in which 0, 1 or 2 members are N and up to 2 members are O or S and at least one member must be either N, O, or S; wherein, optionally, the ring contains 0 to 1 unsaturated bonds, and, optionally, when the ring is of 6 or 7 members, it contains up to 2 unsaturated bonds. The carbon atom ring members that form a heterocycle ring may be fully saturated or partially saturated. The term "heterocyclyl" also includes two 5 membered monocyclic heterocycloalkyl groups bridged to form a bicyclic ring. Such groups are not considered to be fully aromatic and are not referred to as heteroaryl groups. When a heterocycle is bicyclic, both rings of the heterocycle are non-aromatic and at least one of the rings contains a heteroatom ring member. Examples of heterocycle groups include, and are not limited to, pyrrolinyl (including 2H-pyrrole, 2-pyrrolinyl or 3-pyrrolinyl), pyrrolidinyl, imidazolinyl, imidazolidinyl, pyrazolinyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

The term "benzo-fused heterocyclyl" refers to a 5 to 7 membered monocyclic heterocycle ring fused to a benzene ring. The heterocycle ring contains carbon atoms and from 1 to 4 heteroatoms independently selected from N, O, and S. The carbon atom ring members that form the heterocycle ring may be fully saturated or partially saturated. Unless otherwise noted, benzo-fused heterocycle ring is attached to its pendant group at a carbon atom of the benzene ring.

The term "aryl" refers to an unsaturated, aromatic monocyclic or bicyclic ring of 6 to 10 carbon members. Examples of aryl rings include phenyl and naphthalenyl.

The term "heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

The term "halogen" or "halo" refers to fluorine, chlorine, bromine and iodine atoms.

The term "formyl" refers to the group —C(=O)H.

The term "oxo" refers to the group (=O).

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as sub-combinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

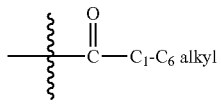

The term "R" at a stereocenter designates that the stereocenter is purely of the R-configuration as defined in the art; likewise, the term "S" means that the stereocenter is purely of the S-configuration. As used herein, the terms "*R" or "*S" at a stereocenter are used to designate that the stereocenter is of pure but unknown configuration. As used herein, the term "RS" refers to a stereocenter that exists as a mixture of the R- and S-configurations. Similarly, the terms "*RS" or "*SR" refer to a stereocenter that exists as a mixture of the R- and S-configurations and is of unknown configuration relative to another stereocenter within the molecule.

Compounds containing one stereocenter drawn without a stereo bond designation are a mixture of 2 enantiomers. Compounds containing 2 stereocenters both drawn without stereo bond designations are a mixture of 4 diastereomers. Compounds with 2 stereocenters both labeled "RS" and drawn with stereo bond designations are a 2-component mixture with relative stereochemistry as drawn. Compounds with 2 stereocenters both labeled "*RS" and drawn with stereo bond designations are a 2-component mixture with relative stereochemistry unknown. Unlabeled stereocenters drawn without stereo bond designations are a mixture of the R- and S-configurations. For unlabeled stereocenters drawn with stereo bond designations, the absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of Formula (I) can be selected by one of ordinary skill in the art to provide compounds that are chemically stable and that can be readily synthesized by techniques known in the art as well as those methods set forth herein.

The term "subject" refers to an animal, preferably a mammal, most preferably a human, who has been the object of treatment, observation or experiment.

The term "therapeutically effective amount" refers to an amount of an active compound or pharmaceutical agent, including a compound of the present invention, which elicits the biological or medicinal response in a tissue system, animal or human that is being sought by a researcher, veterinarian, medical doctor or other clinician, which includes alleviation or partial alleviation of the symptoms of the disease, syndrome, condition, or disorder being treated.

The term "composition" refers to a product that includes the specified ingredients in therapeutically effective amounts, as well as any product that results, directly, or indirectly, from combinations of the specified ingredients in the specified amounts.

The term "MGL inhibitor" is intended to encompass a compound that interacts with MGL to substantially reduce or eliminate its catalytic activity, thereby increasing the concentrations of its substrate(s). The term "MGL-modulated" is used to refer to the condition of being affected by the modulation of the MGL enzyme including the condition of being affected by the inhibition of the MGL enzyme, such as, for example, pain and the diseases that lead to such pain, inflammation and CNS disorders.

As used herein, unless otherwise noted, the term "affect" or "affected" (when referring to a disease, syndrome, condition or disorder that is affected by inhibition of MGL) shall include a reduction in the frequency and/or severity of one or more symptoms or manifestations of said disease, syndrome, condition or disorder; and/or include the prevention of the development of one or more symptoms or manifestations of said disease, syndrome, condition or disorder or the development of the disease, condition, syndrome or disorder.

The compounds of Formula (I) are useful in methods for treating, ameliorating and/or preventing a disease, a syndrome, a condition or a disorder that is affected by the inhibition of MGL. Such methods comprise, consist of and/or consist essentially of administering to a subject, including an animal, a mammal, and a human in need of such treatment, amelioration and/or prevention, a therapeutically effective amount of a compound of Formula (I), or an enantiomer, diastereomer, solvate or pharmaceutically acceptable salt thereof. In particular, the compounds of Formula (I) are useful for treating, ameliorating and/or preventing pain; diseases, syndromes, conditions, or disorders causing such pain; inflammation and/or CNS disorders. More particularly, the compounds of Formula (I) are useful for treating, ameliorating and/or preventing inflammatory pain, inflammatory hypersensitivity conditions and/or neuropathic pain, comprising administering to a subject in need thereof a therapeutically effective amount of a compound of Formula (I), as herein defined.

Examples of inflammatory pain include pain due to a disease, condition, syndrome, disorder, or a pain state including inflammatory bowel disease, visceral pain, migraine, post operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain due to physical trauma, headache, sinus headache, tension headache, or arachnoiditis.

One type of inflammatory pain is inflammatory hyperalgesia/hypersensitivity. Examples of inflammatory hyperalgesia include a disease, syndrome, condition, disorder, or pain state including inflammation, osteoarthritis, rheumatoid arthritis, back pain, joint pain, abdominal pain, musculoskeletal diseases, skin diseases, post operative pain, headaches, toothache, burn, sunburn, insect sting, neurogenic bladder, urinary incontinence, interstitial cystitis, urinary tract infection, cough, asthma, chronic obstructive pulmonary disease, rhinitis, contact dermatitis/hypersensitivity and/or dermal allergy, itch, eczema, pharyngitis, enteritis, irritable bowel syndrome, inflammatory bowel diseases including Crohn's Disease, ulcerative colitis, benign prostatic hypertrophy, and nasal hypersensitivity.

In an embodiment, the present invention is directed to a method for treating, ameliorating and/or preventing inflammatory visceral hyperalgesia in which a enhanced visceral irritability exists, comprising, consisting of, and/or consisting essentially of the step of administering to a subject in need of such treatment a therapeutically effective amount of a compound, salt or solvate of Formula (I). In a further embodiment, the present invention is directed to a method for treating inflammatory somatic hyperalgesia in which a hypersensitivity to thermal, mechanical and/or chemical stimuli exists, comprising administering to a mammal in need of such treatment a therapeutically effective amount of a compound of Formula (I) or an enantiomer, diastereomer, solvate or pharmaceutically acceptable salt thereof.

A further embodiment of the present invention is directed to a method for treating, ameliorating and/or preventing neuropathic pain. Examples of a neuropathic pain include pain due to a disease, syndrome, condition, disorder, or pain state including cancer, neurological disorders, spine and peripheral nerve surgery, brain tumor, traumatic brain injury (TBI), spinal cord trauma, chronic pain syndrome, fibromyalgia, chronic fatigue syndrome, lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngeal neuralgia, migrainous neuralgia, idiopathic neuralgia, intercostals neuralgia, mammary neuralgia, Morton's neuralgia, nasociliary neuralgia, occipital neuralgia, postherpetic neuralgia, causalgia, red neuralgia, Sluder's neuralgia, splenopalatine neuralgia, supraorbital neuralgia, trigeminal neuralgia, vulvodynia, or vidian neuralgia.

One type of neuropathic pain is neuropathic cold allodynia, which can be characterized by the presence of a neuropathy-associated allodynic state in which a hypersensitivity to cooling stimuli exists. Examples of neuropathic cold allodynia include allodynia due to a disease, condition, syndrome, disorder or pain state including neuropathic pain (neuralgia), pain arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS I/II) and radiculopathy.

In a further embodiment, the present invention is directed to a method for treating, ameliorating and/or preventing neuropathic cold allodynia in which a hypersensitivity to a cooling stimuli exists, comprising, consisting of, and/or consisting essentially of the step of administering to a subject in need of such treatment a therapeutically effective amount of a compound of Formula (I) or an enantiomer, diastereomer, solvate or pharmaceutically acceptable salt thereof.

In a further embodiment, the present invention is directed to a method for treating, ameliorating and/or preventing CNS disorders. Examples of CNS disorders include anxieties, such as social anxiety, post-traumatic stress disorder, phobias, social phobia, special phobias, panic disorder, obsessive-compulsive disorder, acute stress disorder, separation anxiety disorder, and generalized anxiety disorder, as well as depression, such as major depression, bipolar disorder, seasonal affective disorder, post natal depression, manic depression, and bipolar depression.

Embodiments of the present invention include a compound of Formula (I)

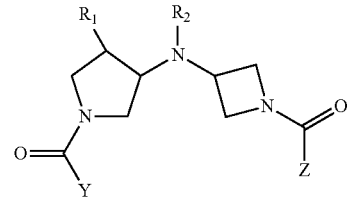

Formula (I)

wherein
a) Y is a $C_{6-10}$aryl or a heteroaryl selected from the group consisting of thiazolyl, thienyl, benzofuranyl, and benzothienyl; wherein Y is unsubstituted or substituted with one or two fluoro substituents;
b) Y is an unsubstituted $C_{6-10}$aryl or an unsubstituted heteroaryl that is thienyl or thiazolyl;
c) Y is an unsubstituted phenyl or an unsubstituted heteroaryl that is thienyl or thiazolyl;
d) Z is
  i) a $C_{6-10}$aryl;
  ii) 9H-fluorenyl;
  iii) phenyl-($R_a$)-phenyl wherein the phenyl ring on phenyl-($R_a$)— is unsubstituted or substituted with one substituent that is trifluoromethyl;
    $R_a$ is CH(F), $CF_2$, or CH(OH);
  iv) a benzo-fused heterocyclyl selected from the group consisting of 1,2,3,4-tetrahydroisoquinolinyl, isoindolinyl, and indolinyl;

wherein the benzo-fused heterocyclyl is unsubstituted or substituted with one substituent that is phenyl or bromo, wherein said phenyl is unsubstituted or substituted with one substituent selected from the group consisting of bromo, chloro, fluoro, methyl, methoxy, or trifluoromethyl; or v) a heteroaryl selected from the group consisting thiazolyl, benzothienyl, benzofuranyl, benzothiazolyl, quinazolinyl, indolyl, and indazolyl;

wherein the $C_{6-10}$aryl and the heteroaryl of Z are unsubstituted or substituted with one or two substitutents each of which is independently selected from the group consisting of bromo, chloro, fluoro, $C_{1-4}$alkyl, $C_{2-4}$alkenyl, trifluoromethyl, trifluoromethoxy, and $R_b$; provided that no more than one substituent is $R_b$;

$R_b$ is selected from the group consisting of 2,2-difluoroethyl; phenylmethyl; $C_{3-6}$ cycloalkyl; N-methyl-N-phenylaminocarbonyl-methyl; thienyl; pyrimidinyl; and phenyl; wherein the phenyl portion of phenylmethyl, and said thienyl, pyrimidinyl, and phenyl of $R_b$ are unsubstituted or substituted with one or two substituents each of which is independently selected from the group consisting of trifluoromethyl, trifluoromethoxy, chloro, and fluoro;

e) Z is
i) a $C_{6-10}$aryl;
ii) 9H-fluorenyl;
iii) phenyl-($R_a$)-phenyl wherein the phenyl ring on phenyl-($R_a$)— is unsubstituted or substituted with one substituent that is trifluoromethyl;
$R_a$ is CH(F), $CF_2$, or CH(OH);
iv) a benzo-fused heterocyclyl selected from the group consisting of 1,2,3,4-tetrahydroisoquinolinyl, isoindolinyl, and indolinyl; wherein the benzo-fused heterocyclyl is unsubstituted or substituted with one substituent that is phenyl or bromo; or
v) a heteroaryl selected from the group consisting thiazolyl, benzothienyl, benzofuranyl, benzothiazolyl, quinazolinyl, indolyl, and indazolyl;

wherein the $C_{6-10}$aryl and the heteroaryl of Z are unsubstituted or substituted with one or two substitutents each of which is independently selected from the group consisting of bromo, chloro, fluoro, $C_{1-4}$alkyl, $C_{2-4}$alkenyl, trifluoromethyl, trifluoromethoxy, and $R_b$; provided that no more than one substituent is $R_b$;

$R_b$ is selected from the group consisting of phenylmethyl; $C_{3-6}$ cycloalkyl; thienyl; pyrimidinyl; and phenyl; wherein the phenyl portion of phenylmethyl, and said thienyl and said phenyl of $R_b$ are unsubstituted or substituted with one or two substituents each of which is independently selected from the group consisting of trifluoromethyl, trifluoromethoxy, chloro, and fluoro;

f) Z is
i) a $C_{6-10}$aryl;
ii) 9H-fluorenyl;
iii) phenyl-($R_a$)-phenyl wherein the phenyl ring on phenyl-($R_a$)— is unsubstituted or substituted with one substituent that is trifluoromethyl;
$R_a$ is $CF_2$ or CH(OH);
iv) indolinyl and said indolinyl is unsubstituted or substituted with one substituent that is phenyl or bromo; or
v) a heteroaryl selected from the group consisting benzothienyl, benzofuranyl, indolyl, and indazolyl;
wherein the $C_{6-10}$aryl and the heteroaryl of Z are unsubstituted or substituted with one or two substitutents each of which is independently selected from the group consisting of bromo, chloro, fluoro, $C_{1-4}$alkyl, $C_{2-4}$alkenyl, trifluoromethyl, trifluoromethoxy, and $R_b$; provided that no more than one substituent is $R_b$; and $R_b$ is selected from the group consisting of phenylmethyl; thienyl; pyrimidinyl; and phenyl; wherein the phenyl portion of phenylmethyl, and said thienyl and said phenyl of $R_b$ are unsubstituted or substituted with one or two substituents each of which is independently selected from the group consisting of trifluoromethyl, chloro, and fluoro;

g) Z is
i) a $C_{6-10}$aryl;
ii) phenyl-($R_a$)-phenyl wherein the phenyl ring on phenyl-($R_a$)— is unsubstituted or substituted with one substituent that is trifluoromethyl;
$R_a$ is $CF_2$ or CH(OH);
iii) indolinyl and said indolinyl is unsubstituted or substituted with one substituent that is phenyl or bromo; or
iv) a heteroaryl selected from the group consisting benzothienyl, benzofuranyl, indolyl, and indazolyl;

wherein the $C_{6-10}$aryl and the heteroaryl of Z are unsubstituted or substituted with one or two substitutents each of which is independently selected from the group consisting of bromo, chloro, fluoro, $C_{1-4}$alkyl, $C_{2-4}$alkenyl, trifluoromethyl, trifluoromethoxy, and $R_b$; provided that no more than one substituent is $R_b$;

$R_b$ is selected from the group consisting of phenylmethyl; thienyl; pyrimidinyl; and phenyl; wherein the phenyl portion of phenylmethyl, and said thienyl and said phenyl of $R_b$ are unsubstituted or substituted with one or two substituents each of which is independently selected from the group consisting of trifluoromethyl, chloro, and fluoro;

h) $R_1$ is hydrogen, fluoro, or hydroxy;
i) $R_1$ is hydrogen or fluoro;
j) $R_2$ is hydrogen, $C_{1-2}$ alkyl, or hydroxy;
k) $R_2$ is hydrogen, methyl, or hydroxy;
l) $R_2$ is hydrogen;

and any combination of embodiments a) through l) above, provided that it is understood that combinations in which different embodiments of the same substituent would be combined are excluded;

and enantiomers, diastereomers, solvates and pharmaceutically acceptable salts thereof.

An embodiment of the present invention includes a compound of Formula (I)

Formula (I)

wherein
Y is a $C_{6-10}$aryl or a heteroaryl selected from the group consisting of thiazolyl, thienyl, benzofuranyl, and benzothienyl; wherein Y is unsubstituted or substituted with one or two fluoro substituents;

Z is
i) a $C_{6-10}$aryl;
ii) 9H-fluorenyl;

iii) phenyl-($R_a$)-phenyl wherein the phenyl ring on phenyl-($R_a$)— is unsubstituted or substituted with one substituent that is trifluoromethyl;

$R_a$ is CH(F), $CF_2$, or CH(OH);

iv) a benzo-fused heterocyclyl selected from the group consisting of 1,2,3,4-tetrahydroisoquinolinyl, isoindolinyl, and indolinyl; wherein the benzo-fused heterocyclyl is unsubstituted or substituted with one substituent that is phenyl or bromo, wherein said phenyl is unsubstituted or substituted with one substituent selected from the group consisting of bromo, chloro, fluoro, methyl, methoxy, or trifluoromethyl; or v) a heteroaryl selected from the group consisting thiazolyl, benzothienyl, benzofuranyl, benzothiazolyl, quinazolinyl, indolyl, and indazolyl;

wherein the $C_{6-10}$aryl and the heteroaryl of Z are unsubstituted or substituted with one or two substitutents each of which is independently selected from the group consisting of bromo, chloro, fluoro, $C_{1-4}$alkyl, $C_{2-4}$alkenyl, trifluoromethyl, trifluoromethoxy, and $R_b$; provided that no more than one substituent is $R_b$;

$R_b$ is selected from the group consisting of 2,2-difluoroethyl; phenylmethyl; $C_{3-6}$ cycloalkyl; N-methyl-N-phenylaminocarbonyl-methyl; thienyl; pyrimidinyl; and phenyl; wherein the phenyl portion of phenylmethyl, and said thienyl, pyrimidinyl, and phenyl of $R_b$ are unsubstituted or substituted with one or two substituents each of which is independently selected from the group consisting of trifluoromethyl, trifluoromethoxy, chloro, and fluoro;

$R_1$ is hydrogen, fluoro or hydroxy;

$R_2$ is hydrogen, methyl, or hydroxy;

and enantiomers, diastereomers, solvates, and pharmaceutically acceptable salt forms thereof.

Another embodiment of the present invention includes a compound of Formula (I)

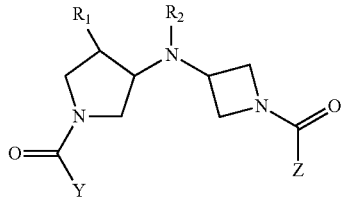

Formula (I)

wherein

Y is an unsubstituted $C_{6-10}$aryl or an unsubstituted heteroaryl that is thienyl or thiazolyl;

Z is i) a $C_{6-10}$aryl;

ii) 9H-fluorenyl;

iii) phenyl-($R_a$)-phenyl wherein the phenyl ring on phenyl-($R_a$)— is unsubstituted or substituted with one substituent that is trifluoromethyl;

$R_a$ is CH(F), $CF_2$, or CH(OH);

iv) a benzo-fused heterocyclyl selected from the group consisting of 1,2,3,4-tetrahydroisoquinolinyl, isoindolinyl, and indolinyl;

wherein the benzo-fused heterocyclyl is unsubstituted or substituted with one substituent that is phenyl or bromo; or v) a heteroaryl selected from the group consisting thiazolyl, benzothienyl, benzofuranyl, benzothiazolyl, quinazolinyl, indolyl, and indazolyl;

wherein the $C_{6-10}$aryl and the heteroaryl of Z are unsubstituted or substituted with one or two substitutents each of which is independently selected from the group consisting of bromo, chloro, fluoro, $C_{1-4}$alkyl, $C_{2-4}$alkenyl, trifluoromethyl, trifluoromethoxy, and $R_b$; provided that no more than one substituent is $R_b$;

$R_b$ is selected from the group consisting of phenylmethyl; $C_{3-6}$ cycloalkyl; thienyl; pyrimidinyl; and phenyl; wherein the phenyl portion of phenylmethyl, and said thienyl and said phenyl of $R_b$ are unsubstituted or substituted with one or two substituents each of which is independently selected from the group consisting of trifluoromethyl, trifluoromethoxy, chloro, and fluoro;

$R_1$ is hydrogen or fluoro;

$R_2$ is hydrogen, $C_{1-2}$ alkyl, or hydroxy;

and enantiomers, diastereomers, solvates, and pharmaceutically acceptable salt forms thereof.

Another embodiment of the present invention includes a compound of Formula (I)

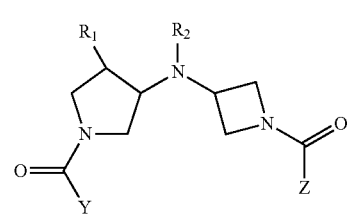

Formula (I)

wherein

Y is an unsubstituted phenyl or an unsubstituted heteroaryl that is thienyl or thiazolyl;

Z is i) a $C_{6-10}$aryl;

ii) 9H-fluorenyl;

iii) phenyl-($R_a$)-phenyl wherein the phenyl ring on phenyl-($R_a$)— is unsubstituted or substituted with one substituent that is trifluoromethyl;

$R_a$ is $CF_2$ or CH(OH);

iv) indolinyl and said indolinyl is unsubstituted or substituted with one substituent that is phenyl or bromo; or v) a heteroaryl selected from the group consisting benzothienyl, benzofuranyl, indolyl, and indazolyl;

wherein the $C_{6-10}$aryl and the heteroaryl of Z are unsubstituted or substituted with one or two substituents each of which is independently selected from the group consisting of bromo, chloro, fluoro, $C_{1-4}$alkyl, $C_{2-4}$alkenyl, trifluoromethyl, trifluoromethoxy, and $R_b$; provided that no more than one substituent is $R_b$; and $R_b$ is selected from the group consisting of phenylmethyl; thienyl; pyrimidinyl; and phenyl; wherein the phenyl portion of phenylmethyl, and said thienyl and said phenyl of $R_b$ are unsubstituted or substituted with one or two substituents each of which is independently selected from the group consisting of trifluoromethyl, chloro, and fluoro;

$R_1$ is hydrogen or fluoro;

$R_2$ is hydrogen, $C_{1-2}$ alkyl, or hydroxy;

and enantiomers, diastereomers, solvates, and pharmaceutically acceptable salt forms thereof.

Another embodiment of the present invention includes a compound of Formula (I)

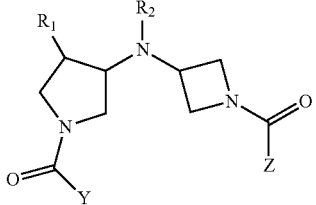

Formula (I)

wherein
Y is an unsubstituted phenyl or an unsubstituted heteroaryl that is thienyl or thiazolyl;
Z is
i) a $C_{6-10}$aryl;
ii) phenyl-($R_a$)-phenyl wherein the phenyl ring on phenyl-($R_a$)— is unsubstituted or substituted with one substituent that is trifluoromethyl;
  $R_a$ is $CF_2$ or CH(OH);
iii) indolinyl and said indolinyl is unsubstituted or substituted with one substituent that is phenyl or bromo; or
iv) a heteroaryl selected from the group consisting benzothienyl, benzofuranyl, indolyl, and indazolyl;
  wherein the $C_{6-10}$aryl and the heteroaryl of Z are unsubstituted or substituted with one or two substitutents each of which is independently selected from the group consisting of bromo, chloro, fluoro, $C_{1-4}$alkyl, $C_{2-4}$alkenyl, trifluoromethyl, trifluoromethoxy, and $R_b$; provided that no more than one substituent is $R_b$;
  $R_b$ is selected from the group consisting of phenylmethyl wherein the phenyl is unsubstituted or substituted with one fluoro substituent; thienyl; pyrimidinyl; and phenyl; wherein the phenyl portion of phenylmethyl, and said thienyl and phenyl of $R_b$ are unsubstituted or substituted with one or two substituents each of which is independently selected from the group consisting of trifluoromethyl, chloro, and fluoro;
$R_1$ is hydrogen or fluoro;
$R_2$ is hydrogen;
and enantiomers, diastereomers, solvates, and pharmaceutically acceptable salt forms thereof.

An embodiment of the present invention includes a compound of Formula (I)

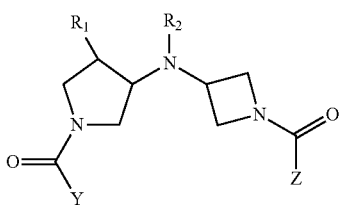

Formula (I)

selected from the group consisting of
(3S)—N-[1-(Biphenyl-4-ylcarbonyl)azetidin-3-yl]-1-(1,3-thiazol-2-ylcarbonyl)pyrrolidin-3-amine,
(3S)—N-[1-(Biphenyl-4-ylcarbonyl)azetidin-3-yl]-1-(phenylcarbonyl)pyrrolidin-3-amine,
(3S)—N-{1-[(4-Benzylphenyl)carbonyl]azetidin-3-yl}-1-(1,3-thiazol-2-ylcarbonyl)pyrrolidin-3-amine,
(3S)—N-{1-[(4-Benzylphenyl)carbonyl]azetidin-3-yl}-1-(phenylcarbonyl)pyrrolidin-3-amine,
(3S)—N-{1-[(4-Benzylphenyl)carbonyl]azetidin-3-yl}-1-(thiophen-3-ylcarbonyl)pyrrolidin-3-amine,
(3R)—N-{1-[(4-Benzylphenyl)carbonyl]azetidin-3-yl}-1-(1,3-thiazol-2-ylcarbonyl)pyrrolidin-3-amine,
(3R)—N-{1-[(4-Benzylphenyl)carbonyl]azetidin-3-yl}-1-(phenylcarbonyl)pyrrolidin-3-amine,
(3S)—N-{1-[(6-Bromo-3,4-dihydroisoquinolin-2(1H)-yl)carbonyl]azetidin-3-yl}-1-(1,3-thiazol-2-ylcarbonyl)pyrrolidin-3-amine,
(3S)—N-{1-[(6-Phenyl-3,4-dihydroisoquinolin-2(1H)-yl)carbonyl]azetidin-3-yl}-1-(1,3-thiazol-2-ylcarbonyl)pyrrolidin-3-amine,
(3S)—N-{1-[(5-Bromo-1,3-dihydro-2H-isoindol-2-yl)carbonyl]azetidin-3-yl}-1-(1,3-thiazol-2-ylcarbonyl)pyrrolidin-3-amine,
(3S)—N-{1-[(5-Phenyl-1,3-dihydro-2H-isoindol-2-yl)carbonyl]azetidin-3-yl}-1-(1,3-thiazol-2-ylcarbonyl)pyrrolidin-3-amine,
(3S)—N-{1-[(4-Benzylphenyl)carbonyl]azetidin-3-yl}-N-methyl-1-(phenylcarbonyl)pyrrolidin-3-amine,
(3S)—N-Methyl-1-(phenylcarbonyl)-N-(1-{[3'-(trifluoromethyl)biphenyl-4-yl]carbonyl}azetidin-3-yl)pyrrolidin-3-amine,
(3S)-1-(Phenylcarbonyl)-N-(1-{[3'-(trifluoromethyl)biphenyl-4-yl]carbonyl}azetidin-3-yl)pyrrolidin-3-amine,
(3S)—N-{1-[(3',5'-Dichlorobiphenyl-4-yl)carbonyl]azetidin-3-yl}-1-(phenylcarbonyl)pyrrolidin-3-amine,
(3S)-1-(Phenylcarbonyl)-N-(1-{[5-(trifluoromethoxy)-1-benzothiophen-2-yl]carbonyl}azetidin-3-yl)pyrrolidin-3-amine,
(3S)-1-(Phenylcarbonyl)-N-(1-{[5-(trifluoromethyl)-1-benzothiophen-2-yl]carbonyl}azetidin-3-yl)pyrrolidin-3-amine,
(3S)-1-(Phenylcarbonyl)-N-(1-{[6-(trifluoromethyl)-1-benzothiophen-2-yl]carbonyl}azetidin-3-yl)pyrrolidin-3-amine,
(3S)—N-{1-[(6-Bromo-3-chloro-1-benzothiophen-2-yl)carbonyl]azetidin-3-yl}-1-(phenylcarbonyl)pyrrolidin-3-amine,
(3S)—N-{1-[(5-Bromonaphthalen-2-yl)carbonyl]azetidin-3-yl}-1-(phenylcarbonyl)pyrrolidin-3-amine,
(3S)-1-(Phenylcarbonyl)-N-{1-[(5-phenylnaphthalen-2-yl)carbonyl]azetidin-3-yl}pyrrolidin-3-amine,
(3S)-1-(Phenylcarbonyl)-N-[1-({5-[2-(trifluoromethyl)phenyl]naphthalen-2-yl}carbonyl)azetidin-3-yl]pyrrolidin-3-amine,
(3S)-1-(Phenylcarbonyl)-N-[1-({5-[3-(trifluoromethyl)phenyl]naphthalen-2-yl}carbonyl)azetidin-3-yl]pyrrolidin-3-amine,
(3S)-1-(Phenylcarbonyl)-N-[1-({5-[4-(trifluoromethoxy)phenyl]naphthalen-2-yl}carbonyl)azetidin-3-yl]pyrrolidin-3-amine,
(3S)—N-[1-(9H-Fluoren-2-ylcarbonyl)azetidin-3-yl]-1-(phenylcarbonyl)pyrrolidin-3-amine,
(3S)—N-(1-{[3-Chloro-6-(trifluoromethyl)-1-benzothiophen-2-yl]carbonyl}azetidin-3-yl)-1-(phenylcarbonyl)pyrrolidin-3-amine,
(3S)—N-{1-[(3'-Chlorobiphenyl-4-yl)carbonyl]azetidin-3-yl}-1-(phenylcarbonyl)pyrrolidin-3-amine,
(3S)—N-{1-[(3',4'-Dichlorobiphenyl-4-yl)carbonyl]azetidin-3-yl}-1-(phenylcarbonyl)pyrrolidin-3-amine,
(3S)—N-{1-[(3-Chloro-6-phenyl-1-benzothiophen-2-yl)carbonyl]azetidin-3-yl}-1-(phenylcarbonyl)pyrrolidin-3-amine, (3S)—N-[1-({3-Chloro-6-[3-(trifluoromethyl)phenyl]-1-benzothiophen-2-yl}carbonyl)azetidin-3-yl]-1-(phenylcarbonyl)pyrrolidin-3-amine,
(3S)—N-[1-({3-Chloro-6-[4-(trifluoromethyl)phenyl]-1-benzothiophen-2-yl}carbonyl)azetidin-3-yl]-1-(phenylcarbonyl)pyrrolidin-3-amine,
(3S)—N-{1-[(5-Bromonaphthalen-2-yl)carbonyl]azetidin-3-yl}-N-hydroxy-1-(phenylcarbonyl)pyrrolidin-3-amine,
(3S)-1-(Phenylcarbonyl)-N-(1-{[4'-(trifluoromethyl)biphenyl-4-yl]carbonyl}azetidin-3-yl)pyrrolidin-3-amine,
(3S)-1-(Phenylcarbonyl)-N-(1-{[4'-(trifluoromethoxy)biphenyl-4-yl]carbonyl}azetidin-3-yl)pyrrolidin-3-amine,
(3S)—N-{1-[(5-Chloro-3-methyl-1-benzothiophen-2-yl)carbonyl]azetidin-3-yl}-1-(phenylcarbonyl)pyrrolidin-3-amine,
(3S)—N-{1-[(6-Bromo-1-benzothiophen-2-yl)carbonyl]azetidin-3-yl}-1-(phenylcarbonyl)pyrrolidin-3-amine,
(3S)—N-{1-[(3-Methyl-5-phenyl-1-benzothiophen-2-yl)carbonyl]azetidin-3-yl}-1-(phenylcarbonyl)pyrrolidin-3-amine,
(3S)—N-[1-({3-Methyl-5-[4-(trifluoromethyl)phenyl]-1-benzothiophen-2-yl}carbonyl)azetidin-3-yl]-1-(phenylcarbonyl)pyrrolidin-3-amine,
(3S)—N-[1-({3-Methyl-5-[3-(trifluoromethyl)phenyl]-1-benzothiophen-2-yl}carbonyl)azetidin-3-yl]-1-(phenylcarbonyl)pyrrolidin-3-amine,
(3S)—N-{1-[(6-Phenyl-1-benzothiophen-2-yl)carbonyl]azetidin-3-yl}-1-(phenylcarbonyl)pyrrolidin-3-amine,
(3S)-1-(Phenylcarbonyl)-N-[1-({6-[4-(trifluoromethyl)phenyl]-1-benzothiophen-2-yl}carbonyl)azetidin-3-yl]pyrrolidin-3-amine,
(3S)-1-(Phenylcarbonyl)-N-[1-({6-[3-(trifluoromethyl)phenyl]-1-benzothiophen-2-yl}carbonyl)azetidin-3-yl]pyrrolidin-3-amine,
(3S)—N-[1-(Biphenyl-4-ylcarbonyl)azetidin-3-yl]-1-[(4-fluorophenyl)carbonyl]pyrrolidin-3-amine,
(3S)—N-[1-(Biphenyl-4-ylcarbonyl)azetidin-3-yl]-1-[(3-fluorophenyl)carbonyl]pyrrolidin-3-amine,
(3S)-1-(1-Benzofuran-2-ylcarbonyl)-N-[1-(biphenyl-4-ylcarbonyl)azetidin-3-yl]pyrrolidin-3-amine,
(3S)-1-(1-Benzothiophen-2-ylcarbonyl)-N-[1-(biphenyl-4-ylcarbonyl)azetidin-3-yl]pyrrolidin-3-amine,
(3S)—N-{1-[(5-Bromo-1-benzothiophen-2-yl)carbonyl]azetidin-3-yl}-1-(phenylcarbonyl)pyrrolidin-3-amine,
(3S)—N-{1-[(5-Phenyl-1-benzothiophen-2-yl)carbonyl]azetidin-3-yl}-1-(phenylcarbonyl)pyrrolidin-3-amine,
(3S)-1-(Phenylcarbonyl)-N-[1-({5-[3-(trifluoromethyl)phenyl]-1-benzothiophen-2-yl}carbonyl)azetidin-3-yl]pyrrolidin-3-amine,
(3S)-1-(Phenylcarbonyl)-N-[1-({5-[4-(trifluoromethyl)phenyl]-1-benzothiophen-2-yl}carbonyl)azetidin-3-yl]pyrrolidin-3-amine,
(3S)—N-Ethyl-1-(phenylcarbonyl)-N-(1-{[3'-(trifluoromethyl)biphenyl-4-yl]carbonyl}azetidin-3-yl)pyrrolidin-3-amine,
(3S)—N-Hydroxy-1-(phenylcarbonyl)-N-(1-{[3'-(trifluoromethyl)biphenyl-4-yl]carbonyl}azetidin-3-yl)pyrrolidin-3-amine,
(3S)—N-{1-[(3-Bromo-1-benzothiophen-2-yl)carbonyl]azetidin-3-yl}-1-(phenylcarbonyl)pyrrolidin-3-amine,
(3S)—N-{1-[(3-Chloro-6-fluoro-1-benzothiophen-2-yl)carbonyl]azetidin-3-yl}-1-(phenylcarbonyl)pyrrolidin-3-amine,
(3S)-1-(Phenylcarbonyl)-N-{1-[(3-phenyl-1H-indol-6-yl)carbonyl]azetidin-3-yl}pyrrolidin-3-amine,
N-[1-(Biphenyl-4-ylcarbonyl)azetidin-3-yl]-4-fluoro-1-(phenylcarbonyl)pyrrolidin-3-amine,
4-Fluoro-1-(phenylcarbonyl)-N-(1-{[3'-(trifluoromethyl)biphenyl-4-yl]carbonyl}azetidin-3-yl)pyrrolidin-3-amine,
(3R)—N-[1-(Biphenyl-4-ylcarbonyl)azetidin-3-yl]-4-fluoro-1-(phenylcarbonyl)pyrrolidin-3-amine,
(3S)—N-[1-(Biphenyl-4-ylcarbonyl)azetidin-3-yl]-4-fluoro-1-(phenylcarbonyl)pyrrolidin-3-amine,
(3R)-4-Fluoro-1-(phenylcarbonyl)-N-(1-{[3'-(trifluoromethyl)biphenyl-4-yl]carbonyl}azetidin-3-yl)pyrrolidin-3-amine,
(3S)-4-Fluoro-1-(phenylcarbonyl)-N-(1-{[3'-(trifluoromethyl)biphenyl-4-yl]carbonyl}azetidin-3-yl)pyrrolidin-3-amine,
(3S)—N-{1-[(1-Methyl-3-phenyl-1H-indol-6-yl)carbonyl]azetidin-3-yl}-1-(phenylcarbonyl)pyrrolidin-3-amine,
(3S)—N-{1-[(3-Phenyl-1-benzothiophen-2-yl)carbonyl]azetidin-3-yl}-1-(phenylcarbonyl)pyrrolidin-3-amine,
(3S)—N-{1-[(3-Cyclopropyl-1-benzothiophen-2-yl)carbonyl]azetidin-3-yl}-1-(phenylcarbonyl)pyrrolidin-3-amine,
{4-[(3-{[(3S)-1-(Phenylcarbonyl)pyrrolidin-3-yl]amino}azetidin-1-yl)carbonyl]phenyl}[4-(trifluoromethyl)phenyl]methanol,
(3S)—N-{1-[(3-Methyl-1-benzothiophen-2-yl)carbonyl]azetidin-3-yl}-1-(phenylcarbonyl)pyrrolidin-3-amine,
N-{1-[(4-{Fluoro[4-(trifluoromethyl)phenyl]methyl}phenyl)carbonyl]azetidin-3-yl}-1-(phenylcarbonyl)pyrrolidin-3-amine,
(3S)—N-{1-[(3-Cyclopropyl-6-fluoro-1-benzothiophen-2-yl)carbonyl]azetidin-3-yl}-1-(phenylcarbonyl)pyrrolidin-3-amine,
(3R,4R)-4-Methoxy-1-(phenylcarbonyl)-N-(1-{[3'-(trifluoromethyl)biphenyl-4-yl]carbonyl}azetidin-3-yl)pyrrolidin-3-amine,
(3R,4R)-1-(Phenylcarbonyl)-4-[(1-{[3'-(trifluoromethyl)biphenyl-4-yl]carbonyl}azetidin-3-yl)amino]pyrrolidin-3-ol,
(3S)—N-[1-({4-[Difluoro(phenyl)methyl]phenyl}carbonyl)azetidin-3-yl]-1-(phenylcarbonyl)pyrrolidin-3-amine,
(3S)-1-(Phenylcarbonyl)-N-(1-{[3-phenyl-6-(trifluoromethyl)-1-benzothiophen-2-yl]carbonyl}azetidin-3-yl)pyrrolidin-3-amine,
(3S)—N-(1-{[3-Cyclopropyl-6-(trifluoromethyl)-1-benzothiophen-2-yl]carbonyl}azetidin-3-yl)-1-(phenylcarbonyl)pyrrolidin-3-amine,
(3S)—N-(1-{[3-(2-Methylprop-1-en-1-yl)-6-(trifluoromethyl)-1-benzothiophen-2-yl]carbonyl}azetidin-3-yl)-1-(phenylcarbonyl)pyrrolidin-3-amine,
(3S)-1-(Phenylcarbonyl)-N-[1-({4-[4-(trifluoromethyl)benzyl]phenyl}carbonyl)azetidin-3-yl]pyrrolidin-3-amine,
(3R,4R)-4-{[1-(Biphenyl-4-ylcarbonyl)azetidin-3-yl]amino}-1-(phenylcarbonyl)pyrrolidin-3-ol,
(3S)—N-{1-[(3-Cyclobutyl-6-fluoro-1-benzothiophen-2-yl)carbonyl]azetidin-3-yl}-1-(phenylcarbonyl)pyrrolidin-3-amine,
(3S)—N-(1-{[3-Methyl-6-(trifluoromethyl)-1-benzothiophen-2-yl]carbonyl}azetidin-3-yl)-1-(phenylcarbonyl)pyrrolidin-3-amine,
N-{1-[(5-Chloro-3-methyl-1-benzothiophen-2-yl)carbonyl]azetidin-3-yl}-N-[(3S)-1-(phenylcarbonyl)pyrrolidin-3-yl]formamide,
N-{1-[(5-Chloro-3-methyl-1-benzothiophen-2-yl)carbonyl]azetidin-3-yl}-N-[(3S)-1-(1,3-thiazol-2-ylcarbonyl)pyrrolidin-3-yl]formamide,
N-{1-[(5-Chloro-3-methyl-1-benzothiophen-2-yl)carbonyl]azetidin-3-yl}-N-[(3S)-1-(1,3-thiazol-4-ylcarbonyl)pyrrolidin-3-yl]formamide, (3S)—N-{1-[(5-Chloro-3-methyl-1-benzothiophen-2-yl)carbonyl]azetidin-3-yl}-1-(1,3-thiazol-2-ylcarbonyl)pyrrolidin-3-amine, (3S)—N-{1-[(5-Chloro-3-methyl-1-benzothiophen-2-yl)carbonyl]azetidin-3-yl}-1-(1,3-thiazol-4-ylcarbonyl)pyrrolidin-3-amine, (3S)—N-{1-[(6-Fluoro-3-methyl-1-benzothiophen-2-yl)carbonyl]azetidin-3-yl}-1-(phenylcarbonyl)pyrrolidin-3-amine, (3S)—N-{1-[(6-Fluoro-3-methyl-1-benzothiophen-2-yl)carbonyl]azetidin-3-yl}-1-(1,3-thiazol-2-ylcarbonyl)pyrrolidin-3-amine, (3S)—N-{1-[(6-Fluoro-3-methyl-1-benzothiophen-2-yl)carbonyl]azetidin-3-yl}-1-(1,3-thiazol-4-ylcarbonyl)pyrrolidin-3-amine, (3S)—N-(1-{[3-Fluoro-6-(trifluoromethyl)-1-benzothiophen-2-yl]carbonyl}azetidin-3-yl)-1-(phenylcarbonyl)pyrrolidin-3-amine, (3S)—N-[1-({3-Methyl-5-[3-(trifluoromethyl)phenyl]-1-benzothiophen-2-yl}carbonyl)azetidin-3-yl]-1-(1,3-thiazol-2-ylcarbonyl)pyrrolidin-3-amine, (3S)—N-[1-({3-Methyl-5-[4-(trifluoromethyl)phenyl]-1-benzothiophen-2-yl}carbonyl)azetidin-3-yl]-1-(1,3-thiazol-2-ylcarbonyl)pyrrolidin-3-amine, (3S)—N-{1-[(3-Methyl-5-phenyl-1-benzothiophen-2-yl)carbonyl]azetidin-3-yl}-1-(1,3-thiazol-2-ylcarbonyl)pyrrolidin-3-amine, (3S)—N-(1-{[5-(3-Fluorophenyl)-3-methyl-1-benzothiophen-2-yl]carbonyl}azetidin-3-yl)-1-(phenylcarbonyl)pyrrolidin-3-amine, (3S)—N-(1-{[5-(4-Fluorophenyl)-3-methyl-1-benzothiophen-2-yl]carbonyl}azetidin-3-yl)-1-(phenylcarbonyl)pyrrolidin-3-amine, (3S)—N-{1-[(6-Bromo-1-benzothiophen-2-yl)carbonyl]azetidin-3-yl}-1-(1,3-thiazol-2-ylcarbonyl)pyrrolidin-3-amine, (3S)—N-{1-[(6-Bromo-1-benzothiophen-2-yl)carbonyl]azetidin-3-yl}-1-(1,3-thiazol-4-ylcarbonyl)pyrrolidin-3-amine, (3S)—N-{1-[(5-Bromo-1-benzothiophen-2-yl)carbonyl]azetidin-3-yl}-1-(1,3-thiazol-2-ylcarbonyl)pyrrolidin-3-amine, (3S)—N-{1-[(5-Bromo-1-benzothiophen-2-yl)carbonyl]azetidin-3-yl}-1-(1,3-thiazol-4-ylcarbonyl)pyrrolidin-3-amine, (3S)-1-(1,3-Thiazol-2-ylcarbonyl)-N-[1-({6-[3-(trifluoromethyl)phenyl]-1-benzothiophen-2-yl}carbonyl)azetidin-3-yl]pyrrolidin-3-amine, (3S)-1-(1,3-Thiazol-4-ylcarbonyl)-N-[1-({6-[3-(trifluoromethyl)phenyl]-1-benzothiophen-2-yl}carbonyl)azetidin-3-yl]pyrrolidin-3-amine, (3S)-1-(Phenylcarbonyl)-N-[1-({3-[4-(trifluoromethyl)phenyl]-1H-indol-6-yl}carbonyl)azetidin-3-yl]pyrrolidin-3-amine, (3S)-1-(1,3-Thiazol-2-ylcarbonyl)-N-[1-({6-[4-(trifluoromethyl)phenyl]-1-benzothiophen-2-yl}carbonyl)azetidin-3-yl]pyrrolidin-3-amine, (3S)-1-(Phenylcarbonyl)-N-[1-({3-[3-(trifluoromethyl)phenyl]-1H-indol-6-yl}carbonyl)azetidin-3-yl]pyrrolidin-3-amine, (3S)-1-(1,3-Thiazol-4-ylcarbonyl)-N-[1-({3-[4-(trifluoromethyl)phenyl]-1H-indol-6-yl}carbonyl)azetidin-3-yl]pyrrolidin-3-amine, (3S)-1-(1,3-Thiazol-2-ylcarbonyl)-N-[1-({3-[3-(trifluoromethyl)phenyl]-1H-indol-6-yl}carbonyl)azetidin-3-yl]pyrrolidin-3-amine, (3S)-1-(1,3-Thiazol-4-ylcarbonyl)-N-[1-({3-[3-(trifluoromethyl)phenyl]-1H-indol-6-yl}carbonyl)azetidin-3-yl]pyrrolidin-3-amine, (3S)—N-{1-[(5-Bromo-1-benzofuran-2-yl)carbonyl]azetidin-3-yl}-1-(phenylcarbonyl)pyrrolidin-3-amine, (3S)-1-(Phenylcarbonyl)-N-{1-[(4-phenylquinazolin-7-yl)carbonyl]azetidin-3-yl}pyrrolidin-3-amine, (3S)-1-(Phenylcarbonyl)-N-[1-({4-[4-(trifluoromethyl)phenyl]quinazolin-7-yl}carbonyl)azetidin-3-yl]pyrrolidin-3-amine, (3S)—N-{1-[(4-Phenylquinazolin-7-yl)carbonyl]azetidin-3-yl}-1-(1,3-thiazol-2-ylcarbonyl)pyrrolidin-3-amine, (3S)-1-(1,3-Thiazol-2-ylcarbonyl)-N-[1-({4-[4-(trifluoromethyl)phenyl]quinazolin-7-yl}carbonyl)azetidin-3-yl]pyrrolidin-3-amine, (3S)—N-{1-[(4-Phenylquinazolin-7-yl)carbonyl]azetidin-3-yl}-1-(1,3-thiazol-4-ylcarbonyl)pyrrolidin-3-amine, (3S)-1-(1,3-Thiazol-2-ylcarbonyl)-N-(1-{[3'-(trifluoromethyl)biphenyl-4-yl]carbonyl}azetidin-3-yl)pyrrolidin-3-amine, (3S)-1-(1,3-Thiazol-4-ylcarbonyl)-N-(1-{[3'-(trifluoromethyl)biphenyl-4-yl]carbonyl}azetidin-3-yl)pyrrolidin-3-amine, (3S)-1-(1,3-Thiazol-2-ylcarbonyl)-N-(1-{[4'-(trifluoromethyl)biphenyl-4-yl]carbonyl}azetidin-3-yl)pyrrolidin-3-amine, (3S)—N-(1-{[3-Fluoro-3'-(trifluoromethyl)biphenyl-4-yl]carbonyl}azetidin-3-yl)-1-(1,3-thiazol-2-ylcarbonyl)pyrrolidin-3-amine, (3S)—N-(1-{[3-Methyl-3'-(trifluoromethyl)biphenyl-4-yl]carbonyl}azetidin-3-yl)-1-(1,3-thiazol-2-ylcarbonyl)pyrrolidin-3-amine, (3S)-1-(1,3-Thiazol-2-ylcarbonyl)-N-[1-({1-[4-(trifluoromethyl)phenyl]-1H-indol-5-yl}carbonyl)azetidin-3-yl]pyrrolidin-3-amine, (3S)—N-{1-[(1-Pyrimidin-2-yl-1H-indol-5-yl)carbonyl]azetidin-3-yl}-1-(1,3-thiazol-2-ylcarbonyl)pyrrolidin-3-amine, (3S)—N-{1-[(1-Phenyl-1H-indazol-5-yl)carbonyl]azetidin-3-yl}-1-(1,3-thiazol-2-ylcarbonyl)pyrrolidin-3-amine, (3S)—N-{1-[(5-Phenyl-1-benzofuran-2-yl)carbonyl]azetidin-3-yl}-1-(phenylcarbonyl)pyrrolidin-3-amine, (3S)—N-(1-{[5-(5-Chlorothiophen-2-yl)-1-benzofuran-2-yl]carbonyl}azetidin-3-yl)-1-(phenylcarbonyl)pyrrolidin-3-amine, (3S)—N-{1-[(3-Methyl-5-phenyl-1-benzothiophen-2-yl)carbonyl]azetidin-3-yl}-1-(1,3-thiazol-4-ylcarbonyl)pyrrolidin-3-amine, (3S)—N-{1-[(6-Phenyl-1-benzothiophen-2-yl)carbonyl]azetidin-3-yl}-1-(1,3-thiazol-4-ylcarbonyl)pyrrolidin-3-amine, (3S)—N-[1-({3-Methyl-5-[3-(trifluoromethyl)phenyl]-1-benzothiophen-2-yl}carbonyl)azetidin-3-yl]-1-(1,3-thiazol-4-ylcarbonyl)pyrrolidin-3-amine, (3S)-1-(Phenylcarbonyl)-N-[1-({4-[3-(trifluoromethyl)benzyl]phenyl}carbonyl)azetidin-3-yl]pyrrolidin-3-amine, (3S)-1-(1,3-Thiazol-4-ylcarbonyl)-N-[1-({4-[3-(trifluoromethyl)benzyl]phenyl}carbonyl)azetidin-3-yl]pyrrolidin-3-amine, (3S)-1-(1,3-Thiazol-4-ylcarbonyl)-N-[1-({6-[4-(trifluoromethyl)phenyl]-1-benzothiophen-2-yl}carbonyl)azetidin-3-yl]pyrrolidin-3-amine, (3S)—N-{1-[(5-Phenyl-1-benzothiophen-2-yl)carbonyl]azetidin-3-yl}-1-(1,3-thiazol-2-ylcarbonyl)pyrrolidin-3-amine, (3S)-1-(1,3-Thiazol-4-ylcarbonyl)-N-[1-({5-[3-(trifluoromethyl)phenyl]-1-benzothiophen-2-yl}carbonyl)azetidin-3-yl]pyrrolidin-3-amine,
(3S)—N-{1-[(5-Phenyl-1-benzothiophen-2-yl)carbonyl]azetidin-3-yl}-1-(1,3-thiazol-4-ylcarbonyl)pyrrolidin-3-amine,
(3S)-1-(1,3-Thiazol-2-ylcarbonyl)-N-[1-({5-[3-(trifluoromethyl)phenyl]-1-benzothiophen-2-yl}carbonyl)azetidin-3-yl]pyrrolidin-3-amine,
(3S)—N-{1-[(2-Phenyl-1,3-benzothiazol-6-yl)carbonyl]azetidin-3-yl}-1-(1,3-thiazol-2-ylcarbonyl)pyrrolidin-3-amine,
(3S)—N-(1-{[2-(2-Fluorophenyl)-4-methyl-1,3-thiazol-5-yl]carbonyl}azetidin-3-yl)-1-(1,3-thiazol-2-ylcarbonyl)pyrrolidin-3-amine,
(3S)—N-(1-{[2-(4-Fluorophenyl)-4-methyl-1,3-thiazol-5-yl]carbonyl}azetidin-3-yl)-1-(1,3-thiazol-2-ylcarbonyl)pyrrolidin-3-amine,
(3S)—N-(1-{[2-(3-Chlorophenyl)-4-methyl-1,3-thiazol-5-yl]carbonyl}azetidin-3-yl)-1-(1,3-thiazol-2-ylcarbonyl)pyrrolidin-3-amine,
(3S)—N-(1-{[2-(4-Chlorophenyl)-4-methyl-1,3-thiazol-5-yl]carbonyl}azetidin-3-yl)-1-(1,3-thiazol-2-ylcarbonyl)pyrrolidin-3-amine,
(3S)-1-(1,3-Thiazol-2-ylcarbonyl)-N-(1-{[6-(trifluoromethyl)-1-benzothiophen-2-yl]carbonyl}azetidin-3-yl)pyrrolidin-3-amine,
(3S)-1-(1,3-Thiazol-4-ylcarbonyl)-N-(1-{[6-(trifluoromethyl)-1-benzothiophen-2-yl]carbonyl}azetidin-3-yl)pyrrolidin-3-amine,
(3S)—N-{1-[(6-Bromo-3-chloro-1-benzothiophen-2-yl)carbonyl]azetidin-3-yl}-1-(1,3-thiazol-2-ylcarbonyl)pyrrolidin-3-amine,
(3S)—N-{1-[(6-Bromo-3-chloro-1-benzothiophen-2-yl)carbonyl]azetidin-3-yl}-1-(1,3-thiazol-4-ylcarbonyl)pyrrolidin-3-amine,
(3S)—N-(1-{[3-Fluoro-1-(4-fluorophenyl)-1H-indol-5-yl]carbonyl}azetidin-3-yl)-1-(phenylcarbonyl)pyrrolidin-3-amine,
(3S)—N-(1-{[3-Fluoro-1-(4-fluorophenyl)-1H-indol-5-yl]carbonyl}azetidin-3-yl)-1-(1,3-thiazol-4-ylcarbonyl)pyrrolidin-3-amine,
(3S)-1-(1,3-Thiazol-4-ylcarbonyl)-N-[1-({4-[4-(trifluoromethyl)benzyl]phenyl}carbonyl)azetidin-3-yl]pyrrolidin-3-amine,
(3S)-1-(1,3-Thiazol-4-ylcarbonyl)-N-(1-{[4'-(trifluoromethyl)biphenyl-4-yl]carbonyl}azetidin-3-yl)pyrrolidin-3-amine,
(3S)—N-{1-[(3-Chloro-6-phenyl-1-benzothiophen-2-yl)carbonyl]azetidin-3-yl}-1-(1,3-thiazol-2-ylcarbonyl)pyrrolidin-3-amine,
(3S)—N-{1-[(3-Chloro-6-phenyl-1-benzothiophen-2-yl)carbonyl]azetidin-3-yl}-1-(1,3-thiazol-4-ylcarbonyl)pyrrolidin-3-amine,
(3S)—N-[1-({3-Chloro-6-[3-(trifluoromethyl)phenyl]-1-benzothiophen-2-yl}carbonyl)azetidin-3-yl]-1-(1,3-thiazol-2-ylcarbonyl)pyrrolidin-3-amine,
(3S)—N-[1-({3-Chloro-6-[3-(trifluoromethyl)phenyl]-1-benzothiophen-2-yl}carbonyl)azetidin-3-yl]-1-(1,3-thiazol-4-ylcarbonyl)pyrrolidin-3-amine,
(3S)—N-[1-({3-Chloro-6-[4-(trifluoromethyl)phenyl]-1-benzothiophen-2-yl}carbonyl)azetidin-3-yl]-1-(1,3-thiazol-2-ylcarbonyl)pyrrolidin-3-amine,
(3S)—N-[1-({3-Chloro-6-[4-(trifluoromethyl)phenyl]-1-benzothiophen-2-yl}carbonyl)azetidin-3-yl]-1-(1,3-thiazol-4-ylcarbonyl)pyrrolidin-3-amine,
(3S)—N-(1-{[3-Fluoro-3'-(trifluoromethyl)biphenyl-4-yl]carbonyl}azetidin-3-yl)-1-(phenylcarbonyl)pyrrolidin-3-amine,
(3S)—N-(1-{[3-Methyl-3'-(trifluoromethyl)biphenyl-4-yl]carbonyl}azetidin-3-yl)-1-(phenylcarbonyl)pyrrolidin-3-amine,
(3S)-1-(Phenylcarbonyl)-N-[1-({1-[4-(trifluoromethyl)phenyl]-1H-indol-5-yl}carbonyl)azetidin-3-yl]pyrrolidin-3-amine,
(3S)-1-(Phenylcarbonyl)-N-{1-[(1-pyrimidin-2-yl-1H-indol-5-yl)carbonyl]azetidin-3-yl}pyrrolidin-3-amine,
(3S)-1-(Phenylcarbonyl)-N-{1-[(1-phenyl-1H-indazol-5-yl)carbonyl]azetidin-3-yl}pyrrolidin-3-amine,
(3S)—N-{1-[(2-Phenyl-1,3-benzothiazol-6-yl)carbonyl]azetidin-3-yl}-1-(phenylcarbonyl)pyrrolidin-3-amine,
(3S)-1-(1,3-Thiazol-4-ylcarbonyl)-N-[1-({1-[4-(trifluoromethyl)phenyl]-1H-indol-5-yl}carbonyl)azetidin-3-yl]pyrrolidin-3-amine,
(3S)—N-(1-{[1-(4-Fluorophenyl)-1H-indol-5-yl]carbonyl}azetidin-3-yl)-1-(1,3-thiazol-2-ylcarbonyl)pyrrolidin-3-amine,
(3S)—N-(1-{[1-(4-Fluorophenyl)-1H-indol-5-yl]carbonyl}azetidin-3-yl)-1-(1,3-thiazol-4-ylcarbonyl)pyrrolidin-3-amine,
(3S)—N-(1-{[1-(4-Fluorophenyl)-1H-indol-5-yl]carbonyl}azetidin-3-yl)-1-(phenylcarbonyl)pyrrolidin-3-amine,
(3S)—N-[1-({1-Methyl-3-[3-(trifluoromethyl)phenyl]-1H-indol-6-yl}carbonyl)azetidin-3-yl]-1-(1,3-thiazol-2-ylcarbonyl)pyrrolidin-3-amine,
(3S)—N-[1-({1-Methyl-3-[4-(trifluoromethyl)phenyl]-1H-indol-6-yl}carbonyl)azetidin-3-yl]-1-(1,3-thiazol-2-ylcarbonyl)pyrrolidin-3-amine,
(3S)—N-[1-({1-Methyl-3-[3-(trifluoromethyl)phenyl]-1H-indol-6-yl}carbonyl)azetidin-3-yl]-1-(1,3-thiazol-4-ylcarbonyl)pyrrolidin-3-amine,
(3S)—N-[1-({1-Methyl-3-[4-(trifluoromethyl)phenyl]-1H-indol-6-yl}carbonyl)azetidin-3-yl]-1-(1,3-thiazol-4-ylcarbonyl)pyrrolidin-3-amine,
(3S)—N-[1-({1-Methyl-3-[3-(trifluoromethyl)phenyl]-1H-indol-6-yl}carbonyl)azetidin-3-yl]-1-(phenylcarbonyl)pyrrolidin-3-amine,
(3S)—N-(1-{[3-Chloro-6-(trifluoromethyl)-1-benzothiophen-2-yl]carbonyl}azetidin-3-yl)-1-(1,3-thiazol-2-ylcarbonyl)pyrrolidin-3-amine,
(3S)—N-(1-{[3-Chloro-6-(trifluoromethyl)-1-benzothiophen-2-yl]carbonyl}azetidin-3-yl)-1-(1,3-thiazol-4-ylcarbonyl)pyrrolidin-3-amine,
(3S)—N-{1-[(1-Methyl-3-phenyl-1H-indol-6-yl)carbonyl]azetidin-3-yl}-1-(1,3-thiazol-2-ylcarbonyl)pyrrolidin-3-amine,
(3S)—N-{1-[(1-Methyl-3-phenyl-1H-indol-6-yl)carbonyl]azetidin-3-yl}-1-(1,3-thiazol-4-ylcarbonyl)pyrrolidin-3-amine,
(3S)—N-{1-[(3-Fluoro-5-phenyl-1-benzothiophen-2-yl)carbonyl]azetidin-3-yl}-1-(1,3-thiazol-2-ylcarbonyl)pyrrolidin-3-amine,
(3S)—N-{1-[(3-Fluoro-5-phenyl-1-benzothiophen-2-yl)carbonyl]azetidin-3-yl}-1-(1,3-thiazol-4-ylcarbonyl)pyrrolidin-3-amine,
(3S)—N-{1-[(3-Fluoro-5-phenyl-1-benzothiophen-2-yl)carbonyl]azetidin-3-yl}-1-(phenylcarbonyl)pyrrolidin-3-amine,
(3S)—N-[1-({3-Fluoro-5-[4-(trifluoromethyl)phenyl]-1-benzothiophen-2-yl}carbonyl)azetidin-3-yl]-1-(1,3-thiazol-2-ylcarbonyl)pyrrolidin-3-amine, (3S)—N-[1-({3-Fluoro-5-[4-(trifluoromethyl)phenyl]-1-benzothiophen-2-yl}carbonyl)azetidin-3-yl]-1-(1,3-thiazol-4-ylcarbonyl)pyrrolidin-3-amine,
(3S)—N-[1-({3-Fluoro-5-[4-(trifluoromethyl)phenyl]-1-benzothiophen-2-yl}carbonyl)azetidin-3-yl]-1-(phenylcarbonyl)pyrrolidin-3-amine,
(3S)—N-[1-({3-Fluoro-6-[4-(trifluoromethyl)phenyl]-1-benzothiophen-2-yl}carbonyl)azetidin-3-yl]-1-(1,3-thiazol-2-ylcarbonyl)pyrrolidin-3-amine,
(3S)—N-[1-({3-Fluoro-6-[4-(trifluoromethyl)phenyl]-1-benzothiophen-2-yl}carbonyl)azetidin-3-yl]-1-(1,3-thiazol-4-ylcarbonyl)pyrrolidin-3-amine,
(3S)—N-[1-({3-Fluoro-6-[4-(trifluoromethyl)phenyl]-1-benzothiophen-2-yl}carbonyl)azetidin-3-yl]-1-(phenylcarbonyl)pyrrolidin-3-amine,
(3S)—N-(1-{[5-Chloro-3-(trifluoromethyl)-1-benzothiophen-2-yl]carbonyl}azetidin-3-yl)-1-(phenylcarbonyl)pyrrolidin-3-amine,
(3S)—N-(1-{[5-Chloro-3-(trifluoromethyl)-1-benzothiophen-2-yl]carbonyl}azetidin-3-yl)-1-(1,3-thiazol-4-ylcarbonyl)pyrrolidin-3-amine,
(3S)—N-(1-{[6-Chloro-3-(trifluoromethyl)-1-benzothiophen-2-yl]carbonyl}azetidin-3-yl)-1-(phenylcarbonyl)pyrrolidin-3-amine,
(3S)—N-(1-{[6-Chloro-3-(trifluoromethyl)-1-benzothiophen-2-yl]carbonyl}azetidin-3-yl)-1-(1,3-thiazol-2-ylcarbonyl)pyrrolidin-3-amine,
(3S)—N-(1-{[5-Methyl-3-(trifluoromethyl)-1-benzothiophen-2-yl]carbonyl}azetidin-3-yl)-1-(1,3-thiazol-4-ylcarbonyl)pyrrolidin-3-amine,
(3S)—N-(1-{[6-Methyl-3-(trifluoromethyl)-1-benzothiophen-2-yl]carbonyl}azetidin-3-yl)-1-(1,3-thiazol-4-ylcarbonyl)pyrrolidin-3-amine,
(3S)—N-(1-{[6-Methyl-3-(trifluoromethyl)-1-benzothiophen-2-yl]carbonyl}azetidin-3-yl)-1-(1,3-thiazol-2-ylcarbonyl)pyrrolidin-3-amine,
(3S)—N-{1-[(3-Phenyl-1H-indol-6-yl)carbonyl]azetidin-3-yl}-1-(1,3-thiazol-2-ylcarbonyl)pyrrolidin-3-amine,
(3S)—N-{1-[(3-Phenyl-1H-indol-6-yl)carbonyl]azetidin-3-yl}-1-(1,3-thiazol-4-ylcarbonyl)pyrrolidin-3-amine,
(3S)—N-(1-{[3-(4-Fluorophenyl)-1H-indol-6-yl]carbonyl}azetidin-3-yl)-1-(1,3-thiazol-2-ylcarbonyl)pyrrolidin-3-amine,
(3S)—N-(1-{[3-(4-Fluorophenyl)-1H-indol-6-yl]carbonyl}azetidin-3-yl)-1-(1,3-thiazol-4-ylcarbonyl)pyrrolidin-3-amine,
(3S)—N-(1-{[3-(4-Fluorophenyl)-1H-indol-6-yl]carbonyl}azetidin-3-yl)-1-(phenylcarbonyl)pyrrolidin-3-amine,
(3S)—N-(1-{[3-(4-Fluorophenyl)-1-methyl-1H-indol-6-yl]carbonyl}azetidin-3-yl)-1-(1,3-thiazol-2-ylcarbonyl)pyrrolidin-3-amine,
(3S)—N-(1-{[3-(4-Fluorophenyl)-1-methyl-1H-indol-6-yl]carbonyl}azetidin-3-yl)-1-(1,3-thiazol-4-ylcarbonyl)pyrrolidin-3-amine,
(3S)—N-(1-{[3-(4-Fluorophenyl)-1-methyl-1H-indol-6-yl]carbonyl}azetidin-3-yl)-1-(phenylcarbonyl)pyrrolidin-3-amine,
(3S)—N-{1-[(1-Methyl-3-phenyl-1H-indazol-5-yl)carbonyl]azetidin-3-yl}-1-(1,3-thiazol-2-ylcarbonyl)pyrrolidin-3-amine,
(3S)—N-{1-[(1-Methyl-3-phenyl-1H-indazol-5-yl)carbonyl]azetidin-3-yl}-1-(1,3-thiazol-4-ylcarbonyl)pyrrolidin-3-amine,
(3S)—N-{1-[(1-Methyl-3-phenyl-1H-indazol-5-yl)carbonyl]azetidin-3-yl}-1-(phenylcarbonyl)pyrrolidin-3-amine,
(3S)—N-(1-{[4-Fluoro-1-(4-fluorophenyl)-1H-indol-5-yl]carbonyl}azetidin-3-yl)-1-(1,3-thiazol-2-ylcarbonyl)pyrrolidin-3-amine,
(3S)—N-(1-{[3-(3-Fluorophenyl)-1-methyl-1H-indazol-5-yl]carbonyl}azetidin-3-yl)-1-(1,3-thiazol-2-ylcarbonyl)pyrrolidin-3-amine,
(3S)—N-(1-{[3-(3-Fluorophenyl)-1-methyl-1H-indazol-5-yl]carbonyl}azetidin-3-yl)-1-(1,3-thiazol-4-ylcarbonyl)pyrrolidin-3-amine,
(3S)—N-(1-{[3-(3-Fluorophenyl)-1-methyl-1H-indazol-5-yl]carbonyl}azetidin-3-yl)-1-(phenylcarbonyl)pyrrolidin-3-amine,
(3S)—N-(1-{[3-(3-Fluorophenyl)-1H-indol-6-yl]carbonyl}azetidin-3-yl)-1-(1,3-thiazol-2-ylcarbonyl)pyrrolidin-3-amine,
(3S)—N-(1-{[3-(3-Fluorophenyl)-1H-indol-6-yl]carbonyl}azetidin-3-yl)-1-(1,3-thiazol-4-ylcarbonyl)pyrrolidin-3-amine,
(3S)—N-(1-{[3-(3-Fluorophenyl)-1H-indol-6-yl]carbonyl}azetidin-3-yl)-1-(phenylcarbonyl)pyrrolidin-3-amine,
(3S)—N-(1-{[3-(3-Fluorophenyl)-1-methyl-1H-indol-6-yl]carbonyl}azetidin-3-yl)-1-(1,3-thiazol-2-ylcarbonyl)pyrrolidin-3-amine,
(3S)—N-(1-{[3-(3-Fluorophenyl)-1-methyl-1H-indol-6-yl]carbonyl}azetidin-3-yl)-1-(1,3-thiazol-4-ylcarbonyl)pyrrolidin-3-amine,
(3S)—N-(1-{[3-(3-Fluorophenyl)-1-methyl-1H-indol-6-yl]carbonyl}azetidin-3-yl)-1-(phenylcarbonyl)pyrrolidin-3-amine,
(3S)—N-(1-{[6-Phenyl-3-(trifluoromethyl)-1-benzothiophen-2-yl]carbonyl}azetidin-3-yl)-1-(1,3-thiazol-2-ylcarbonyl)pyrrolidin-3-amine,
(3S)—N-(1-{[3-(4-Fluorophenyl)-1-methyl-1H-indazol-5-yl]carbonyl}azetidin-3-yl)-1-(1,3-thiazol-2-ylcarbonyl)pyrrolidin-3-amine,
(3S)—N-(1-{[3-(4-Fluorophenyl)-1-methyl-1H-indazol-5-yl]carbonyl}azetidin-3-yl)-1-(1,3-thiazol-4-ylcarbonyl)pyrrolidin-3-amine,
(3S)—N-(1-{[3-(4-Fluorophenyl)-1-methyl-1H-indazol-5-yl]carbonyl}azetidin-3-yl)-1-(phenylcarbonyl)pyrrolidin-3-amine,
(3S)—N-(1-{[6-Fluoro-1-(4-fluorophenyl)-1H-indol-5-yl]carbonyl}azetidin-3-yl)-1-(1,3-thiazol-2-ylcarbonyl)pyrrolidin-3-amine,
(3R)—N-(1-{[1-(2,2-Difluoroethyl)-1H-indol-5-yl]carbonyl}azetidin-3-yl)-1-(1,3-thiazol-2-ylcarbonyl)pyrrolidin-3-amine,
(3S)—N-(1-{[1-(4-Fluorophenyl)-1H-indol-4-yl]carbonyl}azetidin-3-yl)-1-(1,3-thiazol-2-ylcarbonyl)pyrrolidin-3-amine,
(3S)—N-(1-{[1-(4-Fluorophenyl)-1H-indol-4-yl]carbonyl}azetidin-3-yl)-1-(1,3-thiazol-4-ylcarbonyl)pyrrolidin-3-amine,
(3S)—N-(1-{[1-(4-Fluorophenyl)-2,3-dihydro-1H-indol-4-yl]carbonyl}azetidin-3-yl)-1-(1,3-thiazol-2-ylcarbonyl)pyrrolidin-3-amine,
(3S)—N-(1-{[1-(4-Fluorophenyl)-2,3-dihydro-1H-indol-4-yl]carbonyl}azetidin-3-yl)-1-(1,3-thiazol-4-ylcarbonyl)pyrrolidin-3-amine,
(3S)—N-(1-{[1-(3-Fluorophenyl)-1H-indol-3-yl]carbonyl}azetidin-3-yl)-1-(1,3-thiazol-2-ylcarbonyl)pyrrolidin-3-amine,
(3S)—N-(1-{[1-(4-Fluorophenyl)-1H-indol-3-yl]carbonyl}azetidin-3-yl)-1-(1,3-thiazol-2-ylcarbonyl)pyrrolidin-3-amine, (3S)—N-(1-{[1-(4-Fluorophenyl)-2,3-dihydro-1H-indol-5-yl]carbonyl}azetidin-3-yl)-1-(1,3-thiazol-2-ylcarbonyl) pyrrolidin-3-amine, (3S)—N-(1-{[3-(4-Fluorobenzyl)-1-methyl-1H-indol-6-yl]carbonyl}azetidin-3-yl)-1-(1,3-thiazol-2-ylcarbonyl)pyrrolidin-3-amine, N-Methyl-N-phenyl-2-{5-[(3-{[(3S)-1-(1,3-thiazol-2-ylcarbonyl)pyrrolidin-3-yl]amino}azetidin-1-yl)carbonyl]-1H-indol-1-yl}acetamide, (3S)—N-(1-{[4-Chloro-1-(4-fluorophenyl)-1H-indol-5-yl]carbonyl}azetidin-3-yl)-1-(1,3-thiazol-2-ylcarbonyl)pyrrolidin-3-amine, (3S)—N-(1-{[1-(4-Fluorophenyl)-6-methyl-1H-indol-5-yl]carbonyl}azetidin-3-yl)-1-(1,3-thiazol-2-ylcarbonyl)pyrrolidin-3-amine, and (3S)—N-(1-{[6-Chloro-1-(4-fluorophenyl)-1H-indol-5-yl]carbonyl}azetidin-3-yl)-1-(1,3-thiazol-2-ylcarbonyl)pyrrolidin-3-amine, and pharmaceutically acceptable salt forms thereof.

For use in medicine, salts of compounds of Formula (I) refer to non-toxic "pharmaceutically acceptable salts." Other salts may, however, be useful in the preparation of compounds of Formula (I) or of their pharmaceutically acceptable salts thereof. Suitable pharmaceutically acceptable salts of compounds of Formula (I) include acid addition salts that can, for example, be formed by mixing a solution of the compound with a solution of a pharmaceutically acceptable acid such as, hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (I) carry an acidic moiety, suitable pharmaceutically acceptable salts thereof may include alkali metal salts such as, sodium or potassium salts; alkaline earth metal salts such as, calcium or magnesium salts; and salts formed with suitable organic ligands such as, quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, and valerate.

Representative acids and bases that may be used in the preparation of pharmaceutically acceptable salts include acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxoglutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine, and zinc hydroxide.

Embodiments of the present invention include prodrugs of compounds of Formula (I). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula (I).

Where the processes for the preparation of the compounds according to certain embodiments of the invention give rise to mixture of stereoisomers, these isomers may be separated by conventional techniques such as, preparative chromatography. The compounds may be prepared in racemic form, or individual enantiomers may be prepared either by enantiospecific synthesis or by resolution. The compounds may, for example, be resolved into their component enantiomers by standard techniques such as, the formation of diastereomeric pairs by salt formation with an optically active acid such as, (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (I) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as $$\%(+)\text{-enantiomer} = \frac{(\text{mass}(+)\text{-enantiomer})}{(\text{mass}(+)\text{-enantiomer}) + (\text{mass}(-)\text{-enantiomer})} \times 100.$$

Another embodiment of the present invention is a composition, including a pharmaceutical composition, comprising, consisting of, and consisting essentially of the (−)-enantiomer of a compound of Formula (I) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\%(-)\text{-enantiomer} = \frac{(\text{mass}(-)\text{-enantiomer})}{(\text{mass}(+)\text{-enantiomer}) + (\text{mass}(-)\text{-enantiomer})} \times 100.$$

During any of the processes for preparation of the compounds of the various embodiments of the present invention, it may be necessary and/or desirable to protect sensitive or reactive groups on any of the molecules concerned. This may be achieved by means of conventional protecting groups such as those described in *Protective Groups in Organic Chemistry, Second Edition*, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis*, Third Edition, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (I) and at least one pharmaceutically acceptable carrier, pharmaceutically acceptable excipient, and/or pharmaceutically acceptable diluent.

By way of example, in the pharmaceutical compositions of embodiments of the present invention, the compounds of Formula (I) may be admixed with any suitable binder(s), lubricant(s), suspending agent(s), coating agent(s), solubilizing agent(s), and combinations thereof.

Solid oral dosage forms such as, tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of Formula (I) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a wax or soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example, intracavernosally, intravenously, intramuscularly, subcutaneously, intradermally, or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus, for liquid oral preparations such as, suspensions, syrups, elixirs and solutions, suitable carriers, excipients and diluents include water, glycols, oils, alcohols, flavoring agents, preservatives, stabilizers, coloring agents and the like; for solid oral preparations such as, powders, capsules, and tablets, suitable carriers, excipients and diluents include starches, sugars, diluents, granulating agents, lubricants, binders, disintegrating agents and the like. Solid oral preparations also may be optionally coated with substances such as, sugars, or be enterically coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives such as, solubilizers and preservatives.

A therapeutically effective amount of a compound of Formula (I) or a pharmaceutical composition thereof includes a dose range from about 0.1 mg to about 3000 mg, or any particular amount or range therein, in particular from about 1 mg to about 1000 mg, or any particular amount or range therein, or, more particularly, from about 10 mg to about 500 mg, or any particular amount or range therein, of active ingredient in a regimen of about 1 to about 4 times per day for an average (70 kg) human; although, it is apparent to one skilled in the art that the therapeutically effective amount for a compound of Formula (I) will vary as will the diseases, syndromes, conditions, and disorders being treated.

For oral administration, a pharmaceutical composition is preferably provided in the form of tablets containing about 1.0, about 10, about 50, about 100, about 150, about 200, about 250, and about 500 milligrams of a compound of Formula (I).

Advantageously, a compound of Formula (I) may be administered in a single daily dose, or the total daily dosage may be administered in divided doses of two, three and four times daily.

Optimal dosages of a compound of Formula (I) to be administered may be readily determined and will vary with the particular compound used, the mode of administration, the strength of the preparation and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Compounds of Formula (I) may be administered in any of the foregoing compositions and dosage regimens or by means of those compositions and dosage regimens established in the art whenever use of a compound of Formula (I) is required for a subject in need thereof.

As MGL inhibitors, the compounds of Formula (I) are useful in methods for treating and preventing a disease, a syndrome, a condition or a disorder in a subject, including an animal, a mammal and a human in which the disease, the syndrome, the condition or the disorder is affected by the modulation, including inhibition, of the MGL enzyme. Such methods comprise, consist of and/or consist essentially of administering to a subject, including an animal, a mammal, and a human in need of such treatment or prevention a therapeutically effective amount of a compound, salt or solvate of Formula (I).

General Synthetic Methods

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes. The various starting materials used in the schemes and examples are commercially available or may be prepared by methods well within the skill of persons versed in the art. The variables are as defined herein.

Abbreviations used in the instant specification, particularly the schemes and examples, are as follows:
AcCl acetyl chloride
AcOH glacial acetic acid
aq. aqueous
Bn or Bzl benzyl
Boc tert-butyloxycarbonyl
conc. concentrated
dba dibenzylideneacetone
DCC N,N'-dicyclohexyl-carbodiimide
DCE 1,2-dichloroethane
DCM dichloromethane
DIPEA diisopropyl-ethyl amine
DMAP 4-N,N-dimethylaminopyridine
DMF N,N-dimethylformamide
DMSO dimethylsulfoxide
dppf 1,1'-bis(diphenylphosphino)ferrocene
EDC N-(3-dimethylaminopropyl)-N'-ethylcarbodiimide hydrochloride
ESI electrospray ionization
EtOAc ethyl acetate
EtOH ethanol
h hour(s)
HATU O-(1H-7-azabenzotriazol-1-yl)-1,1,3,3-tetramethyluronium hexafluorophosphate
HBTU 0-(1H-benzotriazol-1-yl)-1,1,3,3-tetramethyluronium hexafluorophosphate
HEK human embryonic kidney
HEPES (4-(2-hydroxyethyl)-1-piperazineethane sulfonic acid
HPLC high performance liquid chromatography
mCPBA meta-chloroperoxybenzoic acid
MeCN acetonitrile
MeOH methanol
MHz megahertz
min minutes
MS mass spectrometry
NMR nuclear magnetic resonance
PIPES piperazine-N,N'-bis(2-ethanesulfonic acid)
PyBrOP bromo-tris-pyrrolidinophosphonium hexafluorophosphate
RP reverse-phase
$R_t$ retention time
SPhos 2-dicyclohexylphosphino-2',6'-dimethoxybiphenyl
TEA or $Et_3N$ triethylamine
TFA trifluoroacetic acid
THF tetrahydrofuran
TLC thin layer chromatography
TMS tetramethylsilane
XPhos 2-dicyclohexylphosphino-2',4',6'-triisopropylbiphenyl Scheme A illustrates a route for the synthesis of compounds of Formula (I)-A, wherein Z is a benzo-fused heterocyclyl as defined herein.

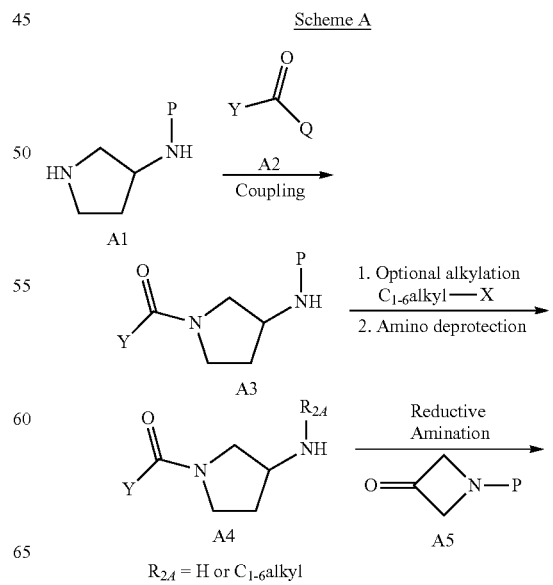

Scheme A

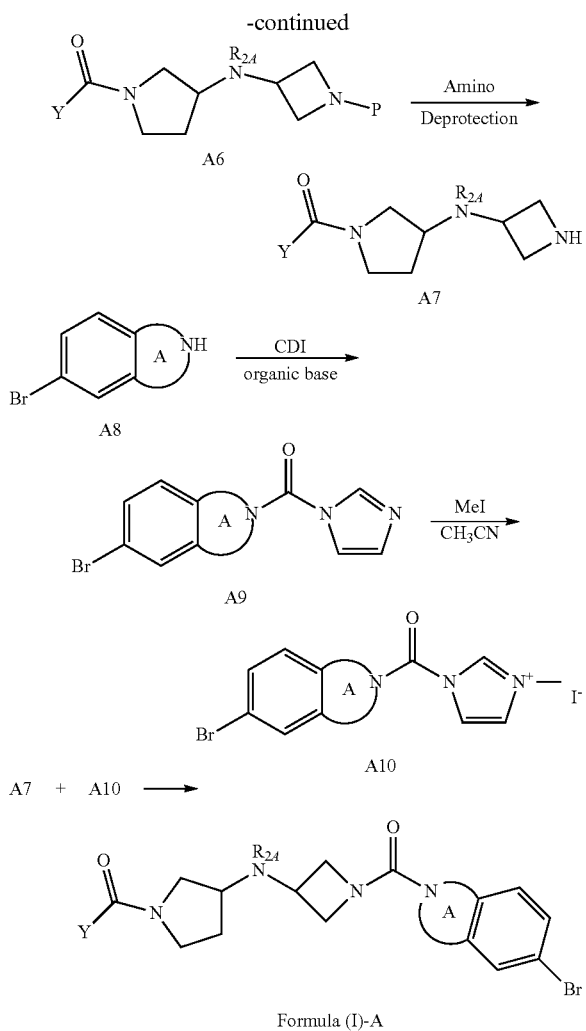

A compound of formula A1 (wherein P is a conventional amino protecting group such as, Boc, Fmoc, Cbz, and the like) is either commercially available or may be prepared by known methods described in the scientific literature. The compound of formula A1 may be treated with a carboxylic acid of formula A2 wherein Q is hydroxy, in the presence of an appropriate coupling agent such as, HATU, DCC, EDC, HBTU, PyBrOP, and the like; and optionally in the presence of a base such as, DIPEA, to afford a compound of Formula A3. Similarly, an acid chloride of formula A2 wherein Q is chloro may be used to effect the acylation of a compound of formula A1. In such case a non-nucleophilic base such as, pyridine, may be added to afford a compound of Formula A3. At this stage, a compound of formula A4 may be alkylated with a compound of formula $C_{1-6}$alkyl-X (wherein X is bromo, chloro, iodo, or triflate), followed by removal of the amino protecting group (P) by conventional methods to afford a compound of formula A4. A compound of formula A4 may undergo a reductive amination with a compound of formula A5 (wherein P is a conventional amino protecting group such as, Boc, Fmoc, Cbz, and the like) in the presence of a hydride source such as, sodium triacetoxyborohydride to afford a compound of formula A6. Removal of amino protecting group P using conventional methods affords a compound of formula A7.

A compound of formula A8, wherein ring A is a 5- to 6-membered heterocycyl containing at least one nitrogen atom, is either commercially available or may be prepared by known methods described in the scientific literature. The compound of formula A8 may be treated with CDI in the presence of an organic base such as triethylamine to afford a compound of formula A9. Treatment with methyl iodide in an anhydrous organic solvent provides a compound of formula A10. The compound of formula A7 may be coupled with a compound of formula A10 in the presence of an organic amine such as triethylamine in an organic solvent such as dichloromethane to afford a compound of Formula (I)-A.

Scheme B illustrates a route for the synthesis of compounds of Formula (I)-B, wherein Z is a benzo-fused heterocyclyl substituted with a phenyl substituent.

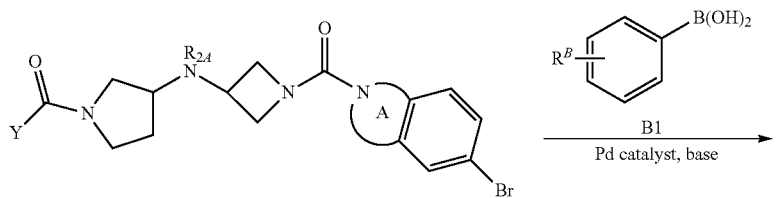

Formula (I)-A

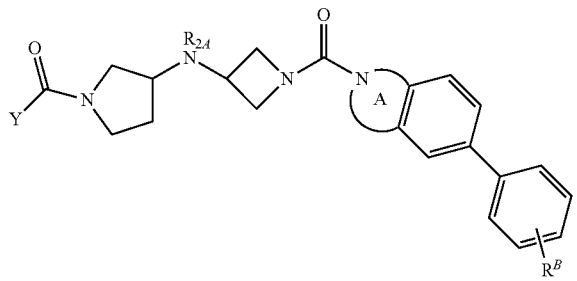

Formula (I)-B

A compound of Formula (I)-A may be treated with a phenylboronic acid of formula B1, wherein $R^B$ is selected from the group consisting of hydrogen, bromo, chloro, fluoro, iodo, $C_{1-4}$alkyl, $C_{2-4}$alkenyl, $C_{1-4}$alkoxy, trifluoromethyl, and trifluoromethoxy, in the presence of a palladium catalyst and appropriate ligands, and in the presence of an inorganic base such as sodium carbonate and the like, to afford a compound of Formula (I)-B.

Scheme C illustrates a route for the synthesis of compounds of Formula (I)-C.

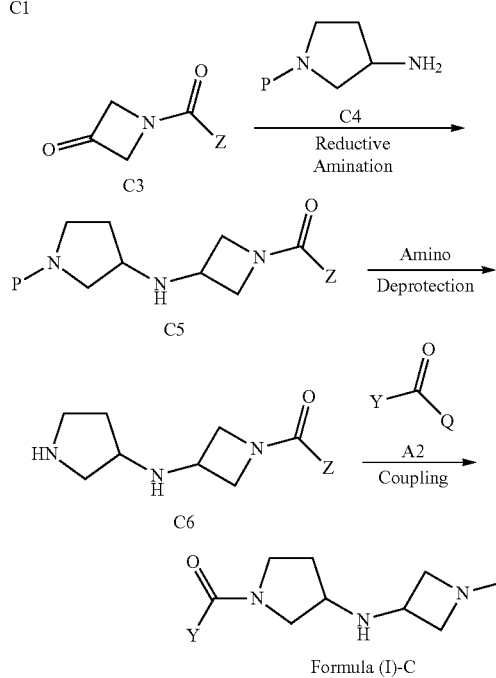

Formula (I)-C

A compound of formula C1 is either commercially available or may be prepared by known methods described in the scientific literature. The compound of formula C2 may be treated with a carboxylic acid of formula C1 wherein Q is hydroxy, in the presence of an appropriate coupling agent such as, HATU, DCC, EDC, HBTU, PyBrOP, and the like; and optionally in the presence of a base such as, DIPEA, to afford a compound of formula C3. Similarly, an acid chloride of formula C1 wherein Q is chloro may be used to effect the acylation of a compound of formula C2. In such case a non-nucleophilic base such as, pyridine or triethylamine, may be added to afford a compound of formula C3. A compound of formula C3 may undergo a reductive amination with a compound of formula C4 (wherein P is a conventional amino protecting group such as, Boc, Fmoc, Cbz, and the like) in the presence of a hydride source such as, sodium triacetoxyborohydride to afford a compound of formula C5. Removal of amino protecting group P using conventional methods affords a compound of formula C6. Coupling with a Y-substituted reagent of formula A2 using the methods described in Scheme A affords the desired compound of Formula (I)-C.

Scheme D illustrates an alternate route for the synthesis of compounds of Formula (I)-C.

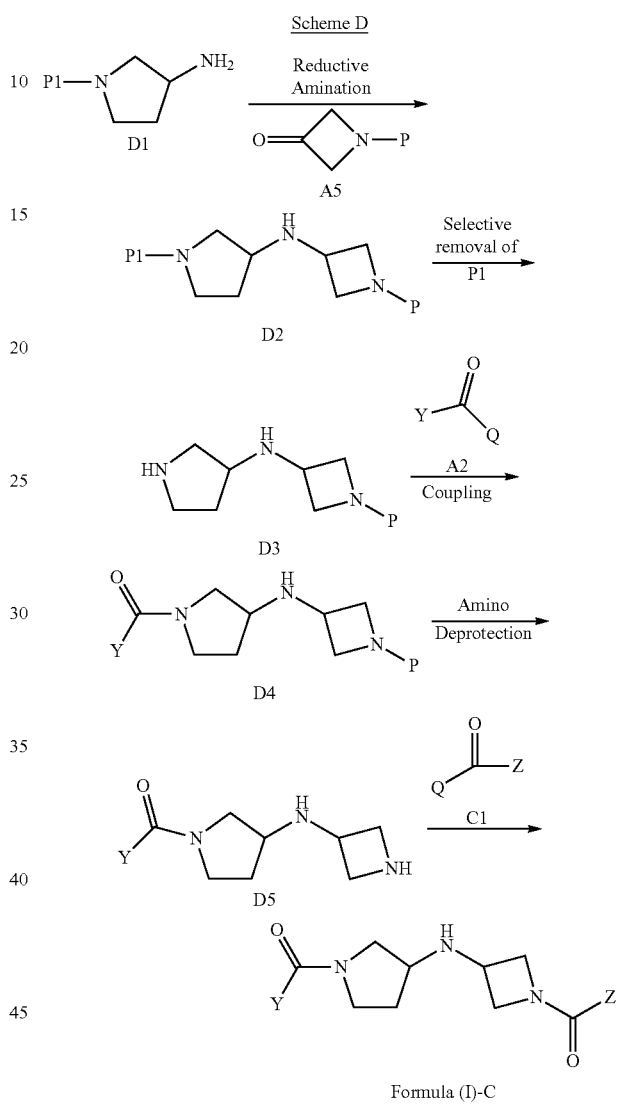

Formula (I)-C

A compound of formula D1 (wherein P1 is a conventional amino protecting group) is either commercially available or may be prepared by known methods described in the scientific literature. A compound of formula D1 may undergo a reductive amination with a compound of formula A5, as described in Scheme A, to afford a compound of formula D2. Selective removal of amino protecting group P1 using conventional methods affords a compound of formula D3. Coupling with a Y-substituted reagent of formula A2 using the methods described in Scheme A affords the desired compound of formula D4. Removal of amino protecting group P using conventional methods affords a compound of formula D5. Coupling with a compound of formula C1 affords a compound of Formula (I)-C.

Scheme E illustrates a route for the synthesis of compounds of Formula (I)-E, wherein $R_2$ is hydroxy.

Scheme E

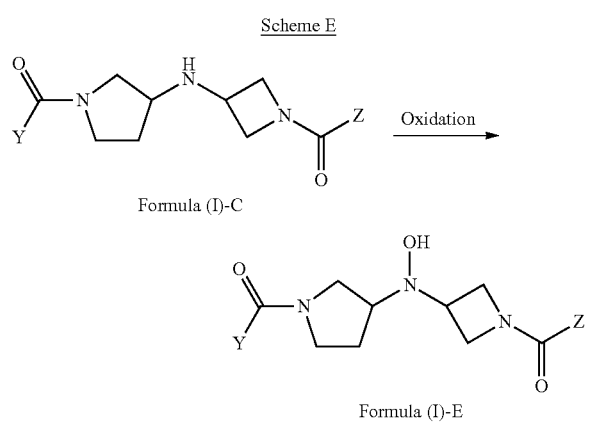

A compound of Formula (I)-C may be treated with an oxidizing agent such as mCPBA, 3,3-dimethyldioxirane, or sodium tungstate/$H_2O_2$ to afford a compound of Formula (I)-E. One of skill in the art will recognize that some Z-substituents may have functional groups sensitive to oxidation conditions. Such functional groups may require the introduction of an appropriate protecting group prior to the oxidation step, and subsequent removal of the protecting group after oxidation.

Scheme F illustrates a route for the synthesis of compounds of Formula (I), wherein Z is a heteroaryl such as benzothienyl, and Z is substituted with $C_{1-4}$alkyl, $C_{2-4}$alkenyl, or $C_{3-6}$cycloalkyl.

Scheme F

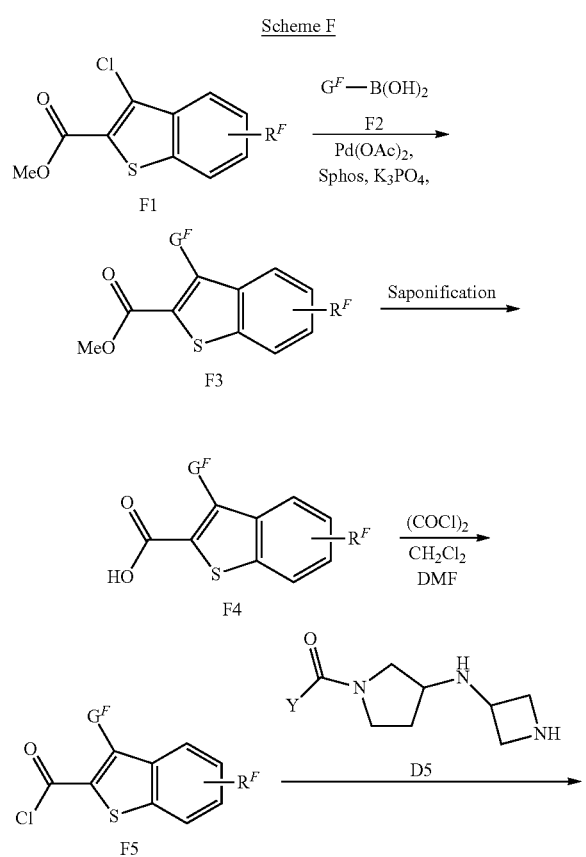

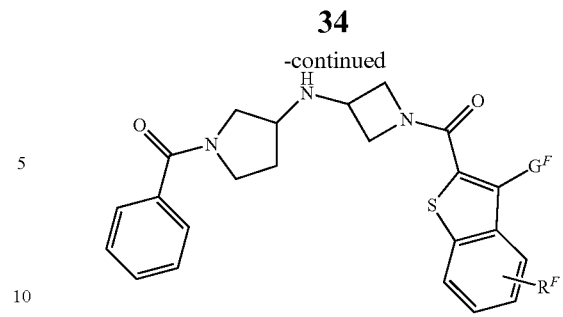

$G^F = C_{1-4}$alkyl, $C_{2-4}$alkenyl, or $C_{3-6}$cycloalkyl

A compound of formula F1 (wherein $R^F$ is chloro, fluoro, $C_{1-4}$alkyl, $C_{1-4}$alkoxy, trifluoromethyl, or $R_b$, wherein $R_b$ is thienyl, pyridinyl, pyrimidinyl, or phenyl) is either commercially available or may be prepared by known methods described in the scientific literature. A compound of formula F1 may be treated with a boronic acid of formula F2 in the presence of a palladium catalyst and appropriate ligands, and in the presence of an inorganic base such as potassium phosphate, to afford a compound of formula F3. Saponification in the presence of hydroxide anion affords a compound of formula F4. Treatment of a compound of formula F4 with oxalyl chloride in the presence of DMF in an organic solvent such as dichloromethane affords the corresponding acid chloride of formula F5. Coupling with a compound of formula D5 in the presence of a non-nucleophilic organic base such as triethylamine, pyridine, or the like, affords a compound of Formula (I)-F.

Scheme G illustrates a route for the synthesis of compounds of Formula (I)-G, wherein Z is a heteroaryl such as, indolyl, and Z is substituted at the indolyl nitrogen atom with $R_b$. Substituent $R_b$ is an optionally substituted thienyl, pyridinyl, pyrimidinyl, or phenyl ring.

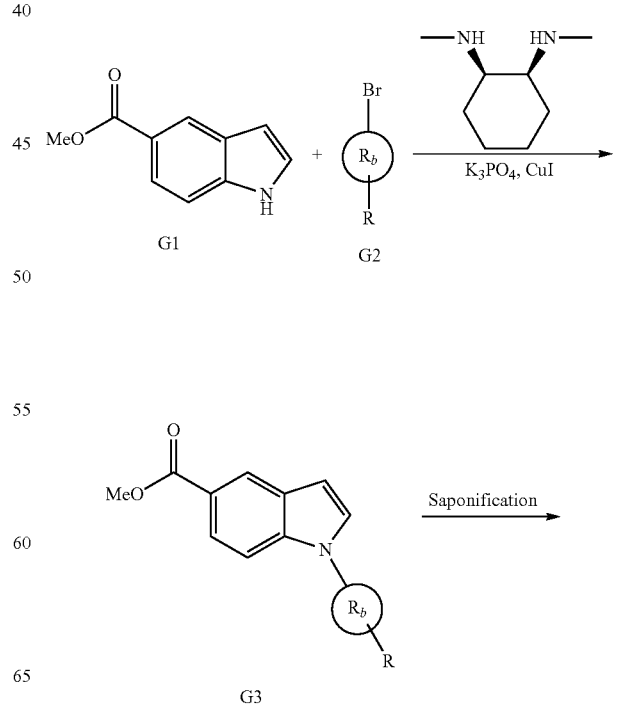

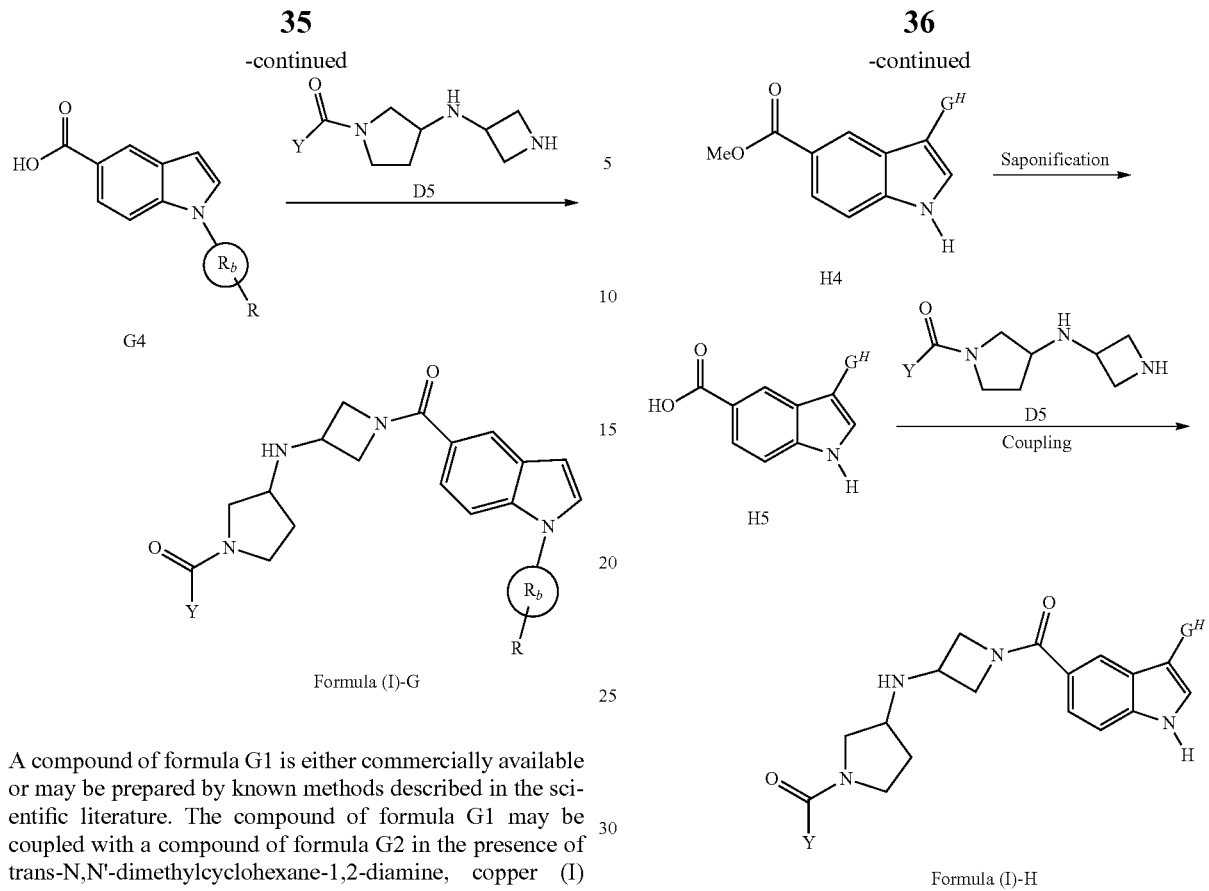

A compound of formula G1 is either commercially available or may be prepared by known methods described in the scientific literature. The compound of formula G1 may be coupled with a compound of formula G2 in the presence of trans-N,N'-dimethylcyclohexane-1,2-diamine, copper (I) iodide, and an inorganic base such as potassium phosphate to afford a compound of formula G3. Saponification affords a carboxylic acid of formula G4. Coupling with a compound of formula D5 in the presence of an appropriate coupling agent such as, HATU, DCC, EDC, HBTU, PyBrOP, and the like; and optionally in the presence of a base such as, DIPEA, affords a compound of Formula (I)-G.

Scheme H illustrates a route for the synthesis of compounds of Formula (I)-H, wherein Z is a heteroaryl such as indolyl, and Z is substituted at a carbon atom with $G^H$, wherein $G^H$ is $C_{1-4}$alkyl or an unsubstituted or substituted phenyl ring as defined by $R_b$.

Scheme H

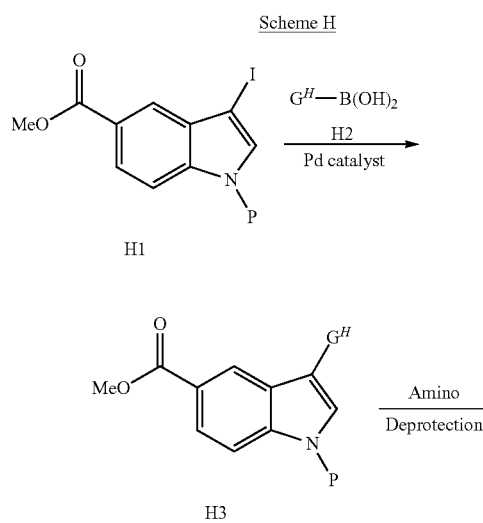

A compound of formula H1 is either commercially available or may be prepared by known methods described in the scientific literature. The compound of formula H1 may be coupled with a boronic acid of formula H2 in the presence of a palladium catalyst and appropriate ligands, and in the presence of an inorganic base such as potassium phosphate, to afford a compound of formula H3. The amino protecting group P may be removed by conventional methods known to one of skill in the art to afford a compound of formula H4. Saponification in the presence of hydroxide ion affords a carboxylic acid of formula H5. A compound of formula H5 may be coupled with a compound of formula D5 as previously described in Scheme G to afford a compound of Formula (I)-H.

Scheme I illustrates a route for the synthesis of compounds of Formula (I)-I, wherein Z is a heteroaryl such as indolyl, and Z is substituted at a carbon atom with $R_b$, wherein $R_b$ is an optionally substituted phenylmethyl as defined herein.

Scheme I

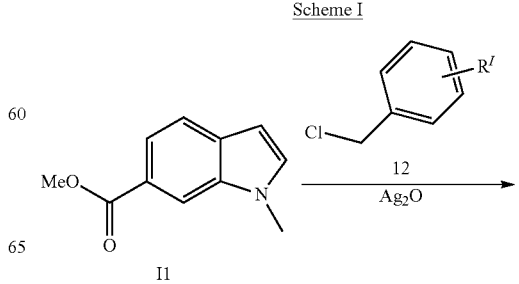

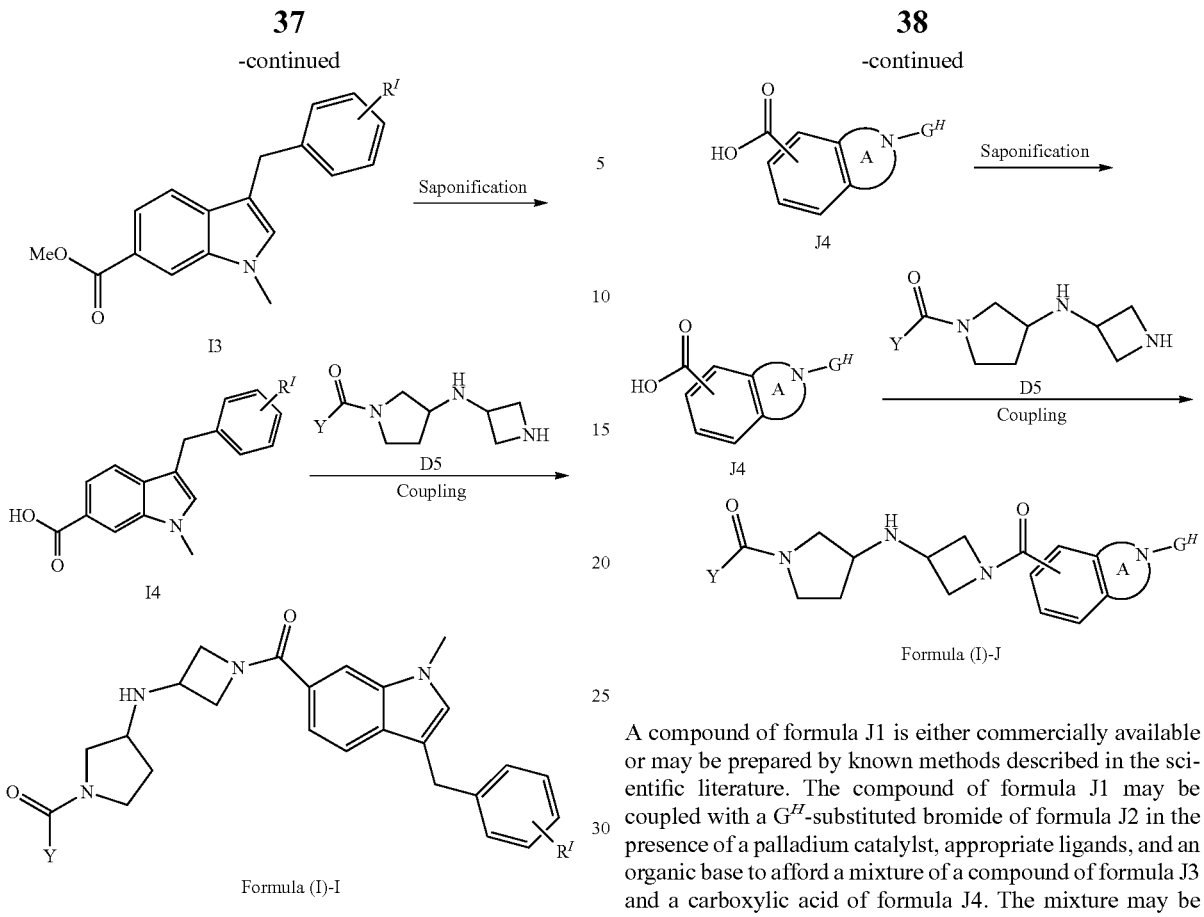

A compound of formula I1 is either commercially available or may be prepared by known methods described in the scientific literature. The compound of formula I1 may be coupled with a benzyl chloride of formula I2 (wherein $R^I$ is defined as trifluoromethyl, trifluoromethoxy, $C_{1-4}$alkyl, chloro, and fluoro) in the presence of a silver oxide, in an organic solvent such as dioxane, to afford a compound of formula I3. Saponification in the presence of hydroxide ion affords a carboxylic acid of formula I4, which may be coupled with a compound of formula D5 as previously described in Scheme G to afford a compound of Formula (I)-I.

Scheme J illustrates a route for the synthesis of compounds of Formula (I)-J, wherein Z is a benzo-fused heterocyclyl attached through a benzo carbon atom.

A compound of formula J1 is either commercially available or may be prepared by known methods described in the scientific literature. The compound of formula J1 may be coupled with a $G^H$-substituted bromide of formula J2 in the presence of a palladium catalylst, appropriate ligands, and an organic base to afford a mixture of a compound of formula J3 and a carboxylic acid of formula J4. The mixture may be subjected to saponification conditions to afford the compound of formula J4, which, subsequently, may be coupled with a compound of formula D5 to afford a compound of Formula (I)-J.

Example 1

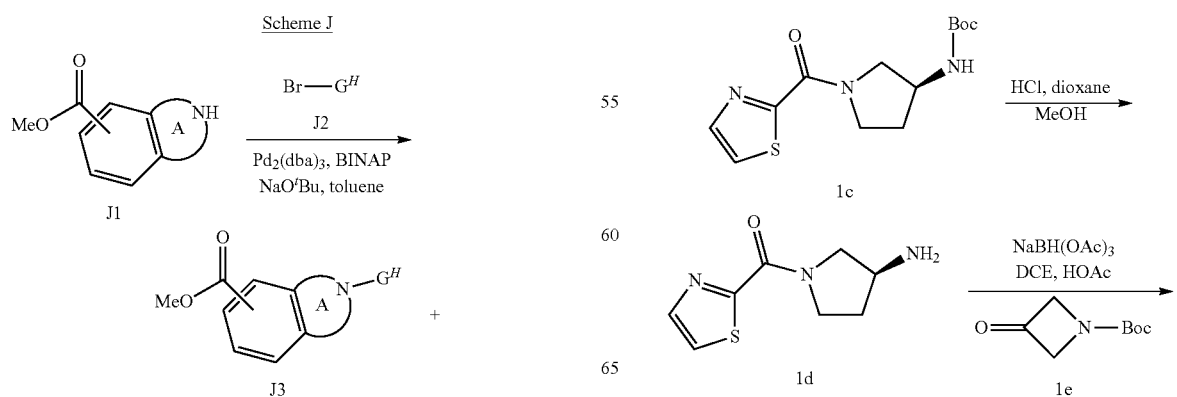

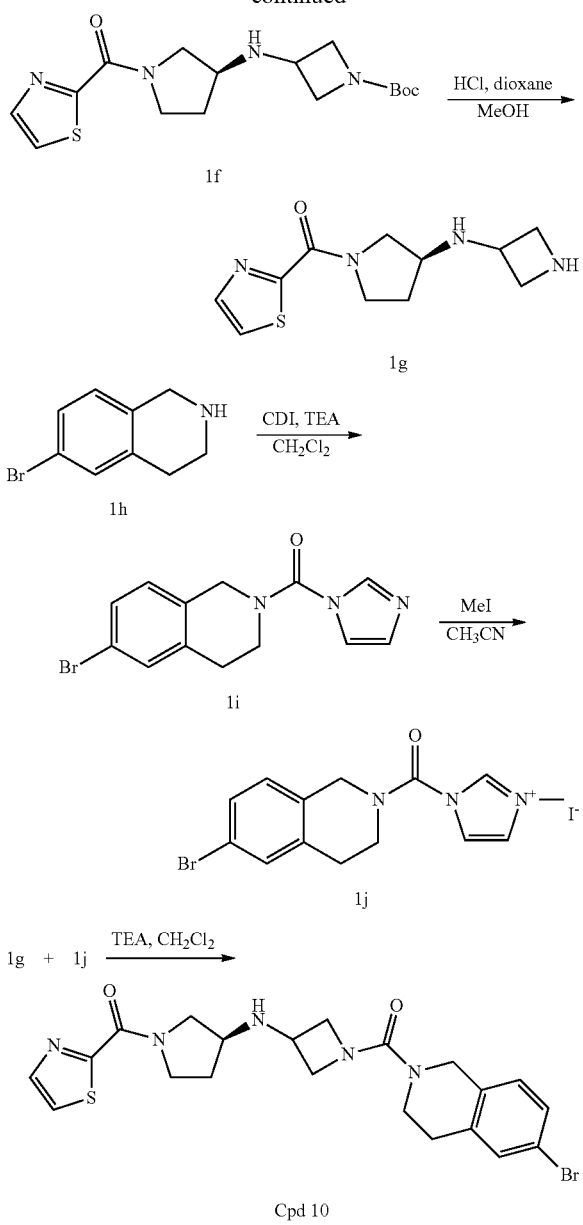

B. (S)-(3-Aminopyrrolidin-1-yl)(thiazol-2-yl)methanone, 1d

To a solution of compound 1c (5.5 g, 18.52 mmol) in MeOH (30 mL) was added an HCl solution in dioxane (4M, 50 mL) at room temperature. The mixture was stirred at room temperature for 4 h. The solvent was removed by evaporation. Ether (100 mL) was added to the residue. The resultant white solid was collected by filtration, washed with hexanes, and dried under reduced pressure. The crude compound 1d was used in the next reaction without further purification. MS m/z (M+H$^+$) 198.

C. (S)-tert-Butyl 3-((1-(thiazole-2-carbonyl)pyrrolidin-3-yl)amino)azetidine-1-carboxylate, 1f To a solution of compound 1d (diHCl salt, 2.7 g, 10 mmol) and N-Boc azetidinone 1e (2.4 g, 14 mmol) in 1,2-DCE (50 mL) was added slowly Et$_3$N (20 mmol) followed by acetic acid (3.5 mL). To this mixture was added Na(OAc)$_3$BH (3.39 g, 16 mmol). The reaction was stirred at room temperature for 5 h. To the reaction mixture was added aq. NaHCO$_3$, and the resultant mixture was extracted with CH$_2$Cl$_2$. The organic layer was dried over Na$_2$SO$_4$ and concentrated. Purification by flash column chromatography (silica gel, 80% EtOAc/heptane) gave compound 1f (2.96 g). $^1$H NMR (300 MHz, CDCl$_3$): δ 7.91 (m, 1H), 7.53 (m, 1H), 4.28 (m, 1H), 4.22-4.11 (m, 2.5H), 3.91 (m, 0.5H), 3.83 (m, 1H), 3.73-3.60 (m, 3.5H), 3.49 (m, 0.5H), 3.41 (m, 1H), 2.11 (m, 1H), 1.89-1.73 (m, 1H), 1.44 (s, 9H).

D. (S)-(3-(Azetidin-3-ylamino)pyrrolidin-1-yl)(thiazol-2-yl)methanone, 1g

To a solution of compound 1f (3 g, 8.52 mmol) in MeOH (10 mL) was added an HCl solution in dioxane (4M, 20 mL) at room temperature. The mixture was stirred at room temperature for 4 h. The solvent was removed by evaporation. Ether (50 mL) was added to the residue. The white solid was collected by filtration, washed with hexanes, and dried under vacuum. The crude compound 1g was used in the next reaction without further purification. MS m/z (M+H$^+$) 253.

E. (6-bromo-3,4-dihydroisoquinolin-2(1H)-yl)(1H-imidazol-1-yl)methanone, 1i

To a suspension of compound 1h (HCl salt, 1.03 g, 4.16 mmol) and CDI (0.74 g, 4.57 mmol) in CH$_2$Cl$_2$ (8 mL) was added Et$_3$N (0.665 mL, 4.78 mmol). The reaction was stirred at room temperature overnight. To the reaction mixture was added water, and the resultant mixture was extracted with CH$_2$Cl$_2$. The organic layer was dried over Na$_2$SO$_4$ and concentrated. The residue was triturated from EtOAc/hexanes to afford compound 1i (1.03 g). The crude compound 1i was used in the next reaction without further purification. MS m/z (M+H$^+$) 306. $^1$H NMR (300 MHz, CDCl$_3$): δ 7.93 (s, 1H), 7.36 (m, 2H), 7.27 (m, 1H), 7.14 (m, 1H), 6.98 (d, 1H, J=6.6 Hz), 4.69 (s, 2H), 3.81 (m, 2H), 2.99 (m, 2H).

F. 1-(6-Bromo-1,2,3,4-tetrahydroisoquinoline-2-carbonyl)-3-methyl-1H-imidazol-3-ium iodide, 1j To a solution of compound 1i (1.03 g, 3.37 mmol) in CH$_3$CN (7 mL) was added MeI (0.84 mL, 13.46 mmol). The reaction was stirred at room temperature overnight. The reaction was concentrated and the residue was washed with Et$_2$O/hexanes to afford compound 1j (1.48 g). $^1$H NMR (300 MHz, A. (S)-tert-Butyl (1-(thiazole-2-carbonyl)pyrrolidin-3-yl)carbamate, 1c To a solution of compound 1a (4.47 g, 24 mmol), 2-thiazole carboxylic acid 1b (2.58 g, 20 mmol), and Et$_3$N (1.4 mL, 100 mmol) in CH$_2$Cl$_2$ (50 mL) was added HATU (9.89 g, 26 mmol). The reaction mixture was stirred at room temperature for 18 h. The resultant mixture was diluted with CH$_2$Cl$_2$ and washed with aq. NaHCO$_3$. The organic phase was dried over Na$_2$SO$_4$, filtered, and concentrated under reduced pressure. Purification of the residue by flash column chromatography (silica gel, 50% EtOAc/hexanes) gave compound 1c (5.5 g). $^1$H NMR (300 MHz, CDCl$_3$): δ 7.89 (m, 1H), 7.52 (m, 1H), 4.65 (m, 1H), 4.39-4.22 (m, 2.5H), 4.03 (m, 0.5H), 3.91 (m, 0.5H), 3.81-3.74 (m, 1H), 3.61 (m, 0.5H), 2.28-2.19 (m, 1H), 2.05-1.86 (m, 1H), 1.44 (s, 9H).

CDCl₃): δ 10.44 (s, br, 1H), 7.65 (s, 1H), 7.31 (m, 3H), 7.23 (m, 1H), 5.02 (m, 2H), 4.31 (s, 3H), 3.98 (m, 2H), 3.04 (m, 2H).

G. (S)-(3-((1-(6-Bromo-1,2,3,4-tetrahydroisoquinoline-2-carbonyl)azetidin-3-yl)amino)pyrrolidin-1-yl)(thiazol-2-yl)methanone, Cpd 10

To a suspension of compound 1g (di-HCl salt, 105 mg, 0.327 mmol) and compound 1j (162 mg, 0.36 mmol) in CH₂Cl₂ (2 mL) was added Et₃N (0.09 mL, 0.65 mmol). The reaction was stirred room temperature overnight. To the reaction mixture was added water, and the resultant mixture was extracted with CH₂Cl₂. The organic layer was dried over Na₂SO₄ and concentrated. Purification by flash column chromatography (silica gel, 5% MeOH/EtOAc+0.5% TEA) gave compound 10 (136 m g). MS m/z (M+H⁺) 490, 492. ¹H NMR (300 MHz, CDCl₃): δ 7.90 (m, 1H), 7.54 (m, 1H), 7.31-7.28 (m, 2H), 6.96 (m, 1H), 4.42 (d, J=3 Hz, 2H), 4.31-4.16 (m, 3H), 3.96-3.68 (m, 4H), 3.53-3.40 (m, 3H), 2.83 (m, 2H), 2.12 (m, 1H), 1.84 (m, 1H).

Following the procedure described above for Example 1 and substituting the appropriate reagents, starting materials and purification methods known to those skilled in the art, the following compounds of the present invention were prepared.

| Cpd | Cpd Name and Data |
|---|---|
| 12 | (3S)-N-{1-[(5-Bromo-1,3-dihydro-2H-isoindol-2-yl)carbonyl]azetidin-3-yl}-1-(1,3-thiazol-2-ylcarbonyl)pyrrolidin-3-amine MS m/z (M + H⁺) 476, 478 |

Example 2

A. (S)-(3-((1-(6-Phenyl-1,2,3,4-tetrahydroisoquinoline-2-carbonyl)azetidin-3-yl)amino)pyrrolidin-1-yl)(thiazol-2-yl)methanone, Cpd 11

A mixture of compound 10 (82 mg, 0.167 mmol), phenyl boronic acid 2a (35 mg, 0.284 mmol), Pd(dppf)Cl₂.CH₂Cl₂ (14 mg, 0.0167 mmol) and Na₂CO₃ (35 mg, 0.334 mmol) in dioxane (0.8 mL) and water (0.2 mL) in a capped vial was heated at 80° C. for 6 h. The reaction mixture was diluted with EtOAc and water. The organic layer was concentrated and purified by chromatography (silica gel, 5% MeOH/EtOAc) to give compound 11 (70 mg). MS m/z (M+H⁺) 488.

Following the procedure described above for Example 2 and substituting the appropriate reagents, starting materials and purification methods known to those skilled in the art, the following compounds of the present invention were prepared.

| Cpd | Cpd Name and Data |
|---|---|
| 13 | (3S)-N-{1-[(5-Phenyl-1,3-dihydro-2H-isoindol-2-yl)carbonyl]azetidin-3-yl}-1-(1,3-thiazol-2-ylcarbonyl)pyrrolidin-3-amine MS m/z (M + H⁺) 474 |

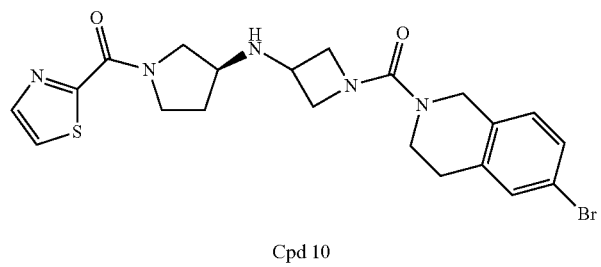

Cpd 10

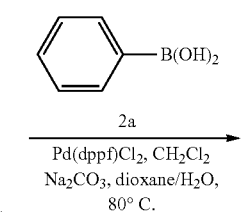

2a

Pd(dppf)Cl₂, CH₂Cl₂
Na₂CO₃, dioxane/H₂O,
80° C.

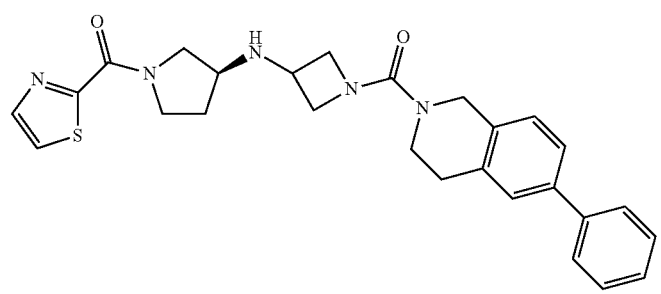

Cpd 11

Example 3

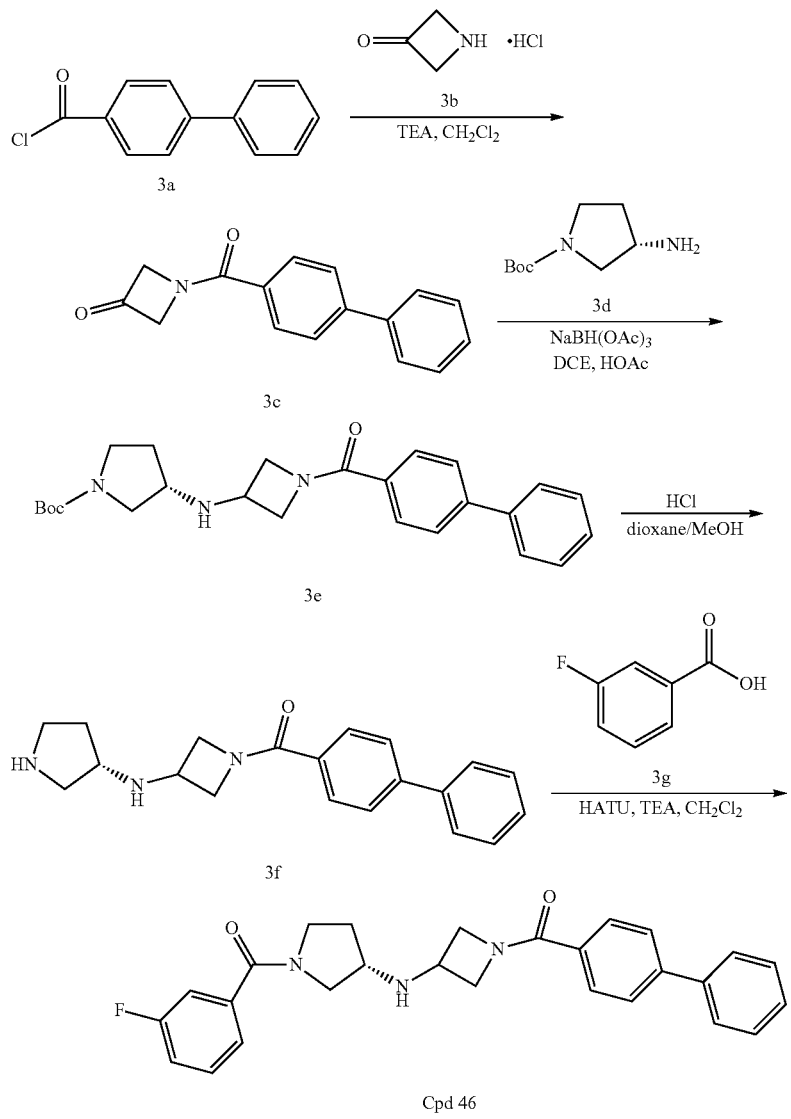

A. 1-([1,1'-Biphenyl]-4-carbonyl)azetidin-3-one, 3c

To a suspension of compound 3b (HCl salt, 0.31 g, 2.88 mmol) in $CH_2Cl_2$ (10 mL) was dropwise added $Et_3N$ (0.87 g, 8.65 mmol) at 0° C. under argon gas followed by a solution of compound 3a (0.685 g, 3.17 mmol) in $CH_2Cl_2$ (3 mL). The reaction was stirred at 0° C. for 1 h and then quenched with water. The aqueous layer was extracted with $CH_2Cl_2$ and the combined organic extracts were concentrated and purified by column chromatography (silica gel, 35% EtOAc/hexanes) to give compound 3c as a white solid (0.6 g). MS m/z (M+H$^+$) 252.

B. (S)-tert-Butyl 3-((1-([1,1'-biphenyl]-4-carbonyl)azetidin-3-yl)amino)pyrrolidine-1-carboxylate, 3e To a solution of compound 3c (0.223 g, 0.89 mmol) and compound 3d (0.25 g, 1.33 mmol) in 1,2-DCE (4 mL) was added acetic acid (0.4 mL). To this mixture was added $Na(OAc)_3BH$ (0.244 g, 1.15 mmol). The reaction was stirred at room temperature for 4 h. To the reaction mixture was added aq. $NaHCO_3$, and the resultant mixture was extracted with $CH_2Cl_2$. The organic layer was dried over $Na_2SO_4$ and concentrated. Purification by flash column chromatography (silica gel, 65% EtOAc/heptane) gave compound 3e (0.3 g). MS m/z (M+H$^+$) 422.2; (M+Na$^+$) 444. $^1$H NMR (300 MHz, $CDCl_3$) δ: 7.70 (m, 2H), 7.62-7.59 (m, 4H), 7.46 (m, 2H), 7.37 (m, 1H), 4.48 (m, 2H), 4.15-4.03 (m, 2H), 3.77 (m, 1H), 3.53-3.31 (m, 4H), 3.08 (m, 1H), 2.04 (m, 2H), 1.46 (s, 9H).

C. (S)-[1,1'-Biphenyl]-4-yl(3-(pyrrolidin-3-ylamino)azetidin-1-yl)methanone, 3f To a solution of compound 3e (2.5 g, 5.92 mmol) in MeOH (7 mL) was added an HCl solution in dioxane (4M, 12 mL) at room temperature. The mixture was stirred at room temperature for 4 h. The solvent was removed by evaporation. Ether (30 mL) was added to the residue. The off-white solid was collected by filtration, washed with hexanes, and dried under vacuum. The crude compound 3f was used in the next reaction without further purification. MS m/z (M+H$^+$) 322.

D. (3S)—N-[1-(Biphenyl-4-ylcarbonyl)azetidin-3-yl]-1-[(3-fluorophenyl)carbonyl]pyrrolidin-3-amine, Cpd 46

To a solution of compound 3f (di-HCl salt, 40 mg, 0.1 mmol), compound 3g (17 mg, 0.12 mmol), and Et$_3$N (0.07 mL, 0.5 mmol) in CH$_2$Cl$_2$ (1 mL) was added HATU (61 mg, 0.16 mmol). The reaction mixture was stirred at room temperature for 18 h. The resultant mixture was diluted with CH$_2$Cl$_2$ and washed with aq. NaHCO$_3$. The organic phase was dried over Na$_2$SO$_4$, filtered, and concentrated under reduced pressure. Purification of the residue by flash column chromatography (silica gel, 50% EtOAc/hexanes) gave compound 46 (41 mg). MS m/z (M+H$^+$) 444.5.

Following the procedure described above for Example 3 and substituting the appropriate reagents, starting materials and purification methods known to those skilled in the art, the following compounds of the present invention were prepared.

| Cpd | Cpd Name and Data |
|---|---|
| 1 | (3S)-N-[1-(Biphenyl-4-ylcarbonyl)azetidin-3-yl]-1-(1,3-thiazol-2-ylcarbonyl)pyrrolidin-3-amine<br>MS m/z (M + H$^+$) 433.5 |
| 2 | (3S)-N-[1-(Biphenyl-4-ylcarbonyl)azetidin-3-yl]-1-(phenylcarbonyl)pyrrolidin-3-amine<br>MS m/z (M + H$^+$) 426 |
| 3 | (3S)-N-{1-[(4-Benzylphenyl)carbonyl]azetidin-3-yl}-1-(1,3-thiazol-2-ylcarbonyl)pyrrolidin-3-amine<br>MS m/z (M + H$^+$) 447 |
| 4 | (3S)-N-{1-[(4-Benzylphenyl)carbonyl]azetidin-3-yl}-1-(phenylcarbonyl)pyrrolidin-3-amine<br>MS m/z (M + H$^+$) 440 |
| 5 | (3S)-N-{1-[(4-Benzylphenyl)carbonyl]azetidin-3-yl}-1-(thiophen-3-ylcarbonyl)pyrrolidin-3-amine<br>MS m/z (M + H$^+$) 446 |
| 6 | (3R)-N-{1-[(4-Benzylphenyl)carbonyl]azetidin-3-yl}-1-(1,3-thiazol-2-ylcarbonyl)pyrrolidin-3-amine<br>MS m/z (M + H$^+$) 447 |
| 7 | (3R)-N-{1-[(4-Benzylphenyl)carbonyl]azetidin-3-yl}-1-(phenylcarbonyl)pyrrolidin-3-amine<br>MS m/z (M + H$^+$) 440 |
| 45 | (3S)-N-[1-(Biphenyl-4-ylcarbonyl)azetidin-3-yl]-1-[(4-fluorophenyl)carbonyl]pyrrolidin-3-amine<br>MS m/z (M + H$^+$) 444.5 |
| 47 | (3S)-1-(1-Benzofuran-2-ylcarbonyl)-N-[1-(biphenyl-4-ylcarbonyl)azetidin-3-yl]pyrrolidin-3-amine<br>MS m/z (M + H$^+$) 466 |
| 48 | (3S)-1-(1-Benzothiophen-2-ylcarbonyl)-N-[1-(biphenyl-4-ylcarbonyl)azetidin-3-yl]pyrrolidin-3-amine<br>MS m/z (M + H$^+$) 482 |
| 71 | trans-4-Methoxy-1-(phenylcarbonyl)-N-(1-{[3'-(trifluoromethyl)biphenyl-4-yl]carbonyl}azetidin-3-yl)pyrrolidin-3-amine<br>MS m/z (M + H$^+$) 524 |
| 72 | trans-1-(Phenylcarbonyl)-4-[(1-{[3'-(trifluoromethyl)biphenyl-4-yl]carbonyl}azetidin-3-yl)amino]pyrrolidin-3-ol<br>MS m/z (M + H$^+$) 510 |
| 78 | trans-4-{[1-(Biphenyl-4-ylcarbonyl)azetidin-3-yl]amino}-1-(phenylcarbonyl)pyrrolidin-3-ol<br>MS m/z (M + H$^+$) 442 |

Example 4

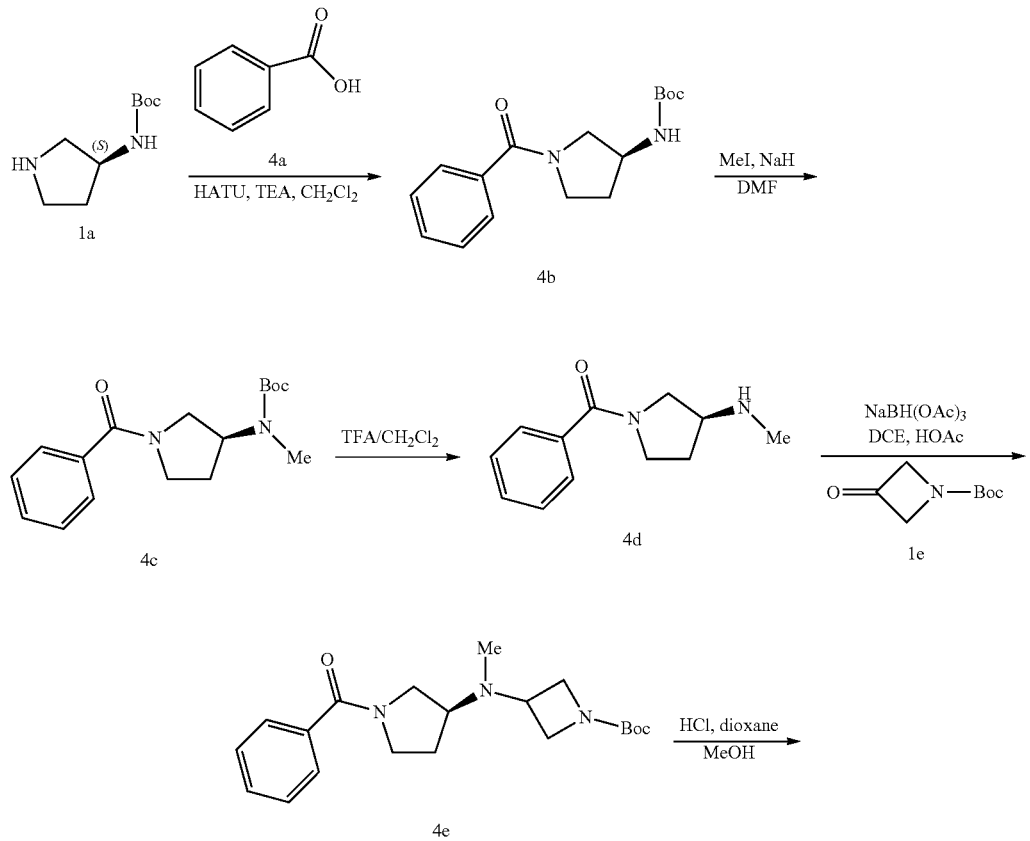

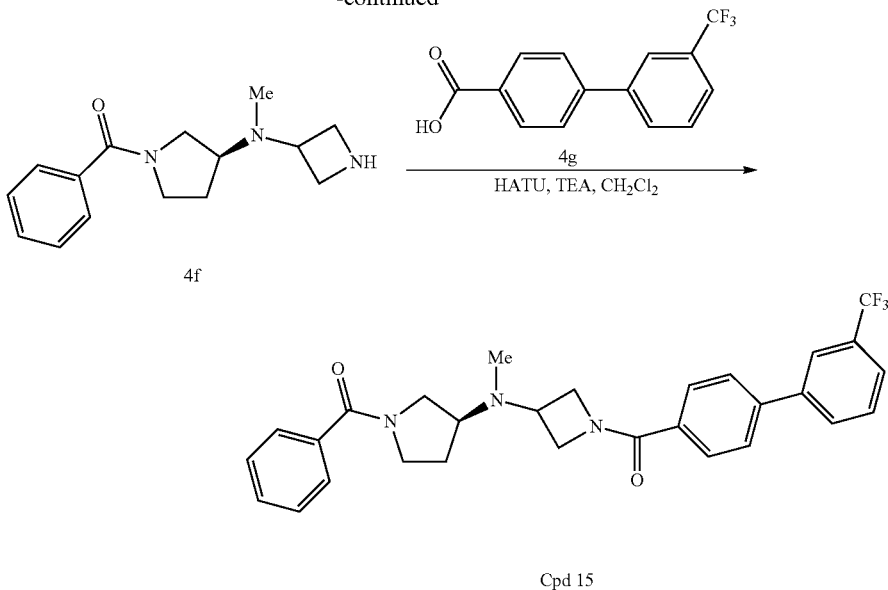

Cpd 15

A. (S)-tert-Butyl (1-benzoylpyrrolidin-3-yl)carbamate, 4b

To a solution of compound 1a (2.53 g, 13.58 mmol), benzoic acid 4a (1.66 g, 13.58 mmol), and Et$_3$N (3.78 mL, 27.2 mmol) in CH$_2$Cl$_2$ (50 mL) was added HATU (6.72 g, 17.65 mmol). The reaction mixture was stirred at room temperature for 18 h. The resultant mixture was diluted with CH$_2$Cl$_2$ and washed with aq. NaHCO$_3$. The organic phase was dried over Na$_2$SO$_4$, filtered, and concentrated under reduced pressure. Purification of the residue by flash column chromatography (silica gel, 50% EtOAc/hexanes) gave compound 4b (3.5 g). MS m/z (M−Boc$^+$) 190.2.

B. (S)-tert-Butyl (1-benzoylpyrrolidin-3-yl)(methyl)carbamate, 4c

To a solution of compound 4b (0.15 g, 0.517 mmol) in DMF (2 mL) was added NaH (60% in mineral, 31 mg, 0.775 mmol) at 0° C. under nitrogen. The reaction was stirred at 0° C. for 30 min and then MeI (0.065 mL, 1.034 mmol) was added. The reaction was allowed to warm to room temperature with continuous stirring for 2 h. To the reaction mixture was added water and EtOAc. The aqueous layer was extracted with EtOAc twice. The organic phase was dried over Na$_2$SO$_4$, filtered, and concentrated under reduced pressure. Purification of the residue by flash column chromatography (silica gel, 35% EtOAc/hexanes) gave compound 4c (0.12 g). MS m/z (M−Boc$^+$) 204.2.

C. (S)-(3-(Methylamino)pyrrolidin-1-yl)(phenyl)methanone, 4d

To a solution of compound 4c (0.12 g, 0.394 mmol) in CH$_2$Cl$_2$ (3 mL) was added trifluoroacetic acid (1 mL) at room temperature. The mixture was stirred at room temperature for 5 h. The solvent was removed by evaporation. Ether (10 mL) was added to the residue. The crude product was collected by filtration, washed with ether, and dried under vacuum. MS m/z (M+H$^+$) 205.2.

D. (S)-tert-Butyl-3-((1-benzoylpyrrolidin-3-yl)(methyl)amino)azetidine-1-carboxylate, 4e To a solution of compound 4d (TFA salt, 124 mg, 0.39 mmol) and compound 1e (94 mg, 0.55 mmol) in 1,2-DCE (2 mL) was added acetic acid (0.1 mL). To this mixture was added Na(OAc)$_3$BH (132 mg, 0.624 mmol). The reaction was stirred at room temperature for 4 h. To the reaction mixture was added aq. NaHCO$_3$, and the resultant mixture was extracted with CH$_2$Cl$_2$. The organic layer was dried over Na$_2$SO$_4$ and concentrated. Purification by flash column chromatography (silica gel, 5% MeOH/EtOAc+0.5% TEA) gave compound 4e (0.11 g). MS m/z (M+H$^+$) 360.5.

E. (S)-(3-(azetidin-3-ylmethyl)amino)pyrrolidin-1-yl)(phenyl)methanone, 4f

To a solution of compound 4e (0.11 g, 0.31 mmol) in MeOH (1 mL) was added HCl solution in dioxane (4M, 1.5 mL) at room temperature. The mixture was stirred at room temperature for 4 h. The solvent was removed by evaporation. Ether (10 mL) was added to the residue. The off-white solid was collected by filtration, washed with hexanes, and dried under vacuum. The crude compound 4f was used in the next reaction without further purification. MS m/z (M+H$^+$) 260.2.

F. (3S)-N-Methyl-1-(phenylcarbonyl)-N-(1-{[3'-(trifluoromethyl)biphenyl-4-yl]carbonyl}azetidin-3-yl)pyrrolidin-3-amine, Cpd 15

To a solution of compound 4f (di-HCl salt, 38 mg, 0.114 mmol), compound 4g (36 mg, 0.137 mmol), and Et$_3$N (0.08 mL, 0.57 mmol) in CH$_2$Cl$_2$ (1 mL) was added HATU (74 mg, 0.194 mmol). The reaction mixture was stirred at room temperature for 18 h. The resultant mixture was diluted with CH$_2$Cl$_2$ and washed with aq. NaHCO$_3$. The organic phase was dried over Na$_2$SO$_4$, filtered, and concentrated under reduced pressure. Purification of the residue by flash column chromatography (silica gel, 5% MeOH/EtOAc+0.5 TEA %) gave compound 15 (36 mg). MS m/z (M+H$^+$) 508.0.

Following the procedure described above for Example 4 and substituting the appropriate reagents, starting materials and purification methods known to those skilled in the art, the following compounds of the present invention were prepared.

| Cpd | Cpd Name and Data |
|---|---|
| 14 | (3S)-N-{1-[(4-Benzylphenyl)carbonyl]azetidin-3-yl}-N-methyl-1-(phenylcarbonyl) pyrrolidin-3-amine<br>MS m/z (M + H⁺) 454.0 |

Example 5

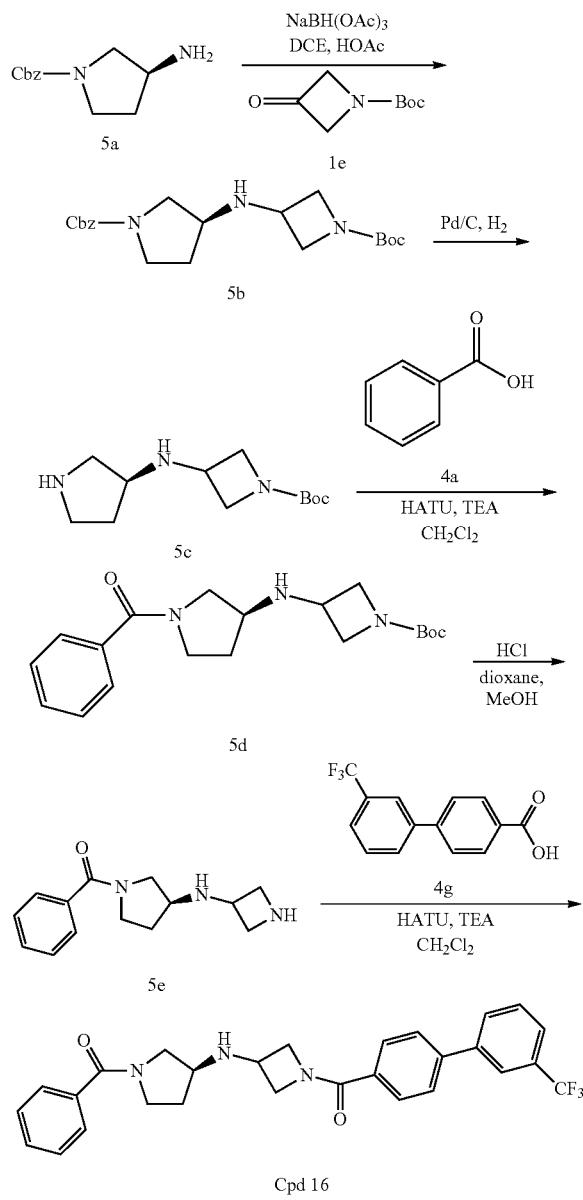

Cpd 16

A. (S)-Benzyl 3-((1-(tert-butoxycarbonyl)azetidin-3-yl)amino)pyrrolidine-1-carboxylate, 5b To a solution of compound 5a (4.25 g, 19.3 mmol) and compound 1e (4.29 g, 25.08 mmol) in DCE (60 mL) was added acetic acid (3 mL). To this mixture was added Na(OAc)$_3$BH (5.73 g, 27 mmol). The reaction was stirred at room temperature for 4 h. To the reaction mixture was added aq. NaHCO$_3$, and the resultant mixture was extracted with CH$_2$Cl$_2$. The organic layer was dried over Na$_2$SO$_4$ and concentrated. Purification by flash column chromatography (silica gel, 2% MeOH/EtOAc+0.5% TEA) gave compound 5b (6.5 g). $^1$H NMR (300 MHz, CDCl$_3$): δ 7.37-7.30 (m, 5H), 5.13 (s, 2H), 4.11 (m, 2H), 3.61 (m, 5H), 3.42 (m, 1H), 3.31 (m, 1H), 3.15 (m, 1H), 2.05 (m, 1H), 1.71 (m, 1H), 1.43 (s, 9H).

B. (S)-tert-Butyl-3-(pyrrolidin-3-ylamino)azetidine-1-carboxylate, 5c

A solution of compound 5b (1.3 g, 3.46 mmol), 10% Pd/C (200 mg) in EtOH (50 mL) was hydrogenated under 40 psi hydrogen pressure in a Parr apparatus for 4.5 h. The reaction was filtered through a pad of diatomaceous earth and the organic solution was concentrated and dried under vacuum to give compound 5c as a thick oil (0.825 g). $^1$H NMR (300 MHz, CDCl$_3$): δ 4.10 (m, 2H), 3.64-3.55 (m, 3H), 3.23 (m, 1H), 3.05 (m, 1H), 2.97-2.85 (m, 2H), 2.68 (m, 1H), 1.97 (m, 1H), 1.51 (m, 1H), 1.43 (s, 9H).

C. (S)-tert-Butyl-3-((1-benzoylpyrrolidin-3-yl)amino)azetidine-1-carboxylate, 5d To a solution of compound 5c (1 g, 4.14 mmol), compound 4a (0.557 g, 4.56 mmol), and Et$_3$N (1.27 mL, 8.28 mmol) in CH$_2$Cl$_2$ (20 mL) was added HATU (2.05 g, 5.38 mmol). The reaction mixture was stirred at room temperature for 18 h. The resultant mixture was diluted with CH$_2$Cl$_2$ and washed with aq. NaHCO$_3$. The organic phase was dried over Na$_2$SO$_4$, filtered, and concentrated under reduced pressure. Purification of the residue by flash column chromatography (silica gel, 5% MeOH/EtOAc+0.5 TEA %) gave compound 5d (0.96 g). MS m/z (M+Na⁺) 368.0.

D. (S)-(3-(Azetidin-3-ylamino)pyrrolidin-1-yl)(phenyl)methanone, 5e

To a solution of compound 5d (0.96 g, 2.78 mmol) in MeOH (5 mL) was added HCl solution in dioxane (4M, 10 mL) at room temperature. The mixture was stirred at room temperature for 4 h. The solvent was removed by evaporation. Ether (50 mL) was added to the residue. The off-white solid was collected by filtration, washed with hexanes, and dried under vacuum. The crude compound 5e was used in the next reaction without further purification. MS m/z (M+H⁺) 246.0.

E. (3S)-1-(Phenylcarbonyl)-N-(1-{[3'-(trifluoromethyl)biphenyl-4-yl]carbonyl}azetidin-3-yl)pyrrolidin-3-amine, Cpd 16

To a solution of compound 5e (di-HCl salt, 300 mg, 0.934 mmol), compound 4g (0.262 g, 0.98° mmol), and Et$_3$N (0.78 mL, 5.58 mmol) in CH$_2$Cl$_2$ (5 mL) was added HATU (74 mg, 0.194 mmol). The reaction mixture was stirred at room temperature for 18 h. The resultant mixture was diluted with CH$_2$Cl$_2$ and washed with aq. NaHCO$_3$. The organic phase was dried over Na$_2$SO$_4$, filtered, and concentrated under reduced pressure. Purification of the residue by flash column chromatography (silica gel, 5% MeOH/EtOAc+0.5 TEA %) gave compound 16 (400 mg). MS m/z (M+H$^+$) 494.0. $^1$H NMR (400 MHz, CDCl$_3$): δ 7.84 (m, 1H), 7.79-7.76 (m, 3H), 7.66-7.57 (m, 4H), 7.52-7.48 (m, 2H), 7.43-7.40 (m, 3H), 4.53-4.38 (m, 2H), 4.08-3.83 (m, 3H), 3.71-3.60 (m, 2H), 3.46 (m, 2H), 3.33 (m, 0.5H), 3.22 (m, 0.5H), 2.16-2.04 (m, 1H), 1.83 (m, 1H).

Following the procedure described above for Example 5 and substituting the appropriate reagents, starting materials and purification methods known to those skilled in the art, the following compounds of the present invention were prepared:

| Cpd | Cpd Name and Data |
|---|---|
| 17 | (3S)-N-{1-[(3',5'-Dichlorobiphenyl-4-yl)carbonyl]azetidin-3-yl}-1-(phenylcarbonyl)pyrrolidin-3-amine MS m/z (M + H$^+$) 494, 495, 496 |
| 18 | (3S)-1-(Phenylcarbonyl)-N-(1-{[5-(trifluoromethoxy)-1-benzothiophen-2-yl]carbonyl}azetidin-3-yl)pyrrolidin-3-amine MS m/z (M + H$^+$) 490 |
| 19 | (3S)-1-(Phenylcarbonyl)-N-(1-{[5-(trifluoromethyl)-1-benzothiophen-2-yl]carbonyl}azetidin-3-yl)pyrrolidin-3-amine MS m/z (M + H$^+$) 474 |
| 20 | (3S)-1-(Phenylcarbonyl)-N-(1-{[6-(trifluoromethyl)-1-benzothiophen-2-yl]carbonyl}azetidin-3-yl)pyrrolidin-3-amine MS m/z (M + H$^+$) 474 |
| 21 | (3S)-N-{1-[(6-Bromo-3-chloro-1-benzothiophen-2-yl)carbonyl]azetidin-3-yl}-1-(phenylcarbonyl)pyrrolidin-3-amine MS m/z (M + H$^+$) 518, 520 |
| 22 | (3S)-N-{1-[(5-Bromonaphthalen-2-yl)carbonyl]azetidin-3-yl}-1-(phenylcarbonyl)pyrrolidin-3-amine MS m/z (M + H$^+$) 478, 480 |
| 27 | (3S)-N-[1-(9H-Fluoren-2-ylcarbonyl)azetidin-3-yl]-1-(phenylcarbonyl)pyrrolidin-3-amine MS m/z (M + H$^+$) 438 |
| 28 | (3S)-N-(1-{[3-Chloro-6-(trifluoromethyl)-1-benzothiophen-2-yl]carbonyl}azetidin-3-yl)-1-(phenylcarbonyl)pyrrolidin-3-amine MS m/z (M + H$^+$) 508 |
| 29 | (3S)-N-{1-[(3'-Chlorobiphenyl-4-yl)carbonyl]azetidin-3-yl}-1-(phenylcarbonyl)pyrrolidin-3-amine MS m/z (M + H$^+$) 460 |
| 30 | (3S)-N-{1-[(3',4'-Dichlorobiphenyl-4-yl)carbonyl]azetidin-3-yl}-1-(phenylcarbonyl)pyrrolidin-3-amine MS m/z (M + H$^+$) 495 |
| 35 | (3S)-1-(Phenylcarbonyl)-N-(1-{[4'-(trifluoromethyl)biphenyl-4-yl]carbonyl}azetidin-3-yl)pyrrolidin-3-amine MS m/z (M + H$^+$) 494 |
| 36 | (3S)-1-(Phenylcarbonyl)-N-(1-{[4'-(trifluoromethoxy)biphenyl-4-yl]carbonyl}azetidin-3-yl)pyrrolidin-3-amine MS m/z (M + H$^+$) 510 |
| 38 | (3S)-N-{1-[(6-Bromo-1-benzothiophen-2-yl)carbonyl]azetidin-3-yl}-1-(phenylcarbonyl)pyrrolidin-3-amine MS m/z (M + H$^+$) 484, 486 |
| 49 | (3S)-N-{1-[(5-Bromo-1-benzothiophen-2-yl)carbonyl]azetidin-3-yl}-1-(phenylcarbonyl)pyrrolidin-3-amine MS m/z (M + H$^+$) 484, 486 |
| 55 | (3S)-N-{1-[(3-Bromo-1-benzothiophen-2-yl)carbonyl]azetidin-3-yl}-1-(phenylcarbonyl)pyrrolidin-3-amine MS m/z (M + H$^+$) 484, 486 |
| 56 | (3S)-N-{1-[(3-Chloro-6-fluoro-1-benzothiophen-2-yl)carbonyl]azetidin-3-yl}-1-(phenylcarbonyl)pyrrolidin-3-amine MS m/z (M + H$^+$) 458 |
| 68 | (3S)-N-{1-[(3-Methyl-1-benzothiphen-2-yl)carbonyl]azetidin-3-yl}-1-(phenylcarbonyl)pyrrolidin-3-amine MS m/z (M + H$^+$) 420 |
| 95 | (3S)-N-{1-[(6-Bromo-1-benzothiophen-2-yl)carbonyl]azetidin-3-yl}-1-(1,3-thiazol-2-ylcarbonyl)pyrrolidin-3-amine MS m/z (M + H$^+$) 491, 493 |
| 96 | (3S)-N-{1-[(6-Bromo-1-benzothiophen-2-yl)carbonyl]azetidin-3-yl}-1-(1,3-thiazol-4-ylcarbonyl)pyrrolidin-3-amine MS m/z (M + H$^+$) 491, 493 |
| 97 | (3S)-N-{1-[(5-Bromo-1-benzothiphen-2-yl)carbonyl]azetidin-3-yl}-1-(1,3-thiazol-2-ylcarbonyl)pyrrolidin-3-amine MS m/z (M + H$^+$) 491, 493 |
| 98 | (3S)-N-{1-[(5-Bromo-1-benzothiophen-2-yl)carbonyl]azetidin-3-yl}-1-(1,3-thiazol-4-ylcarbonyl)pyrrolidin-3-amine MS m/z (M + H$^+$) 491, 493 |
| 107 | (3S)-N-{1-[(5-Bromo-1-benzofuran-2-yl)carbonyl]azetidin-3-yl}-1-(phenylcarbonyl)pyrrolidin-3-amine MS m/z (M + H$^+$) 468, 470 |
| 113 | (3S)-1-(1,3-Thiazol-2-ylcarbonyl)-N-(1-{[3'-(trifluoromethyl)biphenyl-4-yl]carbonyl}azetidin-3-yl)pyrrolidin-3-amine MS m/z (M + H$^+$) 501 |
| 114 | (3S)-1-(1,3-Thiazol-4-ylcarbonyl)-N-(1-{[3'-(trifluoromethyl)biphenyl-4-yl]carbonyl}azetidin-3-yl)pyrrolidin-3-amine MS m/z (M + H$^+$) 501 |
| 115 | (3S)-1-(1,3-Thiazol-2-ylcarbonyl)-N-(1-{[4'-(trifluoromethyl)biphenyl-4-yl]carbonyl}azetidin-3-yl)pyrrolidin-3-amine MS m/z (M + H$^+$) 501 |
| 116 | (3S)-N-(1-{[3-Fluoro-3'-(trifluoromethyl)biphenyl-4-yl]carbonyl}azetidin-3-yl)-1-(1,3-thiazol-2-ylcarbonyl)pyrrolidin-3-amine MS m/z (M + H$^+$) 519 |
| 117 | (3S)-N-(1-{[3-Methyl-3'-(trifluoromethyl)biphenyl-4-yl]carbonyl}azetidin-3-yl)-1-(1,3-thiazol-2-ylcarbonyl)pyrrolidin-3-amine MS m/z (M + H$^+$) 515 |
| 134 | (3S)-N-(1-{[2-(2-Fluorophenyl)-4-methyl-1,3-thiazol-5-yl]carbonyl}azetidin-3-yl)-1-(1,3-thiazol-2-ylcarbonyl)pyrrolidin-3-amine MS m/z (M + H$^+$) 472 |
| 135 | (3S)-N-(1-{[2-(4-Fluorophenyl)-4-methyl-1,3-thiazol-5-yl]carbonyl}azetidin-3-yl)-1-(1,3-thiazol-2-ylcarbonyl)pyrrolidin-3-amine MS m/z (M + H$^+$) 472 |
| 136 | (3S)-N-(1-{[2-(3-Chlorophenyl)-4-methyl-1,3-thiazol-5-yl]carbonyl}azetidin-3-yl)-1-(1,3-thiazol-2-ylcarbonyl)pyrrolidin-3-amine MS m/z (M + H$^+$) 489 |
| 137 | (3S)-N-(1-{[2-(4-Chlorophenyl)-4-methyl-1,3-thiazol-5-yl]carbonyl}azetidin-3-yl)-1-(1,3-thiazol-2-ylcarbonyl)pyrrolidin-3-amine MS m/z (M + H$^+$) 489 |
| 138 | (3S)-1-(1,3-Thiazol-2-ylcarbonyl)-N-(1-{[6-(trifluoromethyl)-1-benzothiophen-2-yl]carbonyl}azetidin-3-yl)pyrrolidin-3-amine MS m/z (M + H$^+$) 481 |
| 139 | (3S)-1-(1,3-Thiazol-4-ylcarbonyl)-N-(1-{[6-(trifluoromethyl)-1-benzothiophen-2-yl]carbonyl}azetidin-3-yl)pyrrolidin-3-amine MS m/z (M + H$^+$) 481 |
| 140 | (3S)-N-{1-[(6-Bromo-3-chloro-1-benzothiophen-2-yl)carbonyl]azetidin-3-yl}-1-(1,3-thiazol-2-ylcarbonyl)pyrrolidin-3-amine MS m/z (M + H$^+$) |
| 141 | (3S)-N-{1-[(6-Bromo-3-chloro-1-benzothiophen-2-yl)carbonyl]azetidin-3-yl}-1-(1,3-thiazol-4-ylcarbonyl)pyrrolidin-3-amine MS m/z (M + H$^+$) 525, 527 |
| 145 | (3S)-1-(1,3-Thiazol-4-ylcarbonyl)-N-(1-{[4'-(trifluoromethyl)biphenyl-4-yl]carbonyl}azetidin-3-yl)pyrrolidin-3-amine MS m/z (M + H$^+$) 501 |
| 167 | (3S)-N-(1-{[3-Chloro-6-(trifluoromethyl)-1-benzothiophen-2-yl]carbonyl}azetidin-3-yl)-1-(1,3-thiazol-2-ylcarbonyl)pyrrolidin-3-amine MS m/z (M + H$^+$) 515 |
| 168 | (3S)-N-(1-{[3-Chloro-6-(trifluoromethyl)-1-benzothiophen-2-yl]carbonyl}azetidin-3-yl)-1-(1,3-thiazol-4-ylcarbonyl)pyrrolidin-3-amine MS m/z (M + H$^+$) 515 |

Example 6

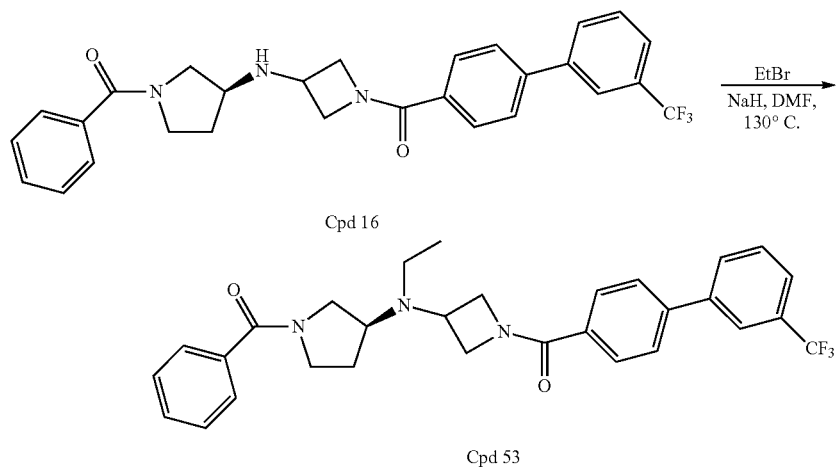

A. (3S)—N-Ethyl-1-(phenylcarbonyl)-N-(1-{[3'-(trifluoromethyl)biphenyl-4-yl]carbonyl}azetidin-3-yl)pyrrolidin-3-amine, Cpd 53

To a solution of Compound 16 (50 mg, 0.101 mmol) in dry DMF (1 mL) was added NaH (6 mg, 0.152 mmol) and the resulting mixture was stirred at room temperature for 20 min. EtBr (0.012 mL, 0.12 mmol) was added and the reaction mixture was heated to 130° C. overnight. The resultant mixture was diluted with EtOAc and water. The organic layer was washed with water and aq. NaHCO$_3$, dried over Na$_2$SO$_4$, filtered, and concentrated under reduced pressure. Purification of the residue by flash column chromatography (silica gel, 5% MeOH/EtOAc+0.5 TEA %) gave compound 53 (9 mg). MS m/z (M+H$^+$) 522.0.

Example 7

A. (3S)—N-Hydroxy-1-(phenylcarbonyl)-N-(1-{[3'-(trifluoromethyl)biphenyl-4-yl]carbonyl}azetidin-3-yl)pyrrolidin-3-amine, Cpd 54

To a solution of Compound 16 (60 mg, 0.12 mmol) in dry CH$_2$Cl$_2$ (1 mL) was added mCPBA (77%, 33 mg, 0.146 mmol) at 0° C. and the resulting mixture was stirred at this temperature for 30 min. The reaction mixture was diluted with CH$_2$Cl$_2$ and water. The organic layer was washed with water and brine, dried over Na$_2$SO$_4$, filtered, and concentrated under reduced pressure. Purification of the residue by flash column chromatography (silica gel, 5% MeOH/EtOAc) gave compound 54 (7 mg). MS m/z (M+Na$^+$) 510.0, MS m/z (M+Na$^+$) 532.0.

Following the procedure described above for Example 7 and substituting the appropriate reagents, starting materials and purification methods known to those skilled in the art, the following compounds of the present invention were prepared:

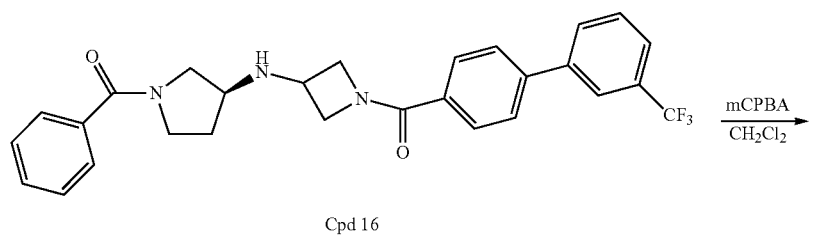

| Cpd | Cpd Name and Data |
|---|---|
| 34 | (3S)-N-{1-[(5-Bromonaphthalen-2-yl)carbonyl]azetidin-3-yl}-N-hydroxy-1-(phenylcarbonyl)pyrrolidin-3-amine<br>MS m/z (M + H⁺) 494, 496 |

Example 8

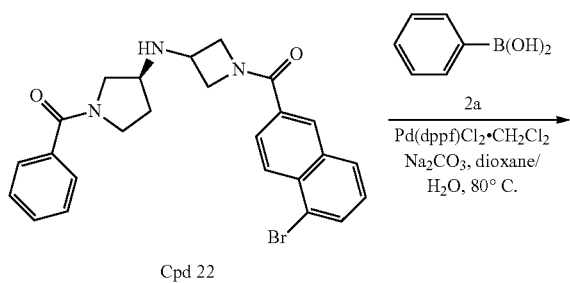

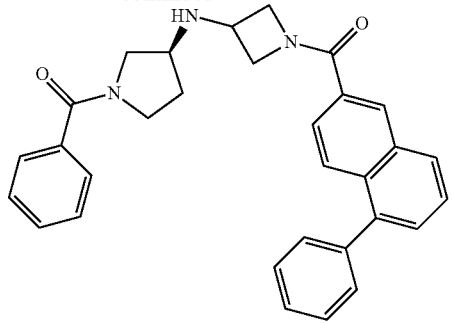

Cpd 23

A. (3S)-1-(Phenylcarbonyl)-N-{1-[(5-phenylnaphthalen-2-yl)carbonyl]azetidin-3-yl}pyrrolidin-3-amine, Cpd 23

A mixture of cpd 22 (50 mg, 0.105 mmol), phenylboronic acid (19 mg, 0.158 mmol), Pd(dppf)Cl$_2$·CH$_2$Cl$_2$ (9 mg, 0.011 mmol), Na$_2$CO$_3$ (22 mg, 0.22 mmol) in dioxane (0.8 mL) and water (0.2 mL) in a capped vial was heated at 80° C. for 6 h. The reaction mixture was diluted with EtOAc and water. The organic layer was concentrated and purified by chromatography (silica gel, 5% MeOH/EtOAc) to give compound 23 (37 mg). MS m/z (M+H⁺) 476.

Following the procedure described above for Example 8 and substituting the appropriate reagents, starting materials and purification methods known to those skilled in the art, the following compounds of the present invention were prepared:

| Cpd | Cpd Name and Data |
|---|---|
| 24 | (3S)-1-(Phenylcarbonyl)-N-[1-({5-[2-(trifluoromethyl)phenyl]naphthalen-2-yl}carbonyl)azetidin-3-yl]pyrrolidin-3-amine<br>MS m/z (M + H⁺) 544 |
| 25 | (3S)-1-(Phenylcarbonyl)-N-[1-({5-[3-(trifluoromethyl)phenyl]naphthalen-2-yl}carbonyl)azetidin-3-yl]pyrrolidin-3-amine<br>MS m/z (M + H⁺) 544 |
| 26 | (3S)-1-(Phenylcarbonyl)-N-[1-({5-[4-(trifluoromethoxy)phenyl]naphthalen-2-yl}carbonyl)azetidin-3-yl]pyrrolidin-3-amine<br>MS m/z (M + H⁺) 560 |
| 31 | (3S)-N-{1-[(3-Chloro-6-phenyl-1-benzothiophen-2-yl)carbonyl]azetidin-3-yl}-1-(phenylcarbonyl)pyrrolidin-3-amine<br>MS m/z (M + H⁺) 517 |
| 32 | (3S)-N-[1-({3-Chloro-6-[3-(trifluoromethyl)phenyl]-1-benzothiophen-2-yl}carbonyl)azetidin-3-yl]-1-(phenylcarbonyl)pyrrolidin-3-amine<br>MS m/z (M + H⁺) 585 |
| 33 | (3S)-N-[1-({3-Chloro-6-[4-(trifluoromethyl)phenyl]-1-benzothiophen-2-yl}carbonyl)azetidin-3-yl]-1-(phenylcarbonyl)pyrrolidin-3-amine<br>MS m/z (M + H⁺) 585 |
| 42 | (3S)-N-{1-[(6-Phenyl-1-benzothiophen-2-yl)carbonyl]azetidin-3-yl}-1-(phenylcarbonyl)pyrrolidin-3-amine<br>MS m/z (M + H⁺) 596 |
| 43 | (3S)-1-(Phenylcarbonyl)-N-[1-({6-[4-(trifluoromethyl)phenyl]-1-benzothiophen-2-yl}carbonyl)azetidin-3-yl]pyrrolidin-3-amine<br>MS m/z (M + H⁺) 550 |
| 44 | (3S)-1-(Phenylcarbonyl)-N-[1-({6-[3-(trifluoromethyl)phenyl]-1-benzothiophen-2-yl}carbonyl)azetidin-3-yl]pyrrolidin-3-amine<br>MS m/z (M + H⁺) 550 |
| 50 | (3S)-N-{1-[(5-Phenyl-1-benzothiophen-2-yl)carbonyl]azetidin-3-yl}-1-(phenylcarbonyl)pyrrolidin-3-amine<br>MS m/z (M + H⁺) 519 |
| 51 | (3S)-1-(Phenylcarbonyl)-N-[1-({5-[3-(trifluoromethyl)phenyl]-1-benzothiophen-2-yl}carbonyl)azetidin-3-yl]pyrrolidin-3-amine<br>MS m/z (M + H⁺) 550 |
| 52 | (3S)-1-(Phenylcarbonyl)-N-[1-({5-[4-(trifluoromethyl)phenyl]-1-benzothiophen-2-yl}carbonyl)azetidin-3-yl]pyrrolidin-3-amine<br>MS m/z (M + H⁺) 550 |

-continued

| Cpd | Cpd Name and Data |
|---|---|
| 65 | (3S)-N-{1-[(3-Phenyl-1-benzothiophen-2-yl)carbonyl]azetidin-3-yl}-1-(phenylcarbonyl)pyrrolidin-3-amine<br>MS m/z (M + H$^+$) 482 |
| 99 | (3S)-1-(1,3-Thiazol-2-ylcarbonyl)-N-[1-({6-[3-(trifluoromethyl)phenyl]-1-benzothiophen-2-yl}carbonyl)azetidin-3-yl]pyrrolidin-3-amine<br>MS m/z (M + H$^+$) 557 |
| 100 | (3S)-1-(1,3-Thiazol-4-ylcarbonyl)-N-[1-({6-[3-(trifluoromethyl)phenyl]-1-benzothiophen-2-yl}carbonyl)azetidin-3-yl]pyrrolidin-3-amine<br>MS m/z (M + H$^+$) 557 |
| 102 | (3S)-1-(1,3-Thiazol-2-ylcarbonyl)-N-[1-({6-[4-(trifluoromethyl)phenyl]-1-benzothiophen-2-yl}carbonyl)azetidin-3-yl]pyrrolidin-3-amine<br>MS m/z (M + H$^+$) 533 |
| 108 | (3S)-1-(Phenylcarbonyl)-N-{1-[(4-phenylquinazolin-7-yl)carbonyl]azetidin-3-yl}pyrrolidin-3-amine<br>MS m/z (M + H$^+$) 478 |
| 109 | (3S)-1-(Phenylcarbonyl)-N-[1-({4-[4-(trifluoromethyl)phenyl]quinazolin-7-yl}carbonyl)azetidin-3-yl]pyrrolidin-3-amine<br>MS m/z (M + H$^+$) 546 |
| 110 | (3S)-N-{1-[(4-Phenylquinazolin-7-yl)carbonyl]azetidin-3-yl}-1-(1,3-thiazol-2-ylcarbonyl)pyrrolidin-3-amine<br>MS m/z (M + H$^+$) 485 |
| 111 | (3S)-1-(1,3-Thiazol-2-ylcarbonyl)-N-[1-({4-[4-(trifluoromethyl)phenyl]quinazolin-7-yl}carbonyl)azetidin-3-yl]pyrrolidin-3-amine<br>MS m/z (M + H$^+$) 553 |
| 112 | (3S)-N-{1-[(4-Phenylquinazolin-7-yl)carbonyl]azetidin-3-yl}-1-(1,3-thiazol-4-ylcarbonyl)pyrrolidin-3-amine<br>MS m/z (M + H$^+$) 485 |
| 121 | (3S)-N-{1-[(5-Phenyl-1-benzofuran-2-yl)carbonyl]azetidin-3-yl}-1-(phenylcarbonyl)pyrrolidin-3-amine<br>MS m/z (M + H$^+$) 466 |
| 122 | (3S)-N-(1-{[5-(5-Chlorothiophen-2-yl)-1-benzofuran-2-yl]carbonyl}azetidin-3-yl)-1-(phenylcarbonyl)pyrrolidin-3-amine<br>MS m/z (M + H$^+$) 507 |
| 124 | (3S)-N-{1-[(6-Phenyl-1-benzothiophen-2-yl)carbonyl]azetidin-3-yl}-1-(1,3-thiazol-4-ylcarbonyl)pyrrolidin-3-amine<br>MS m/z (M + H$^+$) 489 |
| 128 | (3S)-1-(1,3-Thiazol-4-ylcarbonyl)-N-[1-({6-[4-(trifluoromethyl)phenyl]-1-benzothiophen-2-yl}carbonyl)azetidin-3-yl]pyrrolidin-3-amine<br>MS m/z (M + H$^+$) 557 |
| 129 | (3S)-N-{1-[(5-Phenyl-1-benzothiophen-2-yl)carbonyl]azetidin-3-yl}-1-(1,3-thiazol-2-ylcarbonyl)pyrrolidin-3-amine<br>MS m/z (M + H$^+$) 489 |
| 130 | (3S)-1-(1,3-Thiazol-4-ylcarbonyl)-N-[1-({5-[3-(trifluoromethyl)phenyl]-1-benzothiophen-2-yl}carbonyl)azetidin-3-yl]pyrrolidin-3-amine<br>MS m/z (M + H$^+$) 557 |
| 131 | (3S)-N-{1-[(5-Phenyl-1-benzothiophen-2-yl)carbonyl]azetidin-3-yl}-1-(1,3-thiazol-4-ylcarbonyl)pyrrolidin-3-amine<br>MS m/z (M + H$^+$) 489 |
| 132 | (3S)-1-(1,3-Thiazol-2-ylcarbonyl)-N-[1-({5-[3-(trifluoromethyl)phenyl]-1-benzothiophen-2-yl}carbonyl)azetidin-3-yl]pyrrolidin-3-amine<br>MS m/z (M + H$^+$) 557 |
| 146 | (3S)-N-{1-[(3-Chloro-6-phenyl-1-benzothiophen-2-yl)carbonyl]azetidin-3-yl}-1-(1,3-thiazol-2-ylcarbonyl)pyrrolidin-3-amine<br>MS m/z (M + H$^+$) 524 |
| 147 | (3S)-N-{1-[(3-Chloro-6-phenyl-1-benzothiophen-2-yl)carbonyl]azetidin-3-yl}-1-(1,3-thiazol-4-ylcarbonyl)pyrrolidin-3-amine<br>MS m/z (M + H$^+$) 524 |
| 148 | (3S)-N-[1-({3-Chloro-6-[3-(trifluoromethyl)phenyl]-1-benzothiophen-2-yl}carbonyl)azetidin-3-yl]-1-(1,3-thiazol-2-ylcarbonyl)pyrrolidin-3-amine<br>MS m/z (M + H$^+$) 592 |
| 149 | (3S)-N-[1-({3-Chloro-6-[3-(trifluoromethyl)phenyl]-1-benzothiophen-2-yl}carbonyl)azetidin-3-yl]-1-(1,3-thiazol-4-ylcarbonyl)pyrrolidin-3-amine<br>MS m/z (M + H$^+$) 592 |
| 150 | (3S)-N-[1-({3-Chloro-6-[4-(trifluoromethyl)phenyl]-1-benzothiophen-2-yl}carbonyl)azetidin-3-yl]-1-(1,3-thiazol-2-ylcarbonyl)pyrrolidin-3-amine<br>MS m/z (M + H$^+$) 592 |
| 151 | (3S)-N-[1-({3-Chloro-6-[4-(trifluoromethyl)phenyl]-1-benzothiophen-2-yl}carbonyl)azetidin-3-yl]-1-(1,3-thiazol-4-ylcarbonyl)pyrrolidin-3-amine<br>MS m/z (M + H$^+$) 592 |

Example 9

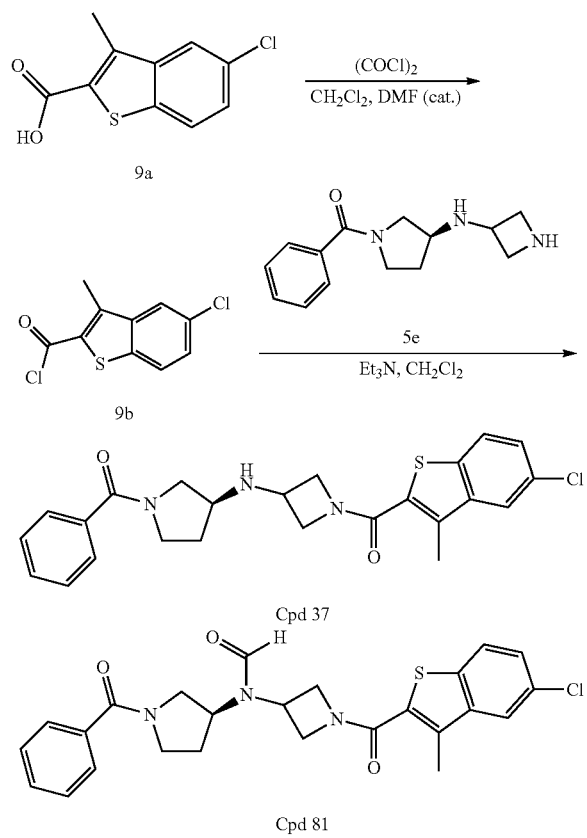

A. 5-Chloro-3-methylbenzo[b]thiophene-2-carbonyl chloride, 9b

To compound 9a (0.651 g, 2.87 mmol) in CH₂Cl₂ (15 mL) at room temperature was added (COCl)₂ (0.267 mL, 3.16 mmol), followed by DMF (0.0556 mL, 0.718 mmol). The reaction mixture was stirred at room temperature for 18 h. The reaction mixture was then concentrated to give compound 9b, which was used in the next reaction without further purification.

B. (3S)—N-{1-[(5-Chloro-3-methyl-1-benzothiophen-2-yl)carbonyl]azetidin-3-yl}-1-(phenylcarbonyl)pyrrolidin-3-amine, Cpd 37 and N-{1-[(5-Chloro-3-methyl-1-benzothiophen-2-yl)carbonyl]azetidin-3-yl}-N-[(3S)-1-(phenylcarbonyl)pyrrolidin-3-yl]formamide, Cpd 81

To a solution of compound 5e (320 mg, 1.006 mmol) and Et₃N (0.56 mL, 4.02 mmol) in CH₂Cl₂ (10 mL) at 0° C. was added a solution of compound 9b (271 mg, 1.106 mmol) in CH₂Cl₂ (1 mL). The reaction was slowly warmed up to room temperature over 4.5 h, diluted with CH₂Cl₂, and washed with aq. NaHCO₃. The organic layer was dried over Na₂SO₄ and concentrated. Purification by flash column chromatography (silica gel, 3% MeOH/CH₂Cl₂) afforded cpd 37 (135 mg), MS m/z (M+H⁺) 454 and cpd 81 (70 mg). MS m/z (M+H⁺) 483.

Following the procedure described above for Example 9 and substituting the appropriate reagents, starting materials and purification methods known to those skilled in the art, the following compounds of the present invention were prepared:

| Cpd | Cpd Name and Data |
|---|---|
| 82 | N-{1-[(5-Chloro-3-methyl-1-benzothiophen-2-yl)carbonyl]azetidin-3-yl}-N-[(3S)-1-(1,3-thiazol-2-ylcarbonyl)pyrrolidin-3-yl]formamide MS m/z (M + H⁺) 490 |
| 83 | N-{1-[(5-Chloro-3-methyl-1-benzothiophen-2-yl)carbonyl]azetidin-3-yl}-N-[(3S)-1-(1,3-thiazol-4-ylcarbonyl)pyrrolidin-3-yl]formamide MS m/z (M + H⁺) 490 |
| 84 | (3S)-N-{1-[(5-Chloro-3-methyl-1-benzothiophen-2-yl)carbonyl]azetidin-3-yl}-1-(1,3-thiazol-2-ylcarbonyl)pyrrolidin-3-amine MS m/z (M + H⁺) 462.2 |
| 85 | (3S)-N-{1-[(5-Chloro-3-methyl-1-benzothiophen-2-yl)carbonyl]azetidin-3-yl}-1-(1,3-thiazol-4-ylcarbonyl)pyrrolidin-3-amine MS m/z (M + H⁺) 462.2 |

Example 10

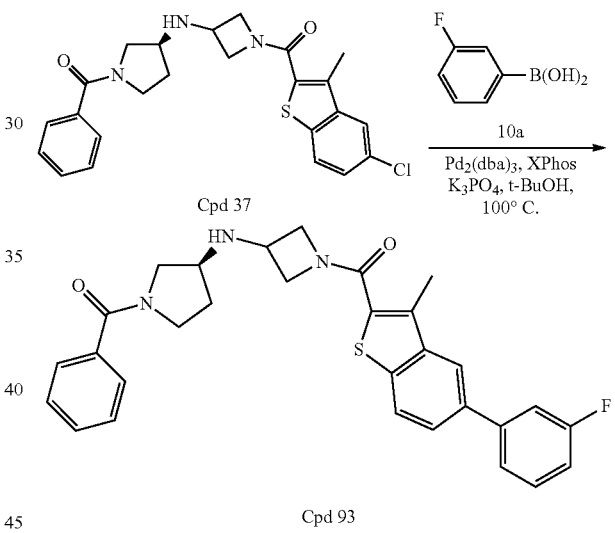

A. (3S)—N-(1-{[5-(3-Fluorophenyl)-3-methyl-1-benzothiophen-2-yl]carbonyl}azetidin-3-yl)-1-(phenylcarbonyl)pyrrolidin-3-amine, Cpd 93

A mixture of cpd 37 (44 mg, 0.0991 mmol), 3-fluorophenyl boronic acid 10a (27 mg, 0.19 mmol), Tris(dibenzylideneacetone)dipalladium (Pd₂(dba)₃)(8.8 mg), 2-Dicyclohexylphosphino-2',4',6'-triisopropylbiphenyl (XPhos) (11 mg) and K₃PO₄ (41 mg) in t-BuOH (0.8 mL) in a capped vial under a N₂ atmosphere was heated at 100° C. for 3 h. The reaction was cooled to room temperature and diluted with water and EtOAc. The organic phase was washed with aq. NaHCO₃. The organic layer was dried over Na₂SO₄ and concentrated. Purification by flash column chromatography (silica gel, 3% MeOH/CH₂Cl₂) afforded cpd 93 (40 mg). MS m/z (M+H⁺) 514

Following the procedure described above for Example 10 and substituting the appropriate reagents, starting materials and purification methods known to those skilled in the art, the following compounds of the present invention were prepared:

| Cpd | Cpd Name and Data |
|---|---|
| 39 | (3S)-N-{1-[(3-Methyl-5-phenyl-1-benzothiophen-2-yl)carbonyl]azetidin-3-yl}-1-(phenylcarbonyl)pyrrolidin-3-amine<br>MS m/z (M + H$^+$) 533 |
| 40 | (3S)-N-[1-({3-Methyl-5-[4-(trifluoromethyl)phenyl]-1-benzothiophen-2-yl}carbonyl)azetidin-3-yl]-1-(phenylcarbonyl)pyrrolidin-3-amine<br>MS m/z (M + H$^+$) 564.5 |
| 41 | (3S)-N-[1-({3-Methyl-5-[3-(trifluoromethyl)phenyl]-1-benzothiophen-2-yl}carbonyl)azetidin-3-yl]-1-(phenylcarbonyl)pyrrolidin-3-amine<br>MS m/z (M + H$^+$) 564.5 |
| 90 | (3S)-N-[1-({3-Methyl-5-[3-(trifluoromethyl)phenyl]-1-benzothiophen-2-yl}carbonyl)azetidin-3-yl]-1-(1,3-thiazol-2-ylcarbonyl)pyrrolidin-3-amine<br>$^1$H NMR (300 MHz, CDCl$_3$) δ: 7.95 (m, 1H), 7.89-7.92 (m, 3H), 7.84 (m, 1H), 7.66 (m, 1H), 7.72 (m, 2H), 7.53 (d, J = 2.8, 1H), 4.44-4.52 (m, 2H), 4.20-4.30 (m, 1.5H), 3.80-4.02 (m, 4.5 H), 3.72-3.76 (m, 0.5H), 3.42-3.55 (m, 1.5H), 2.70 (d, J = 3 Hz, 3H), 2.01-2.11 (m, 1H), 1.79-1.93 (m, 1H)<br>MS m/z (M + H$^+$) 571.3 |
| 91 | (3S)-N-[1-({3-Methyl-5-[4-(trifluoromethyl)phenyl]-1-benzothiophen-2-yl}carbonyl)azetidin-3-yl]-1-(1,3-thiazol-2-ylcarbonyl)pyrrolidin-3-amine<br>MS m/z (M + H$^+$) 571.3 |
| 92 | (3S)-N-{1-[(3-Methyl-5-phenyl-1-benzothiophen-2-yl)carbonyl]azetidin-3-yl}-1-(1,3-thiazol-2-ylcarbonyl)pyrrolidin-3-amine<br>MS m/z (M + H$^+$) 503 |
| 94 | (3S)-N-(1-{[5-(4-Fluorophenyl)-3-methyl-1-benzothiophen-2-yl]carbonyl}azetidin-3-yl)-1-(phenylcarbonyl)pyrrolidin-3-amine<br>MS m/z (M + H$^+$) 514 |
| 123 | (3S)-N-{1-[(3-Methyl-5-phenyl-1-benzothiophen-2-yl)carbonyl]azetidin-3-yl}-1-(1,3-thiazol-4-ylcarbonyl)pyrrolidin-3-amine<br>MS m/z (M + H$^+$) 503 |
| 125 | (3S)-N-[1-({3-Methyl-5-[3-(trifluoromethyl)phenyl]-1-benzothiophen-2-yl}carbonyl)azetidin-3-yl]-1-(1,3-thiazol-4-ylcarbonyl)pyrrolidin-3-amine<br>MS m/z (M + H$^+$) 571 |

Example 10a

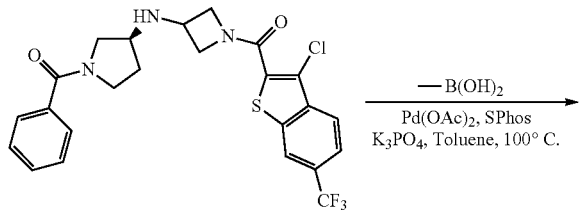

Cpd 28

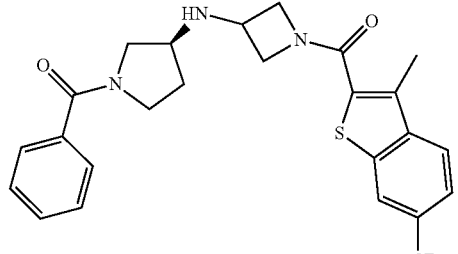

Cpd 80

A. (3S)—N-(1-{[3-Methyl-6-(trifluoromethyl)-1-benzothiophen-2-yl]carbonyl}azetidin-3-yl)-1-(phenylcarbonyl)pyrrolidin-3-amine, Cpd 80

A mixture of compound 28 (60 mg, 0.118 mmol), methylboronic acid (14 mg, 0.236 mmol), Pd(OAc)$_2$ (2.65 mg, 0.012 mmol), 2-Dicyclohexylphosphino-2',6'-dimethoxybiphenyl (SPhos) (12 mg, 0.0295 mmol), and K$_3$PO$_4$ (50 mg, 0.236 mmol) in toluene (0.8 mL) was heated to 100° C. for 3 h in a sealed reaction vessel. The reaction was diluted with EtOAc and water. The organic layer was concentrated and purified by flash column chromatography (silica gel, 10% EtOAc/hexanes) to give cpd 80. MS m/z (M+H$^+$) 488.

Following the procedure described above for Example 10a and substituting the appropriate reagents, starting materials and purification methods known to those skilled in the art, the following compounds of the present invention were prepared:

| Cpd | Cpd Name and Data |
|---|---|
| 66 | (3S)-N-{1-[(3-Cyclopropyl-1-benzothiophen-2-yl)carbonyl]azetidin-3-yl}-1-(phenylcarbonyl)pyrrolidin-3-amine<br>MS m/z (M + H$^+$) 446 |
| 74 | (3S)-1-(Phenylcarbonyl)-N-(1-{[3-phenyl-6-(trifluoromethyl)-1-benzothiophen-2-yl]carbonyl}azetidin-3-yl)pyrrolidin-3-amine<br>MS m/z (M + H$^+$) 550 |
| 75 | (3S)-N-(1-{[3-Cyclopropyl-6-(trifluoromethyl)-1-benzothiophen-2-yl]carbonyl}azetidin-3-yl)-1-(phenylcarbonyl)pyrrolidin-3-amine<br>MS m/z (M + H$^+$) 514 |
| 76 | (3S)-N-(1-{[3-(2-Methylprop-1-en-1-yl)-6-(trifluoromethyl)-1-benzothiophen-2-yl]carbonyl}azetidin-3-yl)-1-(phenylcarbonyl)pyrrolidin-3-amine<br>MS m/z (M + H$^+$) 528 |

Example 11

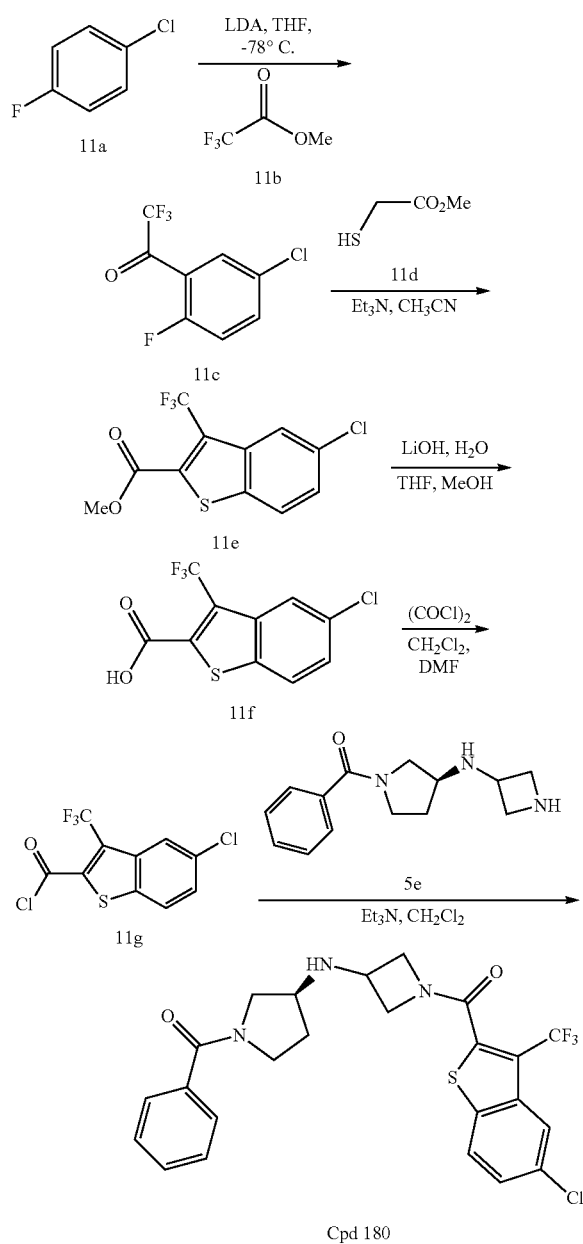

Cpd 180

A. 1-(5-Chloro-2-fluoro-phenyl)-2,2,2-trifluoro-ethanone, 11c

To a solution of LDA (2.0 M in THF/heptane/ethylbenzene, 12.6 mL, 25.3 mmol) in dry THF was slowly added 1-fluoro-4-chloro-benzene 11a (2.45 mL, 23.0 mmol) at −78° C. The mixture was stirred for 1 h at −78° C. and ethyl trifluoroacetate 11b (3.02 mL, 25.3 mmol) was added. The reaction mixture was allowed to warm to room temperature overnight and was quenched with saturated aqueous NH₄Cl solution. The mixture was extracted with EtOAc. The organic extracts were concentrated and purified by flash column chromatography (silica gel, 15% EtOAc/hexanes) to give a mixture of the compound 11c along with a regio-isomeric by-product, 1-(5-fluoro-2-chloro-phenyl)-2,2,2-trifluoro-ethanone, in a ratio of 5:1 (11c is the major product).

B. Methyl 5-chloro-3-(trifluoromethyl)benzo[b]thiophene-2-carboxylate, 11e

A solution of compound 11c (1.5 g, 6.62 mmol), methyl 2-mercaptoacetate 11d (0.6 mL, 6.62 mmol), and Et₃N (1.2 mL, 8.6 mmol) in acetonitrile (12 mL) was heated at 75° C. for 4 h. The reaction was diluted with EtOAc and water. The organic layer was concentrated and purified by flash column chromatography (silica gel, 10% EtOAc/hexanes) to provide compound 11e.

C. 5-Chloro-3-trifluoromethyl-benzo[b]thiophene-2-carboxylic acid, 11f

A mixture of compound 11e (390 mg, 1.33 mmol) and LiOH (159 mg, 6.65 mmol) in THF/MeOH/H₂O (4/4/4 mL) was stirred for 4 h. The reaction was concentrated under reduced pressure and then water was added to the residue. The aqueous mixture was acidified with 1N HCl to pH ~4. A white precipitate was filtered and washed with water and Et₂O. The crude product was dried under vacuum to give compound 11f which was used without purification.

D. 5-Chloro-3-trifluoromethyl-benzo[b]thiophene-2-carbonyl chloride, 11g

The title compound 11g was prepared using the method described in Example 9, substituting compound 11f for compound 9a in Step A.

E. (3S)—N-(1-{[5-Chloro-3-(trifluoromethyl)-1-benzothiophen-2-yl]carbonyl}azetidin-3-yl)-1-(phenylcarbonyl)pyrrolidin-3-amine, Cpd 180

The title compound Cpd 180 was prepared using the method described in Example 9, substituting compound 11g for compound 9b in Step B. MS m/z (M+H⁺) 508.

Following the procedure described above for Example 11 and substituting the appropriate reagents, starting materials and purification methods known to those skilled in the art, the following compounds of the present invention were prepared:

| Cpd | Cpd Name and Data |
|---|---|
| 181 | (3S)-N-(1-{[5-Chloro-3-(trifluoromethyl)-1-benzothiophen-2-yl]carbonyl}azetidin-3-yl)-1-(1,3-thiazol-4-ylcarbonyl)pyrrolidin-3-amine<br>MS m/z (M + H⁺) 515 |

Example 11a

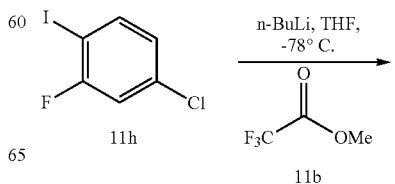

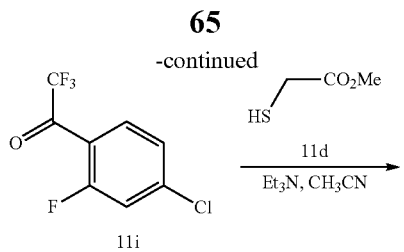
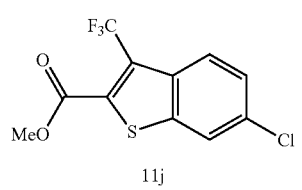
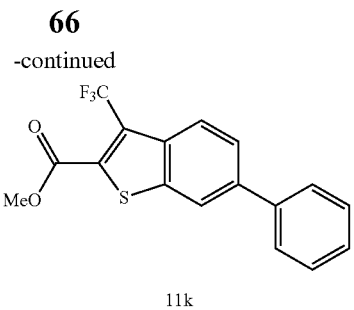

H. Methyl 6-phenyl-3-(trifluoromethyl)benzo[b]thiophene-2-carboxylate, 11k

The title compound 11k was prepared using a similar method to that described in Example 10a, substituting compound 11j for compound 28 and phenyl boronic acid 2a for methyl boronic acid in Step A.

Following the procedure described above for Example 11, Steps C-E, and substituting the appropriate reagents, starting materials and purification methods known to those skilled in the art, the following compounds of the present invention were prepared:

| Cpd | Cpd Name and Data |
|---|---|
| 208 | (3S)-N-(1-{[6-Phenyl-3-(trifluoromethyl)-1-benzothiophen-2-yl]carbonyl}azetidin-3-yl)-1-(1,3-thiazol-2-ylcarbonyl)pyrrolidin-3-amine<br>MS m/z (M + H$^+$) 557 |

F. 1-(4-Chloro-2-fluoro-phenyl)-2,2,2-trifluoro-ethanone, 11i

To a solution of n-BuLi (1.6 M in hexanes, 2.93 mL, 4.68 mmol) in dry THF was slowly added 4-chloro-2-fluoro-1-iodo-benzene 11h (31.0 g, 0.9 mmol) at −78° C. under N$_2$. The mixture was stirred for 1 h at −78° C. and ethyl trifluoroacetate 11b (0.51 mL, 4.29 mmol) was added. The reaction was allowed to warm to room temperature overnight and was quenched with saturated aqueous NH$_4$Cl solution. The mixture was extracted with EtOAc. The organic extracts were concentrated and purified by flash column chromatography (silica gel, 15% EtOAc/hexanes) to give compound 11i.

G. Methyl 6-chloro-3-(trifluoromethyl)benzo[b]thiophene-2-carboxylate, 11j

The title compound 11j was prepared using a similar method to that described in Example 11, substituting compound 11i for compound 11c in Step B.

Following the procedure described above for Example 11, Steps C-E, and substituting the appropriate reagents, starting materials and purification methods known to those skilled in the art, the following compounds of the present invention were prepared:

| Cpd | Cpd Name and Data |
|---|---|
| 182 | (3S)-N-(1-{[6-Chloro-3-(trifluoromethyl)-1-benzothiophen-2-yl]carbonyl}azetidin-3-yl)-1-(phenylcarbonyl)pyrrolidin-3-amine<br>MS m/z (M + H$^+$) 508 |
| 183 | (3S)-N-(1-{[6-Chloro-3-(trifluoromethyl)-1-benzothiophen-2-yl]carbonyl}azetidin-3-yl)-1-(1,3-thiazol-2-ylcarbonyl)pyrrolidin-3-amine<br>MS m/z (M + H$^+$) 515 |

Example 11b

Example 12

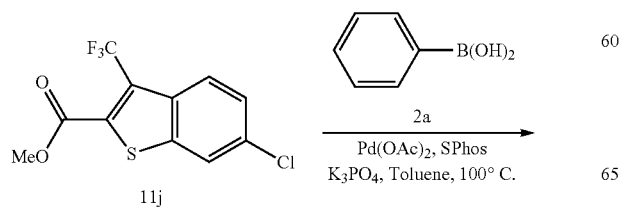

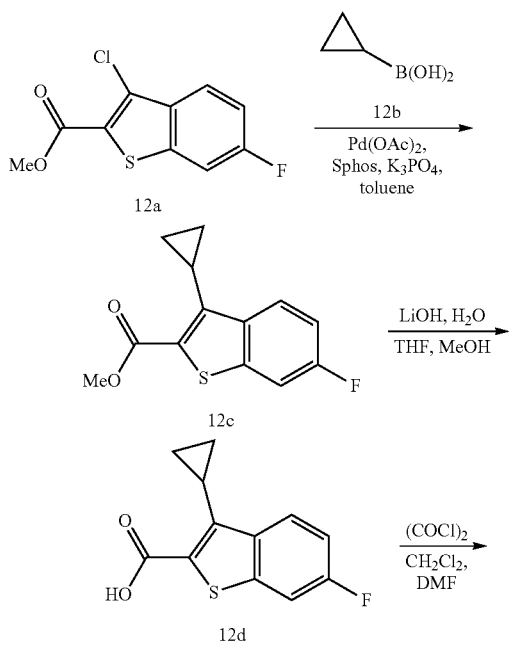

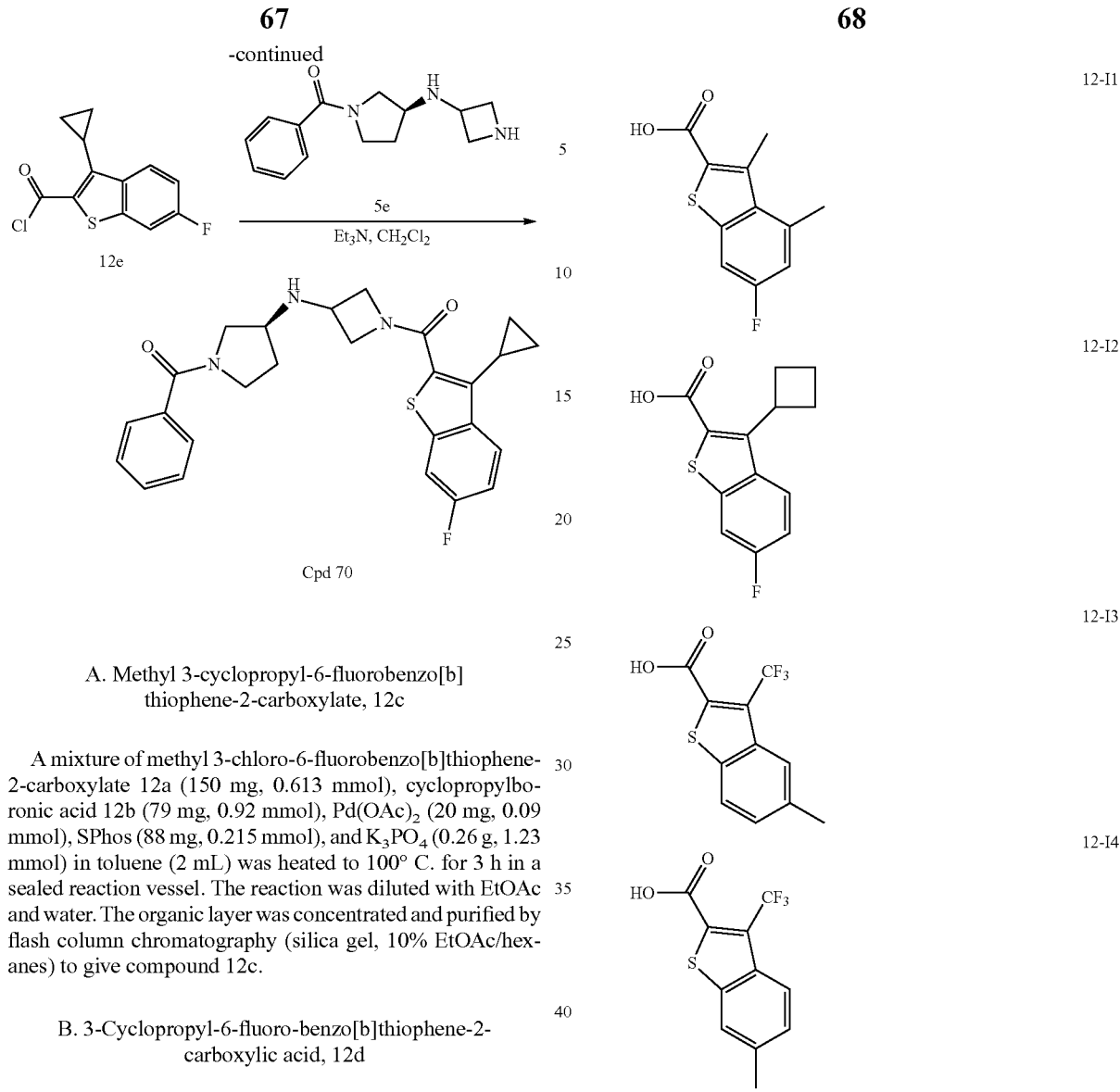

A. Methyl 3-cyclopropyl-6-fluorobenzo[b]thiophene-2-carboxylate, 12c

A mixture of methyl 3-chloro-6-fluorobenzo[b]thiophene-2-carboxylate 12a (150 mg, 0.613 mmol), cyclopropylboronic acid 12b (79 mg, 0.92 mmol), Pd(OAc)$_2$ (20 mg, 0.09 mmol), SPhos (88 mg, 0.215 mmol), and K$_3$PO$_4$ (0.26 g, 1.23 mmol) in toluene (2 mL) was heated to 100° C. for 3 h in a sealed reaction vessel. The reaction was diluted with EtOAc and water. The organic layer was concentrated and purified by flash column chromatography (silica gel, 10% EtOAc/hexanes) to give compound 12c.

B. 3-Cyclopropyl-6-fluoro-benzo[b]thiophene-2-carboxylic acid, 12d

The title compound 12d was prepared using the method described in Example 11, substituting compound 12c for compound 11f in Step C.

C. 3-Cyclopropyl-6-fluoro-benzo[b]thiophene-2-carbonyl chloride, 12e

The title compound 12e was prepared using the method described in Example 9, substituting compound 12d for compound 9a in Step A.

D. 1-{1-[(3-Cyclopropyl-6-fluoro-1-benzothiophen-2-yl)carbonyl]azetidin-3-yl}-4-(1,3-thiazol-2-ylcarbonyl)piperazine, Cpd 70

The title compound Cpd 70 was prepared using the method described in Example 9, substituting compound 12e for compound 9b in Step B. MS m/z (M+H$^+$) 464.

Following the procedure described above for Example 12 and substituting the appropriate reagents, starting materials and purification methods known to those skilled in the art, the following intermediate compounds were prepared:

Following the procedure described above for Example 12 and substituting the appropriate reagents, starting materials and purification methods known to those skilled in the art, the following compounds of the present invention were prepared:

| Cpd | Cpd Name and Data |
|---|---|
| 79 | (3S)-N-{1-[(3-Cyclobutyl-6-fluoro-1-benzothiophen-2-yl)carbonyl]azetidin-3-yl}-1-(phenylcarbonyl)pyrrolidin-3-amine<br>MS m/z (M + H$^+$) 478 |
| 86 | (3S)-N-{1-[(6-Fluoro-3-methyl-1-benzothiophen-2-yl)carbonyl]azetidin-3-yl}-1-(phenylcarbonyl)pyrrolidin-3-amine<br>MS m/z (M + H$^+$) 438 |
| 87 | (3S)-N-{1-[(6-Fluoro-3-methyl-1-benzothiophen-2-yl)carbonyl]azetidin-3-yl}-1-(1,3-thiazol-2-ylcarbonyl)-pyrrolidin-3-amine<br>MS m/z (M + H$^+$) 445 |
| 88 | (3S)-N-{1-[(6-Fluoro-3-methyl-1-benzothiophen-2-yl)carbonyl]azetidin-3-yl}-1-(1,3-thiazol-4-ylcarbonyl)-pyrrolidin-3-amine<br>MS m/z (M + H$^+$) 445 |

-continued

| Cpd | Cpd Name and Data |
|---|---|
| 184 | (3S)-N-(1-{[5-Methyl-3-(trifluoromethyl)-1-benzothiophen-2-yl]carbonyl}azetidin-3-yl)-1-(1,3-thiazol-4-ylcarbonyl)pyrrolidin-3-amine<br>MS m/z (M + H$^+$) 495 |
| 185 | (3S)-N-(1-{[6-Methyl-3-(trifluoromethyl)-1-benzothiophen-2-yl]carbonyl}azetidin-3-yl)-1-(1,3-thiazol-4-ylcarbonyl)-pyrrolidin-3-amine<br>MS m/z (M + H$^+$) 495 |
| 186 | (3S)-N-(1-{[6-Methyl-3-(trifluoromethyl)-1-benzothiophen-2-yl]carbonyl}azetidin-3-yl)-1-(1,3-thiazol-2-ylcarbonyl)pyrrolidin-3-amine<br>MS m/z (M + H$^+$) 495 |

Example 13

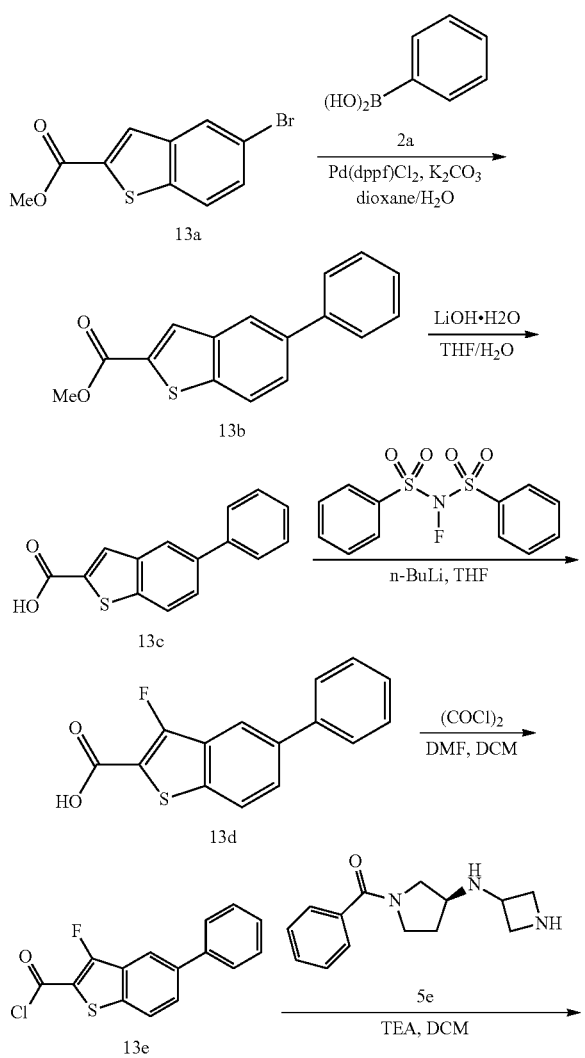

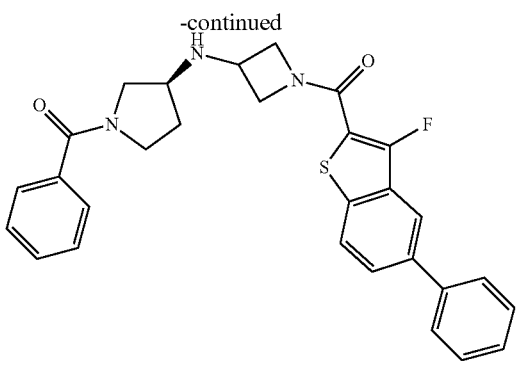

Cpd 173

A. Methyl 5-Phenyl-benzo[b]thiophene-2-carboxylate, 13b

A mixture of compound 13a (542.3 mg, 2 mmol), phenyl boronic acid (2a, 268.2 mg, 2.2 mmol), Pd(dppf)Cl$_2$.CH$_2$Cl$_2$ (98 mg, 0.12 mmol), and K$_2$CO$_3$ (414.6 mg, 3 mmol), in a dioxane (4 mL)/water (1 mL) mixture, was placed in a capped vial and heated at 80° C. overnight. The reaction mixture was then diluted with EtOAc and water. The organic layer was concentrated under reduced pressure and purified by flash column chromatography (silica gel, 2-10% EtOAc/heptane) to give compound 13b (510 mg). MS m/z (M+H$^+$) 269.1.

B. 5-Phenyl-benzo[b]thiophene-2-carboxylic acid, 13c

A solution of compound 13b (510 mg, 1.9 mmol) and LiOH.H$_2$O (319 mg, 7.6 mmol) in THF/H$_2$O (10/10 mL) was stirred at room temperature overnight. The resulting mixture was concentrated and diluted with water. The water layer was acidified with 1N aqueous HCl to pH~4 and extracted with CH$_2$Cl$_2$. The organic solution was dried over Na$_2$SO$_4$ and concentrated to give compound 13c (479 mg), which was used in the next reaction without further purification. MS m/z (M+H$^+$) 255.0.

C. 3-Fluoro-5-phenyl-benzo[b]thiophene-2-carboxylic acid, 13d

To a solution of compound 13c (507 mg, 1.99 mmol) in THF (8 mL) at −70° C. was added n-BuLi (1.6 M in hexane, 2.62 mL, 4.19 mmol). The mixture was stirred at −70° C. for 1 h, then a solution of N-fluorobenzenesulfonimide (817.3 mg, 2.59 mmol) in THF (2 mL) was slowly added. The reaction mixture was allowed to warm to room temperature and was stirred overnight. The resulting mixture was partitioned between dilute aqueous HCl and EtOAc. The organic solution was washed with water and brine, dried over Na$_2$SO$_4$, and concentrated. The residue was tritrated from CH$_2$Cl$_2$, filtered and dried the solid to give compound 13d (391.9 mg). MS m/z (M+H$^+$) 273.0.

D. 3-Fluoro-5-phenyl-benzo[b]thiophene-2-carbonyl chloride, 13e

To a solution of compound 13d (136.2 mg, 0.5 mmol) in CH$_2$Cl$_2$ (5 mL) at room temperature was added (COCl)$_2$ (0.064 mL, 0.75 mmol), followed by DMF (0.01 mL, 0.125 mmol). The reaction mixture was stirred at room temperature for 18 h. The reaction mixture was then concentrated to give compound 13e as a light pink powder, which was used in the next reaction without further purification.

E. (3S)—N-{1-[(3-Fluoro-5-phenyl-1-benzothiophen-2-yl)carbonyl]azetidin-3-yl}-1-(phenylcarbonyl)pyrrolidin-3-amine, Cpd 173

To a solution of compound 5e (42.7 mg, 0.131 mmol) and Et₃N (0.07 mL, 0.5 mmol) in CH₂Cl₂ (2 mL) at 0° C. was slowly added a solution of compound 13e (36.3 mg, 0.125 mmol) in CH₂Cl₂ (1 mL). The reaction was stirred at 0° C. for 2 h, diluted with CH₂Cl₂, and washed with aqueous NaHCO₃. The organic layer was dried over Na₂SO₄ and concentrated. The residue was purified by flash column chromatography (silica gel, % MeOH/EtOAc) to give compound Cpd 173 (16.7 mg). MS m/z (M+H$^+$) 500.

Following the procedure described above for Example 13 and substituting the appropriate reagents, starting materials and purification methods known to those skilled in the art, the following compounds of the present invention were prepared:

| Cpd | Cpd Name and Data |
|---|---|
| 171 | (3S)-N-{1-[(3-Fluoro-5-phenyl-1-benzothiophen-2-yl)carbonyl]azetidin-3-yl}-1-(1,3-thiazol-2-ylcarbonyl)pyrrolidin-3-amine<br>MS m/z (M + H$^+$) 507 |
| 172 | (3S)-N-{1-[(3-Fluoro-5-phenyl-1-benzothiophen-2-yl)carbonyl]azetidin-3-yl}-1-(1,3-thiazol-4-ylcarbonyl)pyrrolidin-3-amine<br>MS m/z (M + H$^+$) 507 |
| 174 | (3S)-N-[1-({3-Fluoro-5-[4-(trifluoromethyl)phenyl]-1-benzothiophen-2-yl}carbonyl)azetidin-3-yl]-1-(1,3-thiazol-2-ylcarbonyl)pyrrolidin-3-amine<br>MS m/z (M + H$^+$) 575 |
| 175 | (3S)-N-[1-({3-Fluoro-5-[4-(trifluoromethyl)phenyl]-1-benzothiophen-2-yl}carbonyl)azetidin-3-yl]-1-(1,3-thiazol-4-ylcarbonyl)pyrrolidin-3-amine<br>MS m/z (M + H$^+$) 575 |
| 176 | (3S)-N-[1-({3-Fluoro-5-[4-(trifluoromethyl)phenyl]-1-benzothiophen-2-yl}carbonyl)azetidin-3-yl]-1-(phenylcarbonyl)pyrrolidin-3-amine<br>MS m/z (M + H$^+$) 568 |
| 177 | (3S)-N-[1-({3-Fluoro-6-[4-(trifluoromethyl)phenyl]-1-benzothiophen-2-yl}carbonyl)azetidin-3-yl]-1-(1,3-thiazol-2-ylcarbonyl)pyrrolidin-3-amine<br>MS m/z (M + H$^+$) 575 |
| 178 | (3S)-N-[1-({3-Fluoro-6-[4-(trifluoromethyl)phenyl]-1-benzothiophen-2-yl}carbonyl)azetidin-3-yl]-1-(1,3-thiazol-4-ylcarbonyl)pyrrolidin-3-amine<br>MS m/z (M + H$^+$) 575 |
| 179 | (3S)-N-[1-({3-Fluoro-6-[4-(trifluoromethyl)phenyl]-1-benzothiophen-2-yl}carbonyl)azetidin-3-yl]-1-(phenylcarbonyl)pyrrolidin-3-amine<br>MS m/z (M + H$^+$) 568 |

Example 14

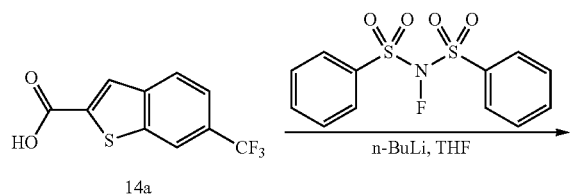

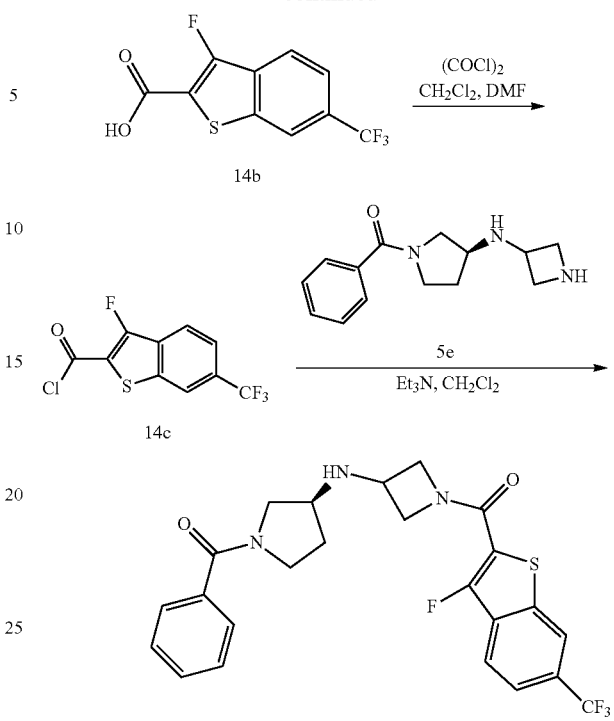

Cpd 89

A. 3-Fluoro-6-trifluoromethyl-benzo[b]thiophene-2-carboxylic acid, 14b

A solution of 6-trifluoromethyl-benzo[b]thiophene-2-carboxylic acid 14a (2.031 mmol, 0.50 g) in THF (8 mL) at −70° C. was treated with a 1.6 M solution of n-BuLi in hexanes (2.66 mL, 4.26 mmol). After 1 h at −70° C., N-fluorobenzenesulfonimide (0.833 g, 2.64 mmol) in THF (2 mL) was slowly added and the reaction was warmed to room temperature. After 1 h the mixture was partitioned between dilute aqueous HCl and EtOAc. The organic layer was washed with water and brine and then concentrated. The residue was triturated with CH₂Cl₂. The off-white precipitate was collected by filtration to provide compound 14b.

B. 3-Fluoro-6-trifluoromethyl-benzo[b]thiophene-2-carbonyl chloride, 14c

The title compound 14c was prepared using the method described in Example 11, substituting compound 14b for compound 11e in Step C.

C. (3S)—N-(1-{[3-Fluoro-6-(trifluoromethyl)-1-benzothiophen-2-yl]carbonyl}azetidin-3-yl)-1-(phenylcarbonyl)pyrrolidin-3-amine, Cpd 89

The title compound Cpd 89 was prepared using the method described in Example 13, substituting compound 14c for compound 13e in Step E. MS m/z (M+H$^+$) 492.

Example 15

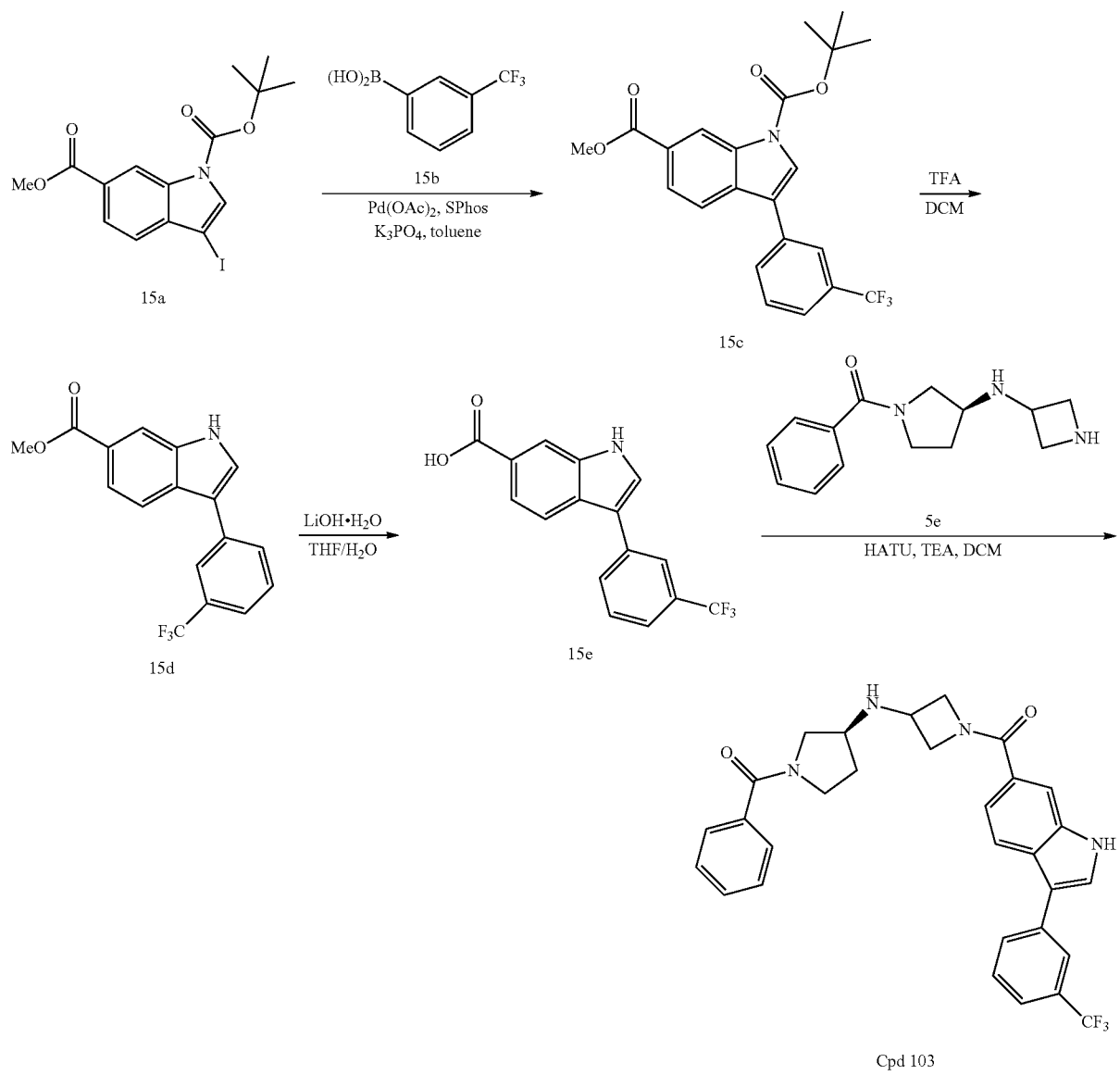

A. 1-tert-Butyl 6-methyl 3-(3-trifluoromethylphenyl)-1H-indole-1,6-dicarboxylate, 15c A mixture of compound 15a (1.00 g, 2.49 mmol), 3-trifluoromethylphenyl boronic acid 15b (710 mg, 3.74 mmol), Pd(OAc)₂ (44.8 mg, 0.2 mmol), 2-dicyclohexylphosphino-2', 6'-dimethoxybiphenyl (SPhos, 204.7 mg, 0.5 mmol), and K₃PO₄ (1.06 g, 4.99 mmol), in toluene (5 mL) was placed in a capped vial and heated at 90° C. under N₂ for 3 h. The reaction mixture was then diluted with EtOAc and water. The organic layer was washed with brine, concentrated under reduced pressure, and purified by flash column chromatography (silica gel, 2-10% EtOAc/heptane) to give compound 15c as a light yellow solid, which was further recrystallized from heptane to obtain a white solid (900 mg). MS m/z (M+H⁺) 420.0.

B. Methyl 3-(3-trifluoromethylphenyl)-1H-indole-6-carboxylate, 15d

To a solution of compound 15c (900 mg, 2.14 mmol) in CH₂Cl₂ (5 mL) was added trifluoroacetic acid (2 mL) at room temperature. The mixture was stirred at room temperature for 2 h. The resulting mixture was concentrated to give compound 15d (840 mg) as a white solid. MS m/z (M+H⁺) 320.0.

C. 3-(3-Trifluoromethyl-phenyl)-1H-indole-6-carboxylic acid, 15e

A solution of compound 15d (TFA salt, 500 mg, 1.15 mmol), and LiOH.H₂O (132.7 mg, 3.16 mmol) in THF/H₂O (10 mL/10 mL) was stirred at 45° C. overnight. The resulting mixture was concentrated and diluted with water. The aqueous layer was acidified with 1N aqueous HCl to pH~4 and extracted with CH₂Cl₂. The organic solution was dried over Na$_2$SO$_4$ and concentrated to give compound 15e (330 mg), which was used in the next reaction without further purification. MS m/z (M+H$^+$) 306.0.

D. (3S)-1-(Phenylcarbonyl)-N-[1-({3-[3-(trifluoromethyl)phenyl]-1H-indol-6-yl}carbonyl)azetidin-3-yl]pyrrolidin-3-amine, Cpd 103

The titled compound 103 was prepared using the method described in Example 5, substituting compound 15d for compound 4g in Step F. MS m/z (M+H$^+$) 533.

Following the procedure described above for Example 15 Step A-C, and substituting the appropriate reagents, starting materials and purification methods known to those skilled in the art, the following intermediate compounds were prepared:

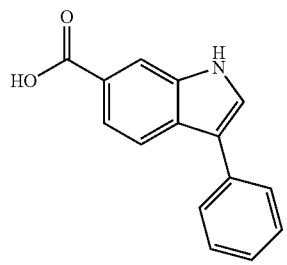

15-I1

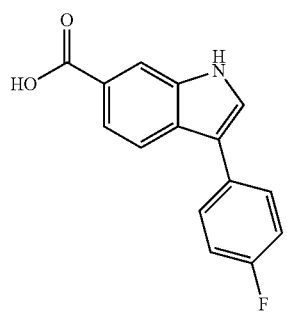

15-I2

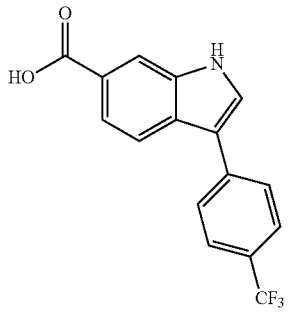

15-I3

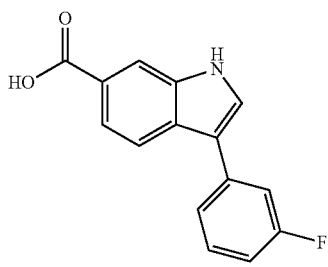

15-I4

Following the procedure described above for Example 15 and substituting the appropriate reagents, starting materials and purification methods known to those skilled in the art, the following compounds of the present invention were prepared:

| Cpd | Cpd Name and Data |
|---|---|
| 57 | (3S)-1-(Phenylcarbonyl)-N-{1-[(3-phenyl-1H-indol-6-yl)carbonyl]azetidin-3-yl}-pyrrolidin-3-amine<br>MS m/z (M + H$^+$) 465 |
| 101 | (3S)-1-(Phenylcarbonyl)-N-[1-({3-[4-(trifluoromethyl)phenyl]-1H-indol-6-yl}carbonyl)azetidin-3-yl]pyrrolidin-3-amine<br>MS m/z (M + H$^+$) 533 |
| 104 | (3S)-1-(1,3-Thiazol-2-ylcarbonyl)-N-[1-({3-[4-(trifluoromethyl)phenyl]-1H-indol-6-yl}carbonyl)azetidin-3-yl]pyrrolidin-3-amine<br>MS m/z (M + H$^+$) 540 |
| 105 | (3S)-1-(1,3-Thiazol-2-ylcarbonyl)-N-[1-({3-[3-(trifluoromethyl)phenyl]-1H-indol-6-yl}carbonyl)azetidin-3-yl]pyrrolidin-3-amine<br>MS m/z (M + H$^+$) 540 |
| 106 | (3S)-1-(1,3-Thiazol-4-ylcarbonyl)-N-[1-({3-[3-(trifluoromethyl)phenyl]-1H-indol-6-yl}carbonyl)azetidin-3-yl]pyrrolidin-3-amine<br>MS m/z (M + H$^+$) 540 |
| 187 | (3S)-N-{1-[(3-Phenyl-1H-indol-6-yl)carbonyl]azetidin-3-yl}-1-(1,3-thiazol-2-ylcarbonyl)pyrrolidin-3-amine<br>MS m/z (M + H$^+$) 472 |
| 188 | (3S)-N-{1-[(3-Phenyl-1H-indol-6-yl)carbonyl]azetidin-3-yl}-1-(1,3-thiazol-4-ylcarbonyl)pyrrolidin-3-amine<br>MS m/z (M + H$^+$) 472 |
| 189 | (3S)-N-(1-{[3-(4-Fluorophenyl)-1H-indol-6-yl]carbonyl}azetidin-3-yl)-1-(1,3-thiazol-2-ylcarbonyl)pyrrolidin-3-amine<br>MS m/z (M + H$^+$) 490 |

| Cpd | Cpd Name and Data |
|---|---|
| 190 | (3S)-N-(1-{[3-(4-Fluorophenyl)-1H-indol-6-yl]carbonyl}azetidin-3-yl)-1-(1,3-thiazol-4-ylcarbonyl)pyrrolidin-3-amine<br>MS m/z (M + H$^+$) 490 |
| 191 | (3S)-N-(1-{[3-(4-Fluorophenyl)-1H-indol-6-yl]carbonyl}azetidin-3-yl)-1-(phenylcarbonyl)pyrrolidin-3-amine<br>MS m/z (M + H$^+$) 483 |
| 202 | (3S)-N-(1-{[3-(3-Fluorophenyl)-1H-indol-6-yl]carbonyl}azetidin-3-yl)-1-(1,3-thiazol-2-ylcarbonyl)pyrrolidin-3-amine<br>MS m/z (M + H$^+$) 490 |
| 203 | (3S)-N-(1-{[3-(3-Fluorophenyl)-1H-indol-6-yl]carbonyl}azetidin-3-yl)-1-(1,3-thiazol-4-ylcarbonyl)pyrrolidin-3-amine<br>MS m/z (M + H$^+$) 490 |
| 204 | (3S)-N-(1-{[3-(3-Fluorophenyl)-1H-indol-6-yl]carbonyl}azetidin-3-yl)-1-(phenylcarbonyl)pyrrolidin-3-amine<br>MS m/z (M + H$^+$) 483 |

Example 15a

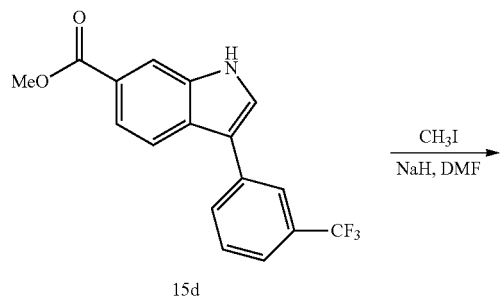

15d

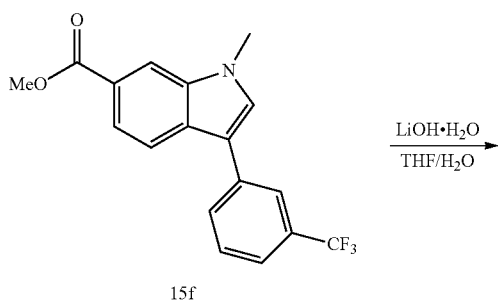

15f

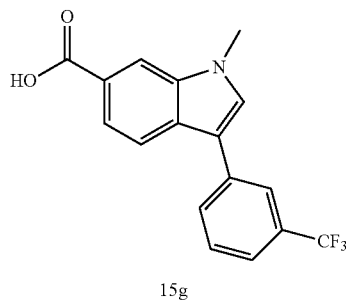

15g

E. Methyl 3-(3-trifluoromethyl-phenyl)-1-methyl-1H-indole-6-carboxylate, 15f To a solution of compound 15d (300 mg, 0.78 mmol) in DMF (3 mL) was added NaH (60% in mineral oil, 68.9 mg, 1.72 mmol) at 0° C. The mixture was stirred at 0° C. for 30 min, then CH$_3$I (0.053 mL, 0.86 mmol) was added and stirring continued at 0° C. for another 1 h. The resulting mixture was diluted with EtOAc and water. The organic layer was washed with brine and concentrated. The residue was recrystallized from heptane, filtered and the solid dried to give compound 15f (265 mg) as a light yellow solid. MS m/z (M+H$^+$) 284.1.

F. 3-(3-Trifluoromethyl-phenyl)-1-methyl-1H-indole-6-carboxylic acid, 15g

A solution of compound 15f (264 mg, 0.93 mmol), and LiOH.H$_2$O (156.4 mg, 3.73 mmol) in THF/H$_2$O (10 mL/10 mL) was stirred at 45° C. for 5 h. The resulting mixture was concentrated and diluted with water. The aqueous layer was acidified with 1N aqueous HCl to pH~4 and extracted with CH$_2$Cl$_2$. The organic solution was dried over Na$_2$SO$_4$ and concentrated to give compound 15g (252 mg), which was used in the next reaction without further purification. MS m/z (M+H$^+$) 270.1.

Following the procedure described above for Example 15a and substituting the appropriate reagents, starting materials and purification methods known to those skilled in the art, the following intermediate compounds were prepared:

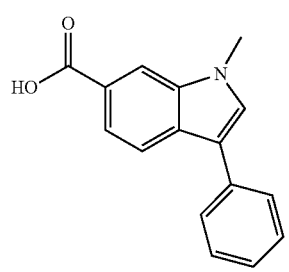

15a-I1

-continued

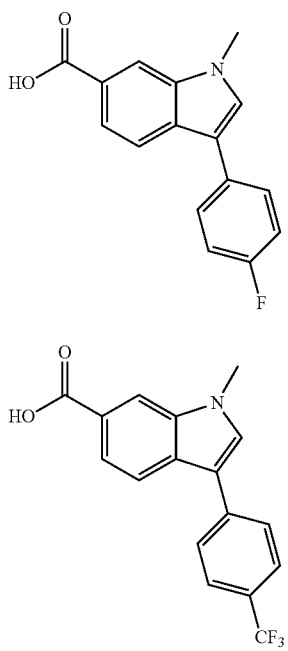

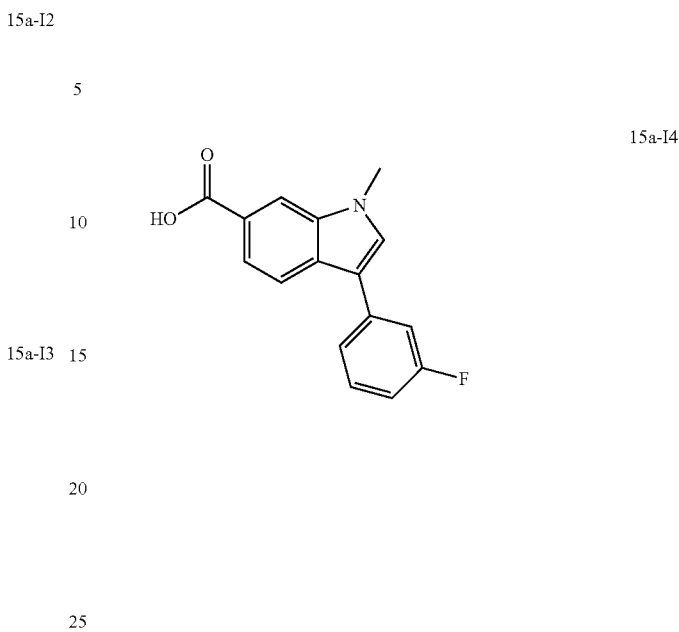

Following the procedure described above for Example 15a and substituting the appropriate reagents, starting materials and purification methods known to those skilled in the art, the following compounds of the present invention were prepared:

| Cpd | Cpd Name and Data |
|---|---|
| 64 | (3S)-N-{1-[(1-Methyl-3-phenyl-1H-indol-6-yl)carbonyl]azetidin-3-yl}-1-(phenylcarbonyl)pyrrolidin-3-amine<br>MS m/z (M + H$^+$) 479 |
| 162 | (3S)-N-[1-({1-Methyl-3-[3-(trifluoromethyl)phenyl]-1H-indol-6-yl}carbonyl)azetidin-3-yl]-1-(1,3-thiazol-2-ylcarbonyl)pyrrolidin-3-amine<br>MS m/z (M + H$^+$) 554.2 |
| 163 | (3S)-N-[1-({1-Methyl-3-[4-(trifluoromethyl)phenyl]-1H-indol-6-yl}carbonyl)azetidin-3-yl]-1-(1,3-thiazol-2-ylcarbonyl)pyrrolidin-3-amine<br>MS m/z (M + H$^+$) 554 |
| 164 | (3S)-N-[1-({1-Methyl-3-[3-(trifluoromethyl)phenyl]-1H-indol-6-yl}carbonyl)azetidin-3-yl]-1-(1,3-thiazol-4-ylcarbonyl)pyrrolidin-3-amine<br>MS m/z (M + H$^+$) 554 |
| 165 | (3S)-N-[1-({1-Methyl-3-[4-(trifluoromethyl)phenyl]-1H-indol-6-yl}carbonyl)azetidin-3-yl]-1-(1,3-thiazol-4-ylcarbonyl)pyrrolidin-3-amine<br>MS m/z (M + H$^+$) 554 |
| 166 | (3S)-N-[1-({1-Methyl-3-[3-(trifluoromethyl)phenyl]-1H-indol-6-yl}carbonyl)azetidin-3-yl]-1-(phenylcarbonyl)pyrrolidin-3-amine<br>MS m/z (M + H$^+$) 547 |
| 169 | (3S)-N-{1-[(1-Methyl-3-phenyl-1H-indol-6-yl)carbonyl]azetidin-3-yl}-1-(1,3-thiazol-2-ylcarbonyl)pyrrolidin-3-amine<br>MS m/z (M + H$^+$) 486 |
| 170 | (3S)-N-{1-[(1-Methyl-3-phenyl-1H-indol-6-yl)carbonyl]azetidin-3-yl}-1-(1,3-thiazol-4-ylcarbonyl)pyrrolidin-3-amine<br>MS m/z (M + H$^+$) 486 |
| 192 | (3S)-N-(1-{[3-(4-Fluorophenyl)-1-methyl-1H-indol-6-yl]carbonyl}azetidin-3-yl)-1-(1,3-thiazol-2-ylcarbonyl)pyrrolidin-3-amine<br>MS m/z (M + H$^+$) 504 |
| 193 | (3S)-N-(1-{[3-(4-Fluorophenyl)-1-methyl-1H-indol-6-yl]carbonyl}azetidin-3-yl)-1-(1,3-thiazol-4-ylcarbonyl)pyrrolidin-3-amine<br>MS m/z (M + H$^+$) 504 |
| 194 | (3S)-N-(1-{[3-(4-Fluorophenyl)-1-methyl-1H-indol-6-yl]carbonyl}azetidin-3-yl)-1-(phenylcarbonyl)pyrrolidin-3-amine<br>MS m/z (M + H$^+$) 497 |
| 205 | (3S)-N-(1-{[3-(3-Fluorophenyl)-1-methyl-1H-indol-6-yl]carbonyl}azetidin-3-yl)-1-(1,3-thiazol-2-ylcarbonyl)pyrrolidin-3-amine<br>MS m/z (M + H$^+$) 504 |
| 206 | (3S)-N-(1-{[3-(3-Fluorophenyl)-1-methyl-1H-indol-6-yl]carbonyl}azetidin-3-yl)-1-(1,3-thiazol-4-ylcarbonyl)pyrrolidin-3-amine<br>MS m/z (M + H$^+$) 504 |

-continued
| Cpd | Cpd Name and Data |
|---|---|
| 207 | (3S)-N-(1-{[3-(3-Fluorophenyl)-1-methyl-1H-indol-6-yl]carbonyl}azetidin-3-yl)-1-(phenylcarbonyl)pyrrolidin-3-amine<br>MS m/z (M + H$^+$) 497 |
Example 16
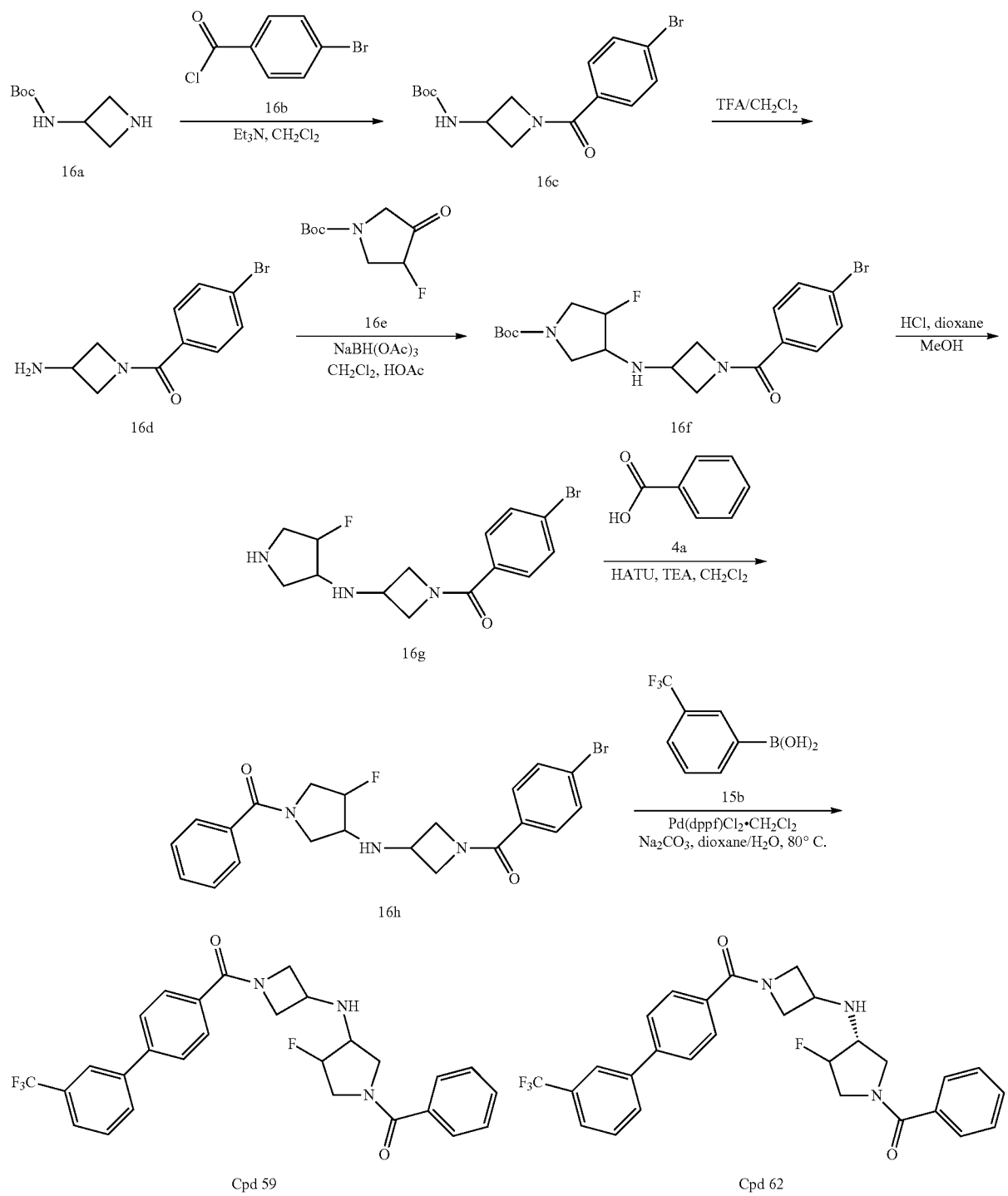
Cpd 59
Cpd 62

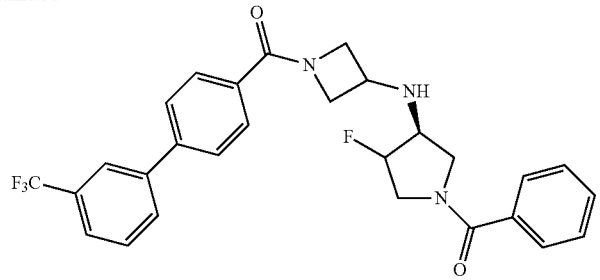

Cpd 63

A. tert-Butyl (1-(4-bromobenzoyl)azetidin-3-yl)carbamate, Cpd 16c

To a solution of compound 16a (1.02 g, 5.92 mmol) and Et₃N (1.24 mL, 8.88 mmol) in CH₂Cl₂ (25 mL) at 0° C. was slowly added a solution of compound 16b (1.36 g, 6.22 mmol) in CH₂Cl₂ (5 mL). The reaction was stirred at 0° C. for 2 h, diluted with CH₂Cl₂, and washed with aqueous NaHCO₃. The organic layer was dried over Na₂SO₄ and concentrated. The residue was purified by flash column chromatography (silica gel, 35% EtOAc/hexanes) to give compound 16c (810 mg). MS m/z (M+H⁺) 356.0.

B. (3-Aminoazetidin-1-yl)(4-bromophenyl)methanone, Cpd 16d

To a solution of compound 16c (810 mg, 2.28 mmol) in CH₂Cl₂ (10 mL) was added trifluoroacetic acid (7 mL) at room temperature. The mixture was stirred at room temperature for 2 h. The resulting mixture was concentrated. To the residue was added CH₂Cl₂ and 1N aqueous NaOH solution until the pH of the aqueous layer was approximately 8. The organic phase was washed with brine, dried over anhydrous Na₂SO₄ and concentrated under reduced pressure to give compound 16d (570 mg). MS m/z (M+H⁺) 254, 256.

C. tert-Butyl 3-((1-(4-bromobenzoyl)azetidin-3-yl)amino)-4-fluoropyrrolidine-1-carboxylate, 16f The title compound 16f was prepared using the method described in Example 5, substituting compound 16d for compound 5a and compound 16e for compound 1e in Step A. MS m/z (M+H⁺) 441, 443.

D. (4-Bromophenyl)(3-((4-fluoropyrrolidin-3-yl)amino)azetidin-1-yl)methanone, 16g The title compound 16g was prepared using the method described in Example 5, substituting compound 16f for compound 5d in Step E. MS m/z (M+H⁺).

E. (3-((1-Benzoyl-4-fluoropyrrolidin-3-yl)amino)azetidin-1-yl)(4-bromophenyl)methanone, 16h The title compound was prepared using the method described in Example 5, substituting compound 16g for compound 5e and compound 4a for compound 4g in Step F. MS m/z (M+H⁺) 341, 343.

F. (3-((1-Benzoyl-4-fluoropyrrolidin-3-yl)amino)azetidin-1-yl)(3'-(trifluoromethyl)-[1,1'-biphenyl]-4-yl)methanone, Cpd 59, (3-(((3R)-1-benzoyl-4-fluoropyrrolidin-3-yl)amino)azetidin-1-yl)(3'-(trifluoromethyl)-[1,1'-biphenyl]-4-yl)methanone, Cpd 62 and (3-(((3S)-1-benzoyl-4-fluoropyrrolidin-3-yl)amino)azetidin-1-yl)(3'-(trifluoromethyl)-[1,1'-biphenyl]-4-yl)methanone, Cpd 63

The title compounds were prepared using the method described in Example 8, substituting compound 16h for compound 22 and compound 15b for phenyl boronic acid. The crude products were purified by column chromatography (silica gel, 10% MeOH/EtOAc+0.5% TEA) to give compound 59. Compound 59 was further separated by a chiral column (Chiralpak AD-H, 50% IPA/hexanes, 0.65 mL/min) to give the first fraction as compound 62 MS m/z (M+H⁺) 548 and the second fraction as compound 63 MS m/z (M+H⁺) 512.

Following the procedure described above for Example 16 and substituting the appropriate reagents, starting materials and purification methods known to those skilled in the art, the following compounds of the present invention were prepared:

| Cpd | Cpd Name and Data |
|---|---|
| 58 | N-[1-(Biphenyl-4-ylcarbonyl)azetidin-3-yl]-4-fluoro-1-(phenylcarbonyl)pyrrolidin-3-amine<br>MS m/z (M + H⁺) 444 |
| 60 | (3R)-N-[1-(Biphenyl-4-ylcarbonyl)azetidin-3-yl]-4-fluoro-1-(phenylcarbonyl)pyrrolidin-3-amine<br>MS m/z (M + H⁺) 444 |
| 61 | (3S)-N-[1-(Biphenyl-4-ylcarbonyl)azetidin-3-yl]-4-fluoro-1-(phenylcarbonyl)pyrrolidin-3-amine<br>MS m/z (M + H⁺) 480 |

Example 17

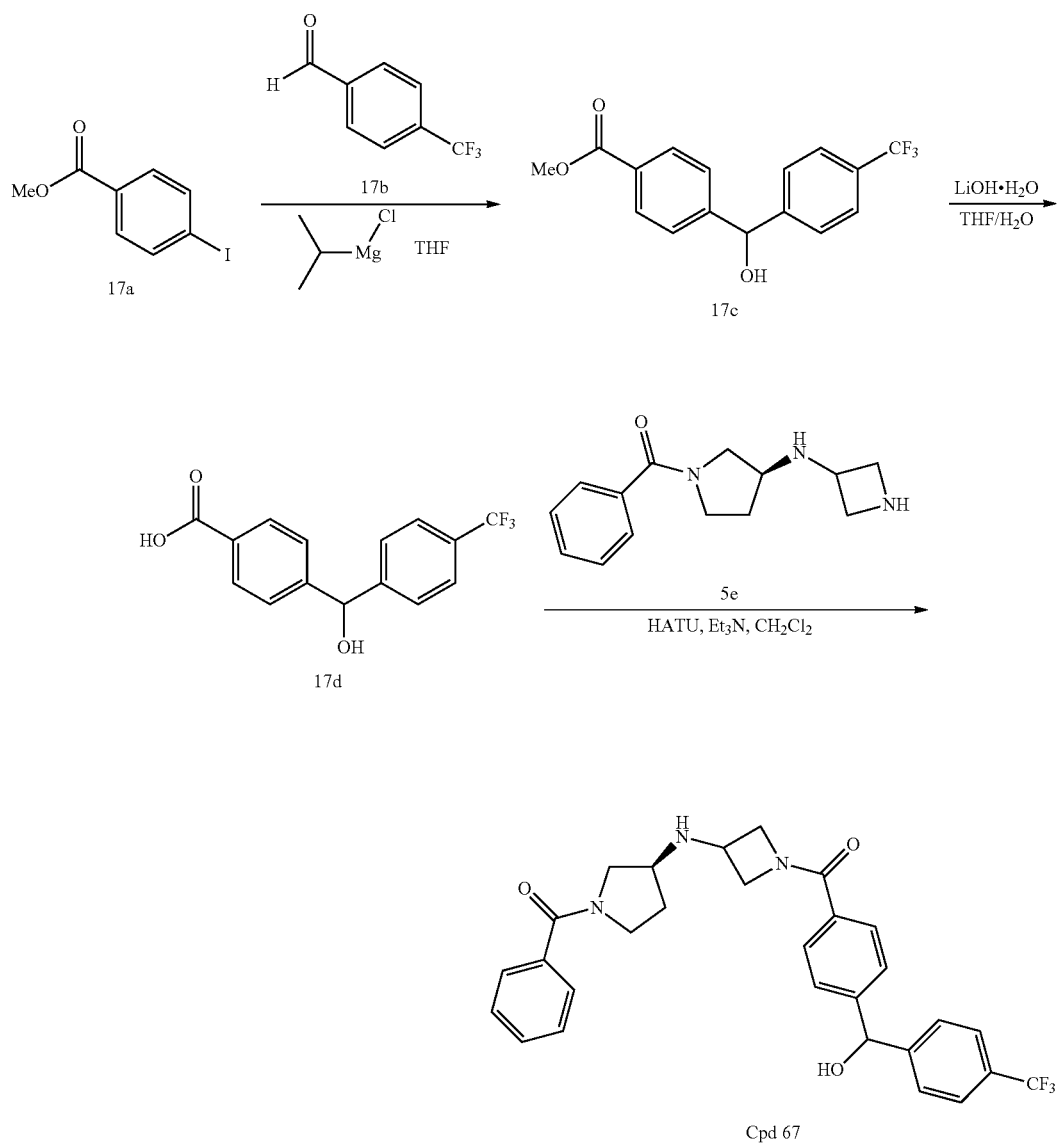

A. Methyl 4-(hydroxy(4-(trifluoromethyl)phenyl)methyl)benzoate, 17c

To a solution of methyl 4-iodobenzoate 17a (2.1 g, 8 mmol) in 10 mL of dry THF was added i-propyl magnesium chloride (2M in THF, 4.2 mL, 8.4 mmol) dropwise under $N_2$ at −20° C. The solution was stirred for 30 min. The THF solution was then added slowly to a solution of 4-trifluoromethylbenzaldehyde 17b (1.1 mL, 8 mmol) in THF (20 mL) at −40° C. After 20 min, the reaction mixture was allowed to warm up slowly to room temperature. The reaction was quenched with saturated aqueous $NH_4Cl$ and extracted with EtOAc. The organic layer was concentrated and purified by flash column chromatography (silica gel, 15% EtOAc/hexanes) to give compound 17c as a white solid.

B. 4-(Hydroxy(4-(trifluoromethyl)phenyl)methyl)benzoic acid, 17d

The title compound 17d was prepared using the method described in Example 13, substituting compound 17c for compound 13b in Step B.

C. ((3-(((S)-1-Benzoylpyrrolidin-3-yl)amino)azetidin-1-yl)(4-(hydroxy(4-(trifluoromethyl)phenyl)methyl)phenyl)methanone, Cpd 67

The title compound 67 was prepared using the method described in Example 5, substituting compound 16g for compound 5e and compound 4a for compound 4g in Step F. MS m/z (M+H$^+$) 526.

Example 17a

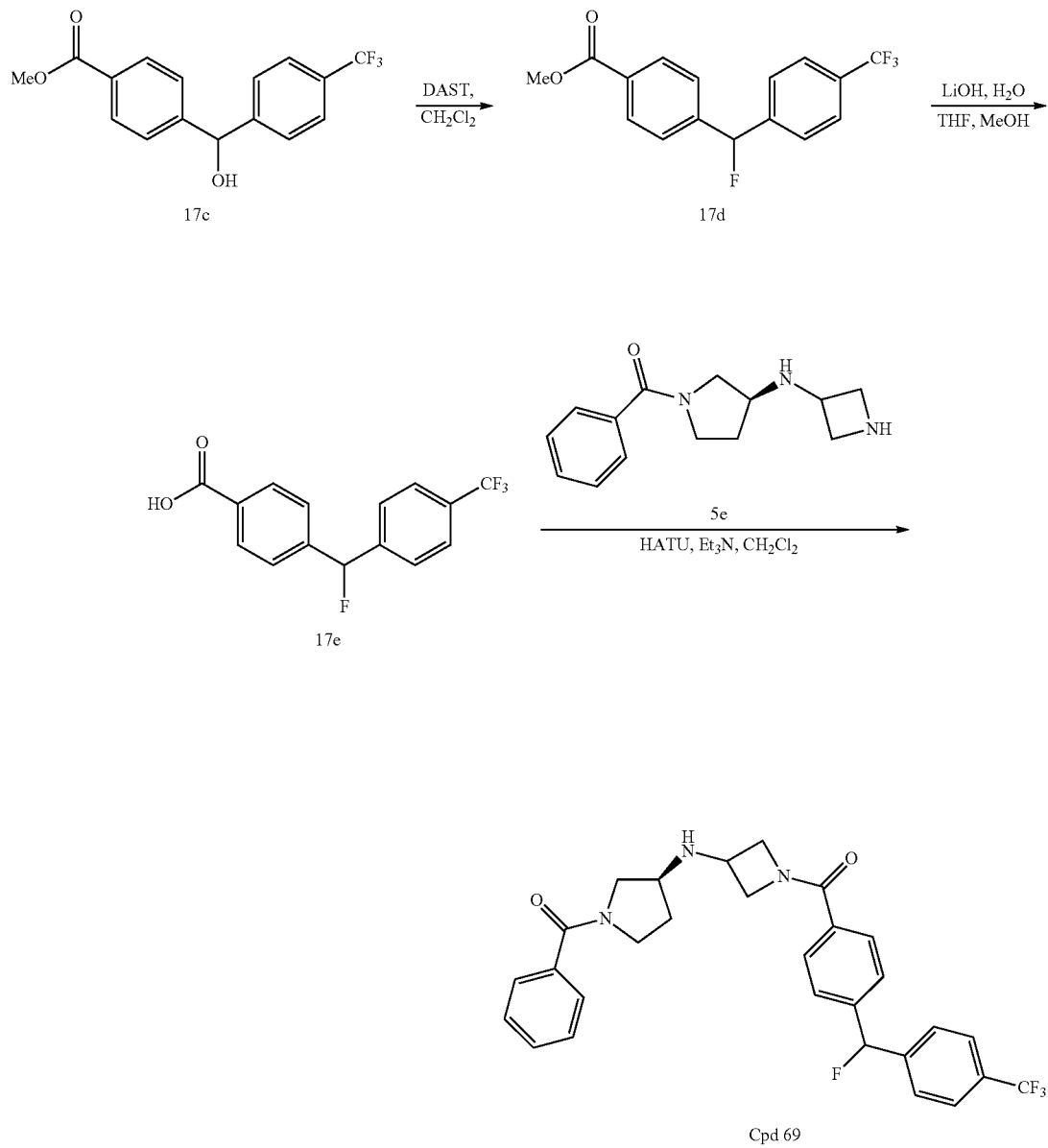

A. 4 Methyl 4-(fluoro(4-(trifluoromethyl)phenyl)methyl)benzoate, 17d

To a solution of compound 63c (300 mg, 0.97 mmol) in CH$_2$Cl$_2$ was added DAST (0.133 mL, 1.015 mmol) dropwise at −78° C. under N$_2$. The reaction was kept at −78° C. for 30 min and then quenched with aqueous NaHCO$_3$ solution at 0° C. The reaction was diluted with CH$_2$Cl$_2$ and the organic solution was concentrated. The crude material was purified flash column chromatography (silica gel, 10% EtOAc/hexanes) to give compound 17d.

B. 4-(Fluoro(4-(trifluoromethyl)phenyl)methyl)benzoic acid, 17e

The title compound 17e was prepared using the method described in Example 13, substituting compound 17d for compound 13b in Step B.

C. N-{1-[(4-{Fluoro[4-(trifluoromethyl)phenyl]methyl}phenyl)carbonyl]azetidin-3-yl}-1-(phenylcarbonyl)pyrrolidin-3-amine, Cpd 69

The title compound 69 was prepared using the method described in Example 5, substituting compound 17e for compound 4g in Step F. MS m/z (M+1-1') 526.

Example 17b

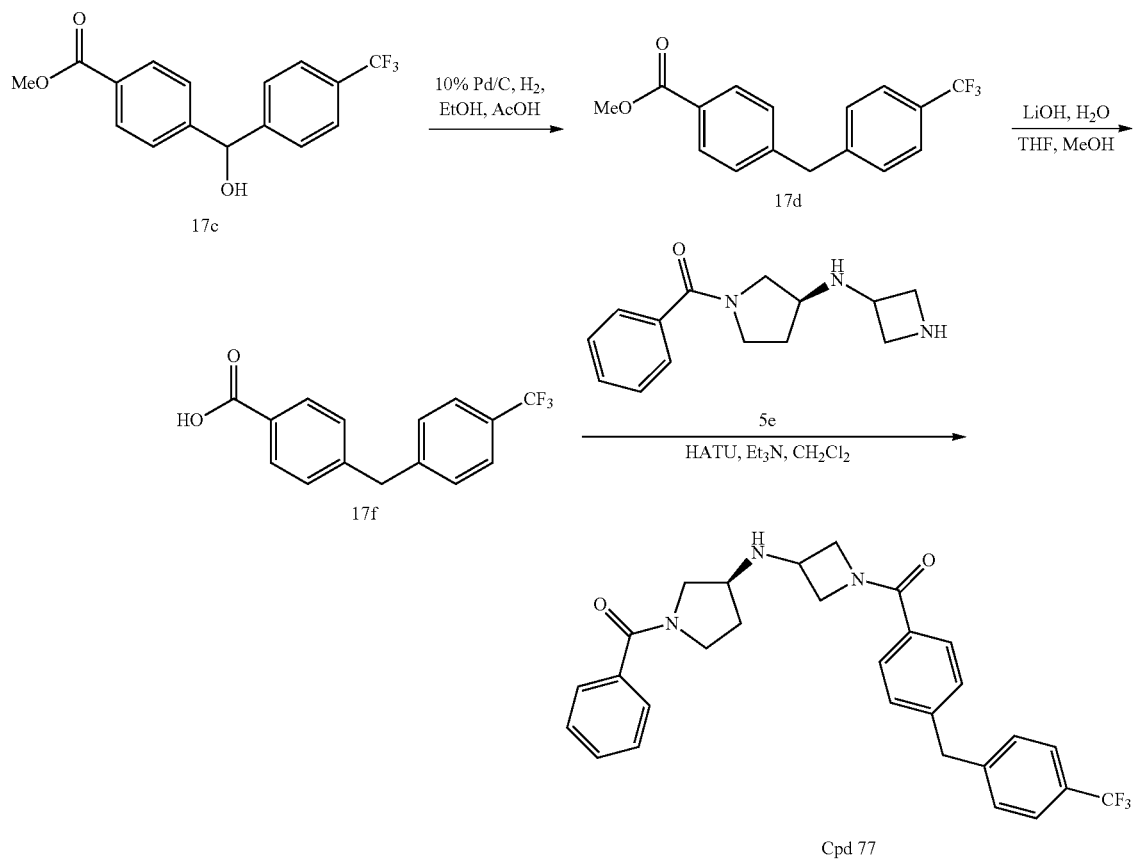

A. Methyl 4-(4-(trifluoromethyl)benzyl)benzoate, Cpd 17d

A solution of compound 17c (250 g, 0.806 mmol), 10% Pd/C (50 mg) in EtOH (18 mL) and AcOH (2 mL) was hydrogenated under 40 psi hydrogen pressure in a Parr apparatus overnight. The reaction was filtered through a pad of diatomaceous earth and the organic solution was concentrated. The crude product was purified by flash column chromatography (silica gel, 10% EtOAc/hexanes) to give compound 17d (120 mg) and unreacted starting material compound 17c (100 mg).

B. 4-(4-(trifluoromethyl)benzyl)benzoic acid, Cpd 17f

The title compound 17f was prepared using the method described in Example 13, substituting compound 17d for compound 13b in Step B.

C. (S)-(3-((1-Benzoylpyrrolidin-3-yl)amino)azetidin-1-yl)(4-(4-(trifluoromethyl)benzyl)phenyl)methanone, Cpd 77

The title compound 77 was prepared using the method described in Example 5, substituting compound 17f for compound 4g in Step F. MS m/z (M+1-1') 508.

Following the procedure described above for Example 17b and substituting the appropriate reagents, starting materials and purification methods known to those skilled in the art, the following compounds of the present invention were prepared:

| Cpd | Cpd Name and Data |
|---|---|
| 144 | (3S)-1-(1,3-Thiazol-4-ylcarbonyl)-N-[1-({4-[4-(trifluoromethyl)benzyl]phenyl}carbonyl)azetidin-3-yl]pyrrolidin-3-amine<br>MS m/z (M + H⁺) 515. |

Example 17c

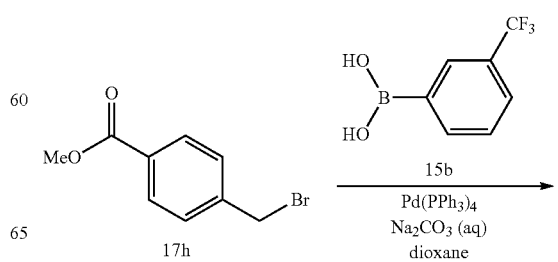

91

-continued

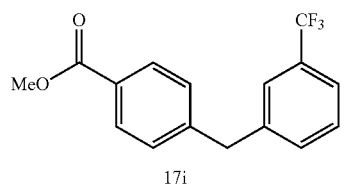

17i

A. Methyl 4-(3-(trifluoromethyl)benzyl)benzoate, Cpd 17i

A mixture of 4-bromomethyl-benzoic acid methyl ester 17h (1 g, 4.37 mmol), 3-trifluoromethylphenylboronic acid 15b (1 g, 5.25 mmol) and Pd(PPh$_3$)$_4$ (50 mg, 0.044 mmol) in dioxane (15 mL) was stirred at room temperature for 1 min. An aqueous solution of Na$_2$CO$_3$ (2M, 4 mL) was added. The resulting solution was heated at 90° C. for 5 h and was then cooled to room temperature. The reaction was partitioned between EtOAc and water. The organic phase was concentrated and purified by flash column chromatography (silica gel, 5% EtOAc/hexanes) to give compound 17i.

Following the procedure described above for Example 17b, Step B and Step C and substituting compound 17i for compound 17d, the following compounds of the present invention were prepared:

| Cpd | Cpd Name and Data |
|---|---|
| 126 | (3S)-1-(Phenylcarbonyl)-N-[1-({4-[3-(trifluoromethyl)benzyl]phenyl}carbonyl)azetidin-3-yl]pyrrolidin-3-amine<br>MS m/z (M + H$^+$) 508 |
| 127 | (3S)-1-(1,3-Thiazol-4-ylcarbonyl)-N-[1-({4-[3-(trifluoromethyl)benzyl]phenyl}carbonyl)azetidin-3-yl]pyrrolidin-3-amine<br>MS m/z (M + H$^+$) 515 |

Example 18

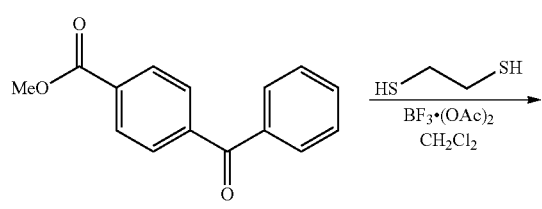

18a

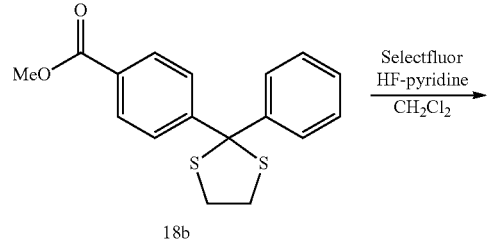

18b

92

-continued

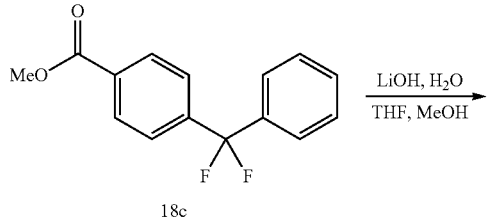

18c

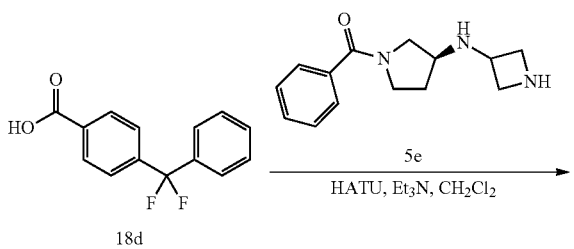

18d

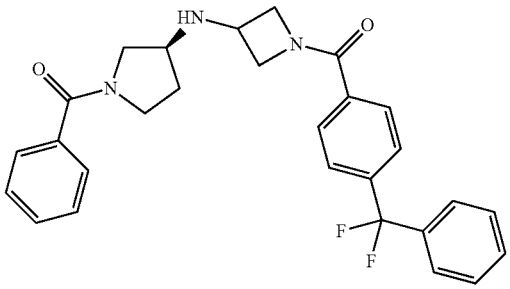

Cpd 73

A. Methyl 4-(2-phenyl-1,3-dithiolan-2-yl)benzoate, 18b

Methyl 4-benzoylbenzoate 18a (0.50 g, 2.08 mmol) and BF$_3$·(OAc)$_2$ (0.73 mL, 5.2 mmol) were dissolved in dry CH$_2$Cl$_2$ under a N$_2$ atmosphere. Ethane-1,2-dithiol (0.333 mL, 3.95 mmol) was added and the solution was stirred overnight. The reaction mixture was partitioned between CH$_2$Cl$_2$ and water. The organic layer was concentrated and purified by flash column chromatography (silica gel, 10% EtOAc/hexanes) to afford compound 18b.

B. Methyl 4-(difluoro(phenyl)methyl)benzoate, 18c

1-Chloromethyl-4-fluoro-1,4-diazoniabicyclo[2.2.2]octane bis(tetrafluoroborate) (Selectfluor) (381 mg, 1.07 mmol) and HF-pyridine reagent (1.5 mL, HF: Pyridine=70:30 wt %) were dissolved in CH$_2$Cl$_2$ (4 mL) in a polyethylene bottle and cooled to 0° C. A solution of compound 18b (162 mg, 0.512 mmol) in CH$_2$Cl$_2$ (2 mL) was slowly added and the mixture was stirred for 45 min at room temperature. The solution was extracted with CH$_2$Cl$_2$, and the combined organics were dried over anhydrous Na$_2$SO$_4$ and concentrated. A crude product was purified by flash column chromatography (silica gel, 5% EtOAc/hexanes) to afford compound 18c as aclear oil.

C. 4-(Difluoro(phenyl)methyl)benzoic acid, 18d

The title compound 18d was prepared using the method described in Example 13, substituting compound 17c for compound 13b in Step B.

D. (3S)—N-[1-({4-[Difluoro(phenyl)methyl] phenyl}carbonyl)azetidin-3-yl]-1-(phenylcarbonyl) pyrrolidin-3-amine, Cpd 73

The title compound 73 was prepared using the method described in Example 5, substituting compound 18d for compound 4g in Step F. MS m/z (M+H$^+$) 476.

Example 19

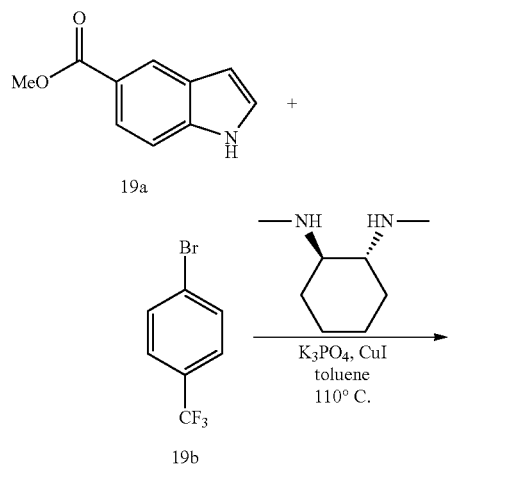

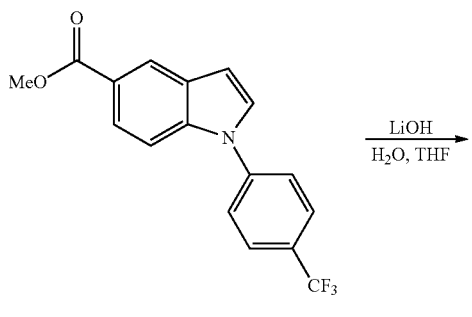

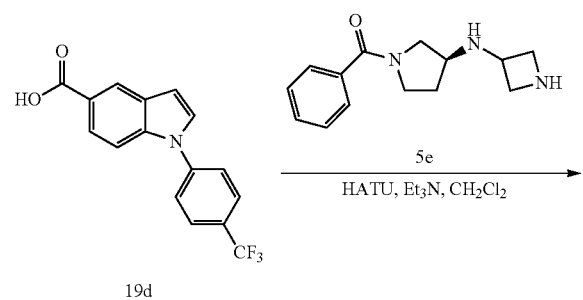

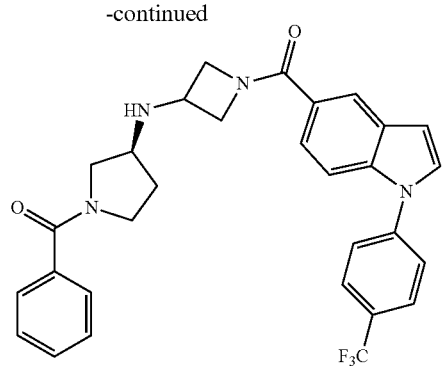

Cpd 154

A. Methyl 1-(4-trifluoromethylphenyl)-indole-5-carboxylate, 19c

A mixture of methyl indole-5-carboxylate 19a (2 g, 11.4 mmol), 1-bromo-4-trifluoromethyl-benzene 19b (2.8 g, 12.5 mmol), CuI (0.22 g, 1.14 mmol), trans-N,N'-dimethylcyclohexane-1,2-diamine (0.54 mL, 3.43 mmol), and K$_3$PO$_4$ (6.06 g, 28.5 mmol) in toluene (12 mL) was heated at 110° C. for 7 h. The reaction mixture was diluted with CH$_2$Cl$_2$ and filtered. The solution was concentrated and the residue was purified by flash column chromatography (silica gel, 20% EtOAc/heptane) to give compound 19c (3.0 g).

B. (4-Trifluoromethylphenyl)-indole-5-carboxylate acid, 19d

The title compound 19d was prepared using the method described in Example 15, substituting compound 19c for compound 15d in Step C.

C. (3S)-1-(Phenylcarbonyl)-N-[1-({1-[4-(trifluoromethyl)phenyl]-1H-indol-5-yl}carbonyl)azetidin-3-yl] pyrrolidin-3-amine, Cpd 154

The title compound 154 was prepared using the method described in Example 5, substituting compound 19d for compound 4g in Step F. MS m/z (M+H$^+$) 533.

Following the procedure described above for Example 19, Steps A and B, and substituting the appropriate reagents, starting materials, and purification methods known to those skilled in the art, the following intermediate compounds were prepared:

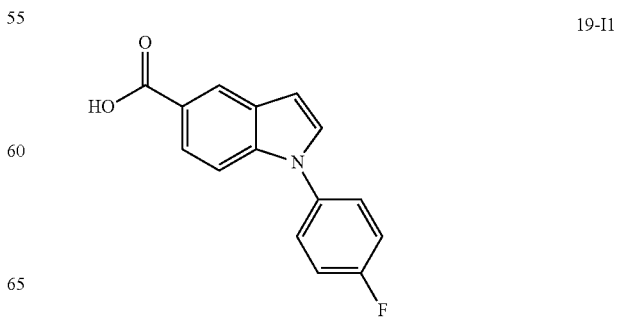

19-I1

-continued

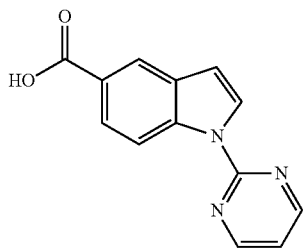
19-I2

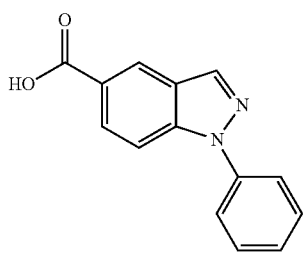
19-I3

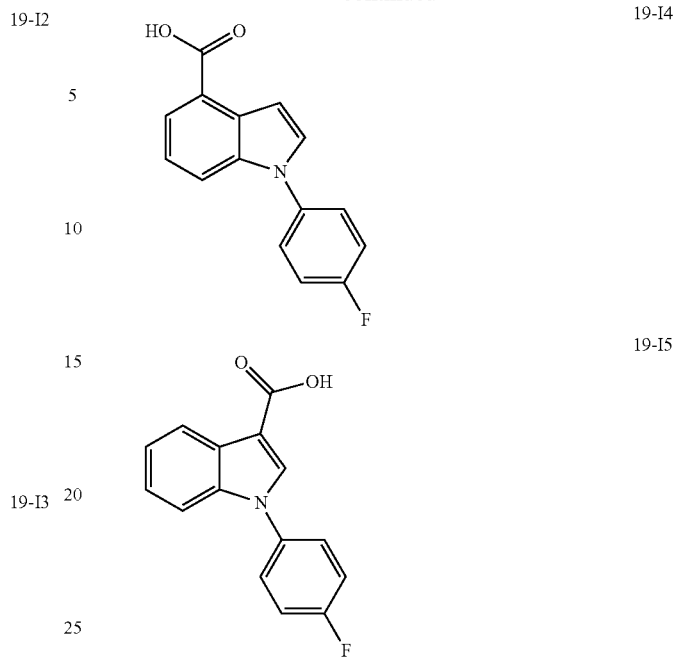

Following the procedure described above for Example 19 and substituting the appropriate reagents, starting materials and purification methods known to those skilled in the art, the following compounds of the present invention were prepared:

| Cpd | Cpd Name and Data |
|---|---|
| 118 | (3S)-1-(1,3-Thiazol-2-ylcarbonyl)-N-[1-({1-[4-(trifluoromethyl)phenyl]-1H-indol-5-yl}carbonyl)azetidin-3-yl]pyrrolidin-3-amine<br>MS m/z (M + H$^+$) 540 |
| 119 | (3S)-N-{1-[(1-Pyrimidin-2-yl-1H-indol-5-yl)carbonyl]azetidin-3-yl}-1-(1,3-thiazol-2-ylcarbonyl)pyrrolidin-3-amine<br>MS m/z (M + H$^+$) 474 |
| 120 | (3S)-N-{1-[(1-Phenyl-1H-indazol-5-yl)carbonyl]azetidin-3-yl}-1-(1,3-thiazol-2-ylcarbonyl)pyrrolidin-3-amine<br>MS m/z (M + H$^+$) 473 |
| 155 | (3S)-N-{1-[(1-Phenyl-1H-indazol-5-yl)carbonyl]azetidin-3-yl}-1-(1,3-thiazol-2-ylcarbonyl)pyrrolidin-3-amine<br>MS m/z (M + H$^+$) 467 |
| 156 | (3S)-1-(Phenylcarbonyl)-N-{1-[(1-phenyl-1H-indazol-5-yl)carbonyl]azetidin-3-yl}pyrrolidin-3-amine<br>MS m/z (M + H$^+$) 466 |
| 158 | (3S)-1-(1,3-Thiazol-4-ylcarbonyl)-N-[1-({1-[4-(trifluoromethyl)phenyl]-1H-indol-5-yl}carbonyl)azetidin-3-yl]pyrrolidin-3-amine<br>MS m/z (M + H$^+$) 540 |
| 159 | (3S)-N-(1-{[1-(4-Fluorophenyl)-1H-indol-5-yl]carbonyl}azetidin-3-yl)-1-(1,3-thiazol-2-ylcarbonyl)pyrrolidin-3-amine<br>MS m/z (M + H$^+$) 490 |
| 160 | (3S)-N-(1-{[1-(4-Fluorophenyl)-1H-indol-5-yl]carbonyl}azetidin-3-yl)-1-(1,3-thiazol-4-ylcarbonyl)pyrrolidin-3-amine<br>MS m/z (M + H$^+$) 490 |
| 161 | (3S)-N-(1-{[1-(4-Fluorophenyl)-1H-indol-5-yl]carbonyl}azetidin-3-yl)-1-(phenylcarbonyl)pyrrolidin-3-amine<br>MS m/z (M + H$^+$) 483 |
| 214 | (3S)-N-(1-{[1-(4-Fluorophenyl)-1H-indol-4-yl]carbonyl}azetidin-3-yl)-1-(1,3-thiazol-2-ylcarbonyl)pyrrolidin-3-amine<br>MS m/z (M + H$^+$) 490 |
| 215 | (3S)-N-(1-{[1-(4-Fluorophenyl)-1H-indol-4-yl]carbonyl}azetidin-3-yl)-1-(1,3-thiazol-4-ylcarbonyl)pyrrolidin-3-amine<br>MS m/z (M + H$^+$) 490 |
| 218 | (3S)-N-(1-{[1-(3-Fluorophenyl)-1H-indol-3-yl]carbonyl}azetidin-3-yl)-1-(1,3-thiazol-2-ylcarbonyl)pyrrolidin-3-amine<br>MS m/z (M + H$^+$) 490 |

| Cpd | Cpd Name and Data |
|---|---|
| 219 | (3S)-N-(1-{[1-(4-Fluorophenyl)-1H-indol-3-yl]carbonyl}azetidin-3-yl)-1-(1,3-thiazol-2-ylcarbonyl)pyrrolidin-3-amine<br>MS m/z (M + H⁺) 490 |

Example 20

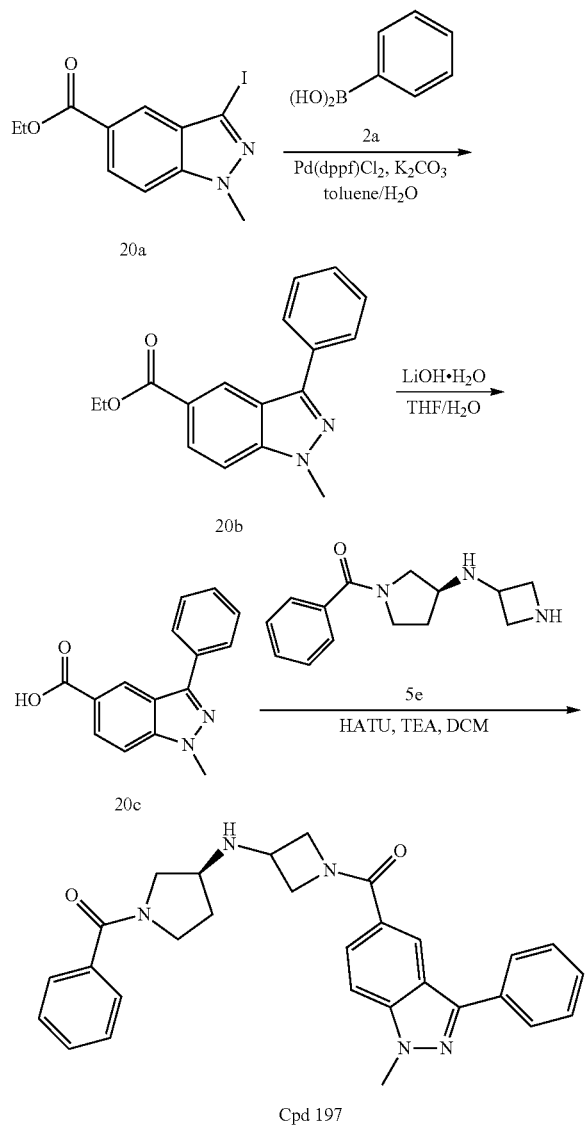

A. Ethyl 1-Methyl-3-phenyl-1H-indazole-5-carboxylate, 20b

A mixture of compound 20a (300 mg, 0.91 mmol), phenyl boronic acid 2a (133 mg, 1.09 mmol), Pd(dppf)Cl$_2$.CH$_2$Cl$_2$ (40 mg, 0.055 mmol), and K$_2$CO$_3$ (251.2 mg, 1.82 mmol), in a toluene (2 mL)/water (0.4 mL) mixture, was placed in a capped vial and heated at 90° C. overnight. The reaction mixture was then partitioned between EtOAc and water. The organic layer was concentrated under reduced pressure and purified by flash column chromatography (silica gel, 2-10% EtOAc/Heptanes) to give compound 20b (231 mg). MS m/z (M+H⁺) 281.1.

B. 1-Methyl-3-phenyl-1H-indazole-5-carboxylic acid, 20c

A solution compound 20b (230 mg, 0.58 mmol), and LiOH.H$_2$O (98 mg, 2.33 mmol) in THF/H$_2$O (10/10 mL) was stirred at 45° C. for 8 h. The resulting mixture was concentrated and diluted with water. The water layer was acidified with 1N aqueous HCl to pH~4 and extracted with CH$_2$Cl$_2$. The organic solution was dried over Na$_2$SO$_4$ and concentrated to give compound 20c (206 mg), which was used in the next reaction without further purification. MS m/z (M+H⁺) 253.1.

C. (3S)—N-{1-[(1-Methyl-3-phenyl-1H-indazol-5-yl)carbonyl]azetidin-3-yl}-1-(phenylcarbonyl)pyrrolidin-3-amine, Cpd 197

The title compound 197 was prepared using the method described in Example 5, substituting compound 20c for compound 4g in Step F. MS m/z (M+H⁺) 480.

Following the procedure described above for Example 20, steps A and B, and substituting the appropriate reagents, starting materials, and purification methods known to those skilled in the art, the following intermediate compounds were prepared:

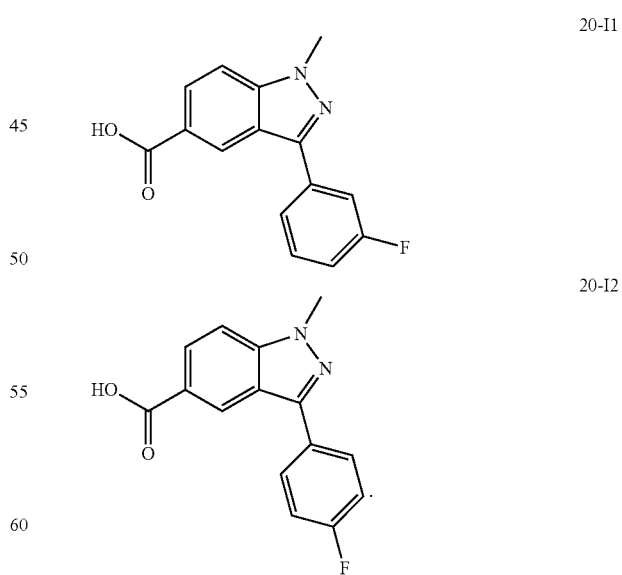

Following the procedure described above for Example 20 and substituting the appropriate reagents, starting materials and purification methods known to those skilled in the art, the following compounds of the present invention were prepared:

| Cpd | Cpd Name and Data |
|---|---|
| 195 | (3S)-N-{1-[(1-Methyl-3-phenyl-1H-indazol-5-yl)carbonyl]azetidin-3-yl}-1-(1,3-thiazol-2-ylcarbonyl)pyrrolidin-3-amine MS m/z (M + H+) 487. |
| 196 | (3S)-N-{1-[(1-Methyl-3-phenyl-1H-indazol-5-yl)carbonyl]azetidin-3-yl}-1-(1,3-thiazol-4-ylcarbonyl)pyrrolidin-3-amine MS m/z (M + H+) 487 |
| 199 | (3S)-N-(1-{[3-(3-Fluorophenyl)-1-methyl-1H-indazol-5-yl]carbonyl}azetidin-3-yl)-1-(1,3-thiazol-2-ylcarbonyl)pyrrolidin-3-amine MS m/z (M + H+) 505 |
| 200 | (3S)-N-(1-{[3-(3-Fluorophenyl)-1-methyl-1H-indazol-5-yl]carbonyl}azetidin-3-yl)-1-(1,3-thiazol-4-ylcarbonyl)pyrrolidin-3-amine MS m/z (M + H+) 505 |
| 201 | (3S)-N-(1-{[3-(3-Fluorophenyl)-1-methyl-1H-indazol-5-yl]carbonyl-}azetidin-3-yl)-1-(phenylcarbonyl)pyrrolidin-3-amine MS m/z (M + H+) 498 |
| 209 | (3S)-N-(1-{[3-(4-Fluorophenyl)-1-methyl-1H-indazol-5-yl]carbonyl}azetidin-3-yl)-1-(1,3-thiazol-2-ylcarbonyl)pyrrolidin-3-amine MS m/z (M + H+) 505 |
| 210 | (3S)-N-(1-{[3-(4-Fluorophenyl)-1-methyl-1H-indazol-5-yl]carbonyl}azetidin-3-yl)-1-(1,3-thiazol-4-ylcarbonyl)pyrrolidin-3-amine MS m/z (M + H+) 505 |
| 211 | (3S)-N-(1-{[3-(4-Fluorophenyl)-1-methyl-1H-indazol-5-yl]carbonyl}azetidin-3-yl)-1-(phenylcarbonyl)pyrrolidin-3-amine MS m/z (M + H+) 498 |

Example 20a

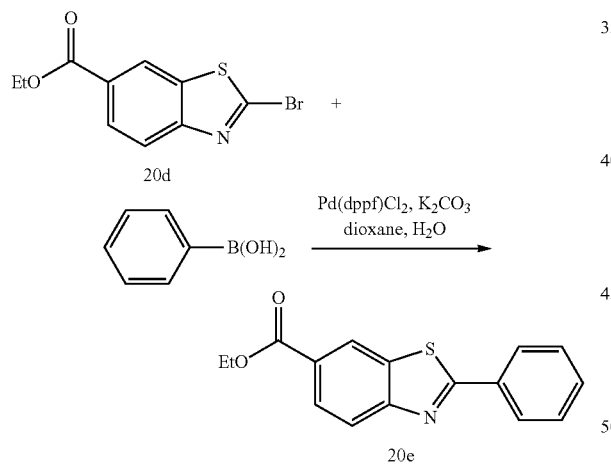

D. Ethyl 2-phenyl-benzothiazole-6-carboxylate, 20e

A mixture of ethyl 2-bromo-benzothiazole-6-carboxylate 20d (300 mg, 1.05 mmol), phenylboronic acid (192 mg, 1.57 mmol), $K_2CO_3$ (188 mg, 1.36 mmol) and Pd(dppf)Cl$_2$·CH$_2$Cl$_2$ (43 mg, 0.05 mmol) in dioxane (2 mL) and H$_2$O (0.4 mL) was heated at 120° C. for 25 min in a microwave reactor. The reaction mixture was diluted with CH$_2$Cl$_2$, washed with H$_2$O, dried over Na$_2$SO$_4$, and concentrated. Purification by flash column chromatography (silica gel, 15% EtOAc/heptane) gave compound 20e (220 mg).

Following the procedure described above for Example 20 and substituting the appropriate reagents, starting materials and purification methods known to those skilled in the art, the following compounds of the present invention were prepared:

| Cpd | Cpd Name and Data |
|---|---|
| 133 | (3S)-N-{1-[(2-Phenyl-1,3-benzothiazol-6-yl)carbonyl]azetidin-3-yl}-1-(1,3-thiazol-2-ylcarbonyl)pyrrolidin-3-amine MS m/z (M + H+) 490 |
| 157 | (3S)-N-{1-[(2-Phenyl-1,3-benzothiazol-6-yl)carbonyl]azetidin-3-yl}-1-(phenylcarbonyl)pyrrolidin-3-amine MS m/z (M + H+) 483. |

Example 21

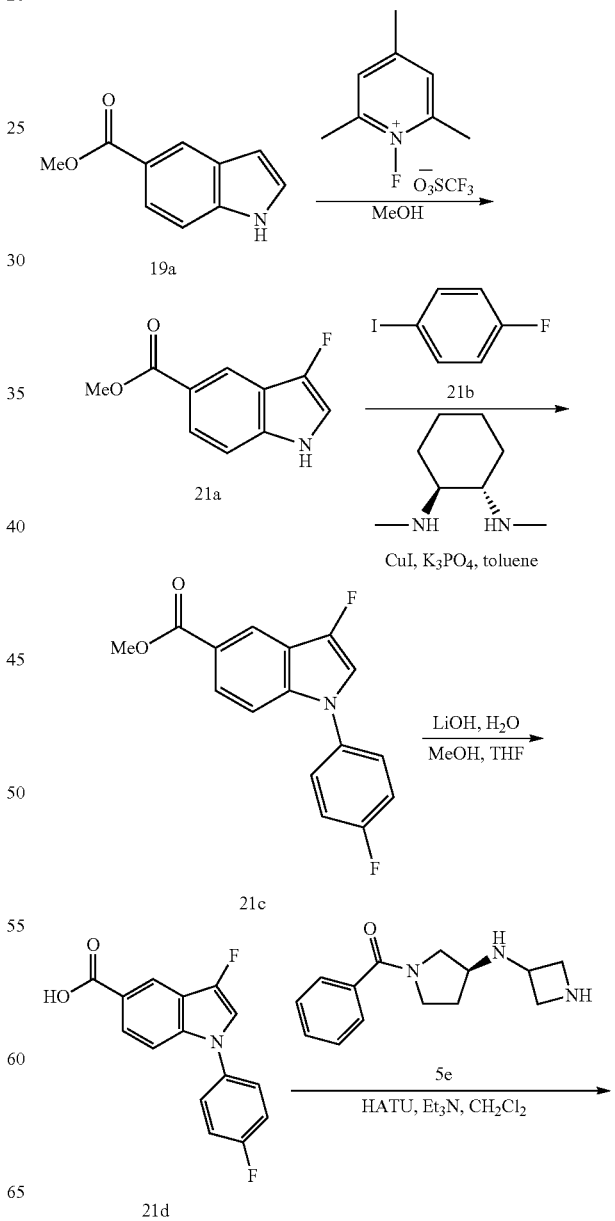

101
-continued

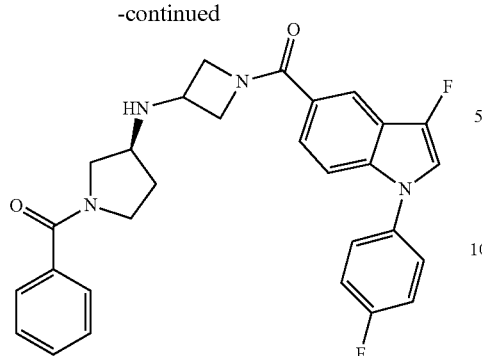

Cpd 142

A. Methyl 3-fluoro-1H-indole-6-carboxylate, 21a

A solution of methyl 1H-indole-6-carboxylate 19a (2.0 g, 11.4 mmol) and N-fluoro-2,4,6-trimethylpyridinium triflate (4.3 g, 14.8 mmol) in MeOH (100 mL) was heated at reflux for 18 h. The reaction mixture was concentrated and purified by flash column chromatography (silica gel, 15-20% EtOAc/hexanes) to give compound 21a as an off-white solid.

B. Methyl 3-fluoro-1-(4-fluorophenyl)-1H-indole-6-carboxylate, 21c

Compound 21a (51 mg, 0.264 mmol), CuI (5 mg, 0.0264 mmol) and $K_3PO_4$ (40 mg, 0.66 mmol) were combined in a sealed reaction tube and the vial was back-flushed with $N_2$. 4-Fluoro-iodobenzene 21b (0.0394 mL, 0.264 mmol) and N,N'-dimethylcyclohexane-1,2-diamine (0.0125 mL, 0.0792 mmol) were added via syringe, followed by toluene. The reaction mixture was heated at 95° C. for 6 h. The reaction was partitioned between EtOAc and water. The organic phase was concentrated and purified by flash column chromatography (silica gel, 20% EtOAc/hexanes) to give compound 21c.

C. 3-Fluoro-1-(4-fluorophenyl)-1H-indole-6-carboxylic acid, 21d

The title compound 21d was prepared using the method described in Example 13, substituting compound 21c for compound 13b in Step B.

D. (3S)—N-(1-{[3-Fluoro-1-(4-fluorophenyl)-1H-indol-5-yl]carbonyl}azetidin-3-yl)-1-(phenylcarbonyl)pyrrolidin-3-amine, Cpd 142

The title compound 142 was prepared using the method described in Example 5, substituting compound 21d for compound 4g in Step F. MS m/z (M+1-1') 501.

Following the procedure described above for Example 21 and substituting the appropriate reagents, starting materials and purification methods known to those skilled in the art, the following compounds of the present invention were prepared:

| Cpd | Cpd Name and Data |
|---|---|
| 143 | (3S)-N-(1-{[3-Fluoro-1-(4-fluorophenyl)-1H-indol-5-yl]carbonyl-}azetidin-3-yl)-1-(1,3-thiazol-4-ylcarbonyl)pyrrolidin-3-amine MS m/z (M + H⁺) 508. |

Example 22

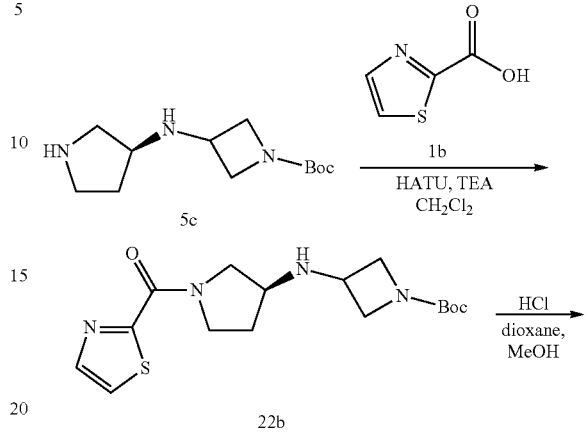

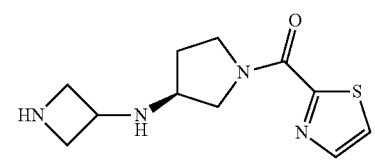

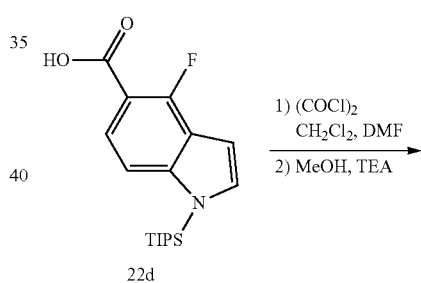

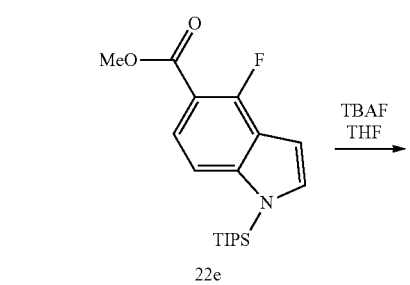

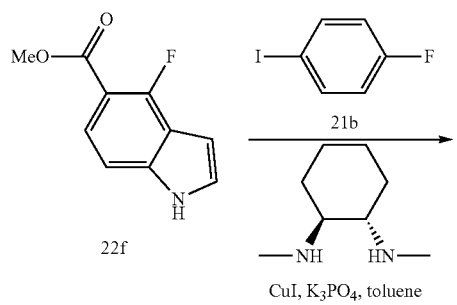

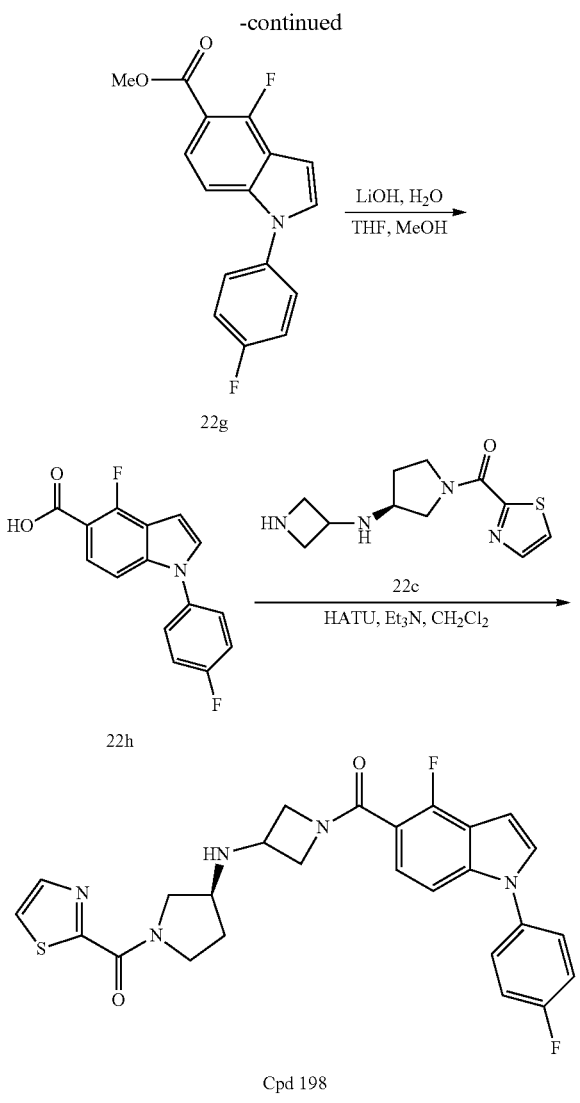

A. (S)-tert-Butyl 3-((1-(thiazole-2-carbonyl)pyrrolidin-3-yl)amino)azetidine-1-carboxylate, 22b The title compound 22b was prepared using the method described in Example 5, substituting compound 1a for compound 4a in Step C.

B. (S)-(3-(Azetidin-3-ylamino)pyrrolidin-1-yl)(thiazol-2-yl)methanone, 22c

The title compound 22c was prepared using the method described in Example 5, substituting compound 22b for compound 5d in Step D.

C. Methyl 4-fluoro-1-triisopropylsilanyl-1H-indole-5-carboxylate, 22e

To a solution of 4-fluoro-1-triisopropylsilanyl-1H-indole-5-carboxylic acid 22d (prepared using the procedure described in *Eur. J. Org. Chem.* 2006, 2956) (2.71 g, 8.08 mmol) in dry CH$_2$Cl$_2$ (20 mL) was added oxalyl chloride (0.82 mL, 9.69 mmol) followed by DMF (0.063 mL, 0.81 mmol). The reaction was stirred at rt for 30 min and then concentrated. The residue was dissolved in CH$_2$Cl$_2$ (20 mL) and cooled to 0° C. Et$_3$N (5.6 mL, 40.4 mmol) was added, followed by slow addition of MeOH. The reaction mixture was stirred at 0° C. for 30 min and concentrated. The residue was partitioned between EtOAc and water. The organic layer was concentrated and purified by flash column chromatography (silica gel, 5% EtOAc/hexanes) to give compound 22e.

D. Methyl 4-fluoro-1H-indole-5-carboxylate, 22f

TBAF (1M solution in THF, 15.8 mL, 15.8 mmol) was added to a solution of compound 22e (2.76 g, 7.9 mmol) in THF at 0° C. After 10 min at room temperature, the reaction was diluted with EtOAc and washed sequentially with brine, saturated NaHCO$_3$, and water. The organic layer was concentrated and purified by flash column chromatography (silica gel, 35% EtOAc/hexanes) to afford compound 22f.

E. Methyl 4-fluoro-1-(4-fluorophenyl)-1H-indole-5-carboxylate, 22g

The title compound 22g was prepared using the method described in Example 21, substituting compound 22f for compound 21b in Step B.

D. 4-Fluoro-1-(4-fluoro-phenyl)-1H-indole-5-carboxylic acid, 22h

The title compound 22h was prepared using the method described in Example 15, substituting compound 22g for compound 15d in Step C.

E. (3S)—N-(1-{[4-Fluoro-1-(4-fluorophenyl)-1H-indol-5-yl]carbonyl}azetidin-3-yl)-1-(1,3-thiazol-2-ylcarbonyl)pyrrolidin-3-amine, Cpd 198

The title compound Cpd 198 was prepared using the method described in Example 5, substituting compound 22h for compound 4g and compound 22c for compound 5e in Step F. MS m/z (M+H$^+$) 508.2.

Following the procedure described above for Example 22, and substituting the appropriate reagents, starting materials, and purification methods known to those skilled in the art, the following intermediate compound was prepared:

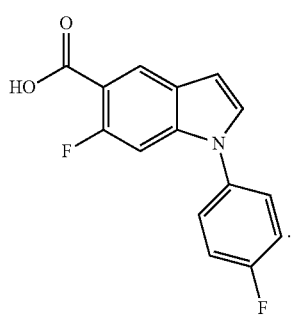

22-I1

Following the procedure described above for Example 22, and substituting the appropriate reagents, starting materials, and purification methods known to those skilled in the art, the following compounds of the present invention were prepared:

| Cpd | Cpd Name and Data |
|---|---|
| 212 | (3S)-N-(1-{[6-Fluoro-1-(4-fluorophenyl)-1H-indol-5-yl]carbonyl-}azetidin-3-yl)-1-(1,3-thiazol-2-ylcarbonyl)pyrrolidin-3-amine<br>$^1$H NMR (400 MHz, CDCl$_3$) δ: 7.80-7.97 (m, 2H), 7.49-7.58 (m, 1H), 7.39-7.49 (m, 2H), 7.19-7.37 (m, 3H), 7.13 (d, J = 11.0 Hz, 1H), 6.69 (d, J = 2.9 Hz, 1H), 4.40-4.56 (m, 1H), 4.23-4.37 (m, 2H), 4.16-4.24 (m, 0.5H), 3.77-4.02 (m, 4.5H), 3.63-3.77 (m, 0.5H), 3.35-3.58 (m, 1.5H), 2.04-2.26 (m, 1H), 1.84-1.97 (m, 0.5H), 1.78 (m, 0.5H)<br>MS m/z (M + H$^+$) 508. |

Example 22a

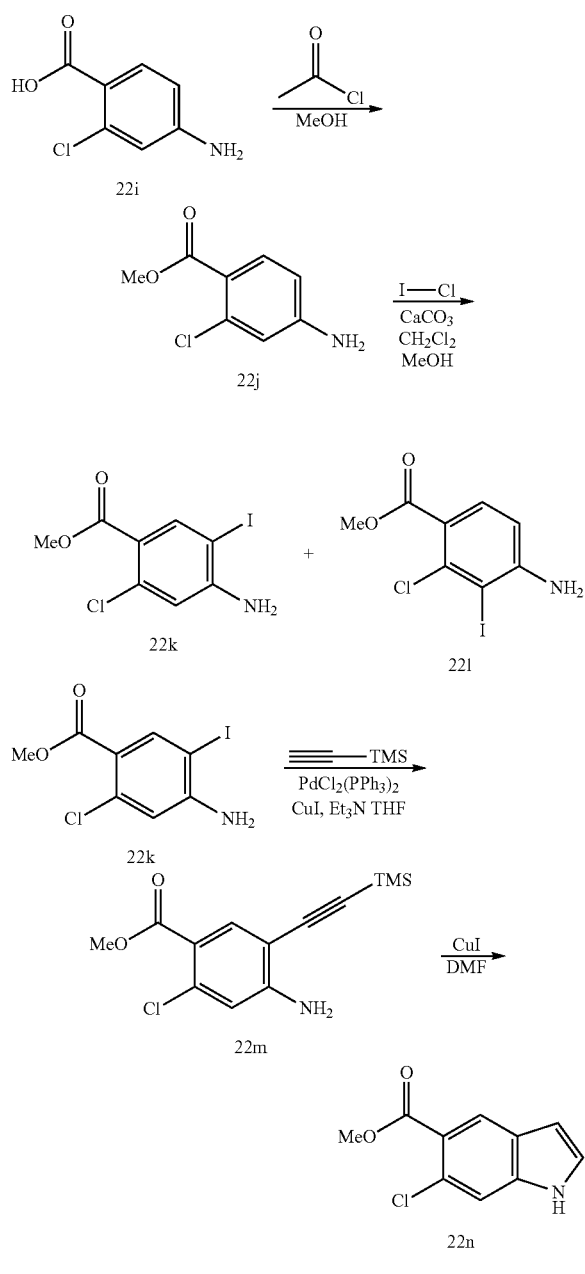

F. Methyl 4-amino-2-chloro-benzoate, 22j

Acetyl chloride (2.5 mL, 35.2 mmol) was added dropwise to a stirring solution of 4-amino-2-chloro-benzoic acid 22i (2.22 g, 12.9 mmol) in methanol (50 mL). The mixture was heated at reflux for 18 h, cooled, and concentrated under reduced pressure. The residue was dissolved in EtOAc, washed sequentially with saturated aqueous NaHCO$_3$ and brine, dried, and concentrated under reduced pressure. The crude product was purified by flash column chromatography (silica gel, 30% EtOAc/hexanes) to give compound 22j.

I. Methyl 4-amino-2-chloro-5-iodo-benzoate, 22k

To a suspension of compound 22j (1.18 g, 6.38 mmol) and CaCO$_3$ (1.28 g, 12.8 mmol) in MeOH (13 mL) was added a solution of iodine monochloride (1.09 g, 6.70 mmol) in CH$_2$Cl$_2$ (6 mL) dropwise at room temperature. The resulting reaction mixture was stirred at room temperature for 1.5 h. The reaction mixture was concentrated and then partitioned between EtOAc and water. The organic layer was concentrated and purified by flash column chromatography (silica gel, 20-25% EtOAc/hexanes) to provide methyl 4-amino-2-chloro-5-iodo-benzoate 22k as the major product and methyl 4-amino-2-chloro-3-iodo-benzoate 22l as the minor product.

J. Methyl 4-amino-2-chloro-5-((trimethylsilyl)ethynyl)benzoate, 22m

To a mixture of compound 22k (200 mg, 0.642 mmol), CuI (12.2 mg, 0.064 mmol) and Pd(PPh$_3$)$_2$Cl$_2$ (45 mg, 0.064 mmol) in THF (2 mL) was added ethynyltrimethylsilane (95 mg, 0.963 mmol) followed by Et$_3$N (1 mL, 7.19 mmol) under N$_2$. The reaction mixture was stirred at room temperature for 1.5 h and then partitioned between EtOAc and water. The organic layer was concentrated and purified by flash column chromatography (silica gel, 15% EtOAc/hexanes) to give compound 22m.

K. Methyl 6-chloro-1H-indole-5-carboxylate, 22n

A mixture of compound 22m (150 mg, 0.532 mmol) and CuI (60 mg, 0.32 mmol) in DMF (1.5 mL) was heated at 110° C. for 5 h and them cooled to room temperature. The reaction was quenched with water and extracted with EtOAc. The organic layer was concentrated and purified by flash column chromatography (silica gel, 15% EtOAc/hexanes) to give compound 22n.

Following the procedure described above for Example 22a and Example 22, and substituting the appropriate reagents, starting materials, and purification methods known to those skilled in the art, the following intermediate compounds were prepared:

22a-I1

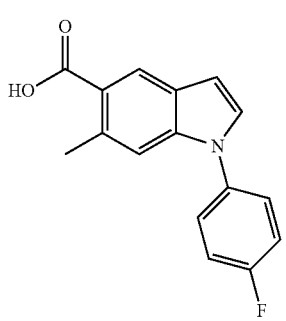

107
-continued

22a-I2

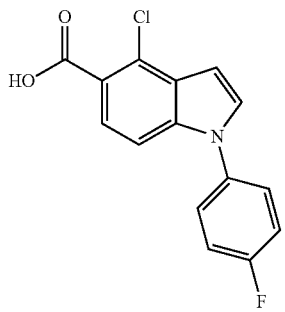

Following the procedure described above for Example 22, and substituting the appropriate reagents, starting materials, and purification methods known to those skilled in the art, the following compounds of the present invention were prepared:

| Cpd | Cpd Name and Data |
|---|---|
| 223 | (3S)-N-(1-{[4-Chloro-1-(4-fluorophenyl)-1H-indol-5-yl]carbonyl-}azetidin-3-yl)-1-(1,3-thiazol-2-ylcarbonyl)pyrrolidin-3-amine<br>$^1$H NMR (400 MHz, CDCl$_3$) δ: 7.85-7.94 (m, 1H), 7.48-7.56 (m, 1H), 7.39-7.48 (m, 2H), 7.31-7.38 (m, 2H), 7.16-7.28 (m, 3H), 6.83 (d, J = 3.2 Hz, 1H), 4.46-4.50 (m, 1H), 4.23-4.36 (m, 1H), 4.12-4.22 (m, 1.5H), 3.66-4.02 (m, 5H), 3.35-3.57 (m, 1.5H), 2.03-2.24 (m, 1H), 1.88 (m, 0.5H), 1.70-1.82 (m, 0.5H) MS m/z (M + H$^+$) 525 |
| 224 | (3S)-N-(1-{[1-(4-Fluorophenyl)-6-methyl-1H-indol-5-yl]carbonyl-}azetidin-3-yl)-1-(1,3-thiazol-2-ylcarbonyl)pyrrolidin-3-amine<br>MS m/z (M + H$^+$) 504 |
| 225 | (3S)-N-(1-{[6-Chloro-1-(4-fluorophenyl)-1H-indol-5-yl]carbonyl-}azetidin-3-yl)-1-(1,3-thiazol-2-ylcarbonyl)pyrrolidin-3-amine<br>MS m/z (M + H$^+$) 525 |

Example 23

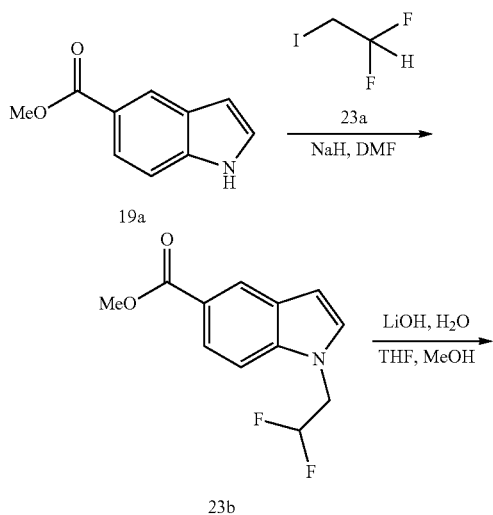

108
-continued

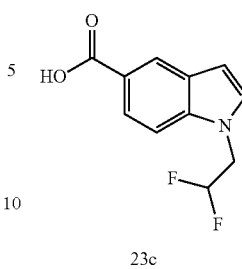

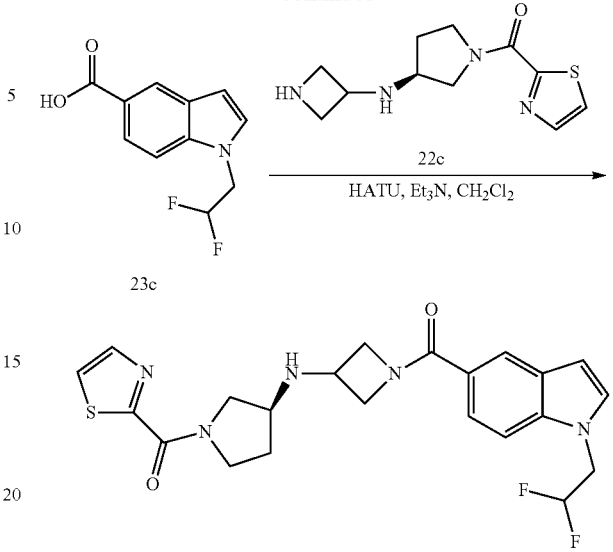

Cpd 213

A. Methyl 1-(2,2-difluoroethyl)-1H-indole-5-carboxylate, 23b

To a suspension of NaH (60% dispersion in mineral oil, 59 mg, 1.48 mmol) in DMF (2 mL) was slowly added a solution of 1H-indole-5-carboxylic acid methyl ester 19a (200 mg, 1.14 mmol) in DMF (1 mL) at 0° C. The resulting solution was stirred at 0° C. for 20 min and 1,1-difluoro-2-iodoethane 23a (263 mg, 1.37 mmol) was added. The reaction was warmed to room temperature and stirred for 2 h. The reaction was quenched with water and extracted with EtOAc. The organic layer was concentrated and purified by flash column chromatography (silica gel, 20% EtOAc/hexanes) to afford compound 23b.

B. 1-(2,2-Difluoroethyl)-1H-indole-5-carboxylic acid, 23c

The title compound 23c was prepared using the method described in Example 15, substituting compound 23b for compound 15d in Step C.

C. (3S)—N-(1-{[1-(2,2-Difluoroethyl)-1H-indol-5-yl]carbonyl}azetidin-3-yl)-1-(1,3-thiazol-2-ylcarbonyl)pyrrolidin-3-amine, Cpd 213

The title compound 213 was prepared using the method described in Example 5, substituting compound 22h for compound 4g and compound 22c for compound 5e in Step F. MS m/z (M+H$^+$) 460.

Following the procedure described above for Example 23, and substituting the appropriate reagents, starting materials, and purification methods known to those skilled in the art, the following compounds of the present invention were prepared:

| Cpd | Cpd Name and Data |
|---|---|
| 222 | N-Methyl-N-phenyl-2-{5-[(3-{[(3S)-1-(1,3-thiazol-2-ylcarbonyl)pyrrolidin-3-yl]amino}azetidin-1-yl)carbonyl]- |

| Cpd | Cpd Name and Data |
|---|---|
| | 1H-indol-1-yl}acetamide<br>MS m/z (M + H⁺) 543 |

Example 24

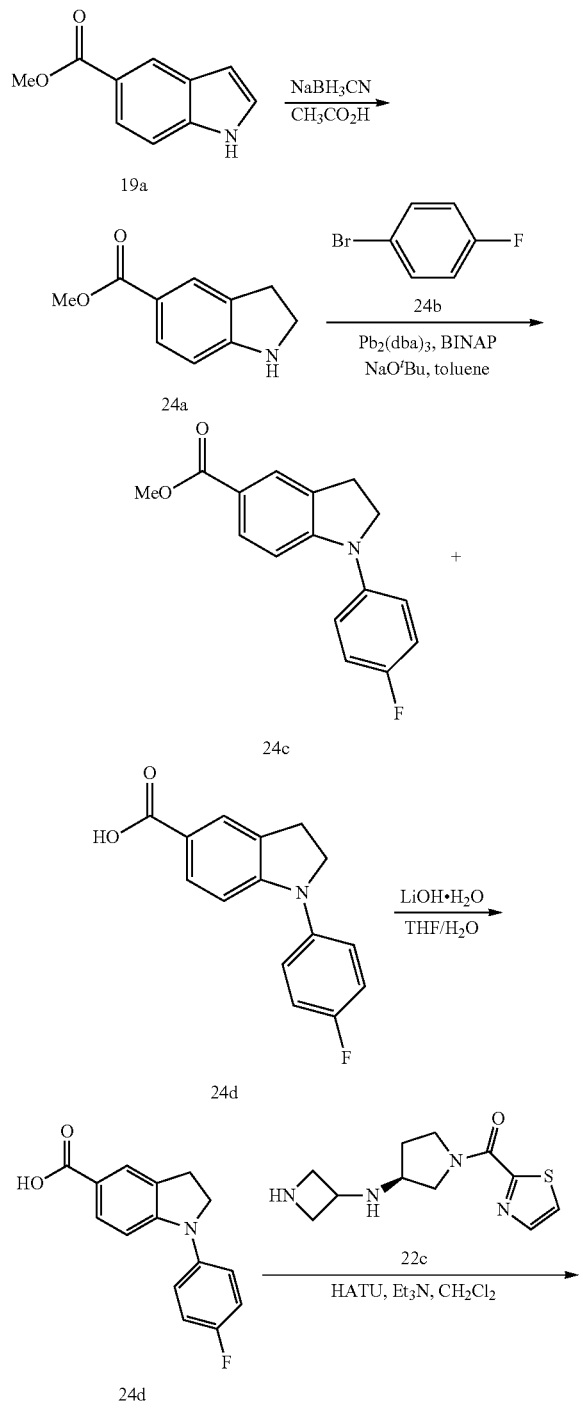

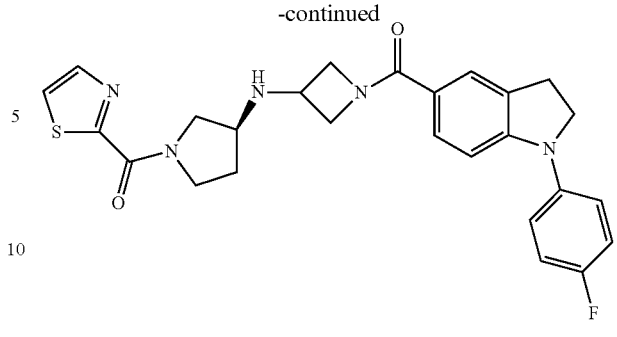

Cpd 220

A. Methyl 2,3-dihydro-1H-indole-5-carboxylate, 24a

To a solution of methyl 1H-indole-5-carboxylate 19a (2 g, 11.4 mmol) in glacial acetic acid (15 mL) at 0° C. was slowly added sodium cyanoborohydride (1.08 g, 17.2 mmol). The mixture was allowed to warm up and stirred at room temperature for 2 h. Water was added to the resulting mixture at 0° C., and the solution was adjusted to pH~12 with 1N aqueous NaOH. The mixture was extracted with $CH_2Cl_2$ and the organic layer was washed with brine and dried over $Na_2SO_4$. The solution was concentrated and purified by flash column chromatography (silica gel, 15% EtOAc/heptane) to give compound 24a (1.79 g). MS m/z (M+H⁺) 178.1.

B. Methyl 1-(4-fluoro-phenyl)-2,3-dihydro-1H-indole-5-carboxylate, 24c, and 1-(4-fluoro-phenyl)-2,3-dihydro-1H-indole-5-carboxylic acid, 24d A mixture of compound 24a (500 mg, 2.82 mmol), 1-bromo-4-fluoro-benzene 24b (0.31 mL, 2.82 mmol), $Pd_2(dba)_3$ (129 mg, 0.14 mmol), BINAP (132 mg, 0.21 mmol), and sodium t-butoxide (325 mg, 3.39 mmol) in toluene (25 mL) was placed in a capped vial and heated at 80° C. overnight. The reaction mixture was then diluted with EtOAc and water, and the water layer was basified to pH~8 with 1N aqueous NaOH. The organic layer was concentrated under reduced pressure and purified by flash column chromatography (silica gel, 5-30% EtOAc/heptane) to give a mixture of compound 24c (145 mg), MS m/z (M+H⁺) 272.1, and compound 24d (232 mg), MS m/z (M+H⁺) 258.0.

C. 1-(4-Fluoro-phenyl)-2,3-dihydro-1H-indole-5-carboxylic acid, 24d

The title compound 24d was prepared using the method described in Example 15, substituting compound 24c for compound 15d in Step C.

D. (3S)—N-(1-{[1-(2,2-Difluoroethyl)-1H-indol-5-yl]carbonyl}azetidin-3-yl)-1-(1,3-thiazol-2-ylcarbonyl)pyrrolidin-3-amine, Cpd 220

The title compound Cpd 220 was prepared using the method described in Example 5, substituting compound 24d for compound 4g and compound 22c for compound 5e in Step F. MS m/z (M+H⁺) 492.

Following the procedure described above for Example 24 and substituting the appropriate reagents, starting materials and purification methods known to those skilled in the art, the following intermediate compound was prepared:

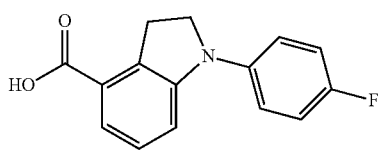 [SMILES: O=C(O)c1cccc2c1CCN2c1ccc(F)cc1]

Following the procedure described above for Example 24, and substituting the appropriate reagents, starting materials, and purification methods known to those skilled in the art, the following compounds of the present invention were prepared:

| Cpd | Cpd Name and Data |
|---|---|
| 216 | (3S)-N-(1-{[1-(4-Fluorophenyl)-2,3-dihydro-1H-indol-4-yl]carbonyl}azetidin-3-yl)-1-(1,3-thiazol-2-ylcarbonyl)pyrrolidin-3-amine<br>MS m/z (M + H$^+$) 492. |
| 217 | (3S)-N-(1-{[1-(4-Fluorophenyl)-2,3-dihydro-1H-indol-4-yl]carbonyl}azetidin-3-yl)-1-(1,3-thiazol-4-ylcarbonyl)pyrrolidin-3-amine<br>MS m/z (M + H$^+$) 492. |

Example 25

A. Methyl 3-(4-fluorobenzyl)-1-methyl-1H-indole-6-carboxylate, 25c

To a solution of compound 25a (500 mg), 2.64 mmol) and compound 25b (0.35 mL, 2.91 mmol) in dioxane (5 mL) was added silver oxide (683.6 mg, 2.91 mmol). The mixture was stirred at 80° C. overnight. The resultant mixture was filtered through diatomaceous earth and washed with EtOAc. The filtrate was concentrated and the residue was purified by flash column chromatography (silica gel, 20-60% CH$_2$Cl$_2$/heptanes) to give compound 25c (175 mg). MS m/z (M+H$^+$) 298.2.

B. 3-Benzyl-1-methyl-1H-indole-6-carboxylic acid, 25d

A solution of compound 25c (175 mg, 0.59 mmol), and LiOH.H$_2$O (101 mg, 2.41 mmol) in THF/H$_2$O (3/3 mL) was stirred at room temperature for 6 h. The resultant mixture was concentrated and partitioned between CH$_2$Cl$_2$ and water. The aqueous layer was acidified with 1N HCl(aq) to pH~4. The

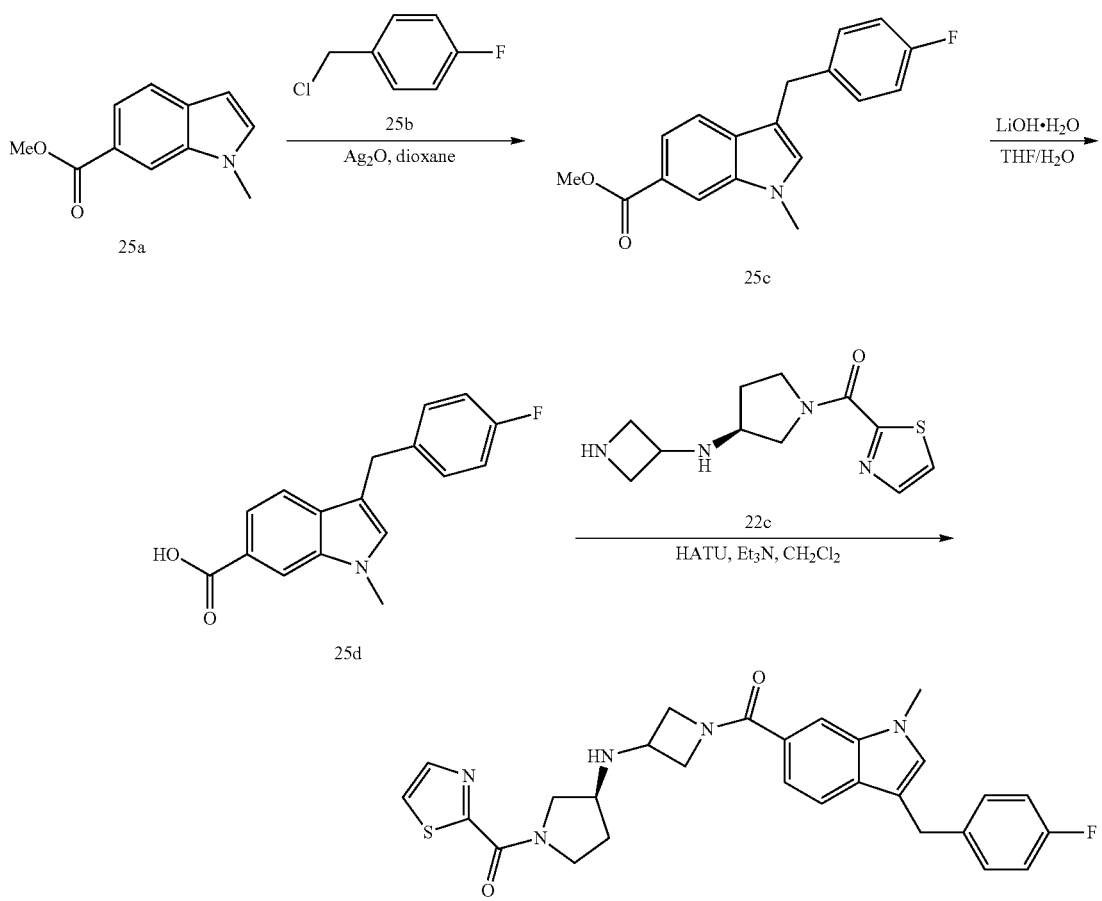

organic layer was dried over $Na_2SO_4$ and concentrated to give compound 25d (163 mg), which was used in the next reaction without further purification.

C. (3S)—N-(1-{[3-(4-Fluorobenzyl)-1-methyl-1H-indol-6-yl]carbonyl}azetidin-3-yl)-1-(1,3-thiazol-2-ylcarbonyl)pyrrolidin-3-amine, Cpd 221

The title compound Cpd 221 was prepared using the method described in Example 5, substituting compound 25d for compound 4g and compound 22c for compound 5e in Step F. MS m/z (M+H⁺) 518.

Example 26

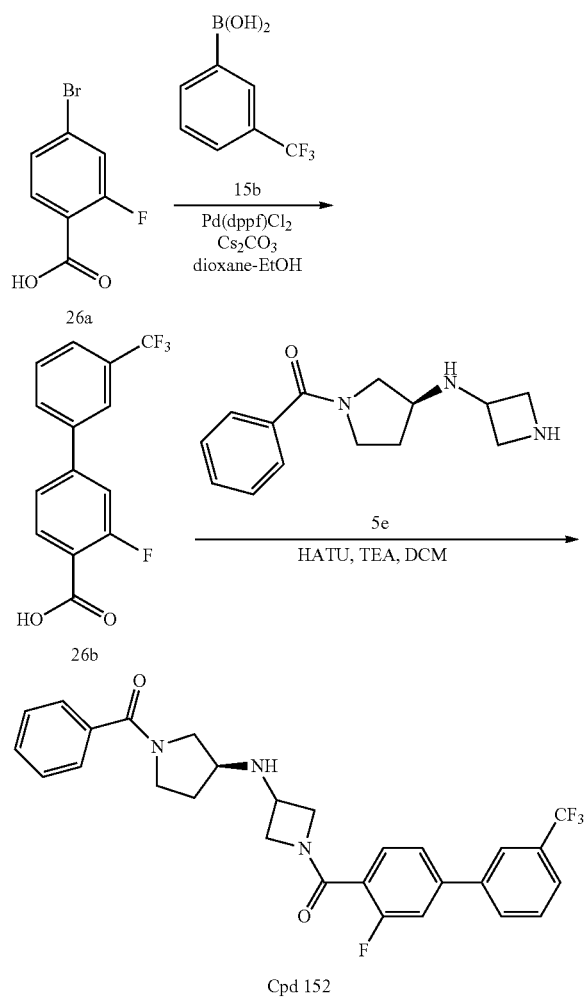

A. 3-Fluoro-3'-(trifluoromethyl)-[1,1'-biphenyl]-4-carboxylic acid, 26b

To a suspension of compound 26a (75 mg, 0.345 mmol), compound 15b (80 mg, 0.42 mmol), and $Cs_2CO_3$ (282 mg, 0.864 mmol) in dioxane (9 mL) and EtOH (3 mL) was added $Pd(dppf)Cl_2$ (0.0252 g, 0.0345 mmol). The reaction mixture was stirred at 80° C. for 3 h. After cooling, the solid was removed by filtration and washed with $CH_3OH$. The filtrate was concentrated. The crude compound 26b was purified by reverse phase chromatography.

B. (3S)—N-(1-{[3-Fluoro-3'-(trifluoromethyl)biphenyl-4-yl]carbonyl}azetidin-3-yl)-1-(phenylcarbonyl)pyrrolidin-3-amine, Cpd 152

The title compound Cpd 152 was prepared using the method described in Example 5, substituting compound 26b for compound 4g in Step F. MS m/z (M+H⁺) 512.

Following the procedure described above for Example 26, Step A and substituting the appropriate reagents, starting materials and purification methods known to those skilled in the art, the following intermediate compounds were prepared:

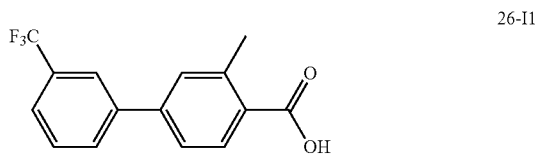 [SMILES: Cc1cc(-c2cccc(C(F)(F)F)c2)ccc1C(=O)O]

26-I1

Following the procedure described above for Example 26, and substituting the appropriate reagents, starting materials, and purification methods known to those skilled in the art, the following compounds of the present invention were prepared:

| Cpd | Cpd Name and Data |
|---|---|
| 153 | (3S)-N-(1-{[3-Methyl-3'-(trifluoromethyl)biphenyl-4-yl]carbonyl}azetidin-3-yl)-1-(phenylcarbonyl)pyrrolidin-3-amine<br>MS m/z (M + H⁺) 508. |

BIOLOGICAL EXAMPLES

In Vitro Methods

Example 1

MGL Enzyme Activity Assay

All rate-based assays were performed in black 384-well polypropylene PCR microplates (Abgene) in a total volume of 30 µL. Substrate 4-methylumbelliferyl butyrate (4MU-B; Sigma) and either purified mutant MGL (mut-MGLL 11-313 L179S L186S) or purified wild type MGL (wt-MGLL 6H-11-313) were diluted separately into 20 mM PIPES buffer (pH=7.0), containing 150 mM NaCl and 0.001% Tween 20. Compounds of Formula (I) were pre-dispensed (50 mL) into the assay plate using a Cartesian Hummingbird prior to adding 4MU-B (25 µL of 1.2× solution to a final concentration of 10 µM) followed by enzyme (5 µL of a 6× solution to a final concentration of 5 nM) to initiate the reaction. Final compound concentrations ranged from 17 to 0.0003 µM. The fluorescence change due to 4MU-B cleavage was monitored with excitation and emission wavelengths of 335 and 440 nm, respectively, and a bandwidth of 10 nm (Safire², Tecan) at 37° C. for 5 min.

The $IC_{50}$ values for the following compounds were determined using Microsoft Office Excel from a fit of the equation to the concentration-response plot of the fractional activity as a function of inhibitor concentration.

BIOLOGICAL DATA TABLE 1

| Cpd | MGL mutant inh $IC_{50}$ (μM) | MGL wild type inh $IC_{50}$ (μM) |
|---|---|---|
| 1 | 0.116 | |
| 2 | 0.122 | |
| 3 | 0.0218 | |
| 4 | 0.0120 | |
| 5 | <0.005 | |
| 6 | 0.490 | |
| 7 | 2.06 | |
| 10 | 2.91 | |
| 11 | 0.344 | |
| 12 | 6.21 | |
| 13 | 0.720 | |
| 14 | 0.0050 | |
| 15 | 0.0117 | 0.0265 |
| 16 | <0.005 | 0.0167 |
| 17 | 0.0410 | |
| 18 | 0.0168 | 0.0176 |
| 19 | 0.361 | |
| 20 | 0.0804 | |
| 21 | 0.0050 | |
| 22 | 0.0335 | |
| 23 | 0.0149 | |
| 24 | 0.0085 | |
| 25 | 0.0070 | <0.005 |
| 26 | 0.125 | |
| 27 | 0.0967 | |
| 28 | <0.005 | |
| 29 | 0.0110 | 0.0098 |
| 30 | 0.0088 | 0.0070 |
| 31 | 0.0050 | <0.005 |
| 32 | <0.005 | <0.005 |
| 33 | <0.005 | <0.005 |
| 34 | 0.0132 | |
| 35 | 0.158 | |
| 36 | 0.189 | |
| 37 | 0.0477 | |
| 38 | 0.301 | |
| 39 | 0.0110 | 0.0080 |
| 40 | 0.0189 | 0.0160 |
| 41 | 0.0063 | <0.005 |
| 42 | 0.0075 | 0.0100 |
| 43 | 0.267 | |
| 44 | 0.0317 | 0.0090 |
| 45 | 1.63 | |
| 46 | 0.336 | |
| 47 | 10.9 | |
| 48 | 8.97 | |
| 49 | 0.357 | 0.480 |
| 50 | 0.0060 | 0.0087 |
| 51 | 0.229 | <0.005 |
| 52 | 0.226 | 0.0066 |
| 53 | 0.0100 | 0.286 |
| 54 | <0.005 | 0.0588 |
| 55 | <0.005 | 0.0202 |
| 56 | <0.005 | 0.0684 |
| 57 | 0.0443 | 0.179 |
| 58 | 0.0330 | 0.464 |
| 59 | <0.005 | 0.0414 |
| 60 | >16.7 | |
| 61 | 0.0133 | 0.856 |
| 62 | 5.86 | >16.6686 |
| 63 | 0.0063 | 0.0666 |
| 64 | 0.0395 | 0.0709 |
| 65 | 0.103 | |
| 66 | 0.214 | |
| 67 | | 0.0097 |
| 68 | 0.0845 | |
| 69 | 0.198 | |
| 70 | 0.0255 | |
| 71 | 5.58 | |
| 72 | 0.757 | |
| 73 | 0.0158 | |
| 74 | | 0.277 |
| 75 | | 0.210 |
| 76 | | 0.0618 |
| 77 | | <0.005 |
| 78 | 13.4 | |
| 79 | | 0.281 |
| 80 | | 0.0226 |
| 81 | | 4.88 |
| 82 | | 0.231 |
| 83 | | 2.44 |
| 84 | | <0.005 |
| 85 | | 0.0482 |
| 86 | | 0.298 |
| 87 | | 0.0341 |
| 88 | | 0.152 |
| 89 | | 0.154 |
| 90 | | <0.005 |
| 91 | | <0.005 |
| 92 | | <0.005 |
| 93 | | <0.005 |
| 94 | | <0.005 |
| 95 | | 0.410 |
| 96 | | 1.05 |
| 97 | | 0.133 |
| 98 | | 3.10 |
| 99 | | <0.005 |
| 100 | | <0.005 |
| 101 | | 0.0440 |
| 102 | | <0.005 |
| 103 | | 0.0150 |
| 104 | | 0.0222 |
| 105 | | 0.0180 |
| 106 | | <0.005 |
| 107 | | >16.6686 |
| 108 | | 1.03 |
| 109 | | 0.857 |
| 110 | | 0.311 |
| 111 | | 0.179 |
| 112 | | 1.66 |
| 113 | | <0.005 |
| 114 | | 0.0167 |
| 115 | | 0.0100 |
| 116 | | <0.005 |
| 117 | | <0.005 |
| 118 | | <0.005 |
| 119 | | 0.0488 |
| 120 | | 0.372 |
| 121 | | 1.75 |
| 122 | | 0.0597 |
| 123 | | <0.005 |
| 124 | | 0.0060 |
| 125 | | <0.005 |
| 126 | | <0.005 |
| 127 | | <0.005 |
| 128 | | 0.0050 |
| 129 | | <0.005 |
| 130 | | <0.005 |
| 131 | | <0.005 |
| 132 | | <0.005 |
| 133 | | 0.145 |
| 134 | | 2.93 |
| 135 | | 1.13 |
| 136 | | 0.165 |
| 137 | | 0.446 |
| 138 | | 0.0160 |
| 139 | | 0.311 |
| 140 | | 0.0124 |
| 141 | | 0.0190 |
| 142 | | 0.0565 |
| 143 | | 0.0465 |
| 144 | | <0.005 |
| 145 | | 0.0964 |
| 146 | | <0.005 |
| 147 | | <0.005 |
| 148 | | <0.005 |
| 149 | | <0.005 |
| 150 | | <0.005 |
| 151 | | <0.005 |
| 152 | | 0.0352 |
| 153 | | 0.176 |
| 154 | | 0.0134 |
| 155 | | 1.28 |
| 156 | | 0.482 |

BIOLOGICAL DATA TABLE 1-continued

| Cpd | MGL mutant inh IC$_{50}$ (µM) | MGL wild type inh IC$_{50}$ (µM) |
|---|---|---|
| 157 | | 0.211 |
| 158 | | 0.0160 |
| 159 | | 0.0060 |
| 160 | | 0.0124 |
| 161 | | 0.0550 |
| 162 | | 0.0063 |
| 163 | | 0.0107 |
| 164 | | 0.0251 |
| 165 | | 0.0445 |
| 166 | | 0.0498 |
| 167 | | 0.0110 |
| 168 | | 0.0322 |
| 169 | | 0.0139 |
| 170 | | 0.350 |
| 171 | | <0.005 |
| 172 | | <0.005 |
| 173 | | <0.005 |
| 174 | | 0.0100 |
| 175 | | <0.005 |
| 176 | | 0.0060 |
| 177 | | 0.0160 |
| 178 | | <0.005 |
| 179 | | 0.0120 |
| 180 | | 0.0427 |
| 181 | | 0.0396 |
| 182 | | 0.217 |
| 183 | | 0.0231 |
| 184 | | 0.205 |
| 185 | | 0.488 |
| 186 | | 0.0905 |
| 187 | | <0.005 |
| 188 | | 0.0749 |
| 189 | | 0.0125 |
| 190 | | 0.114 |
| 191 | | 0.297 |
| 192 | | <0.005 |
| 193 | | 0.0190 |
| 194 | | 0.0449 |
| 195 | | 0.0224 |
| 196 | | 0.298 |
| 197 | | 0.199 |
| 198 | | <0.005 |
| 199 | | 0.107 |
| 200 | | 0.843 |
| 201 | | 0.459 |
| 202 | | 0.0110 |
| 203 | | 0.0504 |
| 204 | | 0.344 |
| 205 | | <0.005 |
| 206 | | 0.0810 |
| 207 | | 0.0639 |
| 208 | | 0.0134 |
| 209 | | 0.279 |
| 210 | | 2.04 |
| 211 | | 0.943 |
| 212 | | <0.005 |
| 213 | | 1.39 |
| 214 | | 0.106 |
| 215 | | 0.668 |
| 216 | | 0.0945 |
| 217 | | 0.723 |
| 218 | | 1.89 |
| 219 | | 4.98 |
| 220 | | 0.0120 |
| 221 | | <0.005 |
| 222 | | 1.68 |
| 223 | | 0.0140 |
| 224 | | 0.224 |
| 225 | | 0.0392 |

Example 2

2-AG Accumulation Assay

To measure the accumulation of 2-AG due to inhibition of MGL, one g rat brain was homogenized using a Polytron homogenizer (Brinkmann, PT300) in 10 mL of 20 mM HEPES buffer (pH=7.4), containing 125 mM NaCl, 1 mM EDTA, 5 mM KCl and 20 mM glucose. Compounds of Formula (I) (10 µM) were pre-incubated with rat brain homogenate (50 mg). After a 15-min incubation time at 37° C., CaCl$_2$ (final concentration=10 mM) was added and then incubated for 15 min at 37° C. in a total volume of 5 mL. The reactions were stopped with 6 mL organic solvent extraction solution of 2:1 chloroform/methanol. Accumulated 2-AG in the organic phase was measured by a HPLC/MS method, according to the following equation:

percent vehicle=(2-AG accumulation in the presence of compound/2-AG accumulation in vehicle)×100.

BIOLOGICAL DATA TABLE 2

| Cpd No | Rat Brain 2AG % VehCntrl (%) @1 µM | Rat Brain 2AG % VehCntrl (%) @10 µM |
|---|---|---|
| 3 | | 844 |
| 4 | | 1033 |
| 5 | | 962 |
| 14 | 484 | |
| 15 | 649 | |
| 16 | 220 | |
| 17 | 441 | |
| 18 | 229 | |
| 20 | 304 | |
| 21 | 596 | |
| 22 | 223 | |
| 23 | 293 | |
| 24 | 706 | |
| 25 | 823 | |
| 27 | 125 | |
| 28 | 511 | |
| 29 | 163 | |
| 30 | 155 | |
| 31 | 323 | |
| 32 | 524 | |
| 33 | 499 | |
| 34 | 645 | |
| 37 | 381 | |
| 39 | 885 | |
| 40 | 1145 | |
| 41 | 1102 | |
| 42 | 211 | |
| 44 | 839 | |
| 50 | 264 | |
| 53 | 164 | |
| 54 | 242 | |
| 55 | 247 | |
| 56 | 222 | |
| 57 | 154 | |
| 59 | 389 | |
| 63 | 696 | |
| 64 | 182 | |
| 67 | 928 | |
| 68 | 161 | |
| 70 | 217 | |
| 73 | 441 | |
| 76 | 522 | |
| 77 | 506 | |
| 80 | 174 | |
| 84 | 433 | |
| 85 | 335 | |
| 87 | 385 | |
| 90 | 1130 | |
| 92 | 624 | |

BIOLOGICAL DATA TABLE 2-continued

| Cpd No | Rat Brain 2AG % VehCntrl (%) @1 μM | Rat Brain 2AG % VehCntrl (%) @10 μM |
|---|---|---|
| 93 | 963 | |
| 94 | 445 | |
| 99 | 644 | |
| 100 | 546 | |
| 101 | 141 | |
| 102 | 529 | |
| 103 | 332 | |
| 104 | 195 | |
| 105 | 812 | |
| 106 | 389 | |
| 113 | 832 | |
| 114 | 311 | |
| 115 | 310 | |
| 116 | 733 | |
| 117 | 400 | |
| 118 | 626 | |
| 119 | 255 | |
| 122 | 152 | |
| 123 | 661 | |
| 124 | 227 | |
| 126 | 715 | |
| 127 | 618 | |
| 128 | 491 | |
| 129 | 590 | |
| 130 | 747 | |
| 131 | 385 | |
| 132 | 1233 | |
| 138 | 340 | |
| 140 | 742 | |
| 141 | 388 | |
| 142 | 247 | |
| 143 | 244 | |
| 144 | 992 | |
| 145 | 193 | |
| 146 | 680 | |
| 147 | 506 | |
| 148 | 942 | |
| 149 | 811 | |
| 150 | 759 | |
| 151 | 495 | |
| 152 | 404 | |
| 154 | 582 | |
| 158 | 415 | |
| 159 | 476 | |
| 160 | 338 | |
| 161 | 485 | |
| 162 | 911 | |
| 163 | 274 | |
| 164 | 458 | |
| 165 | 228 | |
| 166 | 322 | |
| 167 | 695 | |
| 168 | 611 | |
| 169 | 482 | |
| 171 | 614 | |
| 172 | 532 | |
| 173 | 628 | |
| 174 | 791 | |
| 175 | 734 | |
| 176 | 832 | |
| 177 | 766 | |
| 178 | 297 | |
| 179 | 259 | |
| 180 | 333 | |
| 181 | 241 | |
| 183 | 316 | |
| 186 | 563 | |
| 187 | 242 | |
| 188 | 140 | |
| 189 | 277 | |
| 192 | 374 | |
| 193 | 219 | |
| 194 | 178 | |
| 195 | 472 | |
| 198 | 937 | |
| 202 | 363 | |
| 203 | 238 | |
| 205 | 446 | |
| 206 | 267 | |
| 207 | 238 | |
| 208 | 359 | |
| 212 | 582 | |
| 214 | 524 | |
| 216 | 260 | |
| 220 | 421 | |
| 221 | 878 | |

Example 3

MGL ThermoFluor® Assay-Mutant

The ThermoFluor (TF) assay is a 384-well plate-based binding assay that measures thermal stability of proteins[1,2]. The experiments were carried out using instruments available from Johnson & Johnson Pharmaceutical Research & Development, LLC. TF dye used in all experiments was 1,8-ANS (Invitrogen: A-47). Final TF assay conditions used for MGL studies were 0.07 mg/ml of mutant MGL, 100 μM ANS, 200 mM NaCl, 0.001% Tween-20 in 50 mM PIPES (pH=7.0).

Screening compound plates contained 100% DMSO compound solutions at a single concentration. For follow-up concentration-response studies, compounds were arranged in a pre-dispensed plate (Greiner Bio-one: 781280), wherein compounds were serially diluted in 100% DMSO across 11 columns within a series. Columns 12 and 24 were used as DMSO reference and contained no compound. For both single and multiple compound concentration-repsonse experiments, the compound aliquots (46 mL) were robotically predispensed directly into 384-well black assay plates (Abgene: TF-0384/k) using the Hummingbird liquid handler. Following compound dispension, protein and dye solutions were added to achieve the final assay volume of 3 μL. The assay solutions were overlayed with 1 μL of silicone oil (Fluka, type DC 200: 85411) to prevent evaporation.

Bar-coded assay plates were robotically loaded onto a thermostatically controlled PCR-type thermal block and then heated from 40 to 90° C. degrees at a ramp-rate of 1° C./min for all experiments. Fluorescence was measured by continuous illumination with UV light (Hamamatsu LC6), supplied via fiber optics and filtered through a band-pass filter (380-400 nm; >6 OD cutoff). Fluorescence emission of the entire 384-well plate was detected by measuring light intensity using a CCD camera (Sensys, Roper Scientific) filtered to detect 500±25 nm, resulting in simultaneous and independent readings of all 384 wells. A single image with 20-sec exposure time was collected at each temperature, and the sum of the pixel intensity in a given area of the assay plate was recorded vs temperature and fit to standard equations to yield the $T_m$[1].

1. Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) *J Biomol Screen* 6, 429-40.
2. Matulis, D., Kranz, J. K., Salemme, F. R., and Todd, M. J. (2005) *Biochemistry* 44, 5258-66.

The $K_d$ values for certain compounds of Formula (I) were determined from a fit of the equation to the concentration-response plot of the fractional activity as a function of $T_m$. For some experiments, quantitative NMR spectroscopy (qNMR) was used to measure concentration of the initial 100% DMSO compound solutions and, using the same fitting method, $qK_d$ values were determined.

BIOLOGICAL DATA TABLE 3

| Cpd No | MGL mutant ThermoFluor qKd (µM) |
|---|---|
| 202 | 0.0563 |
| 203 | 0.264 |
| 204 | 0.186 |
| 205 | 0.0214 |
| 206 | 0.122 |
| 207 | 0.100 |
| 213 | 0.963 |
| 214 | 0.530 |
| 215 | 1.44 |
| 216 | 0.462 |
| 217 | 1.96 |
| 218 | 3.45 |
| 219 | 4.98 |
| 220 | 0.0603 |
| 221 | 0.0885 |
| 222 | 3.24 |
| 223 | 0.143 |
| 224 | 0.218 |
| 225 | 0.102 |

In Vitro Methods

Example 4

CFA-Induced Paw Radiant Heat Hypersensitivity

Each rat was placed in a test chamber on a warm glass surface and allowed to acclimate for approximately 10 min. A radiant thermal stimulus (beam of light) was focused through the glass onto the plantar surface of each hind paw in turn. The thermal stimulus was automatically shut off by a photoelectric relay when the paw was moved or when the cut-off time was reached (20 sec for radiant heat at ~5 amps). An initial (baseline) response latency to the thermal stimulus was recorded for each animal prior to the injection of complete Freund's adjuvant (CFA). Twenty-four hours following intraplantar CFA injection, the response latency of the animal to the thermal stimulus was re-evaluated and compared to the animal's baseline response time. Only rats that exhibited at least a 25% reduction in response latency (i.e., are hyperalgesic) were included in further analysis. Immediately following the post-CFA latency assessment, the indicated test compound or vehicle was administered orally. Post-compound treatment withdrawal latency was assessed at fixed time intervals, typically 30, 60, 120, 180, and 300 min.

The percent reversal (% R) of hypersensitivity was calculated in one of two different ways: 1) using group mean values or 2) using individual animal values. More specifically:

Method 1. For all compounds, the % R of hypersensitivity was calculated using the mean value for groups of animals at each time point according to the following formula:

% reversal=[(group treatment response−group CFA response)/(group baseline response−group CFA response)]×100

Results are given for the maximum % reversal observed for each compound at any time point tested.

Method 2. For some compounds, the % R of hypersensitivity was calculated separately for each animal according to the following formula:

% reversal=[(individual treatment response−individual CFA response)/(individual baseline response−individual CFA response)]×100.

Results are given as a mean of the maximum % reversal values calculated for each individual animal.

| | | Biological Data Table ##: CFA thermal hypersensitivity | | | | |
|---|---|---|---|---|---|---|
| Cpd No. | dose (mg/kg, p.o.) | vehicle | no. of animals | last time point (min) | Method 1: peak % reversal | Method 2: peak % reversal |
| 16 | 30 | 20% HPβCD | 8 | 300 | 78.0 | 87.7 |
| 39 | 30 | 20% HPβCD | 8 | 300 | 22.5 | |
| 40 | 30 | 20% HPβCD | 8 | 300 | 15.9 | 17.3 |
| 63 | 30 | 20% HPβCD | 8 | 300 | −8.2 | |
| 103 | 30 | 20% HPβCD | 8 | 300 | 28.0 | |
| 105 | 30 | 20% HPβCD | 8 | 300 | 37.2 | |
| 114 | 30 | 20% HPβCD | 8 | 300 | 25.1 | |
| 159 | 30 | 20% HPβCD | 8 | 300 | 56.5 | |
| 162 | 30 | 20% HPβCD | 8 | 300 | 69.7 | |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of Formula (I)

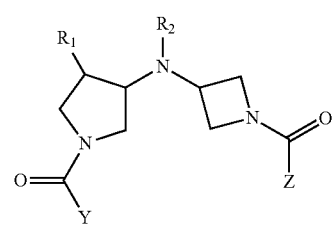

Formula (I)

wherein
Y is a $C_{6-10}$aryl or a heteroaryl selected from the group consisting of thiazolyl, thienyl, benzofuranyl, and benzothienyl; wherein Y is unsubstituted or substituted with one or two fluoro substituents;
Z is
i) a $C_{6-10}$aryl;
ii) 9H-fluorenyl;
iii) phenyl-($R_a$)-phenyl wherein the phenyl ring on phenyl-($R_a$)— is unsubstituted or substituted with one substituent that is trifluoromethyl;
  $R_a$ is CH(F), $CF_2$, or CH(OH);
iv) a benzo-fused heterocyclyl selected from the group consisting of 1,2,3,4-tetrahydroisoquinolinyl, isoindolinyl, and indolinyl;
  wherein the benzo-fused heterocyclyl is unsubstituted or substituted with one substituent that is phenyl or bromo, wherein said phenyl is unsubstituted or substituted with one substituent selected from the group consisting of bromo, chloro, fluoro, methyl, methoxy, or trifluoromethyl; or v) a heteroaryl selected from the group consisting thiazolyl, benzothienyl, benzofuranyl, benzothiazolyl, quinazolinyl, indolyl, and indazolyl;
wherein the $C_{6-10}$aryl and the heteroaryl of Z are unsubstituted or substituted with one or two substitutents each of which is independently selected from the group consisting of bromo, chloro, fluoro, $C_{1-4}$alkyl, $C_{2-4}$alkenyl, trifluoromethyl, trifluoromethoxy, and $R_b$; provided that no more than one substituent is $R_b$; and
$R_b$ is selected from the group consisting of 2,2-difluoroethyl; phenylmethyl; $C_{3-6}$ cycloalkyl; N-methyl-N-phenylaminocarbonyl-methyl; thienyl; pyrimidinyl; and phenyl; wherein the phenyl portion of phenylmethyl, and said thienyl, pyrimidinyl, and phenyl of $R_b$ are unsubstituted or substituted with one or two substituents each of which is independently selected from the group consisting of trifluoromethyl, trifluoromethoxy, chloro, and fluoro;
$R_1$ is hydrogen, fluoro or hydroxy;
$R_2$ is hydrogen, methyl, or hydroxy;
and enantiomers, diastereomers, and pharmaceutically acceptable salt forms thereof.

2. A compound of Formula (I)

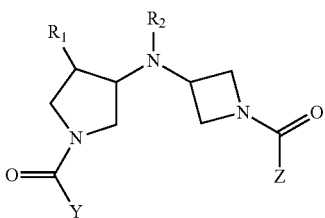

Formula (I)

wherein
Y is an unsubstituted $C_{6-10}$aryl or an unsubstituted heteroaryl that is thienyl or thiazolyl;
Z is
i) a $C_{6-10}$aryl;
ii) 9H-fluorenyl;
iii) phenyl-($R_a$)-phenyl wherein the phenyl ring on phenyl-($R_a$)— is unsubstituted or substituted with one substituent that is trifluoromethyl;
$R_a$ is CH(F), CF$_2$, or CH(OH);
iv) a benzo-fused heterocyclyl selected from the group consisting of 1,2,3,4-tetrahydroisoquinolinyl, isoindolinyl, and indolinyl; wherein the benzo-fused heterocyclyl is unsubstituted or substituted with one substituent that is phenyl or bromo; or
v) a heteroaryl selected from the group consisting thiazolyl, benzothienyl, benzofuranyl, benzothiazolyl, quinazolinyl, indolyl, and indazolyl;
wherein the $C_{6-10}$aryl and the heteroaryl of Z are unsubstituted or substituted with one or two substitutents each of which is independently selected from the group consisting of bromo, chloro, fluoro, $C_{1-4}$-alkyl, $C_{2-4}$alkenyl, trifluoromethyl, trifluoromethoxy, and $R_b$; provided that no more than one substituent is $R_b$;
$R_b$ is selected from the group consisting of phenylmethyl; $C_{3-6}$ cycloalkyl; thienyl; pyrimidinyl; and phenyl; wherein the phenyl portion of phenylmethyl, and said thienyl and said phenyl of $R_b$ are unsubstituted or substituted with one or two substituents each of which is independently selected from the group consisting of trifluoromethyl, trifluoromethoxy, chloro, and fluoro;
$R_1$ is hydrogen or fluoro;
$R_2$ is hydrogen, $C_{1-2}$ alkyl, or hydroxy;
and enantiomers, diastereomers, and pharmaceutically acceptable salt forms thereof.

3. A compound of Formula (I)

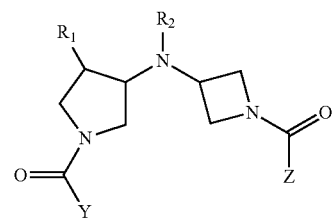

Formula (I)

wherein
Y is an unsubstituted phenyl or an unsubstituted heteroaryl that is thienyl or thiazolyl;
Z is
i) a $C_{6-10}$aryl;
ii) 9H-fluorenyl;
iii) phenyl-($R_a$)-phenyl wherein the phenyl ring on phenyl-($R_a$)— is unsubstituted or substituted with one substituent that is trifluoromethyl;
$R_a$ is CF$_2$ or CH(OH);
iv) indolinyl and said indolinyl is unsubstituted or substituted with one substituent that is phenyl or bromo; or
v) a heteroaryl selected from the group consisting benzothienyl, benzofuranyl, indolyl, and indazolyl;
wherein the $C_{6-10}$aryl and the heteroaryl of Z are unsubstituted or substituted with one or two substituents each of which is independently selected from the group consisting of bromo, chloro, fluoro, $C_{1-4}$alkyl, $C_{2-4}$alkenyl, trifluoromethyl, trifluoromethoxy, and $R_b$; provided that no more than one substituent is $R_b$; and
$R_b$ is selected from the group consisting of phenylmethyl; thienyl; pyrimidinyl; and phenyl; wherein the phenyl portion of phenylmethyl, and said thienyl and said phenyl of $R_b$ are unsubstituted or substituted with one or two substituents each of which is independently selected from the group consisting of trifluoromethyl, chloro, and fluoro;
$R_1$ is hydrogen or fluoro;
$R_2$ is hydrogen, $C_{1-2}$ alkyl, or hydroxy;
and enantiomers, diastereomers, and pharmaceutically acceptable salt forms thereof.

4. A compound of Formula (I)

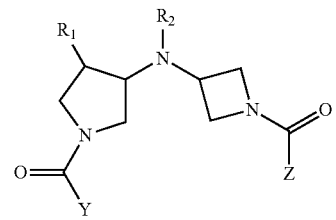

Formula (I)

wherein
Y is an unsubstituted phenyl or an unsubstituted heteroaryl that is thienyl or thiazolyl;
Z is
i) a $C_{6-10}$aryl;
ii) phenyl-($R_a$)-phenyl wherein the phenyl ring on phenyl-($R_a$)— is unsubstituted or substituted with one substituent that is trifluoromethyl;
$R_a$ is $CF_2$ or CH(OH);
iii) indolinyl and said indolinyl is unsubstituted or substituted with one substituent that is phenyl or bromo; or
iv) a heteroaryl selected from the group consisting benzothienyl, benzofuranyl, indolyl, and indazolyl;
wherein the $C_{6-10}$aryl and the heteroaryl of Z are unsubstituted or substituted with one or two substitutents each of which is independently selected from the group consisting of bromo, chloro, fluoro, $C_{1-4}$-alkyl, $C_{2-4}$alkenyl, trifluoromethyl, trifluoromethoxy, and $R_b$; provided that no more than one substituent is $R_b$;
$R_b$ is selected from the group consisting of phenylmethyl; thienyl; pyrimidinyl; and phenyl; wherein the phenyl portion of phenylmethyl, and said thienyl and said phenyl of $R_b$ are unsubstituted or substituted with one or two substituents each of which is independently selected from the group consisting of trifluoromethyl, chloro, and fluoro;
$R_1$ is hydrogen or fluoro;
$R_2$ is hydrogen;
and enantiomers, diastereomers, and pharmaceutically acceptable salt forms thereof.

5. A compound of Formula (I)

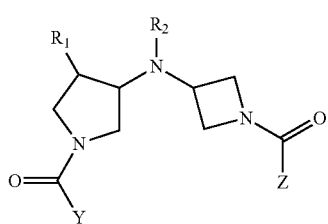

Formula (I)

selected from the group consisting of
(3S)—N-[1-(Biphenyl-4-ylcarbonyl)azetidin-3-yl]-1-(1,3-thiazol-2-ylcarbonyl)pyrrolidin-3-amine,
(3S)—N-[1-(Biphenyl-4-ylcarbonyl)azetidin-3-yl]-1-(phenylcarbonyl)pyrrolidin-3-amine,
(3S)—N-{1-[(4-Benzylphenyl)carbonyl]azetidin-3-yl}-1-(1,3-thiazol-2-ylcarbonyl)pyrrolidin-3-amine,
(3S)—N-{1-[(4-Benzylphenyl)carbonyl]azetidin-3-yl}-1-(phenylcarbonyl)pyrrolidin-3-amine,
(3S)—N-{1-[(4-Benzylphenyl)carbonyl]azetidin-3-yl}-1-(thiophen-3-ylcarbonyl)pyrrolidin-3-amine,
(3R)—N-{1-[(4-Benzylphenyl)carbonyl]azetidin-3-yl}-1-(1,3-thiazol-2-ylcarbonyl)pyrrolidin-3-amine,
(3R)—N-{1-[(4-Benzylphenyl)carbonyl]azetidin-3-yl}-1-(phenylcarbonyl)pyrrolidin-3-amine,
(3S)—N-{1-[(6-Bromo-3,4-dihydroisoquinolin-2(1H)-yl)carbonyl]azetidin-3-yl}-1-(1,3-thiazol-2-ylcarbonyl)pyrrolidin-3-amine,
(3S)—N-{1-[(6-Phenyl-3,4-dihydroisoquinolin-2(1H)-yl)carbonyl]azetidin-3-yl}-1-(1,3-thiazol-2-ylcarbonyl)pyrrolidin-3-amine,
(3S)—N-{1-[(5-Bromo-1,3-dihydro-2H-isoindol-2-yl)carbonyl]azetidin-3-yl}-1-(1,3-thiazol-2-ylcarbonyl)pyrrolidin-3-amine,
(3S)—N-{1-[(5-Phenyl-1,3-dihydro-2H-isoindol-2-yl)carbonyl]azetidin-3-yl}-1-(1,3-thiazol-2-ylcarbonyl)pyrrolidin-3-amine,
(3S)—N-{1-[(4-Benzylphenyl)carbonyl]azetidin-3-yl}-N-methyl-1-(phenylcarbonyl)pyrrolidin-3-amine,
(3S)—N-Methyl-1-(phenylcarbonyl)-N-(1-{[3'-(trifluoromethyl)biphenyl-4-yl]carbonyl}azetidin-3-yl)pyrrolidin-3-amine,
(3S)-1-(Phenylcarbonyl)-N-(1-{[3'-(trifluoromethyl)biphenyl-4-yl]carbonyl}azetidin-3-yl)pyrrolidin-3-amine,
(3S)—N-{1-[(3',5'-Dichlorobiphenyl-4-yl)carbonyl]azetidin-3-yl}-1-(phenylcarbonyl)pyrrolidin-3-amine,
(3S)-1-(Phenylcarbonyl)-N-(1-{[5-(trifluoromethoxy)-1-benzothiophen-2-yl]carbonyl}azetidin-3-yl)pyrrolidin-3-amine,
(3S)-1-(Phenylcarbonyl)-N-(1-{[5-(trifluoromethyl)-1-benzothiophen-2-yl]carbonyl}azetidin-3-yl)pyrrolidin-3-amine,
(3S)-1-(Phenylcarbonyl)-N-(1-{[6-(trifluoromethyl)-1-benzothiophen-2-yl]carbonyl}azetidin-3-yl)pyrrolidin-3-amine,
(3S)—N-{1-[(6-Bromo-3-chloro-1-benzothiophen-2-yl)carbonyl]azetidin-3-yl}-1-(phenylcarbonyl)pyrrolidin-3-amine,
(3S)—N-{1-[(5-Bromonaphthalen-2-yl)carbonyl]azetidin-3-yl}-1-(phenylcarbonyl)pyrrolidin-3-amine,
(3S)-1-(Phenylcarbonyl)-N-{1-[(5-phenylnaphthalen-2-yl)carbonyl]azetidin-3-yl}pyrrolidin-3-amine,
(3S)-1-(Phenylcarbonyl)-N-[1-({5-[2-(trifluoromethyl)phenyl]naphthalen-2-yl}carbonyl)azetidin-3-yl]pyrrolidin-3-amine,
(3S)-1-(Phenylcarbonyl)-N-[1-({5-[3-(trifluoromethyl)phenyl]naphthalen-2-yl}carbonyl)azetidin-3-yl]pyrrolidin-3-amine,
(3S)-1-(Phenylcarbonyl)-N-[1-({5-[4-(trifluoromethoxy)phenyl]naphthalen-2-yl}carbonyl)azetidin-3-yl]pyrrolidin-3-amine,
(3S)—N-[1-(9H-Fluoren-2-ylcarbonyl)azetidin-3-yl]-1-(phenylcarbonyl)pyrrolidin-3-amine,
(3S)—N-(1-{[3-Chloro-6-(trifluoromethyl)-1-benzothiophen-2-yl]carbonyl}azetidin-3-yl)-1-(phenylcarbonyl)pyrrolidin-3-amine,
(3S)—N-{1-[(3'-Chlorobiphenyl-4-yl)carbonyl]azetidin-3-yl}-1-(phenylcarbonyl)pyrrolidin-3-amine,
(3S)—N-{1-[(3',4'-Dichlorobiphenyl-4-yl)carbonyl]azetidin-3-yl}-1-(phenylcarbonyl)pyrrolidin-3-amine,
(3S)—N-{1-[(3-Chloro-6-phenyl-1-benzothiophen-2-yl)carbonyl]azetidin-3-yl}-1-(phenylcarbonyl)pyrrolidin-3-amine,
(3S)—N-[1-({3-Chloro-6-[3-(trifluoromethyl)phenyl]-1-benzothiophen-2-yl}carbonyl)azetidin-3-yl]-1-(phenylcarbonyl)pyrrolidin-3-amine,
(3S)—N-[1-({3-Chloro-6-[4-(trifluoromethyl)phenyl]-1-benzothiophen-2-yl}carbonyl)azetidin-3-yl]-1-(phenylcarbonyl)pyrrolidin-3-amine,
(3S)—N-{1-[(5-Bromonaphthalen-2-yl)carbonyl]azetidin-3-yl}-N-hydroxy-1-(phenylcarbonyl)pyrrolidin-3-amine,
(3S)-1-(Phenylcarbonyl)-N-(1-{[4'-(trifluoromethyl)biphenyl-4-yl]carbonyl}azetidin-3-yl)pyrrolidin-3-amine,
(3S)-1-(Phenylcarbonyl)-N-(1-{[4'-(trifluoromethoxy)biphenyl-4-yl]carbonyl}azetidin-3-yl)pyrrolidin-3-amine, (3S)—N-{1-[(5-Chloro-3-methyl-1-benzothiophen-2-yl)carbonyl]azetidin-3-yl}-1-(phenylcarbonyl)pyrrolidin-3-amine,
(3S)—N-{1-[(6-Bromo-1-benzothiophen-2-yl)carbonyl]azetidin-3-yl}-1-(phenylcarbonyl)pyrrolidin-3-amine,
(3S)—N-{1-[(3-Methyl-5-phenyl-1-benzothiophen-2-yl)carbonyl]azetidin-3-yl}-1-(phenylcarbonyl)pyrrolidin-3-amine,
(3S)—N-[1-({3-Methyl-5-[4-(trifluoromethyl)phenyl]-1-benzothiophen-2-yl}carbonyl)azetidin-3-yl]-1-(phenylcarbonyl)pyrrolidin-3-amine,
(3S)—N-[1-({3-Methyl-5-[3-(trifluoromethyl)phenyl]-1-benzothiophen-2-yl}carbonyl)azetidin-3-yl]-1-(phenylcarbonyl)pyrrolidin-3-amine,
(3S)—N-{1-[(6-Phenyl-1-benzothiophen-2-yl)carbonyl]azetidin-3-yl}-1-(phenylcarbonyl)pyrrolidin-3-amine,
(3S)-1-(Phenylcarbonyl)-N-[1-({6-[4-(trifluoromethyl)phenyl]-1-benzothiophen-2-yl}carbonyl)azetidin-3-yl]pyrrolidin-3-amine,
(3S)-1-(Phenylcarbonyl)-N-[1-({6-[3-(trifluoromethyl)phenyl]-1-benzothiophen-2-yl}carbonyl)azetidin-3-yl]pyrrolidin-3-amine,
(3S)—N-[1-(Biphenyl-4-ylcarbonyl)azetidin-3-yl]-1-[(4-fluorophenyl)carbonyl]pyrrolidin-3-amine,
(3S)—N-[1-(Biphenyl-4-ylcarbonyl)azetidin-3-yl]-1-[(3-fluorophenyl)carbonyl]pyrrolidin-3-amine,
(3S)-1-(1-Benzofuran-2-ylcarbonyl)-N-[1-(biphenyl-4-ylcarbonyl)azetidin-3-yl]pyrrolidin-3-amine,
(3S)-1-(1-Benzothiophen-2-ylcarbonyl)-N-[1-(biphenyl-4-ylcarbonyl)azetidin-3-yl]pyrrolidin-3-amine,
(3S)—N-{1-[(5-Bromo-1-benzothiophen-2-yl)carbonyl]azetidin-3-yl}-1-(phenylcarbonyl)pyrrolidin-3-amine,
(3S)—N-{1-[(5-Phenyl-1-benzothiophen-2-yl)carbonyl]azetidin-3-yl}-1-(phenylcarbonyl)pyrrolidin-3-amine,
(3S)-1-(Phenylcarbonyl)-N-[1-({5-[3-(trifluoromethyl)phenyl]-1-benzothiophen-2-yl}carbonyl)azetidin-3-yl]pyrrolidin-3-amine,
(3S)-1-(Phenylcarbonyl)-N-[1-({5-[4-(trifluoromethyl)phenyl]-1-benzothiophen-2-yl}carbonyl)azetidin-3-yl]pyrrolidin-3-amine,
(3S)—N-Ethyl-1-(phenylcarbonyl)-N-(1-{[3'-(trifluoromethyl)biphenyl-4-yl]carbonyl}azetidin-3-yl)pyrrolidin-3-amine,
(3S)—N-Hydroxy-1-(phenylcarbonyl)-N-(1-{[3'-(trifluoromethyl)biphenyl-4-yl]carbonyl}azetidin-3-yl)pyrrolidin-3-amine,
(3S)—N-{1-[(3-Bromo-1-benzothiophen-2-yl)carbonyl]azetidin-3-yl}-1-(phenylcarbonyl)pyrrolidin-3-amine,
(3S)—N-{1-[(3-Chloro-6-fluoro-1-benzothiophen-2-yl)carbonyl]azetidin-3-yl}-1-(phenylcarbonyl)pyrrolidin-3-amine,
(3S)-1-(Phenylcarbonyl)-N-{1-[(3-phenyl-1H-indol-6-yl)carbonyl]azetidin-3-yl}pyrrolidin-3-amine,
N-[1-(Biphenyl-4-ylcarbonyl)azetidin-3-yl]-4-fluoro-1-(phenylcarbonyl)pyrrolidin-3-amine,
4-Fluoro-1-(phenylcarbonyl)-N-(1-{[3'-(trifluoromethyl)biphenyl-4-yl]carbonyl}azetidin-3-yl)pyrrolidin-3-amine,
(3R)—N-[1-(Biphenyl-4-ylcarbonyl)azetidin-3-yl]-4-fluoro-1-(phenylcarbonyl)pyrrolidin-3-amine,
(3S)—N-[1-(Biphenyl-4-ylcarbonyl)azetidin-3-yl]-4-fluoro-1-(phenylcarbonyl)pyrrolidin-3-amine,
(3R)-4-Fluoro-1-(phenylcarbonyl)-N-(1-{[3'-(trifluoromethyl)biphenyl-4-yl]carbonyl}azetidin-3-yl)pyrrolidin-3-amine,
(3S)-4-Fluoro-1-(phenylcarbonyl)-N-(1-{[3'-(trifluoromethyl)biphenyl-4-yl]carbonyl}azetidin-3-yl)pyrrolidin-3-amine,
(3S)—N-{1-[(1-Methyl-3-phenyl-1H-indol-6-yl)carbonyl]azetidin-3-yl}-1-(phenylcarbonyl)pyrrolidin-3-amine,
(3S)—N-{1-[(3-Phenyl-1-benzothiophen-2-yl)carbonyl]azetidin-3-yl}-1-(phenylcarbonyl)pyrrolidin-3-amine,
(3S)—N-{1-[(3-Cyclopropyl-1-benzothiophen-2-yl)carbonyl]azetidin-3-yl}-1-(phenylcarbonyl)pyrrolidin-3-amine,
{4-[(3-{[(3S)-1-(Phenylcarbonyl)pyrrolidin-3-yl]amino}azetidin-1-yl)carbonyl]phenyl}[4-(trifluoromethyl)phenyl]methanol,
(3S)—N-{1-[(3-Methyl-1-benzothiophen-2-yl)carbonyl]azetidin-3-yl}-1-(phenylcarbonyl)pyrrolidin-3-amine,
N-{1-[(4-{Fluoro[4-(trifluoromethyl)phenyl]methyl}phenyl)carbonyl]azetidin-3-yl}-1-(phenylcarbonyl)pyrrolidin-3-amine,
(3S)—N-{1-[(3-Cyclopropyl-6-fluoro-1-benzothiophen-2-yl)carbonyl]azetidin-3-yl}-1-(phenylcarbonyl)pyrrolidin-3-amine,
(3R,4R)-4-Methoxy-1-(phenylcarbonyl)-N-(1-{[3'-(trifluoromethyl)biphenyl-4-yl]carbonyl}azetidin-3-yl)pyrrolidin-3-amine,
(3R,4R)-1-(Phenylcarbonyl)-4-[(1-{[3'-(trifluoromethyl)biphenyl-4-yl]carbonyl}azetidin-3-yl)amino]pyrrolidin-3-ol,
(3S)—N-[1-({4-[Difluoro(phenyl)methyl]phenyl}carbonyl)azetidin-3-yl]-1-(phenylcarbonyl)pyrrolidin-3-amine,
(3S)-1-(Phenylcarbonyl)-N-(1-{[3-phenyl-6-(trifluoromethyl)-1-benzothiophen-2-yl]carbonyl}azetidin-3-yl)pyrrolidin-3-amine,
(3S)—N-(1-{[3-Cyclopropyl-6-(trifluoromethyl)-1-benzothiophen-2-yl]carbonyl}azetidin-3-yl)-1-(phenylcarbonyl)pyrrolidin-3-amine,
(3S)—N-(1-{[3-(2-Methylprop-1-en-1-yl)-6-(trifluoromethyl)-1-benzothiophen-2-yl]carbonyl}azetidin-3-yl)-1-(phenylcarbonyl)pyrrolidin-3-amine,
(3S)-1-(Phenylcarbonyl)-N-[1-({4-[4-(trifluoromethyl)benzyl]phenyl}carbonyl)azetidin-3-yl]pyrrolidin-3-amine,
(3R,4R)-4-{[1-(Biphenyl-4-ylcarbonyl)azetidin-3-yl]amino}-1-(phenylcarbonyl)pyrrolidin-3-ol,
(3S)—N-{1-[(3-Cyclobutyl-6-fluoro-1-benzothiophen-2-yl)carbonyl]azetidin-3-yl}-1-(phenylcarbonyl)pyrrolidin-3-amine,
(3S)—N-(1-{[3-Methyl-6-(trifluoromethyl)-1-benzothiophen-2-yl]carbonyl}azetidin-3-yl)-1-(phenylcarbonyl)pyrrolidin-3-amine,
N-{1-[(5-Chloro-3-methyl-1-benzothiophen-2-yl)carbonyl]azetidin-3-yl}-N-[(3S)-1-(phenylcarbonyl)pyrrolidin-3-yl]formamide,
N-{1-[(5-Chloro-3-methyl-1-benzothiophen-2-yl)carbonyl]azetidin-3-yl}-N-[(3S)-1-(1,3-thiazol-2-ylcarbonyl)pyrrolidin-3-yl]formamide,
N-{1-[(5-Chloro-3-methyl-1-benzothiophen-2-yl)carbonyl]azetidin-3-yl}-N-[(3S)-1-(1,3-thiazol-4-ylcarbonyl)pyrrolidin-3-yl]formamide,
(3S)—N-{1-[(5-Chloro-3-methyl-1-benzothiophen-2-yl)carbonyl]azetidin-3-yl}-1-(1,3-thiazol-2-ylcarbonyl)pyrrolidin-3-amine,
(3S)—N-{1-[(5-Chloro-3-methyl-1-benzothiophen-2-yl)carbonyl]azetidin-3-yl}-1-(1,3-thiazol-4-ylcarbonyl)pyrrolidin-3-amine, (3S)—N-{1-[(6-Fluoro-3-methyl-1-benzothiophen-2-yl)carbonyl]azetidin-3-yl}-1-(phenylcarbonyl)pyrrolidin-3-amine,
(3S)—N-{1-[(6-Fluoro-3-methyl-1-benzothiophen-2-yl)carbonyl]azetidin-3-yl}-1-(1,3-thiazol-2-ylcarbonyl)pyrrolidin-3-amine,
(3S)—N-{1-[(6-Fluoro-3-methyl-1-benzothiophen-2-yl)carbonyl]azetidin-3-yl}-1-(1,3-thiazol-4-ylcarbonyl)pyrrolidin-3-amine,
(3S)—N-(1-{[3-Fluoro-6-(trifluoromethyl)-1-benzothiophen-2-yl]carbonyl}azetidin-3-yl)-1-(phenylcarbonyl)pyrrolidin-3-amine,
(3S)—N-[1-({3-Methyl-5-[3-(trifluoromethyl)phenyl]-1-benzothiophen-2-yl}carbonyl)azetidin-3-yl]-1-(1,3-thiazol-2-ylcarbonyl)pyrrolidin-3-amine,
(3S)—N-[1-({3-Methyl-5-[4-(trifluoromethyl)phenyl]-1-benzothiophen-2-yl}carbonyl)azetidin-3-yl]-1-(1,3-thiazol-2-ylcarbonyl)pyrrolidin-3-amine,
(3S)—N-{1-[(3-Methyl-5-phenyl-1-benzothiophen-2-yl)carbonyl]azetidin-3-yl}-1-(1,3-thiazol-2-ylcarbonyl)pyrrolidin-3-amine,
(3S)—N-(1-{[5-(3-Fluorophenyl)-3-methyl-1-benzothiophen-2-yl]carbonyl}azetidin-3-yl)-1-(phenylcarbonyl)pyrrolidin-3-amine,
(3S)—N-(1-{[5-(4-Fluorophenyl)-3-methyl-1-benzothiophen-2-yl]carbonyl}azetidin-3-yl)-1-(phenylcarbonyl)pyrrolidin-3-amine,
(3S)—N-{1-[(6-Bromo-1-benzothiophen-2-yl)carbonyl]azetidin-3-yl}-1-(1,3-thiazol-2-ylcarbonyl)pyrrolidin-3-amine,
(3S)—N-{1-[(6-Bromo-1-benzothiophen-2-yl)carbonyl]azetidin-3-yl}-1-(1,3-thiazol-4-ylcarbonyl)pyrrolidin-3-amine,
(3S)—N-{1-[(5-Bromo-1-benzothiophen-2-yl)carbonyl]azetidin-3-yl}-1-(1,3-thiazol-2-ylcarbonyl)pyrrolidin-3-amine,
(3S)—N-{1-[(5-Bromo-1-benzothiophen-2-yl)carbonyl]azetidin-3-yl}-1-(1,3-thiazol-4-ylcarbonyl)pyrrolidin-3-amine,
(3S)-1-(1,3-Thiazol-2-ylcarbonyl)-N-[1-({6-[3-(trifluoromethyl)phenyl]-1-benzothiophen-2-yl}carbonyl)azetidin-3-yl]pyrrolidin-3-amine,
(3S)-1-(1,3-Thiazol-4-ylcarbonyl)-N-[1-({6-[3-(trifluoromethyl)phenyl]-1-benzothiophen-2-yl}carbonyl)azetidin-3-yl]pyrrolidin-3-amine,
(3S)-1-(Phenylcarbonyl)-N-[1-({3-[4-(trifluoromethyl)phenyl]-1H-indol-6-yl}carbonyl)azetidin-3-yl]pyrrolidin-3-amine,
(3S)-1-(1,3-Thiazol-2-ylcarbonyl)-N-[1-({6-[4-(trifluoromethyl)phenyl]-1-benzothiophen-2-yl}carbonyl)azetidin-3-yl]pyrrolidin-3-amine,
(3S)-1-(Phenylcarbonyl)-N-[1-({3-[3-(trifluoromethyl)phenyl]-1H-indol-6-yl}carbonyl)azetidin-3-yl]pyrrolidin-3-amine,
(3S)-1-(1,3-Thiazol-2-ylcarbonyl)-N-[1-({3-[4-(trifluoromethyl)phenyl]-1H-indol-6-yl}carbonyl)azetidin-3-yl]pyrrolidin-3-amine,
(3S)-1-(1,3-Thiazol-2-ylcarbonyl)-N-[1-({3-[3-(trifluoromethyl)phenyl]-1H-indol-6-yl}carbonyl)azetidin-3-yl]pyrrolidin-3-amine,
(3S)-1-(1,3-Thiazol-4-ylcarbonyl)-N-[1-({3-[3-(trifluoromethyl)phenyl]-1H-indol-6-yl}carbonyl)azetidin-3-yl]pyrrolidin-3-amine,
(3S)—N-{1-[(5-Bromo-1-benzofuran-2-yl)carbonyl]azetidin-3-yl}-1-(phenylcarbonyl)pyrrolidin-3-amine,
(3S)-1-(Phenylcarbonyl)-N-{1-[(4-phenylquinazolin-7-yl)carbonyl]azetidin-3-yl}pyrrolidin-3-amine,
(3S)-1-(Phenylcarbonyl)-N-[1-({4-[4-(trifluoromethyl)phenyl]quinazolin-7-yl}carbonyl)azetidin-3-yl]pyrrolidin-3-amine,
(3S)—N-{1-[(4-Phenylquinazolin-7-yl)carbonyl]azetidin-3-yl}-1-(1,3-thiazol-2-ylcarbonyl)pyrrolidin-3-amine,
(3S)-1-(1,3-Thiazol-2-ylcarbonyl)-N-[1-({4-[4-(trifluoromethyl)phenyl]quinazolin-7-yl}carbonyl)azetidin-3-yl]pyrrolidin-3-amine,
(3S)—N-{1-[(4-Phenylquinazolin-7-yl)carbonyl]azetidin-3-yl}-1-(1,3-thiazol-4-ylcarbonyl)pyrrolidin-3-amine,
(3S)-1-(1,3-Thiazol-2-ylcarbonyl)-N-(1-{[3'-(trifluoromethyl)biphenyl-4-yl]carbonyl}azetidin-3-yl)pyrrolidin-3-amine,
(3S)-1-(1,3-Thiazol-4-ylcarbonyl)-N-(1-{[3'-(trifluoromethyl)biphenyl-4-yl]carbonyl}azetidin-3-yl)pyrrolidin-3-amine,
(3S)-1-(1,3-Thiazol-2-ylcarbonyl)-N-(1-{[4'-(trifluoromethyl)biphenyl-4-yl]carbonyl}azetidin-3-yl)pyrrolidin-3-amine,
(3S)—N-(1-{[3-Fluoro-3'-(trifluoromethyl)biphenyl-4-yl]carbonyl}azetidin-3-yl)-1-(1,3-thiazol-2-ylcarbonyl)pyrrolidin-3-amine,
(3S)—N-(1-{[3-Methyl-3'-(trifluoromethyl)biphenyl-4-yl]carbonyl}azetidin-3-yl)-1-(1,3-thiazol-2-ylcarbonyl)pyrrolidin-3-amine,
(3S)-1-(1,3-Thiazol-2-ylcarbonyl)-N-[1-({1-[4-(trifluoromethyl)phenyl]-1H-indol-5-yl}carbonyl)azetidin-3-yl]pyrrolidin-3-amine,
(3S)—N-{1-[(1-Pyrimidin-2-yl-1H-indol-5-yl)carbonyl]azetidin-3-yl}-1-(1,3-thiazol-2-ylcarbonyl)pyrrolidin-3-amine,
(3S)—N-{1-[(1-Phenyl-1H-indazol-5-yl)carbonyl]azetidin-3-yl}-1-(1,3-thiazol-2-ylcarbonyl)pyrrolidin-3-amine,
(3S)—N-{1-[(5-Phenyl-1-benzofuran-2-yl)carbonyl]azetidin-3-yl}-1-(phenylcarbonyl)pyrrolidin-3-amine,
(3S)—N-(1-{[5-(5-Chlorothiophen-2-yl)-1-benzofuran-2-yl]carbonyl}azetidin-3-yl)-1-(phenylcarbonyl)pyrrolidin-3-amine,
(3S)—N-{1-[(3-Methyl-5-phenyl-1-benzothiophen-2-yl)carbonyl]azetidin-3-yl}-1-(1,3-thiazol-4-ylcarbonyl)pyrrolidin-3-amine,
(3S)—N-{1-[(6-Phenyl-1-benzothiophen-2-yl)carbonyl]azetidin-3-yl}-1-(1,3-thiazol-4-ylcarbonyl)pyrrolidin-3-amine,
(3S)—N-[1-({3-Methyl-5-[3-(trifluoromethyl)phenyl]-1-benzothiophen-2-yl}carbonyl)azetidin-3-yl]-1-(1,3-thiazol-4-ylcarbonyl)pyrrolidin-3-amine,
(3S)-1-(Phenylcarbonyl)-N-[1-({4-[3-(trifluoromethyl)benzyl]phenyl}carbonyl)azetidin-3-yl]pyrrolidin-3-amine,
(3S)-1-(1,3-Thiazol-4-ylcarbonyl)-N-[1-({4-[3-(trifluoromethyl)benzyl]phenyl}carbonyl)azetidin-3-yl]pyrrolidin-3-amine,
(3S)-1-(1,3-Thiazol-4-ylcarbonyl)-N-[1-({6-[4-(trifluoromethyl)phenyl]-1-benzothiophen-2-yl}carbonyl)azetidin-3-yl]pyrrolidin-3-amine,
(3S)—N-{1-[(5-Phenyl-1-benzothiophen-2-yl)carbonyl]azetidin-3-yl}-1-(1,3-thiazol-2-ylcarbonyl)pyrrolidin-3-amine,
(3S)-1-(1,3-Thiazol-4-ylcarbonyl)-N-[1-({5-[3-(trifluoromethyl)phenyl]-1-benzothiophen-2-yl}carbonyl)azetidin-3-yl]pyrrolidin-3-amine, (3S)—N-{1-[(5-Phenyl-1-benzothiophen-2-yl)carbonyl]azetidin-3-yl}-1-(1,3-thiazol-4-ylcarbonyl)pyrrolidin-3-amine, (3S)-1-(1,3-Thiazol-2-ylcarbonyl)-N-[1-({5-[3-(trifluoromethyl)phenyl]-1-benzothiophen-2-yl}carbonyl)azetidin-3-yl]pyrrolidin-3-amine, (3S)—N-{1-[(2-Phenyl-1,3-benzothiazol-6-yl)carbonyl]azetidin-3-yl}-1-(1,3-thiazol-2-ylcarbonyl)pyrrolidin-3-amine, (3S)—N-(1-{[2-(2-Fluorophenyl)-4-methyl-1,3-thiazol-5-yl]carbonyl}azetidin-3-yl)-1-(1,3-thiazol-2-ylcarbonyl)pyrrolidin-3-amine, (3S)—N-(1-{[2-(4-Fluorophenyl)-4-methyl-1,3-thiazol-5-yl]carbonyl}azetidin-3-yl)-1-(1,3-thiazol-2-ylcarbonyl)pyrrolidin-3-amine, (3S)—N-(1-{[2-(3-Chlorophenyl)-4-methyl-1,3-thiazol-5-yl]carbonyl}azetidin-3-yl)-1-(1,3-thiazol-2-ylcarbonyl)pyrrolidin-3-amine, (3S)—N-(1-{[2-(4-Chlorophenyl)-4-methyl-1,3-thiazol-5-yl]carbonyl}azetidin-3-yl)-1-(1,3-thiazol-2-ylcarbonyl)pyrrolidin-3-amine, (3S)-1-(1,3-Thiazol-2-ylcarbonyl)-N-(1-{[6-(trifluoromethyl)-1-benzothiophen-2-yl]carbonyl}azetidin-3-yl)pyrrolidin-3-amine, (3S)-1-(1,3-Thiazol-4-ylcarbonyl)-N-(1-{[6-(trifluoromethyl)-1-benzothiophen-2-yl]carbonyl}azetidin-3-yl)pyrrolidin-3-amine, (3S)—N-{1-[(6-Bromo-3-chloro-1-benzothiophen-2-yl)carbonyl]azetidin-3-yl}-1-(1,3-thiazol-2-ylcarbonyl)pyrrolidin-3-amine, (3S)—N-{1-[(6-Bromo-3-chloro-1-benzothiophen-2-yl)carbonyl]azetidin-3-yl}-1-(1,3-thiazol-4-ylcarbonyl)pyrrolidin-3-amine, (3S)—N-(1-{[3-Fluoro-1-(4-fluorophenyl)-1H-indol-5-yl]carbonyl}azetidin-3-yl)-1-(phenylcarbonyl)pyrrolidin-3-amine, (3S)—N-(1-{[3-Fluoro-1-(4-fluorophenyl)-1H-indol-5-yl]carbonyl}azetidin-3-yl)-1-(1,3-thiazol-4-ylcarbonyl)pyrrolidin-3-amine, (3S)-1-(1,3-Thiazol-4-ylcarbonyl)-N-[1-({4-[4-(trifluoromethyl)benzyl]phenyl}carbonyl)azetidin-3-yl]pyrrolidin-3-amine, (3S)-1-(1,3-Thiazol-4-ylcarbonyl)-N-(1-{[4'-(trifluoromethyl)biphenyl-4-yl]carbonyl}azetidin-3-yl)pyrrolidin-3-amine, (3S)—N-{1-[(3-Chloro-6-phenyl-1-benzothiophen-2-yl)carbonyl]azetidin-3-yl}-1-(1,3-thiazol-2-ylcarbonyl)pyrrolidin-3-amine, (3S)—N-{1-[(3-Chloro-6-phenyl-1-benzothiophen-2-yl)carbonyl]azetidin-3-yl}-1-(1,3-thiazol-4-ylcarbonyl)pyrrolidin-3-amine, (3S)—N-[1-({3-Chloro-6-[3-(trifluoromethyl)phenyl]-1-benzothiophen-2-yl}carbonyl)azetidin-3-yl]-1-(1,3-thiazol-2-ylcarbonyl)pyrrolidin-3-amine, (3S)—N-[1-({3-Chloro-6-[3-(trifluoromethyl)phenyl]-1-benzothiophen-2-yl}carbonyl)azetidin-3-yl]-1-(1,3-thiazol-4-ylcarbonyl)pyrrolidin-3-amine, (3S)—N-[1-({3-Chloro-6-[4-(trifluoromethyl)phenyl]-1-benzothiophen-2-yl}carbonyl)azetidin-3-yl]-1-(1,3-thiazol-2-ylcarbonyl)pyrrolidin-3-amine, (3S)—N-[1-({3-Chloro-6-[4-(trifluoromethyl)phenyl]-1-benzothiophen-2-yl}carbonyl)azetidin-3-yl]-1-(1,3-thiazol-4-ylcarbonyl)pyrrolidin-3-amine, (3S)—N-(1-{[3-Fluoro-3'-(trifluoromethyl)biphenyl-4-yl]carbonyl}azetidin-3-yl)-1-(phenylcarbonyl)pyrrolidin-3-amine, (3S)—N-(1-{[3-Methyl-3'-(trifluoromethyl)biphenyl-4-yl]carbonyl}azetidin-3-yl)-1-(phenylcarbonyl)pyrrolidin-3-amine, (3S)-1-(Phenylcarbonyl)-N-[1-({1-[4-(trifluoromethyl)phenyl]-1H-indol-5-yl}carbonyl)azetidin-3-yl]pyrrolidin-3-amine, (3S)-1-(Phenylcarbonyl)-N-{1-[(1-pyrimidin-2-yl-1H-indol-5-yl)carbonyl]azetidin-3-yl}pyrrolidin-3-amine, (3S)-1-(Phenylcarbonyl)-N-{1-[(1-phenyl-1H-indazol-5-yl)carbonyl]azetidin-3-yl}pyrrolidin-3-amine, (3S)—N-{1-[(2-Phenyl-1,3-benzothiazol-6-yl)carbonyl]azetidin-3-yl}-1-(phenylcarbonyl)pyrrolidin-3-amine, (3S)-1-(1,3-Thiazol-4-ylcarbonyl)-N-[1-({1-[4-(trifluoromethyl)phenyl]-1H-indol-5-yl}carbonyl)azetidin-3-yl]pyrrolidin-3-amine, (3S)—N-(1-{[1-(4-Fluorophenyl)-1H-indol-5-yl]carbonyl}azetidin-3-yl)-1-(1,3-thiazol-2-ylcarbonyl)pyrrolidin-3-amine, (3S)—N-(1-{[1-(4-Fluorophenyl)-1H-indol-5-yl]carbonyl}azetidin-3-yl)-1-(1,3-thiazol-4-ylcarbonyl)pyrrolidin-3-amine, (3S)—N-(1-{[1-(4-Fluorophenyl)-1H-indol-5-yl]carbonyl}azetidin-3-yl)-1-(phenylcarbonyl)pyrrolidin-3-amine, (3S)—N-[1-({1-Methyl-3-[3-(trifluoromethyl)phenyl]-1H-indol-6-yl}carbonyl)azetidin-3-yl]-1-(1,3-thiazol-2-ylcarbonyl)pyrrolidin-3-amine, (3S)—N-[1-({1-Methyl-3-[4-(trifluoromethyl)phenyl]-1H-indol-6-yl}carbonyl)azetidin-3-yl]-1-(1,3-thiazol-2-ylcarbonyl)pyrrolidin-3-amine, (3S)—N-[1-({1-Methyl-3-[3-(trifluoromethyl)phenyl]-1H-indol-6-yl}carbonyl)azetidin-3-yl]-1-(1,3-thiazol-4-ylcarbonyl)pyrrolidin-3-amine, (3S)—N-[1-({1-Methyl-3-[4-(trifluoromethyl)phenyl]-1H-indol-6-yl}carbonyl)azetidin-3-yl]-1-(1,3-thiazol-4-ylcarbonyl)pyrrolidin-3-amine, (3S)—N-[1-({1-Methyl-3-[3-(trifluoromethyl)phenyl]-1H-indol-6-yl}carbonyl)azetidin-3-yl]-1-(phenylcarbonyl)pyrrolidin-3-amine, (3S)—N-(1-{[3-Chloro-6-(trifluoromethyl)-1-benzothiophen-2-yl]carbonyl}azetidin-3-yl)-1-(1,3-thiazol-2-ylcarbonyl)pyrrolidin-3-amine, (3S)—N-(1-{[3-Chloro-6-(trifluoromethyl)-1-benzothiophen-2-yl]carbonyl}azetidin-3-yl)-1-(1,3-thiazol-4-ylcarbonyl)pyrrolidin-3-amine, (3S)—N-{1-[(1-Methyl-3-phenyl-1H-indol-6-yl)carbonyl]azetidin-3-yl}-1-(1,3-thiazol-2-ylcarbonyl)pyrrolidin-3-amine, (3S)—N-{1-[(1-Methyl-3-phenyl-1H-indol-6-yl)carbonyl]azetidin-3-yl}-1-(1,3-thiazol-4-ylcarbonyl)pyrrolidin-3-amine, (3S)—N-{1-[(3-Fluoro-5-phenyl-1-benzothiophen-2-yl)carbonyl]azetidin-3-yl}-1-(1,3-thiazol-2-ylcarbonyl)pyrrolidin-3-amine, (3S)—N-{1-[(3-Fluoro-5-phenyl-1-benzothiophen-2-yl)carbonyl]azetidin-3-yl}-1-(1,3-thiazol-4-ylcarbonyl)pyrrolidin-3-amine, (3S)—N-{1-[(3-Fluoro-5-phenyl-1-benzothiophen-2-yl)carbonyl]azetidin-3-yl}-1-(phenylcarbonyl)pyrrolidin-3-amine, (3S)—N-[1-({3-Fluoro-5-[4-(trifluoromethyl)phenyl]-1-benzothiophen-2-yl}carbonyl)azetidin-3-yl]-1-(1,3-thiazol-2-ylcarbonyl)pyrrolidin-3-amine, (3S)—N-[1-({3-Fluoro-5-[4-(trifluoromethyl)phenyl]-1-benzothiophen-2-yl}carbonyl)azetidin-3-yl]-1-(1,3-thiazol-4-ylcarbonyl)pyrrolidin-3-amine, (3S)—N-[1-({3-Fluoro-5-[4-(trifluoromethyl)phenyl]-1-benzothiophen-2-yl}carbonyl)azetidin-3-yl]-1-(phenylcarbonyl)pyrrolidin-3-amine,
(3S)—N-[1-({3-Fluoro-6-[4-(trifluoromethyl)phenyl]-1-benzothiophen-2-yl}carbonyl)azetidin-3-yl]-1-(1,3-thiazol-2-ylcarbonyl)pyrrolidin-3-amine,
(3S)—N-[1-({3-Fluoro-6-[4-(trifluoromethyl)phenyl]-1-benzothiophen-2-yl}carbonyl)azetidin-3-yl]-1-(1,3-thiazol-4-ylcarbonyl)pyrrolidin-3-amine,
(3S)—N-[1-({3-Fluoro-6-[4-(trifluoromethyl)phenyl]-1-benzothiophen-2-yl}carbonyl)azetidin-3-yl]-1-(phenylcarbonyl)pyrrolidin-3-amine,
(3S)—N-(1-{[5-Chloro-3-(trifluoromethyl)-1-benzothiophen-2-yl]carbonyl}azetidin-3-yl)-1-(phenylcarbonyl)pyrrolidin-3-amine,
(3S)—N-(1-{[5-Chloro-3-(trifluoromethyl)-1-benzothiophen-2-yl]carbonyl}azetidin-3-yl)-1-(1,3-thiazol-4-ylcarbonyl)pyrrolidin-3-amine,
(3S)—N-(1-{[6-Chloro-3-(trifluoromethyl)-1-benzothiophen-2-yl]carbonyl}azetidin-3-yl)-1-(phenylcarbonyl)pyrrolidin-3-amine,
(3S)—N-(1-{[6-Chloro-3-(trifluoromethyl)-1-benzothiophen-2-yl]carbonyl}azetidin-3-yl)-1-(1,3-thiazol-2-ylcarbonyl)pyrrolidin-3-amine,
(3S)—N-(1-{[5-Methyl-3-(trifluoromethyl)-1-benzothiophen-2-yl]carbonyl}azetidin-3-yl)-1-(1,3-thiazol-4-ylcarbonyl)pyrrolidin-3-amine,
(3S)—N-(1-{[6-Methyl-3-(trifluoromethyl)-1-benzothiophen-2-yl]carbonyl}azetidin-3-yl)-1-(1,3-thiazol-4-ylcarbonyl)pyrrolidin-3-amine,
(3S)—N-(1-{[6-Methyl-3-(trifluoromethyl)-1-benzothiophen-2-yl]carbonyl}azetidin-3-yl)-1-(1,3-thiazol-2-ylcarbonyl)pyrrolidin-3-amine,
(3S)—N-{1-[(3-Phenyl-1H-indol-6-yl)carbonyl]azetidin-3-yl}-1-(1,3-thiazol-2-ylcarbonyl)pyrrolidin-3-amine,
(3S)—N-{1-[(3-Phenyl-1H-indol-6-yl)carbonyl]azetidin-3-yl}-1-(1,3-thiazol-4-ylcarbonyl)pyrrolidin-3-amine,
(3S)—N-(1-{[3-(4-Fluorophenyl)-1H-indol-6-yl]carbonyl}azetidin-3-yl)-1-(1,3-thiazol-2-ylcarbonyl)pyrrolidin-3-amine,
(3S)—N-(1-{[3-(4-Fluorophenyl)-1H-indol-6-yl]carbonyl}azetidin-3-yl)-1-(1,3-thiazol-4-ylcarbonyl)pyrrolidin-3-amine,
(3S)—N-(1-{[3-(4-Fluorophenyl)-1H-indol-6-yl]carbonyl}azetidin-3-yl)-1-(phenylcarbonyl)pyrrolidin-3-amine,
(3S)—N-(1-{[3-(4-Fluorophenyl)-1-methyl-1H-indol-6-yl]carbonyl}azetidin-3-yl)-1-(1,3-thiazol-2-ylcarbonyl)pyrrolidin-3-amine,
(3S)—N-(1-{[3-(4-Fluorophenyl)-1-methyl-1H-indol-6-yl]carbonyl}azetidin-3-yl)-1-(1,3-thiazol-4-ylcarbonyl)pyrrolidin-3-amine,
(3S)—N-(1-{[3-(4-Fluorophenyl)-1-methyl-1H-indol-6-yl]carbonyl}azetidin-3-yl)-1-(phenylcarbonyl)pyrrolidin-3-amine,
(3S)—N-{1-[(1-Methyl-3-phenyl-1H-indazol-5-yl)carbonyl]azetidin-3-yl}-1-(1,3-thiazol-2-ylcarbonyl)pyrrolidin-3-amine,
(3S)—N-{1-[(1-Methyl-3-phenyl-1H-indazol-5-yl)carbonyl]azetidin-3-yl}-1-(1,3-thiazol-4-ylcarbonyl)pyrrolidin-3-amine,
(3S)—N-{1-[(1-Methyl-3-phenyl-1H-indazol-5-yl)carbonyl]azetidin-3-yl}-1-(phenylcarbonyl)pyrrolidin-3-amine,
(3S)—N-(1-{[4-Fluoro-1-(4-fluorophenyl)-1H-indol-5-yl]carbonyl}azetidin-3-yl)-1-(1,3-thiazol-2-ylcarbonyl)pyrrolidin-3-amine,
(3S)—N-(1-{[3-(3-Fluorophenyl)-1-methyl-1H-indazol-5-yl]carbonyl}azetidin-3-yl)-1-(1,3-thiazol-2-ylcarbonyl)pyrrolidin-3-amine,
(3S)—N-(1-{[3-(3-Fluorophenyl)-1-methyl-1H-indazol-5-yl]carbonyl}azetidin-3-yl)-1-(1,3-thiazol-4-ylcarbonyl)pyrrolidin-3-amine,
(3S)—N-(1-{[3-(3-Fluorophenyl)-1-methyl-1H-indazol-5-yl]carbonyl}azetidin-3-yl)-1-(phenylcarbonyl)pyrrolidin-3-amine,
(3S)—N-(1-{[3-(3-Fluorophenyl)-1H-indol-6-yl]carbonyl}azetidin-3-yl)-1-(1,3-thiazol-2-ylcarbonyl)pyrrolidin-3-amine,
(3S)—N-(1-{[3-(3-Fluorophenyl)-1H-indol-6-yl]carbonyl}azetidin-3-yl)-1-(1,3-thiazol-4-ylcarbonyl)pyrrolidin-3-amine,
(3S)—N-(1-{[3-(3-Fluorophenyl)-1H-indol-6-yl]carbonyl}azetidin-3-yl)-1-(phenylcarbonyl)pyrrolidin-3-amine,
(3S)—N-(1-{[3-(3-Fluorophenyl)-1-methyl-1H-indol-6-yl]carbonyl}azetidin-3-yl)-1-(1,3-thiazol-2-ylcarbonyl)pyrrolidin-3-amine,
(3S)—N-(1-{[3-(3-Fluorophenyl)-1-methyl-1H-indol-6-yl]carbonyl}azetidin-3-yl)-1-(1,3-thiazol-4-ylcarbonyl)pyrrolidin-3-amine,
(3S)—N-(1-{[3-(3-Fluorophenyl)-1-methyl-1H-indol-6-yl]carbonyl}azetidin-3-yl)-1-(phenylcarbonyl)pyrrolidin-3-amine,
(3S)—N-(1-{[6-Phenyl-3-(trifluoromethyl)-1-benzothiophen-2-yl]carbonyl}azetidin-3-yl)-1-(1,3-thiazol-2-ylcarbonyl)pyrrolidin-3-amine,
(3S)—N-(1-{[3-(4-Fluorophenyl)-1-methyl-1H-indazol-5-yl]carbonyl}azetidin-3-yl)-1-(1,3-thiazol-2-ylcarbonyl)pyrrolidin-3-amine,
(3S)—N-(1-{[3-(4-Fluorophenyl)-1-methyl-1H-indazol-5-yl]carbonyl}azetidin-3-yl)-1-(1,3-thiazol-4-ylcarbonyl)pyrrolidin-3-amine,
(3S)—N-(1-{[3-(4-Fluorophenyl)-1-methyl-1H-indazol-5-yl]carbonyl}azetidin-3-yl)-1-(phenylcarbonyl)pyrrolidin-3-amine,
(3S)—N-(1-{[6-Fluoro-1-(4-fluorophenyl)-1H-indol-5-yl]carbonyl}azetidin-3-yl)-1-(1,3-thiazol-2-ylcarbonyl)pyrrolidin-3-amine,
(3R)—N-(1-{[1-(2,2-Difluoroethyl)-1H-indol-5-yl]carbonyl}azetidin-3-yl)-1-(1,3-thiazol-2-ylcarbonyl)pyrrolidin-3-amine,
(3S)—N-(1-{[1-(4-Fluorophenyl)-1H-indol-4-yl]carbonyl}azetidin-3-yl)-1-(1,3-thiazol-2-ylcarbonyl)pyrrolidin-3-amine,
(3S)—N-(1-{[1-(4-Fluorophenyl)-1H-indol-4-yl]carbonyl}azetidin-3-yl)-1-(1,3-thiazol-4-ylcarbonyl)pyrrolidin-3-amine,
(3S)—N-(1-{[1-(4-Fluorophenyl)-2,3-dihydro-1H-indol-4-yl]carbonyl}azetidin-3-yl)-1-(1,3-thiazol-2-ylcarbonyl)pyrrolidin-3-amine,
(3S)—N-(1-{[1-(4-Fluorophenyl)-2,3-dihydro-1H-indol-4-yl]carbonyl}azetidin-3-yl)-1-(1,3-thiazol-4-ylcarbonyl)pyrrolidin-3-amine,
(3S)—N-(1-{[1-(3-Fluorophenyl)-1H-indol-3-yl]carbonyl}azetidin-3-yl)-1-(1,3-thiazol-2-ylcarbonyl)pyrrolidin-3-amine,
(3S)—N-(1-{[1-(4-Fluorophenyl)-1H-indol-3-yl]carbonyl}azetidin-3-yl)-1-(1,3-thiazol-2-ylcarbonyl)pyrrolidin-3-amine,
(3S)—N-(1-{[1-(4-Fluorophenyl)-2,3-dihydro-1H-indol-5-yl]carbonyl}azetidin-3-yl)-1-(1,3-thiazol-2-ylcarbonyl)pyrrolidin-3-amine, (3S)—N-(1-{[3-(4-Fluorobenzyl)-1-methyl-1H-indol-6-yl]carbonyl}azetidin-3-yl)-1-(1,3-thiazol-2-ylcarbonyl)pyrrolidin-3-amine, N-Methyl-N-phenyl-2-{5-[(3-{[(3S)-1-(1,3-thiazol-2-ylcarbonyl)pyrrolidin-3-yl]amino}azetidin-1-yl)carbonyl]-1H-indol-1-yl}acetamide, (3S)—N-(1-{[4-Chloro-1-(4-fluorophenyl)-1H-indol-5-yl]carbonyl}azetidin-3-yl)-1-(1,3-thiazol-2-ylcarbonyl)pyrrolidin-3-amine, (3S)—N-(1-{[1-(4-Fluorophenyl)-6-methyl-1H-indol-5-yl]carbonyl}azetidin-3-yl)-1-(1,3-thiazol-2-ylcarbonyl)pyrrolidin-3-amine, and (3S)—N-(1-{[6-Chloro-1-(4-fluorophenyl)-1H-indol-5-yl]carbonyl}azetidin-3-yl)-1-(1,3-thiazol-2-ylcarbonyl)pyrrolidin-3-amine, and pharmaceutically acceptable salt forms thereof.

6. A pharmaceutical composition comprising the compound of claim 1 or 5 and a member selected from the group consisting of a pharmaceutically acceptable carrier, a pharmaceutically acceptable excipient, and a pharmaceutically acceptable diluent.

7. A pharmaceutical composition of claim 6, wherein the composition is a solid oral dosage form.

8. A pharmaceutical composition of claim 6, wherein the composition is selected from the group consisting of a syrup, an elixir, and a suspension.

9. A method for treating inflammatory pain in a subject in need thereof comprising administering a therapeutically effective amount of the compound of claim 1 or 5 to the subject.

10. The method of claim 9 wherein the inflammatory pain is due to inflammatory bowel disease, visceral pain, migraine, post operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain, pain due to physical trauma, headache, sinus headache, tension headache, or arachnoiditis.

* * * * *